US009663535B2

(12) United States Patent
Breslin et al.

(10) Patent No.: US 9,663,535 B2
(45) Date of Patent: May 30, 2017

(54) ATAXIA TELENGIECTASIA AND RAD3-RELATED (ATR) PROTEIN KINASE INHIBITORS

(71) Applicant: Atrin Pharmaceuticals LLC, Ambler, PA (US)

(72) Inventors: Henry Joseph Breslin, Lansdale, PA (US); Oren Gilad, Ambler, PA (US)

(73) Assignee: Atrin Pharmaceuticals LLC, Ambler, PA (US)

( * ) Notice: Subject to any disclaimer, the term of this patent is extended or adjusted under 35 U.S.C. 154(b) by 0 days.

(21) Appl. No.: 14/881,680

(22) Filed: Oct. 13, 2015

(65) Prior Publication Data

US 2016/0102104 A1    Apr. 14, 2016

Related U.S. Application Data

(60) Provisional application No. 62/063,176, filed on Oct. 13, 2014, provisional application No. 62/104,274, filed on Jan. 16, 2015.

(51) Int. Cl.
| | |
|---|---|
| *C07D 498/08* | (2006.01) |
| *C07D 515/08* | (2006.01) |
| *C07D 498/18* | (2006.01) |
| *A61K 31/4985* | (2006.01) |
| *A61K 31/5377* | (2006.01) |
| *A61K 45/06* | (2006.01) |

(52) U.S. Cl.
CPC ........ *C07D 498/08* (2013.01); *A61K 31/4985* (2013.01); *A61K 31/5377* (2013.01); *A61K 45/06* (2013.01); *C07D 498/18* (2013.01); *C07D 515/08* (2013.01)

(58) Field of Classification Search
CPC .. C07D 498/08; C07D 515/08; C07D 498/18; A61K 31/4985; A61K 45/06; A61K 31/5377
See application file for complete search history.

(56) References Cited

U.S. PATENT DOCUMENTS

| 2005/0009840 A1 | 1/2005 | Cui et al. |
| 2013/0252961 A1 | 9/2013 | Bailey et al. |
| 2014/0031351 A1 | 1/2014 | Breslin et al. |

FOREIGN PATENT DOCUMENTS

| WO | WO 2013-132376 A1 | 9/2013 | |
| WO | WO 2015050989 A2 * | 4/2015 | ........... C07D 491/18 |
| WO | WO 2016-061097 | 4/2016 | |

OTHER PUBLICATIONS

Brown, E, and Baltimore, D., "ATR Disruption Leads to Chromosomal Fragmentation and Early Embryonic Lethality", Genes & Development, Feb. 15, 2000, 14, 397-402.
Bryant H. E. et al., "Specific Killing of BRCA2-deficient Tumours With Inhibitors of Poly(ADP-ribose) Polymerase", Nature, Apr. 14, 2005, 434(7035), 913-917.
Charrier et al, "Discovery of Potent and Selective Inhibitors of Ataxia Telangiectasia Mutated and Rad3 Related (ATR) Protein Kinase as Potential Anticancer Agents", Journal of Medicinal Chemistry, Mar. 17, 2011, 54(7), 2320-2330.
Cimprich, K. and Cortez, D., "ATR: An Essential Regulator of Genome Integrity", Nature Reviews Molecular Cell Biology, Aug. 2008, 9(8), 616-627.
Di Micco R. et al., "Oncogene-Induced Senescence Is A DNA Damage Response Triggered by DNA Hyper-Replication", Nature, Nov. 30, 2006, 444(7119), 638-642.
Fong et al., "Inhibition of Poly(ADP-Ribose) Polymerase in Tumors from BRCA Mutation Carriers", New England Journal of Medicine, Jul. 9, 2009, 361(2),123-134.
Gilad O. et al., "Combining ATR Suppression With Oncogenic Ras Synergistically Increases Genomic Instability", Cancer Research, Dec. 1, 2010, 70(23), 9693-702.
Gygi et al, "Similarity and Categorization of Environmental Sounds", Perception & Psychophysics, Aug. 2007, 69(6), 839-855.
International Application No. PCT/US2015/055317: International Search Report and the Written Opinion dated Feb. 5, 2016, 16 pages.
Menezes D.L. et al., "A Synthetic Lethal Screen Reveals Enhanced Sensitivity to ATR Inhibitor Treatment in Mantle Cell Lymphoma with ATM Loss-of-Function", Molecular Cancer Research, Jan. 2015,13(1),120-129.
Negrini S. et al., "Genomic Instability—An Evolving Hallmark of Cancer", Nature Reviews Molecular Cell Biology, Mar. 2010, 11(3), 220-222.
Reaper P.M. et al., "Selective Killing of ATM- or p53- Deficient Cancer Cells Through Inhibition of ATR", Nature Chemical Biology, Apr. 13, 2011, 7(7), 428-430.
Schoppy et al, "Oncogenic Stress Sensitizes Murine Cancers to Hypomorphic Suppression of ATR", The Journal of Clinical Investigation, Jan. 2012, 122(1), 241-252.
International Preliminary Report on Patentability dated Oct. 21, 2016, 15 pages.

* cited by examiner

*Primary Examiner* — Samantha Shterengarts
*Assistant Examiner* — Matt Mauro
(74) *Attorney, Agent, or Firm* — Baker & Hostetler LLP

(57) ABSTRACT

Macrocyclic compounds having the structure of Formula (A), or pharmaceutically acceptable salts thereof, are provided,

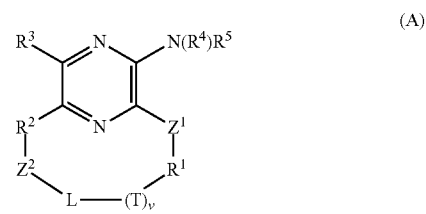

wherein $R^1$, $R^2$, $Z^1$, $Z^2$, v, T, L, $R^3$, $R^4$ and $R^5$ are defined herein. Also provided are pharmaceutical compositions comprising the macrocyclic compound and methods for treating cancer in a patient comprising administering to the patient the macrocyclic compound.

54 Claims, 4 Drawing Sheets

Figure 1: Compound P(1)'s effect on ATR mediated S-phase arrest (conc. = 10 μM)
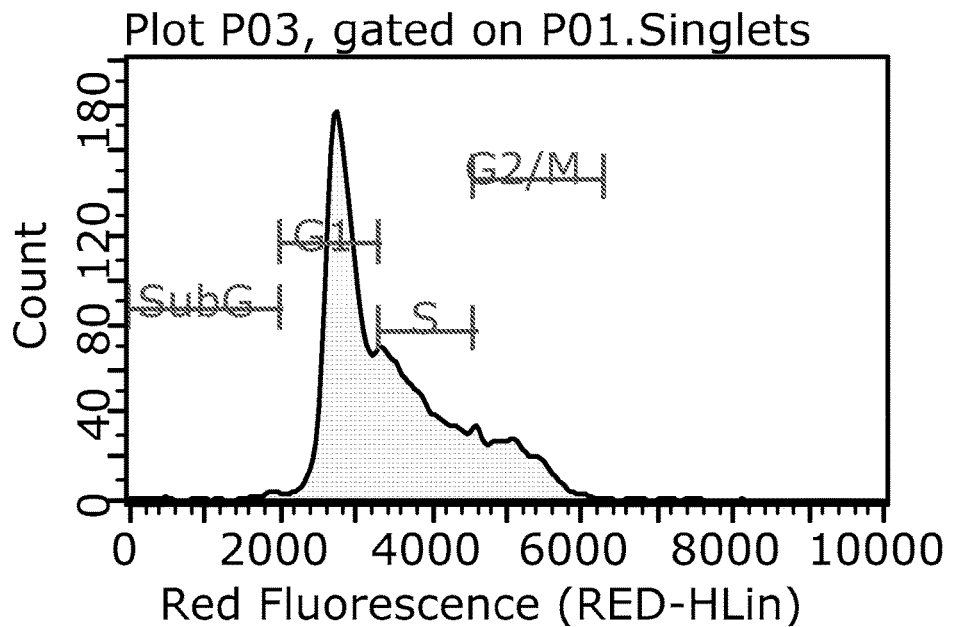
Figure 2: Compound P(1)'s effect on ATR mediated S-phase arrest (conc. = 2.5 μM)
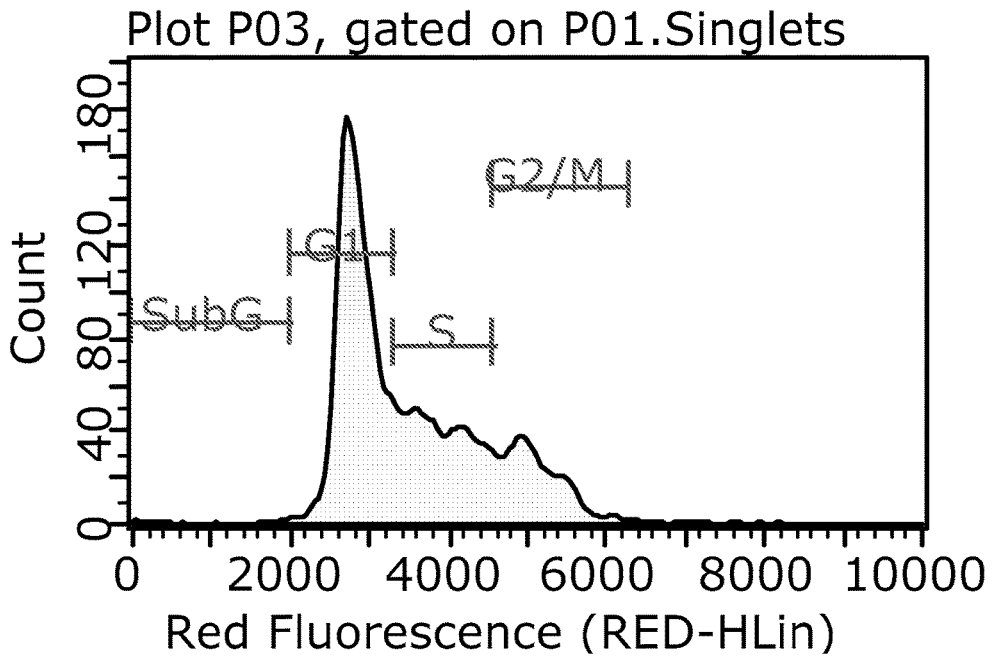

Figure 3A: Compound P(1)'s effect on ATR mediated S-phase arrest (conc. = 1.25 μM)
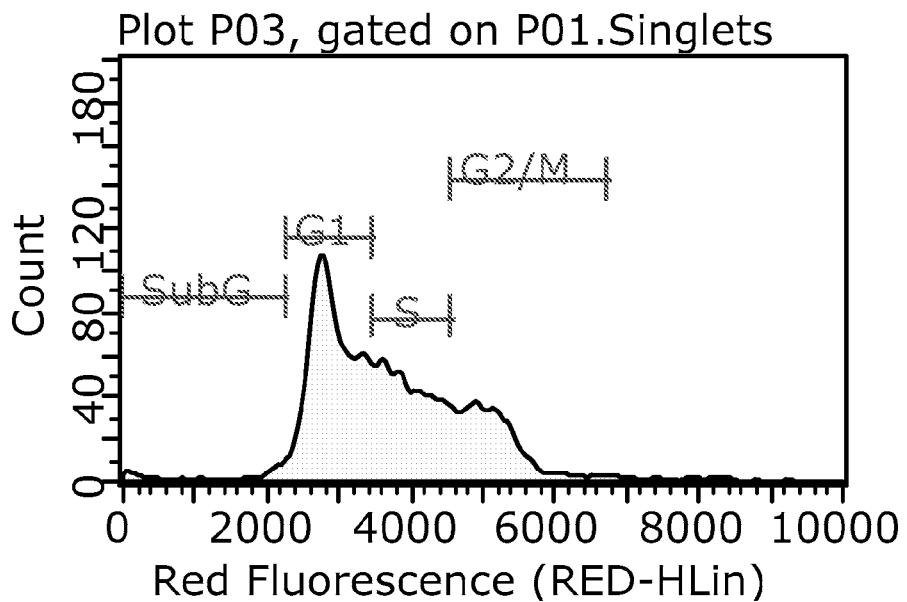
Figure 3B: Compound IM11 effect on ATR mediated S-phase arrest (conc. = 1.25 μM)
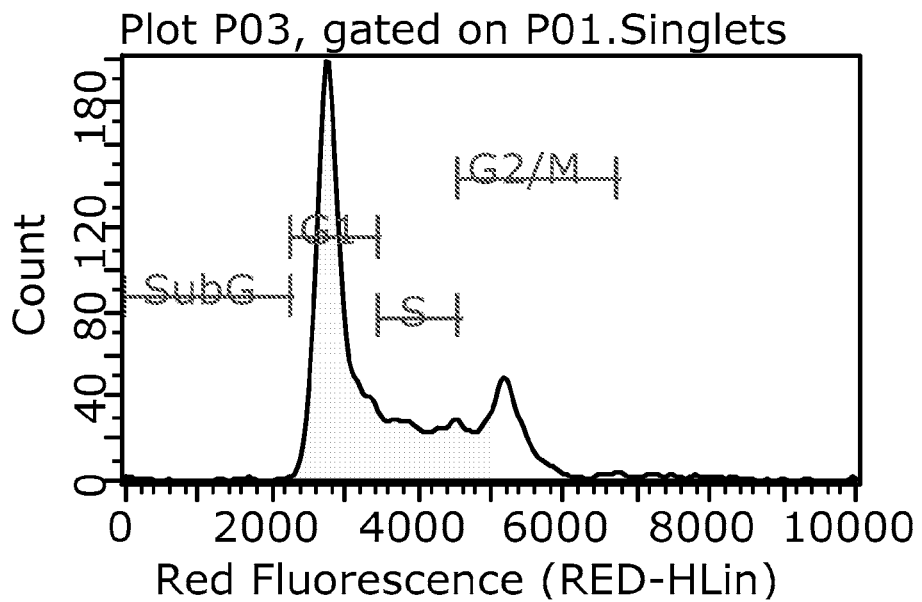

Figure 4A: Compound P(4) replicates the S-phase stalling observed upon ATR knock-down in cells under replicative stress.
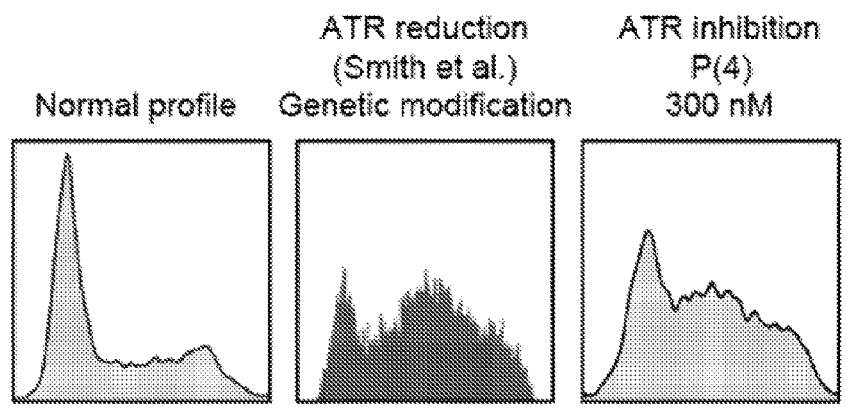
Figure 4B: Compound P(4) inhibits Chk1 phosphorylation at doses as low as 0.03 µM.
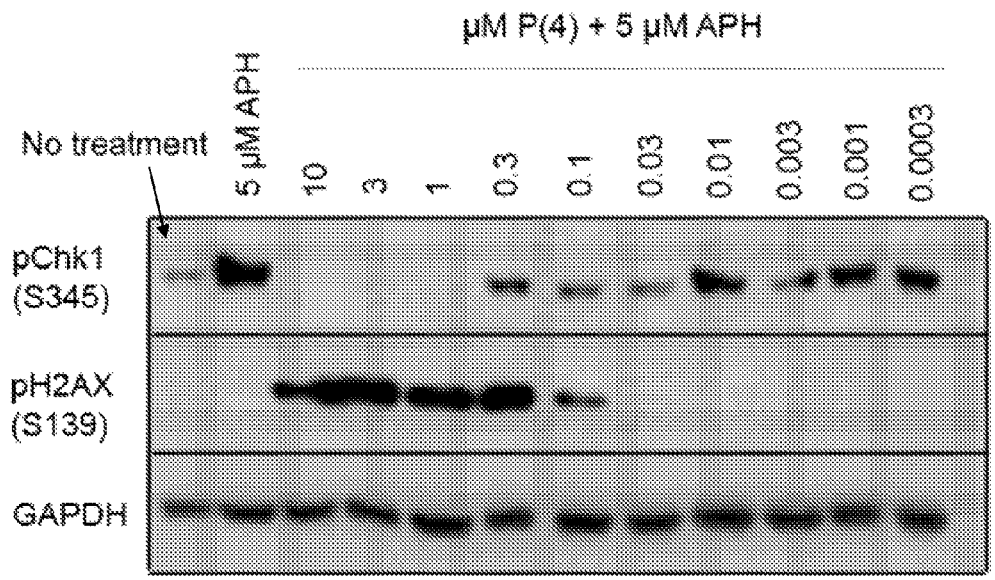

Figure 4C: Compound P(4) does not inhibit Chk2 phosphorylation.
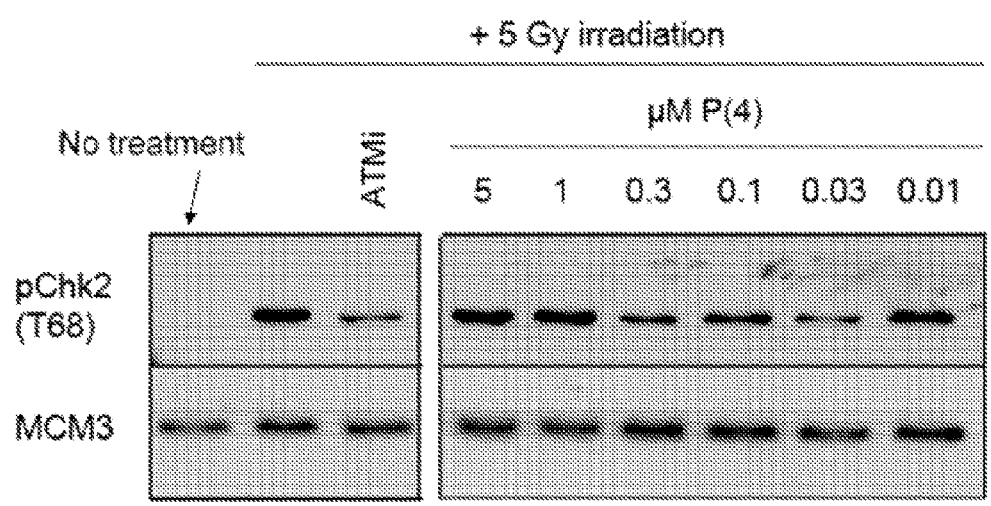

ATAXIA TELENGIECTASIA AND RAD3-RELATED (ATR) PROTEIN KINASE INHIBITORS

CROSS REFERENCE TO RELATED APPLICATIONS

The present application claims the benefit of U.S. Provisional Application No. 62/063,176 filed Oct. 13, 2014 and U.S. Provisional Application No. 62/104,274 filed Jan. 16, 2015, which are incorporated herein by reference in their entireties.

BACKGROUND OF THE INVENTION

This invention relates to: (i) chemical compounds that are generally useful as pharmaceutically active agents, and in particular as ataxia telengiectasia and Rad3-related (ATR) protein kinase inhibitors; (ii) pharmaceutical compositions comprising one or more of these ATR protein kinase inhibitors; (iii) a process for chemical synthesis of the ATR protein kinase inhibitors; and (iv) methods of using the ATR protein kinase inhibitors to treat various biological disorders, including cancer.

BRIEF SUMMARY OF THE INVENTION

In one aspect, the present invention provides a macrocyclic compound having the structure of Formula (A):

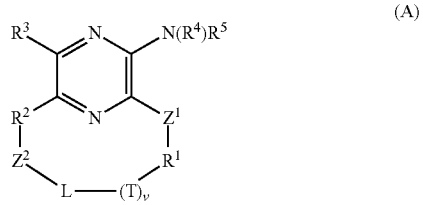

wherein each of $R^1$ and $R^2$ is independently (i) a 5-6 membered monocyclic aromatic ring containing 0-4 heteroatoms independently selected from nitrogen, oxygen, or sulfur; or (ii) an 8-10 membered bicyclic aromatic ring containing 0-6 heteroatoms independently selected from nitrogen, oxygen, or sulfur;

each $R^1$ and $R^2$ may independently be substituted by 0, 1, 2, 3, or 4 substituents;

$Z^1$ represents a covalent bond, an atom, or a functional group comprising a grouping of atoms, wherein the grouping of atoms includes at least one heteroatom selected from the group consisting of N, O, P, and S;

or $Z^1$ represents (i) a 5-6 membered monocyclic aromatic ring containing 0-4 heteroatoms independently selected from nitrogen, oxygen, or sulfur; or (ii) an 8-10 membered bicyclic aromatic ring containing 0-6 heteroatoms independently selected from nitrogen, oxygen, or sulfur;

$Z^2$ represents a covalent bond, an atom, or a functional group comprising a grouping of atoms, wherein the grouping of atoms includes at least one heteroatom selected from the group consisting of N, O, P, and S;

v is an integer having a value of 1 or 0; T is a carbon atom, a nitrogen atom, a sulfur atom, or an oxygen atom;

L is a linking group covalently bonded to T when v has a value of 1 or L is covalently bonded to $R^1$ when v has a value of 0;

wherein L is covalently bonded to $Z^2$ when $Z^2$ is an atom or a functional group comprising grouping of atoms or L is covalently bonded to $R^2$ when $Z^2$ is a covalent bond; and each of $R^3$, $R^4$ and $R^5$ may be the same as or different from each other and each is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of the macrocyclic compound of the present invention, each of $R^1$ and $R^2$ is independently selected from the group consisting of phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyrazinyl, pyrimidinyl, oxadiazolyl, benzimidazolyl, and triazinyl.

In at least one embodiment of the macrocyclic compound of the present invention, each of $R^1$ and $R^2$ is independently selected from the group consisting of phenyl, pyridyl, and isoxazolyl.

In at least one embodiment of the macrocyclic compound of the present invention, each of $Z^1$ and $Z^2$ is independently selected from the group consisting of —SO—, —SO$_2$—, —S(=O)N($R^6$)—, —S(=O)C($R^7$)($R^6$)—, —S(=O)$_2$N($R^6$)—, —S(=O)$_2$C($R^7$)($R^6$)—, —C(=O)—, —C(=O)N($R^6$)—, —C(=O)C($R^7$)($R^6$)—, —C(S)C($R^7$)($R^6$)- and —C(S)N($R^6$)—, wherein each of $R^6$ and $R^7$ is independently selected from the group consisting of hydrogen, alkyl, alkenyl, alkynyl, cycloalkyl, cycloalkenyl, heterocyclyl, aryl, heteroaryl, aralkyl, or heteraralkyl; and when there is a plurality of $R^6$ or $R^7$ in the structure of the macrocyclic compound each instance of $R^6$ or $R^7$ may be the same as or different from another instance of $R^6$ or $R^7$.

In at least one embodiment of the macrocyclic compound of the present invention, each of $Z^1$ is —C(=O)N($R^6$)—, wherein $R^6$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of the macrocyclic compound of the present invention, $Z^2$ is —S(=O)$_2$N($R^6$)—, wherein $R^6$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of the macrocyclic compound of the present invention, $Z^2$ is —S(=O)$_2$N($R^6$)— and $Z^1$ is —C(=O)N($R^6$)—, wherein $R^6$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of the macrocyclic compound of the present invention, each of $R^1$ and $R^2$ is phenyl; and $Z^2$ is —S(=O)$_2$N($R^6$)— and $Z^1$ is —C(=O)N($R^6$)—, wherein $R^6$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of the macrocyclic compound of the present invention, $Z^1$ is selected from the group consisting of phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyzazinyl, pyrimidinyl, oxadiazolyl, benzimidazolyl, and triazinyl.

In at least one embodiment of the macrocyclic compound of the present invention, L represents a backbone chain having at least 2 atoms.

In at least one embodiment of the macrocyclic compound of the present invention, L-(T)$_v$ represents a backbone chain having at least 2 atoms and at most 25 atoms, wherein L, T, and v are as defined for the compound of Formula (A).

In at least one embodiment of the macrocyclic compound of the present invention, L represents an aliphatic backbone chain having at least 3 atoms.

In at least one embodiment of the macrocyclic compound of the present invention, L-(T)$_v$ represents an aliphatic backbone chain having at least 3 carbon atoms and at most 25 carbon atoms, wherein L, T, and v are as defined for the compound of Formula (A).

In at least one embodiment of the macrocyclic compound of the present invention, L represents an aliphatic backbone chain having at least 2 atoms, wherein the aliphatic backbone chain is one or more times interrupted by one or more heteroatoms independently selected from the group consisting of O, S, N and P.

In at least one embodiment of the macrocyclic compound of the present invention, L represents an aliphatic backbone chain having at least 2 carbon atoms, wherein the aliphatic backbone chain is one or more times interrupted by one or more heteroatoms independently selected from the group consisting of O, S, N and P, and wherein L-(T)$_v$ represents a backbone chain having at most 25 atoms, wherein T, and v are as defined for the compound of Formula (A).

In another aspect, the present invention provides a pharmaceutical composition comprising a macrocyclic compound according to the present invention. In at least one embodiment of the pharmaceutical composition, the macrocyclic compound is an ATR protein kinase inhibitor or a pharmaceutically acceptable salt thereof. In at least one embodiment, the pharmaceutical composition of the present invention includes a pharmaceutically acceptable carrier. In at least one embodiment of the pharmaceutical composition, the pharmaceutical composition includes the ATR protein kinase inhibitor in an effective amount to inhibit an ATR protein kinase.

In another aspect, the present invention provides a method of treatment comprising administering to a patient in need of the treatment, an ATR protein kinase inhibitor comprising a macrocyclic compound according to the present invention. In at least one embodiment of the method of treatment of the present invention, the ATR protein kinase inhibitor is administered to the patient in an effective amount to inhibit an ATR protein kinase. In at least one embodiment of the method of treatment of the present invention, inhibition of an ATR protein kinase by a compound according to the present invention prevents and/or treats a cancer in the patient. In at least one embodiment of the method of treatment of the present invention, the patient has a cancer selected from the group consisting of Breast Cancer, Prostate Cancer, Pancreatic Cancer, Lung Cancer, Colon Cancer, Ovarian Cancer, Liver Cancer, Melanoma, Renal Cancer, Central Nervous System Cancer and Leukemia Lymphoma.

BRIEF DESCRIPTION OF THE DRAWINGS

The foregoing summary, as well as the following detailed description of embodiments of the invention, will be better understood when read in conjunction with the appended drawings of an exemplary embodiment. It should be understood, however, that the invention is not limited to the precise arrangements and instrumentalities shown.

In the drawings:

FIG. 1 illustrates an effect of compound P(1) on ATR mediated S-phase arrest of Jurkat cells at 10 μM concentration;

FIG. 2 illustrates an effect of compound P(1) on ATR mediated S-phase arrest of Jurkat cells at 2.5 μM concentration;

FIGS. 3A-3B illustrate effects of compound P(1) and precursor compound IM11, on ATR mediated S-phase arrest of Jurkat cells at 1.25 μM concentration; and FIGS. 4A-4C illustrate effects of compound P(4) on: ATR mediated S-phase arrest of Jurkat cells at 300 nM concentration (FIG. 4A); CHK1 phosphorylation, and H2AX phosphorylation (at 10 to 0.0003 μM) in HCT119 cells (FIG. 4B); and CHK2 phosphorylation in HCT119 cells (at 5 to 0.01 μM) (FIG. 4C).

DETAILED DESCRIPTION OF THE INVENTION

Referring to the drawings in detail, wherein like reference numerals indicate like elements throughout, there are shown in FIGS. 1A to 4 biological effects of exemplary compounds P(1) and P(4) on various cells, including human T lymphocyte cells (Jurkat cells). In FIG. 4 is shown the biological effect of exemplary compound P(4) on HCT119 human colon cancer cell line. In the following descriptions of exemplary embodiments of the present invention, all references, including publications, patent applications, and patents, cited herein are incorporated by reference into this application to the same extent as if each reference were individually and specifically indicated to be incorporated by reference and were set forth in its entirety herein.

That ATR suppression to clinically relevant levels has the potential to be effective in a wide spectrum of cancers is supported by several lines of evidence. Ataxia telengiectasia and rad3-related (ATR) protein kinase is integral to the replication stress response. ATR belongs to a family of kinases, i.e., phosphatidyl inositol 3' kinase-related kinases (PIKKs), that are involved in the signaling and repair of DNA damage. While other members of this family (ataxiatelangiectasia mutated (ATM) and DNA-dependent protein kinase catalytic subunit (DNA-PKcs)) are required for the repair of double strand breaks (DSBs), ATR is recruited to, and activated by, single strand DNA (ssDNA) generated at stalled replication forks or as an intermediate in the repair of DSBs. Upon replication fork stalling activated ATR phosphorylates the downstream kinase Chk1 resulting in stabilization of the replication fork and inhibition of cell-cycle progression, thus allowing time for resolution of the stress and continued replication. When the ATR-Chk1 pathway is disrupted stalled replication forks collapse into DSBs, thus if unresolved, replication stress can cause genomic instability and negatively impact cell survival (Karlene A. Cimprich & David Cortez, ATR: an essential regulator of genome integrity, *Nature Reviews Molecular Cell Biology*, August 2008, 9, 616-627). Due to its vital role in replication, loss of ATR is early-embryonic lethal in mice (Eric J. Brown and David Baltimore, ATR disruption leads to chromosomal fragmentation and early embryonic lethality, *Genes & Development*, 2000, 14, 397-402). However, it is important to note that significant suppression of ATR activity (by more than 90%) by mutations in ATR (as would be replicated by treatment with the inhibitors discussed and disclosed herein) is well tolerated by bone marrow and intestinal epithelium, the tissues that are most sensitive to traditional chemotherapeutics (David W. Schoppy et al., Oncogenic stress sensitizes murine cancers to hypomorphic suppression of ATR, *The Journal of Clinical Investigation*, 2012, 122(1), 241-252).

ATR inhibition is synthetically lethal in cancers with mutations that cause oncogenic stress or disruption of the DNA damage response (DDR). Genetic changes associated with cancer promote the activation of the replicative stress response and other DNA damage response (DDR) pathways (Di Micco R. et al., Oncogene-induced senescence is a DNA damage response triggered by DNA hyper-replication, *Nature* 2006 Nov. 30, 444(7119):638-42; Negrini S. et al., Genomic instability—an evolving hallmark of cancer, *Nat. Rev. Mol. Cell Biol.* 2010 March, 11(3):220-22). Such oncogenic stress inducing alterations include K-Ras$^{G12D}$ and H-Ras$^{G12V}$ mutations, and c-Myc amplification. Activation of the DDR by oncogenic stress has been proposed to contribute to selection for mutation, and loss of, p53 and ATM (Negrini S. et al., Genomic instability—an evolving hallmark of cancer, *Nat. Rev. Mol. Cell Biol.* 2010 March, 11(3):220-228). Mutations in the tumor suppressor p53 are found in ~50% of all human cancers. Similar mutation frequencies are observed in the oncogene Myc, while significant numbers of cancers also harbor mutations in the Ras family of genes (~16%) and to a lesser degree the DDR protein ATM. Alterations in these genes cause an increased reliance on the ATR-Chk1 pathway for genome maintenance. Studies have found that ATR inhibition elicits synthetic lethality under each of these cancer associated conditions (Gilad O. et al., Combining ATR suppression with oncogenic Ras synergistically increases genomic instability, *Cancer Res.* 2010, 70(23), 9693-702; Schoppy et. al., *J. Clin. Invest*, 2012; Reaper P. M. et al., Selective killing of ATM- or p53-deficient cancer cells through inhibition of ATR, *Nat. Chem. Biol.*, 2011, 7(7), 428-30; Menezes D. L. et al., A Synthetic Lethal Screen Reveals Enhanced Sensitivity to ATR Inhibitor Treatment in Mantle Cell Lymphoma with ATM Loss-of-function, *Mol Cancer Res.* 2015 January; 13(1):120-9).

Cancers deficient in components of the homologous recombination pathway, such as those harboring mutations in BRCA1 and BRCA2, are highly sensitive to PARP inhibition (Fong et al., Inhibition of Poly(ADP-Ribose) Polymerase in Tumors from BRCA Mutation Carriers, *N Engl J Med* 2009; 361:123-134, 2009). While PARP is required for the repair of single strand breaks (SSBs), preventing their collapse into DSBs, ATR stabilizes replication forks, similarly preventing collapse and formation of DSBs. Loss of PARP and ATR activities therefore both force cells to rely on the DSB repair pathway. It is the inability of BRCA mutant cells to repair DSBs that renders them sensitive to PARP inhibition (Bryant H. E. et al., Specific killing of BRCA2-deficient tumours with inhibitors of poly(ADP-ribose) polymerase, *Nature* 2005 Apr. 14, 434(7035), 913-7), it is therefore reasonable to suppose that cells deficient in the DDR, such as those harboring BRCA mutations, would also be sensitive to ATR inhibition.

I. DEFINITIONS

"Alkyl" refers to a straight or branched hydrocarbon chain radical consisting of carbon and hydrogen atoms, containing no unsaturation, and may be straight or branched, substituted or unsubstituted. In some preferred embodiments, the alkyl group may consist of 1 to 12 carbon atoms, e.g. 1 carbon atom, 2 carbon atoms, 3 carbon atoms, 4 carbon atoms etc., up to and including 12 carbon atoms. Exemplary alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl and decyl. The alkyl moiety may be attached to the rest of the molecule by a single bond, such as for example, methyl (Me), ethyl (Et), n-propyl (Pr), 1-methylethyl (isopropyl), n-butyl, n-pentyl, 1,1-dimethylethyl (t-butyl) and 3-methylhexyl. Unless stated otherwise specifically in the specification, an alkyl group is optionally substituted by one or more of any suitable substituents. An alkyl group can be mono-, di-, tri- or tetra-valent, as appropriate to satisfy valence requirements. The term "alkylene," by itself or as part of another substituent, means a divalent radical derived from an alkyl moiety, as exemplified, but not limited to, by —CH$_2$CH$_2$CH$_2$CH$_2$—.

Generally, suitable substituents for substituted groups disclosed herein independently include, but are not limited to, alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$, —N(R$^a$)S(O)$_2$R$^a$, —S(O)OR$^a$, —S(O)$_2$OR$^a$, —S(O)N(R$^a$)$_2$, —S(O)$_2$N(R$^a$)$_2$, or PO$_3$(R$^a$)$_2$ where each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

"Alkylaryl" refers to an -(alkyl)aryl radical where aryl and alkyl are as disclosed herein and which are optionally substituted by one or more of the substituents described herein as suitable substituents for aryl and alkyl respectively.

"Alkylhetaryl" refers to an -(alkyl)hetaryl radical where hetaryl and alkyl are as disclosed herein and which are optionally substituted by one or more of the substituents described as suitable substituents for aryl and alkyl respectively.

"Alkylheterocycloalkyl" refers to an -(alkyl)heterocycyl radical where alkyl and heterocycloalkyl are as disclosed herein and which are optionally substituted by one or more of the substituents described as suitable substituents for heterocycloalkyl and alkyl respectively.

An "alkene" moiety refers to a group consisting of at least two carbon atoms and at least one carbon-carbon double bond.

An "alkyne" moiety refers to a group consisting of at least two carbon atoms and at least one carbon-carbon triple bond. The alkynyl moiety, may be branched, straight chain, or cyclic.

"Alkenyl" refers to a straight or branched hydrocarbon chain radical group consisting of carbon and hydrogen atoms, and containing at least one double bond. In some preferred embodiments, the alkenyl group may contain from 2 carbon atoms to 12 carbon atoms, e.g., the alkenyl group may consist of 2 carbon atoms, 3 carbon atoms, 4 carbon atoms etc., up to and including 12 carbon atoms. The alkenyl moiety may be attached to the rest of the molecule by a single bond, such as for example, ethenyl (i.e., vinyl), prop-1-enyl (i.e., allyl), but-1-enyl, pent-1-enyl and penta-1,4-dienyl, or by a double bond. Unless stated otherwise specifically in the specification, an alkenyl group is optionally substituted by one or more substituents which are independently alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively.

"Alkynyl" refers to a straight or branched hydrocarbon chain radical group consisting of carbon and hydrogen atoms, containing at least one triple bond. In some preferred embodiments, the alkynyl group may contain from two to twelve carbon atoms, and may be designated as ($C_{2-12}$) alkynyl or $C_{2-12}$ alkynyl. Whenever it appears herein, a numerical range such as "2 to 12" in ($C_{2-12}$)alkynyl or ($C_{2-12}$)alkynyl refers to each integer in the given range—e.g., "2 to 10 carbon atoms" means that the alkynyl group may consist of 2 carbon atoms, 3 carbon atoms, 4 carbon atoms etc., up to and including 12 carbon atoms. The alkynyl may be attached to the rest of the molecule by a single bond, for example, ethynyl, propynyl, butynyl, pentynyl and hexynyl. Unless stated otherwise specifically in the specification, an alkynyl group is optionally substituted by one or more substituents described as suitable substituents for alkynl.

"Alkynyl-cycloalkyl" refers to an -(alkynyl)cycloalkyl radical where alkynyl and cycloalkyl are as disclosed herein and which are optionally substituted by one or more of the substituents described as suitable substituents for alkynyl and cycloalkyl respectively.

"Carboxaldehyde" refers to a —(C=O)H radical.

"Carboxyl" refers to a —(C=O)OH radical.

"Cyano" refers to a —CN radical.

"Cycloalkyl" refers to a monocyclic or polycyclic radical that contains carbon and hydrogen, and may be saturated, or partially unsaturated. In some preferred embodiments, cycloalkyl groups include groups having from 3 to 12 ring atoms (i.e. ($C_{3-12}$)cycloalkyl or $C_{(3-12)}$cycloalkyl). Whenever it appears herein, a numerical range such as "3 to 12" in ($C_{3-12}$)cycloalkyl or $C_{(3-12)}$cycloalkyl refers to each integer in the given range—e.g., "3 to 12 carbon atoms" means that the cycloalkyl group may consist of 3 carbon atoms, 4 carbon atoms, 5 carbon atoms, etc., up to and including 12 carbon atoms. Illustrative examples of cycloalkyl groups include, but are not limited to cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. Unless stated otherwise specifically in the specification, a cycloalkyl group is optionally substituted by one or more substituents is optionally substituted by one or more substituents described as suitable substituents for alkyl and cycloalkyl respectively.

"Cycloalkyl-alkenyl" refers to a -(cycloalkyl)alkenyl radical where cycloalkyl and alkenyl are as disclosed herein and which are optionally substituted by one or more of the substituents described as suitable substituents for cycloalkyl and alkenyl, respectively.

"Cycloalkyl-heterocycloalkyl" refers to a -(cycloalkyl)heterocycloalkyl radical where cycloalkyl and heterocycloalkyl are as disclosed herein and which are optionally substituted by one or more of the substituents described as suitable substituents for cycloalkyl and heterocycloalkyl, respectively.

"Cycloalkyl-heteroaryl" refers to a -(cycloalkyl)heteroaryl radical where cycloalkyl and heteroaryl are as disclosed herein and which are optionally substituted by one or more of the substituents described as suitable substituents for cycloalkyl and heteroaryl, respectively.

The term "alkoxy" refers to the group —O-alkyl. In some preferred embodiments, the alkoxy group contains from 1 to 12 carbon atoms of a straight, branched, cyclic configuration and combinations thereof attached to the parent structure through an oxygen. Whenever it appears herein, a numerical range such as "1 to 12" refers to each integer in the given range—e.g., "1 to 12 carbon atoms" means that group may consist of 3 carbon atoms, 4 carbon atoms, 5 carbon atoms, etc., up to and including 12 carbon atoms. Examples of alkoxy include, but are not limited to, methoxy, ethoxy, propoxy, isopropoxy, cyclopropyloxy and cyclohexyloxy. "Lower alkoxy" refers to alkoxy groups containing one to six carbons.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which is described as suitable substituents for alkyl.

The term "alkoxycarbonyl" refers to a group of the formula (alkoxy)(C=O)— attached through the carbonyl carbon wherein the alkoxy group has the indicated number of carbon atoms. In some preferred embodiments, the alkoxycarbonyl group contain from 1 to 12 carbon atoms, e.g., ($C_{1-12}$)alkoxycarbonyl group. Whenever it appears herein, a numerical range such as "1 to 12" refers to each integer in the given range—e.g., "1 to 12 carbon atoms" in ($C_{1-12}$)alkoxycarbonyl means that the alkoxycarbonyl group may consist of 1 carbon atom, 2 carbon atoms, 3 carbon atoms, etc., up to and including 12 carbon atoms. "Lower alkoxycarbonyl" refers to an alkoxycarbonyl group wherein the alkoxy group is a lower alkoxy group.

The term "substituted alkoxycarbonyl" refers to the group (substituted alkyl)-O—C(O)— wherein the group is attached to the parent structure through the carbonyl functionality. Unless stated otherwise specifically in the specification, the alkyl moiety of an alkoxycarbonyl group is optionally substituted by one or more substituents which is described herein as suitable substitution groups.

"Acyl" refers to $R^c$—C(O)— wherein $R^c$ include, but is not limited to, alkyl, heteroalkyl, alkenyl, alkynyl, cycloalkyl, heterocycloalkyl, aryl, arylalkyl, heteroaryl, heteroarylalkyl, and wherein the group is attached to the parent structure through the carbonyl functionality. Unless stated otherwise specifically in the specification, the substituent (e.g. alkyl, aryl, heteroaryl moiety, etc.,) of the acyl group is optionally substituted by one or more substituents which are described herein as suitable substitution groups.

"Acyloxy" refers to a $R^c$(C=O)O— radical wherein $R^c$ include, but is not limited to, alkyl, heteroalkyl, alkenyl, alkynyl, cycloalkyl, heterocycloalkyl, aryl, arylalkyl, heteroaryl, heteroarylalkyl, and wherein the acyloxy group is attached to the parent structure through the oxy functionality. Unless stated otherwise specifically in the specification, the "$R^c$" of an acyloxy group is optionally substituted by one or more substituents which are described herein as suitable substitution groups.

"Amino" or "amine" refers to a —N($R^a$)$_2$ radical group, where each $R^a$ is independently hydrogen, alkyl, (halo)alkyl, alkenyl, alkynyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —N($R^a$)$_2$ group has two $R^a$ substituents other than hydrogen, they can be combined with the nitrogen atom to form a 4-, 5-, 6- or 7-membered ring. For example, —N($R^a$)$_2$ is intended to include, but is not limited to, 1-pyrrolidinyl, 4-piperazinyl, and 4-morpholinyl. Unless stated otherwise specifically in the specification, an amino group is optionally substituted by one or more substituents which are described herein as suitable substitution groups.

The term "substituted amino" also refers to N-oxides of the groups —NH$R^a$, and N$R^a$$R^a$ each as described above. N-oxides can be prepared by treatment of the corresponding amino group with, for example, hydrogen peroxide or m-chloroperoxybenzoic acid.

"Amide" or "amido" refers to a chemical moiety with formula —C(O)N($R^d$)$_2$ or —NHC(O)$R^d$, where $R^d$ is selected from the group consisting of hydrogen, alkyl, alkenyl, alkynyl, carbocyclyl, carbocyclylalkyl, cycloalkyl, aryl, heteroaryl (bonded through a ring carbon) and heteroalicyclic (bonded through a ring carbon), each of which moiety may itself be optionally substituted with any of the substituents described herein as suitable substitution groups.

The $R^d$ of —N($R^d$)$_2$ of the amide may optionally be taken together with the nitrogen to which it is attached to form a 4-, 5-, 6- or 7-membered ring. Unless stated otherwise specifically in the specification, an amido group is optionally substituted independently by one or more of the substituents as described herein as suitable substitution groups.

The procedures and specific groups to make such amides are known to those of skill in the art and can readily be found in seminal sources such as Greene and Wuts, Protective Groups in Organic Synthesis, 3$^{rd}$ Ed., John Wiley & Sons, New York, 1999, which is incorporated herein by reference in its entirety.

"Aromatic" means an unsaturated, cyclic and planar hydrocarbon group with a delocalized conjugated π system having 4n+2π electrons, where n is an integer having a value of 0, 1, 2, 3, and so on. In some embodiments, the aromatic group is an "aryl" (abbreviated as Ar), which refers to an aromatic radical with six to ten ring atoms (e.g., (C$_{6-10}$) aromatic or (C$_{6-10}$)aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., 6 to 10 ring atoms in (C$_{6-10}$)aromatic or (C$_{6-10}$)aryl means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety is optionally substituted by one or more substituents which are described herein as suitable substitution groups.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively.

"Ester" refers to a chemical radical of formula —COO$R^e$, where $R^e$ includes, but is not limited to, alkyl, alkenyl, alkynyl, alkyl, alkenyl, alkynyl, cycloalkyl, cycloalkenyl, heterocyclyl, aryl, heteroaryl, aralkyl, and heteraralkyl. The procedures and specific groups to make esters are known to those of skill in the art and can readily be found in seminal sources such as Greene and Wuts, Protective Groups in Organic Synthesis, 3$^{rd}$ Ed., John Wiley & Sons, New York, N.Y., 1999, which is incorporated herein by reference in its entirety. Unless stated otherwise specifically in the specification, an ester group is optionally substituted by one or more substituents which are described herein as suitable substitution groups.

"Haloalkyl" refers to an alkyl radical, as defined above, that is substituted by one or more halogen atoms. Examples of haloalkyl include, but are not limited to, trifluoromethyl, difluoromethyl, 2,2,2-trifluoroethyl, 1-fluoromethyl-2-fluoroethyl, and the like. The alkyl part of the haloalkyl radical may be optionally substituted as defined above for an alkyl group.

"Halo", "halide", or, alternatively, "halogen" is intended to mean fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl", "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given—e.g., (C$_{1-12}$)heteroalkyl which refers to number of carbon atoms in the alkyl chain, the range refers to each integer in the given range—e.g., "1 to 12 carbon atoms" in (C$_{1-12}$)heteroalkyl means that the heteroalkyl group may contain 1 carbon atom, 2 carbon atoms, 3 carbon atoms, etc., up to and including 12 carbon atoms. A heteroalkyl group may be substituted with one or more substituents which are described herein as suitable substitution groups.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl, respectively.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl, respectively.

"Heteroalkylheterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl, respectively.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl, respectively.

"Heteroaryl" or "heteroaromatic refers to a 5- to 18-membered aromatic radical (e.g., ($C_{5-13}$)heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may contain 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene. An N-containing "heteroaromatic" or "heteroaryl" moiety refers to an aromatic group in which at least one of the skeletal atoms of the ring is a nitrogen atom. The polycyclic heteroaryl group may be fused or non-fused. The heteroatom(s) in the heteroaryl radical are optionally oxidized. One or more nitrogen atoms, if present, are optionally quaternized. The heteroaryl may be attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl(benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —$C(O)R^a$, —$C(O)OR^a$, —OC(O)$N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$ (where t is 1 or 2), —$S(O)_tOR^a$ (where t is 1 or 2), —$S(O)_tN(R^a)_2$ (where t is 1 or 2), or $PO_3(R^a)_2$, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

"Heteroarylalkyl" refers to a moiety having an aryl moiety, as described herein, connected to an alkylene moiety, as described herein, wherein the connection to the remainder of the molecule is through the alkylene group.

"Heterocycloalkyl" refers to a stable 3- to 18-membered non-aromatic ring radical that comprises two to twelve carbon atoms and from one to six heteroatoms selected from nitrogen, oxygen and sulfur. Whenever it appears herein, a numerical range such as "3 to 18" refers to each integer in the given range—e.g., "3 to 18 ring atoms" means that the heterocycloalkyl group may consist of 3 ring atoms, 4 ring atoms, etc., up to and including 18 ring atoms. Unless stated otherwise specifically in the specification, the heterocycloalkyl radical is a monocyclic, bicyclic, tricyclic or tetracyclic ring system, which may include fused or bridged ring systems. The heteroatoms in the heterocycloalkyl radical may be optionally oxidized. One or more nitrogen atoms, if present, are optionally quaternized. The heterocycloalkyl radical is partially or fully saturated. The heterocycloalkyl may be attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, a heterocycloalkyl moiety is optionally substituted by one or more substituents which are described herein as suitable substitution groups.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteroatoms independently selected from oxygen, sulfur, and nitrogen and is not aromatic.

"Isomers" are different compounds that have the same molecular formula. "Stereoisomers" are isomers that differ only in the way the atoms are arranged in space—i.e., having a different stereochemical configuration. "Enantiomers" are a pair of stereoisomers that are non-superimposable mirror images of each other. A 1:1 mixture of a pair of enantiomers is a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon can be specified by either (R) or (S). Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R) or (S). The present chemical entities, pharmaceutical compositions and methods are meant to include all such possible isomers, including racemic mixtures, optically pure forms and intermediate mixtures. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which may potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)-isomer and 20% (R)-isomer, the enantiomeric purity of the compound with respect to the (S)-isomeric form is 80%. The enantiomeric purity of a compound can be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or Pirkle's reagents, or derivatization of a compounds using a chiral compound such as Mosher's acid followed by chromatography or nuclear magnetic resonance spectroscopy.

In preferred embodiments, the enantiomerically enriched composition has a higher potency with respect to therapeutic utility per unit mass than does the racemic mixture of that composition. Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., Enantiomers, Racemates and Resolutions, Wiley Interscience, New York, 1981; Eliel, Stereochemistry of Carbon Compounds, McGraw-Hill, N Y, 1962; and Eliel and Wilen, Stereochemistry of Organic Compounds, Wiley-Interscience, New York, 1994.

The terms "enantiomerically enriched" and "non-racemic," as used herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, or such as at least 80% by weight. In some embodiments, the enrichment can be significantly greater than 80% by weight, providing a "substantially enantiomerically enriched" or a "substantially non-racemic" preparation, which refers to preparations of compositions which have at least 85% by weight of one enantiomer relative to other enantiomer, such as at least 90% by weight, or such as at least 95% by weight. The terms "enantiomerically pure" or "substantially enantiomerically pure" refers to a composition that comprises at least 98% of a single enantiomer and less than 2% of the opposite enantiomer.

"Moiety" refers to a specific segment or functional group of a molecule. Chemical moieties are often recognized chemical entities embedded in or appended to a molecule.

"Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under selected reaction conditions, cleave from the starting material, thus promoting reaction at a specified site. Examples of such groups, unless otherwise specified, include halogen atoms and mesyloxy, p-nitrobenzensulphonyloxy and tosyloxy groups.

"Protecting group" is intended to mean a group that selectively blocks one or more reactive sites in a multifunctional compound such that a chemical reaction can be carried out selectively on another unprotected reactive site and the group can then be readily removed after the selective reaction is complete. A variety of protecting groups are disclosed, for example, in T. H. Greene and P. G. M. Wuts, Protective Groups in Organic Synthesis, Third Edition, John Wiley & Sons, New York (1999).

"Solvate" refers to a compound in physical association with one or more molecules of a pharmaceutically acceptable solvent.

"Substituted" means that the referenced group may have attached one or more additional groups, radicals or moieties individually and independently selected from, for example, acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfoxyl, sulfonate, urea, and amino, including mono- and di-substituted amino groups, and protected derivatives thereof. The substituents themselves may be substituted, for example, a cycloalkyl substituent may itself have a halide substituent at one or more of its ring carbons. The term "optionally substituted" means optional substitution with the specified groups, radicals or moieties.

"Sulfanyl" refers to groups that include —S-(optionally substituted alkyl), —S-(optionally substituted aryl), —S-(optionally substituted heteroaryl) and —S-(optionally substituted heterocycloalkyl).

"Sulfinyl" refers to groups that include —S(O)—H, —S(O)-(optionally substituted alkyl), —S(O)-(optionally substituted amino), —S(O)-(optionally substituted aryl), —S(O)-(optionally substituted heteroaryl) and —S(O)-(optionally substituted heterocycloalkyl).

"Sulfonyl" refers to groups that include —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NR$^f$R$^f$ radical, where each R$^f$ is selected independently from the group consisting of hydrogen, alkyl, cycloalkyl, aryl, heteroaryl (bonded through a ring carbon) and heteroalicyclic (bonded through a ring carbon). The R$^f$ groups in —NR$^f$R$^f$ of the —S(=O)$_2$—NR$^f$R$^f$ radical may be taken together with the nitrogen to which it is attached to form a 4-, 5-, 6- or 7-membered ring. A sulfonamido group is optionally substituted by one or more of the substituents described for alkyl, cycloalkyl, aryl, heteroaryl, respectively.

"Sulfoxyl" refers to a —S(=O)$_2$OH radical.

"Sulfonate" refers to a —S(=O)$_2$—OR radical, where R is selected from the group consisting of alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, heteroaryl, respectively.

The symbol , displayed perpendicular to a bond, indicates the point at which the displayed moiety is attached to the remainder of the molecule.

Pharmaceutically Acceptable Salts

The compounds of this invention can exist in free form for treatment, or where appropriate, as a pharmaceutically acceptable salt.

A "pharmaceutically acceptable salt" means any nontoxic salt of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of the ATR protein kinase.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisul-fate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, hep-tanoate, hexanoate, hydrochloride, hydrobromide, hydroio-dide, 2-hydroxy-ethanesulfonate, lactobionate, lactate, laurate, lauryl sulfate, malate, maleate, malonate, methane-sulfonate, 2-naphthalenesulfonate, nicotinate, nitrate, oleate, oxalate, palmitate, palmoate, pectinate, persulfate, 3-phenyl-propionate, phosphate, picrate, pivalate, propionate, salicylate, stearate, succinate, sulfate, tartrate, thiocyanate, p-tolu-enesulfonate, undecanoate, valerate salts, and the like.

Base addition salts can be prepared by 1) reacting the purified compound in its acid form with a suitable oiganic or inoiganic base and 2) isolating the salt thus formed. Salts derived from appropriate bases include alkali metal (e.g., sodium, lithium, and potassium), alkaline earth metal (e.g., magnesium and calcium), ammonium and N+(C1^alkyl)$_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

Pharmaceutically Acceptable Derivatives or Prodrugs

In addition to the compounds of this invention, pharmaceutically acceptable derivatives or prodrugs of the compounds of this invention may also be employed in compositions to treat or prevent the herein identified disorders.

The compounds of this invention can also exist as pharmaceutically acceptable derivatives.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters, pegylated adducts and antibody conjugated adducts.

A "pharmaceutically acceptable derivative or prodrug" means any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

Pharmaceutical Compositions

The present invention also provides compounds and compositions that are useful as inhibitors of ATR kinase.

One aspect of this invention provides pharmaceutically acceptable compositions that comprise any of the compounds as described herein, and optionally comprise a pharmaceutically acceptable carrier, adjuvant or vehicle.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E.

W. Martin (Mack Publishing Co., Easton, Pa., 1980) discloses various carriers used in formulating pharmaceutically acceptable compositions and known techniques for the preparation thereof. Except in so far as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Combination Therapies

Another aspect of this invention is directed towards a method of treating cancer in a subject in need thereof, comprising administration of a compound of this invention or a pharmaceutically acceptable salt thereof, and an additional therapeutic agent. In some embodiments, said method comprises the sequential or co-administration of the compound or a pharmaceutically acceptable salt thereof, and the additional therapeutic agent.

In some embodiments, said additional therapeutic agent is an anti-cancer agent. In other embodiments, said additional therapeutic agent is a DNA-damaging agent. In yet other embodiments, said additional therapeutic agent is selected from radiation therapy, chemotherapy, or other agents typically used in combination with radiation therapy or chemotherapy, such as radiosensitizers and chemosensi-tizers. In yet other embodiments, said additional therapeutic agent is ionizing radiation.

As would be known by one of skill in the art, radiosensitizers are agents that can be used in combination with radiation therapy. Radiosensitizers work in various different ways, including, but not limited to, making cancer cells more sensitive to radiation therapy, working in synergy with radiation therapy to provide an improved synergistic effect, acting additively with radiation therapy, or protecting surrounding healthy cells from damage caused by radiation therapy. Likewise chemosensitizers are agents that can be used in combination with chemotherapy. Similarly, chemosensitizers work in various different ways, including, but not limited to, making cancer cells more sensitive to chemotherapy, working in synergy with chemotherapy to provide an improved synergistic effect, acting additively to chemotherapy, or protecting surrounding healthy cells from damage caused by chemotherapy.

[Examples of DNA-damaging agents that may be used in combination with compounds of this invention include, but are not limited to Platinating agents, such as Carboplatin, Nedaplatin, Satraplatin and other derivatives; Topo I inhibitors, such as Topotecan, irinotecan/SN38, rubitecan and other derivatives; Antimetabolites, such as Folic family (Methotrexate, Pemetrexed and relatives); Purine antagonists and Pyrimidine antagonists (Thioguanine, Fludarabine, Cladribine, Cytarabine, Gemcitabine, 6-Mer-captopurine, 5-Fluorouracil (5FU) and relatives); Alkylating agents, such as Nitrogen mustards (Cyclophosphamide, Mel-phalan, Chlorambucil, mechlorethamine, Ifosfamide and relatives); nitrosoureas (eg Carmustine); Triazenes (Dacarba-zine, temozolomide); Alkyl sulphonates (eg Busulfan); Procarbazine and Aziridines; Antibiotics, such as Hydroxyurea, Anthracyclines (doxorubicin, daunorubicin, epirubicin and other derivatives); Anthracenediones (Mitoxantrone and relatives); Streptomyces family (Bleomycin, Mitomycin C, acti-nomycin); and Ultraviolet light.

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, the DNA damaging agents listed herein, spindle poisons (Vinblastine, Vincristine, Vinorelbine, Paclitaxel), podophyllotoxins (Etoposide, Irinotecan, Topotecan), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtu-zumabb (Campath®); alitretinoin (Panretin®); allopurinol (Zyloprim®); altretamine (Hexylen®); amifostine (Ethyol®); anastrozole (Arimidex®); arsenic trioxide (Trise-nox®); asparaginase (Elspar®); azacitidine (Vidaza); bev-acuzimab (Avastin); bexarotene capsules (Targretin); bexaro-tene gel (Targretin); bleomycin (Blenoxane®); bortezomib (Velcade); busulfan intravenous (Busulfex); busulfan oral (Myleran®); calusterone (Methosarb); capecitabine (Xeloda carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux); chlorambucil (Leukeran®); cisplatin (Platinol®); cladribine (Leustatin®, 2-CdA); clofarabine (Clolar®); cyclophosphamide (Cytoxan®, Neosar®); cyclophosphamide (CytoxanInjection®); cyclophosph-amide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome); daunorubicin, daunomycin (Daunorubicin®); daunorubicin, daunomycin (Cerubidine®); Denileukin diftitox (Ontak); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib.
(Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (MyIo-targ®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (RoferonA®); Interferon alfa-2b (Intron AC); irinotecan (Camptosar®); lenali-domide (Revlimid®); letrozole (Ferrara®); leucovorin (Wellcovorin®, Leucovorin®); Leuprolide Acetate (Eli-gard®); levamisole (Eigamisol®); lomustine, CCNU (CeeBU®); meclorethamine, nitrogen mustard (Mustar-gen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamy-cin®); mitotane (Lysodren®); mitoxantrone (Novantrone®); nandrolone phenpropionate (Durabolin-50®); nelarabine (ArranonC); Nofetumomab (Verluma®); Oprelvekin (Neu-mega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pem-etrexed disodium (Alimta®); pentostatin (Nipent®); pipo-broman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); saigramostim (Leukine®); Saigramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hy-camtin®); toremifene (Fareston®); Tositumomab (Bexxar®); Tositumomab/1-131 tositumomab (Bexxar®); Trastuzumab (Herceptin®); tretinoin, *ATRA* (Vesanoid®); Uracil Mustard (Uracil Mustard Capsules®); valrubicin (Val-star®); vinblastine (Velban®); vincristine (Oncovin®); vinorelbine (Navelbine®); zoledronate (Zometa®) and vori-nostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Compositions for Administration into a Subject.

The ATR kinase inhibitors or pharmaceutical salts thereof may be formulated into pharmaceutical compositions for administration to animals or humans. These pharmaceutical compositions, which comprise an amount of the ATR inhibitor effective to treat or prevent the diseases or conditions described herein and a pharmaceutically acceptable carrier, are another embodiment of the present invention.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

In some embodiments, these compositions optionally further comprise one or more additional therapeutic agents. For example, chemotherapeutic agents or other antiproliferative agents may be combined with the compounds of this invention to treat proliferative diseases and cancer. Examples of known agents with which these compositions can be combined are listed above under the "Combination Therapies" section and also throughout the specification. Some embodiments provide a simultaneous, separate or sequential use of a combined preparation.

Modes of Administration and Dosage Forms

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally at dosage levels of about 0.01 mg/kg to about 100 mg/kg, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofur-furyl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.R and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle.

Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, manni-tol, and silicic acid, b) binders such as, for example, car-boxymethylcellulose, alginates, gelatin, polyvinylpyrrolidi-none, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, poly-oxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cefyl esters wax, cetearyl alcohol, 2-ocfyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a one or more times a day dosage form will vary depending upon the host treated, the particular mode of administration. Preferably, the compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

Administering with Another Agent.

Depending upon the particular protein kinase-mediated conditions to be treated or prevented, additional drugs, which are normally administered to treat or prevent that condition, may be administered together with the compounds of this invention.

Those additional agents maybe administered separately, as part of a multiple dosage regimen, from the protein kinase inhibitor-containing compound or composition. Alternatively, those agents may be part of a single dosage form, mixed together with the protein kinase inhibitor in a single composition.

Another aspect of this invention is directed towards a method of treating cancer in a subject in need thereof, comprising the sequential or co-administration of a compound of this invention or a pharmaceutically acceptable salt thereof, and an anti-cancer agent. In some embodiments, said anti-cancer agent is selected from Platinating agents, such as Cisplatin, Oxaliplatin, Carboplatin, Nedaplatin, or Satrapl-atin and other derivatives; Topo I inhibitors, such as Camp-tothecin, Topotecan, irinotecan/SN38, rubitecan and other derivatives; Antimetabolites, such as Folic family (Methotrexate, Pemetrexed and relatives); Purine family (Thioguanine, Fludarabine, Cladribine, 6-Mercaptopurine and relatives); Pyrimidine family (Cytarabine, Gemcitabine, 5-Fluorouracil and relatives); Alkylating agents, such as Nitrogen mustards (Cyclophosphamide, Melphalan, Chlorambucil, mechlorethamine, Ifosfamide, and relatives); nitrosoureas (e.g. Carmustine); Triazenes (Dacarbazine, temozolomide); Alkyl sulphonates (e.g. Busulfan); Procarbazine and Aziridines; Antibiotics, such as Hydroxyurea; Anthracyclines (doxorubicin, daunorubicin, epirubicin and other derivatives); Anthracenediones (Mitoxantrone and relatives); Streptomyces family (Bleomycin, Mitomycin C, acti-nomycin) and Ultraviolet light.

Another embodiment provides administering a compound of this invention with an additional therapeutic agent that inhibits or modulates a base excision repair protein. In some embodiments, the base excision repair protein is selected from UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly (ADP-Ribose) Polymerases); PolB, PolG (polymerases); FEN1 (endonuclease) or Aprataxin. In other embodiments, the base excision repair protein is selected from PARP1, PARP2, or PolB. In yet other embodiments, the base excision repair protein is selected from PARP1 or PARP2. In some embodiments, the agent is selected from Olaparib (also known as AZD2281 or KU-0059436), Iniparib (also known as BSI-201 or SAR240550), Veliparib (also known as ABT-888), Rucaparib (also known as PF-01367338), CEP-9722, INO-1001, MK-4827, E7016, BMN673, or AZD2461.

II. COMPOSITION

In one aspect, the present invention provides a macrocyclic compound having the structure of Formula (A):

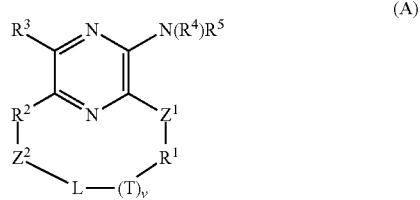

wherein each of $R^1$ and $R^2$ is independently (i) a 5-6 membered monocyclic aromatic ring containing 0-4 heteroatoms independently selected from nitrogen, oxygen, or sulfur; or (ii) an 8-10 membered bicyclic aromatic ring containing 0-6 heteroatoms independently selected from nitrogen, oxygen, or sulfur;
each $R^1$ and $R^2$ may independently be substituted by 0, 1, 2, 3, or 4 substituents; $Z^1$ represents a covalent bond, an atom, or a functional group comprising a grouping of atoms, wherein the grouping of atoms includes at least one heteroatom selected from the group consisting of N, O, P, and S; or $Z^1$ is (i) a 5-6 membered monocyclic aromatic ring containing 0-4 heteroatoms independently selected from nitrogen, oxygen, or sulfur; or (ii) an 8-10 membered bicyclic aromatic ring containing 0-6 heteroatoms independently selected from nitrogen, oxygen, or sulfur; $Z^2$ represents a covalent bond, an atom, or a functional group comprising a grouping of atoms, wherein the grouping of atoms includes at least one heteroatom selected from the group consisting of N, O, P, and S; v is an integer having a value of 1 or 0; L is a linking group covalently bonded to T when v has a value of 1; or L is covalently bonded to $R^1$ when v has a value of 0,
wherein L is covalently bonded to $Z^2$ when $Z^2$ is an atom or a functional group comprising grouping of atoms, or L is covalently bonded to $R^2$ when $Z^2$ is a covalent bond; and each of $R^3$, $R^4$ and $R^5$ may be the same as or different from each other and each is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of the macrocyclic compound of Formula (A), $Z^1$ is selected from the group consisting of phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyazinyl, pyrimidinyl, oxadiazolyl, benzimidazolyl, and triazinyl.

In at least one embodiment of the macrocyclic compound of Formula (A), $Z^1$ is selected from the group consisting of —SO—, —SO$_2$—, —S(=O)N(R$^6$)—, —S(=O)C(R$^7$)(R$^6$)—, —S(=O)$_2$N(R$^6$)—, —S(=O)$_2$C(R$^7$)(R$^6$)—, —C(=O)—, —C(=O)N(R$^6$)—, —C(=O)C(R$^7$)(R$^6$)—, —C(S)C(R$^7$)(R$^6$)— and —C(S)N(R$^6$)—; wherein each of $R^6$ and $R^7$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; when there is a plurality of either $R^6$ or $R^7$ in the structure of the macrocyclic compound each instance of $R^6$ or $R^7$ may be the same as or different from other instances of $R^6$ or $R^7$.

In at least one embodiment of the macrocyclic compound of Formula (A), $Z^1$ is —C(=O)N(R$^6$)—, wherein $R^6$ is selected from the group consisting of hydrogen, alkyl, alkenyl, or alkynyl.

In at least one embodiment of the macrocyclic compound of Formula (A), $Z^1$ is —SO—.

In at least one embodiment of the macrocyclic compound of Formula (A), $Z^1$ is —SO$_2$—.

In at least one embodiment of the macrocyclic compound of Formula (A), $Z^1$ is —S(=O)N(R$^6$)—.

In at least one embodiment of the macrocyclic compound of Formula (A), $Z^1$ is —S(=O)C(R$^7$)(R$^6$)—.

In at least one embodiment of the macrocyclic compound of Formula (A), $Z^1$ is —S(=O)$_2$N(R$^6$)—

In at least one embodiment of the macrocyclic compound of Formula (A)' $Z^1$ is —C(=O)—.

In at least one embodiment of the macrocyclic compound of Formula (A), $Z^1$ is —C(=O)N(R$^6$)—.

In at least one embodiment of the macrocyclic compound of Formula (A), $Z^1$ is —C(=O)C(R$^7$)(R$^6$)—.

In at least one embodiment of the macrocyclic compound of Formula (A), $Z^2$ is selected from the group consisting of —SO—, —SO$_2$—, —S(=O)N(R$^6$)—, —S(=O)C(R$^7$)(R$^6$)—, —S(=O)$_2$N(R$^6$)—, —S(=O)$_2$C(R$^7$)(R$^6$)—, —C(=O)—, —C(=O)N(R$^6$)—, —C(=O)C(R$^7$)(R$^6$)—, —C(S)C(R$^7$)(R$^6$)— and —C(S)N(R$^6$)—; wherein each of $R^6$ and $R^7$ is independently selected from the group consisting of hydrogen, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; when there is a plurality of either $R^6$ or $R^7$ in the structure of the macrocyclic compound each instance of $R^6$ or $R^7$ may be the same as or different from other instances of $R^6$ or $R^7$.

In at least one embodiment of the macrocyclic compound of Formula (A), $Z^2$ is —C(=O)N(R$^6$)—, wherein $R^6$ is selected from the group consisting of hydrogen, alkyl, alkenyl, or alkynyl.

In at least one embodiment of the macrocyclic compound of Formula (A), $Z^1$ and $Z^2$ are —C(=O)N($R^6$)—, wherein $R^6$ is selected from the group consisting of hydrogen, alkyl, alkenyl, or alkynyl.

In at least one embodiment of the macrocyclic compound of Formula (A), $Z^2$ is —SO—.

In at least one embodiment of the macrocyclic compound of Formula (A), $Z^2$ is —$SO_2$—.

In at least one embodiment of the macrocyclic compound of Formula (A), $Z^2$ is —S(=O)N($R^6$)—.

In at least one embodiment of the macrocyclic compound of Formula (A), $Z^2$ is —S(=O)C($R^7$)($R^6$)—.

In at least one embodiment of the macrocyclic compound of Formula (A), $Z^2$ is —S(=O)$_2$N($R^6$)—

In at least one embodiment of the macrocyclic compound of Formula (A), $Z^2$ is —C(=O)—.

In at least one embodiment of the macrocyclic compound of Formula (A), $Z^2$ is —C(=O)N($R^6$)—

In at least one embodiment of the macrocyclic compound of Formula (A), $Z^2$ is —C(=O)C($R^7$)($R^6$)—.

In at least one embodiment of the macrocyclic compound of Formula (A), $Z^2$ is —C(S)C($R^7$)($R^6$)— and —C(S)N($R^6$)—.

In at least one embodiment of the macrocyclic compound of Formula (A), $R^1$ is selected from the group consisting of phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyzazinyl, pyrimidinyl, and triazinyl.

In at least one embodiment of the macrocyclic compound of Formula (A), $R^2$ is selected from the group consisting of phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyzazinyl, pyrimidinyl, and triazinyl.

In at least one embodiment of the macrocyclic compound of Formula (A), $R^1$ and $R^2$ are independently selected from the group consisting of phenyl, thienyl, furanyl, pyrimidinyl, oxazoyl, thiazolyl, pyridyl, naphthyl, quinolinyl, indolyl, benzothiophenyl, benzofuranyl, pyrrolyl, imidazolyl, pyrazole, triazolyl, isoxazolyl, pyridazinyl, pyzazinyl, pyrimidinyl, oxadiazolyl, benzimidazolyl, and triazinyl.

In at least one embodiment of the macrocyclic compound of Formula (A), L represents a backbone chain of at least 2 atoms in length.

In at least one embodiment of the macrocyclic compound of Formula (A), L represents a backbone chain of at least 2 atoms and L-(T)$_v$ represents a backbone chain having at most 25 atoms in length, wherein T, and v are as defined for the compound of Formula (A).

In at least one embodiment of the macrocyclic compound of Formula (A), L comprises a backbone chain of at least 3 atoms in length.

In at least one embodiment of the macrocyclic compound of Formula (A), L represents a backbone chain of at least 3 atoms in length and L-(T)$_v$ represents a backbone chain having at most 25 atoms in length, wherein T, and v are as defined for the compound of Formula (A).

In at least one embodiment of the macrocyclic compound of Formula (A), L comprises a backbone chain of at least 4 atoms in length.

In at least one embodiment of the macrocyclic compound of Formula (A), L represents a backbone chain of at least 4 atoms in length and L-(T)$_v$ represents a backbone chain having at most 25 atoms in length, wherein T, and v are as defined for the compound of Formula (A).

In at least one embodiment of the macrocyclic compound of Formula (A), L comprises a backbone chain of at least 5 atoms in length.

In at least one embodiment of the macrocyclic compound of Formula (A), L represents a backbone chain of at least 5 atoms in length and L-(T)$_v$ represents a backbone chain having at most 25 atoms in length, wherein T, and v are as defined for the compound of Formula (A).

In at least one embodiment of the macrocyclic compound of Formula (A), L comprises a backbone chain of at least 6 atoms in length.

In at least one embodiment of the macrocyclic compound of Formula (A), L represents a backbone chain of at least 6 atoms in length and L-(T)$_v$ represents a backbone chain having at most 25 atoms in length, wherein T, and v are as defined for the compound of Formula (A).

In at least one embodiment of the macrocyclic compound of Formula (A), L comprises a backbone chain of at least 7 atoms in length.

In at least one embodiment of the macrocyclic compound of Formula (A), L represents a backbone chain of at least 7 atoms in length and L-(T)$_v$ represents a backbone chain having at most 25 atoms in length, wherein T, and v are as defined for the compound of Formula (A).

In at least one embodiment of the macrocyclic compound of Formula (A), L comprises a backbone chain of at least 8 atoms in length.

In at least one embodiment of the macrocyclic compound of Formula (A), L represents a backbone chain of at least 8 atoms in length and L-(T)$_v$ represents a backbone chain having at most 25 atoms in length, wherein T, and v are as defined for the compound of Formula (A).

In at least one embodiment of the macrocyclic compound of Formula (A), L comprises a backbone chain of at least 9 atoms in length.

In at least one embodiment of the macrocyclic compound of Formula (A), L represents a backbone chain of at least 9 atoms in length and L-(T)$_v$ represents a backbone chain having at most 25 atoms in length, wherein T, and v are as defined for the compound of Formula (A).

In at least one embodiment of the macrocyclic compound of Formula (A), L comprises a backbone chain of at least 10 atoms in length.

In at least one embodiment of the macrocyclic compound of Formula (A), L represents a backbone chain of at least 10 atoms in length and L-(T)$_v$ represents a backbone chain having at most 25 atoms in length, wherein T, and v are as defined for the compound of Formula (A).

In at least one embodiment of the macrocyclic compound of Formula (A), L comprises a backbone chain of at least 11 atoms in length.

In at least one embodiment of the macrocyclic compound of Formula (A), L represents a backbone chain of at least 11 atoms in length and L-(T)$_v$ represents a backbone chain having at most 25 atoms in length, wherein T, and v are as defined for the compound of Formula (A).

In at least one embodiment of the macrocyclic compound of Formula (A), L comprises a backbone chain having from 2 atoms in length to 17 atoms in length.

In at least one embodiment of the macrocyclic compound of Formula (A), L comprises a backbone chain having from 3 atoms in length to 17 atoms in length.

In at least one embodiment of the macrocyclic compound of Formula (A), L comprises a backbone chain having from 4 atoms in length to 17 atoms in length.

In at least one embodiment of the macrocyclic compound of Formula (A), L comprises a backbone chain having from 5 atoms in length to 17 atoms in length.

In at least one embodiment of the macrocyclic compound of Formula (A), L comprises a backbone chain having from 6 atoms in length to 17 atoms in length.

In at least one embodiment of the macrocyclic compound of Formula (A), L comprises a backbone chain having from 7 atoms in length to 17 atoms in length.

In at least one embodiment of the macrocyclic compound of Formula (A), L comprises a backbone chain having from 8 atoms in length to 17 atoms in length.

In at least one embodiment of the macrocyclic compound of Formula (A), L comprises a backbone chain having from 9 atoms in length to 17 atoms in length.

In at least one embodiment of the macrocyclic compound of Formula (A), L comprises a backbone chain having from 10 atoms in length to 17 atoms in length.

In at least one embodiment of the macrocyclic compound of Formula (A), L comprises a backbone chain having from 11 atoms in length to 17 atoms in length.

In at least one embodiment of the macrocyclic compound of Formula (A), L represents an aliphatic backbone chain having at least 3 atoms in length.

In at least one embodiment of the macrocyclic compound of Formula (A), L represents an alkylene backbone one or more times interrupted with a heteroatom.

In at least one embodiment of the macrocyclic compound of Formula (A), L represents an alkylene backbone one or more times interrupted with a heteroatom, wherein L-(T)$_v$ represents a backbone chain having at most 25 atoms in length, wherein T, and v are as defined for the compound of Formula (A).

In at least one embodiment of the macrocyclic compound of Formula (A), L represents an alkylene backbone one or more times interrupted by one or more heteroatoms independently selected from the group consisting of O, S, N and P. In at least one embodiment of the macrocyclic compound of Formula (A), L represents an alkylene backbone one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of the macrocyclic compound of Formula (A), L represents an aliphatic backbone chain having at least two contiguous carbon atoms, wherein L is interrupted by one or more —O—, —S—, —N(R$^g$)—,

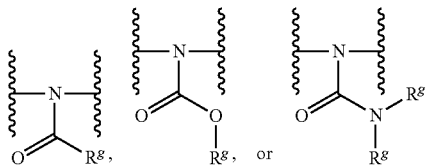

moieties, wherein each R$^g$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of the macrocyclic compound of Formula (A), L represents an aliphatic backbone chain having at least two contiguous carbon atoms, wherein L is interrupted by one or more —O—, —S—, —N(R$^g$)—,

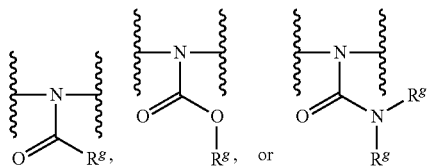

moieties, wherein each R$^g$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents, and wherein L-(T)$_v$ represents a backbone chain having at most 25 atoms in length, wherein T, and v are as defined for the compound of Formula (A).

In at least one embodiment of the macrocyclic compound of Formula (A), L represents an aliphatic backbone chain having at least two contiguous carbon atoms, wherein L is interrupted by one or more —O—, —S—, —N(R$^g$)—,

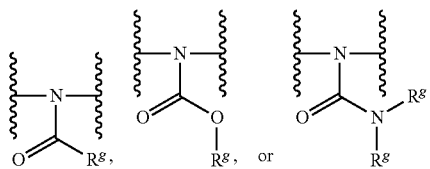

moieties, provided that each —O—, —S—, —N(R$^g$)—,

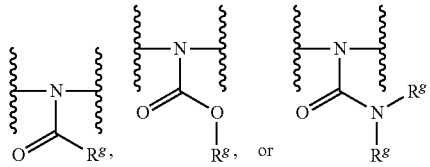

moiety, if present, is not contiguous with another —O—, —S—, —N(R$^g$)—,

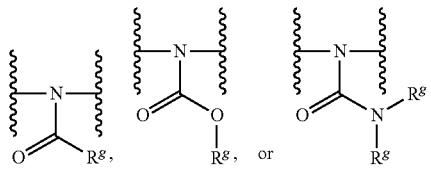

moiety, wherein each R$^g$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of the macrocyclic compound of Formula (A), L represents an aliphatic backbone chain having at least two contiguous carbon atoms, wherein L is interrupted by one or more —O—, —S—, —N(R$^g$)—,

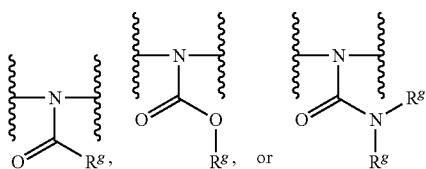

moieties, provided that each —O—, —S—, N(R$^g$)—,

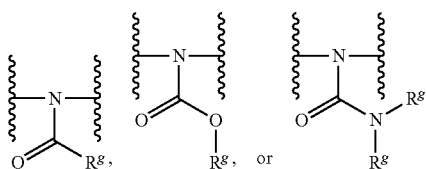

moiety, if present, is not contiguous with another —O—, —S—, N(R$^g$)—,

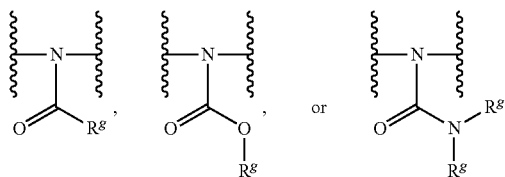

moiety, wherein each R$^g$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents, and wherein L-(T)$_v$ represents a backbone chain having at most 25 atoms in length, wherein T, and v are as defined for the compound of Formula (A).

In at least one embodiment of the macrocyclic compound of Formula (A), L represents a polyalkylene oxide backbone.

In at least one embodiment of the macrocyclic compound of Formula (A), L represents a polyalkylene oxide backbone, wherein L-(T)$_v$ represents a backbone chain having at most 25 atoms in length, wherein T, and v are as defined for the compound of Formula (A).

In at least one embodiment of the macrocyclic compound of Formula (A), L represents a polyalkylene oxide backbone, wherein the polyalkylene oxide backbone comprises polyethylene oxide (PEO), polypropyleneoxide (PPO), polybutyleneoxide (PBO) or a mixture thereof.

In at least one embodiment of the macrocyclic compound of Formula (A), L represents a polyalkylene oxide backbone, wherein the polyalkylene oxide backbone comprises polyethylene oxide (PEO), polypropyleneoxide (PPO), polybutyleneoxide (PBO) or a mixture thereof, and wherein L-(T)$_v$ represents a backbone chain having at most 25 atoms in length, wherein T, and v are as defined for the compound of Formula (A).

In at least one embodiment of the macrocyclic compound of Formula (A), L comprises an aliphatic backbone chain of at least 3 atoms one or more times interrupted by one or more heteroatoms independently selected from the group consisting of O, S, N and P.

In at least one embodiment of the macrocyclic compound of Formula (A), L comprises an aliphatic backbone chain of at least 3 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of the macrocyclic compound of Formula (A), L comprises an aliphatic backbone chain of at least 4 atoms one or more times interrupted by one or more heteroatoms independently selected from the group consisting of O, S, N and P.

In at least one embodiment of the macrocyclic compound of Formula (A), L comprises an aliphatic backbone chain of at least 4 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of the macrocyclic compound of Formula (A), L comprises an aliphatic backbone chain of at least 5 atoms one or more times interrupted by one or more heteroatoms independently selected from the group consisting of O, S, N and P.

In at least one embodiment of the macrocyclic compound of Formula (A), L comprises an aliphatic backbone chain of at least 5 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of the macrocyclic compound of Formula (A), L comprises an aliphatic backbone chain of at least 6 atoms one or more times interrupted by one or more heteroatoms independently selected from the group consisting of O, S, N and P.

In at least one embodiment of the macrocyclic compound of Formula (A), L comprises an aliphatic backbone chain of at least 6 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of the macrocyclic compound of Formula (A), L comprises an aliphatic backbone chain of at least 7 atoms one or more times interrupted by one or more heteroatoms independently selected from the group consisting of O, S, N and P.

In at least one embodiment of the macrocyclic compound of Formula (A), L comprises an aliphatic backbone chain of at least 7 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of the macrocyclic compound of Formula (A), L comprises an aliphatic backbone chain of at least 8 atoms one or more times interrupted by one or more heteroatoms independently selected from the group consisting of O, S, N and P.

In at least one embodiment of the macrocyclic compound of Formula (A), L comprises an aliphatic backbone chain of at least 8 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A). In at least one embodiment of the macrocyclic compound of Formula (A), L comprises an aliphatic backbone chain of at least 9 atoms one or more times interrupted by one or more heteroatoms independently selected from the group consisting of O, S, N and P.

In at least one embodiment of the macrocyclic compound of Formula (A), L comprises an aliphatic backbone chain of at least 9 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of the macrocyclic compound of Formula (A), L comprises an aliphatic backbone chain of at least 10 atoms one or more times interrupted by one or more heteroatoms independently selected from the group consisting of O, S, N and P.

In at least one embodiment of the macrocyclic compound of Formula (A), L comprises an aliphatic backbone chain of at least 10 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of the macrocyclic compound of Formula (A), L comprises an aliphatic backbone chain of at least 11 atoms one or more times interrupted by one or more heteroatoms independently selected from the group consisting of O, S, N and P.

In at least one embodiment of the macrocyclic compound of Formula (A), L comprises an aliphatic backbone chain of at least 11 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of the macrocyclic compound of Formula (A), L comprises an aliphatic backbone of at least 2 atoms in length to 17 atoms in length, wherein the aliphatic backbone chain is one or more times interrupted by one or more heteroatoms independently selected from the group consisting of O, S, N and P.

In at least one embodiment of the macrocyclic compound of Formula (A), L comprises an aliphatic backbone of at least 3 atoms in length to 17 atoms in length, wherein the aliphatic backbone chain is one or more times interrupted by one or more heteroatoms independently selected from the group consisting of O, S, N and P.

In at least one embodiment of the macrocyclic compound of Formula (A), L comprises an aliphatic backbone of at least 4 atoms in length to 17 atoms in length, wherein the aliphatic backbone chain is one or more times interrupted by one or more heteroatoms independently selected from the group consisting of O, S, N and P.

In at least one embodiment of the macrocyclic compound of Formula (A), L comprises an aliphatic backbone of at least 5 atoms in length to 17 atoms in length, wherein the aliphatic backbone chain is one or more times interrupted by one or more heteroatoms independently selected from the group consisting of O, S, N and P.

In at least one embodiment of the macrocyclic compound of Formula (A), L comprises an aliphatic backbone of at least 6 atoms in length to 17 atoms in length, wherein the aliphatic backbone chain is one or more times interrupted by one or more heteroatoms independently selected from the group consisting of O, S, N and P.

In at least one embodiment of the macrocyclic compound of Formula (A), L comprises an aliphatic backbone of at least 7 atoms in length to 17 atoms in length, wherein the aliphatic backbone chain is one or more times interrupted by one or more heteroatoms independently selected from the group consisting of O, S, N and P.

In at least one embodiment of the macrocyclic compound of Formula (A), L comprises an aliphatic backbone of at least 8 atoms in length to 17 atoms in length, wherein the aliphatic backbone chain is one or more times interrupted by one or more heteroatoms independently selected from the group consisting of O, S, N and P.

In at least one embodiment of the macrocyclic compound of Formula (A), L comprises an aliphatic backbone of at least 9 atoms in length to 17 atoms in length, wherein the aliphatic backbone chain is one or more times interrupted by one or more heteroatoms independently selected from the group consisting of O, S, N and P.

In at least one embodiment of the macrocyclic compound of Formula (A), L comprises an aliphatic backbone of at least 10 atoms in length to 17 atoms in length, wherein the aliphatic backbone chain is one or more times interrupted by one or more heteroatoms independently selected from the group consisting of O, S, N and P.

In at least one embodiment of the macrocyclic compound of Formula (A), L comprises an aliphatic backbone of at least 11 atoms in length to 17 atoms in length, wherein the aliphatic backbone chain is one or more times interrupted by one or more heteroatoms independently selected from the group consisting of O, S, N and P.

In some embodiments, the macrocyclic compound having the structure of Formula (A) has the structure of Formula (A1):

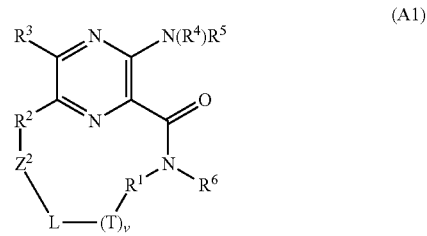

(A1)

wherein $R^1$, $R^2$, $R^3$, $R^4$, $R^5$, L v, T, and $Z^2$ are as defined for the compound of Formula (A); and $R^6$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In some embodiments, the macrocyclic compound having the structure of Formula (A) has the structure of Formula (B):

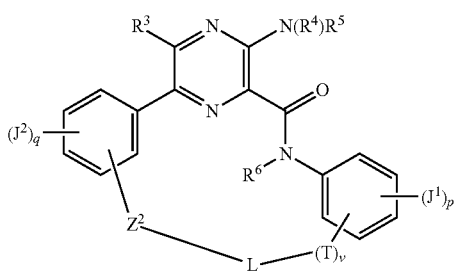

(B)

wherein each of $J^1$ and $J^2$ is independently a hydrogen atom or any suitable substituent and wherein each of p and q is an integer independently ranging in value from 1 to 4; whenever it appears herein, an integer such as "1 to 4" refers to each value in the given range up to and including 4—e.g., "each of p and q is an integer independently ranging in value from 1 to 4" means that each of p and q may have any one of the integer values 1, 2, 3 and 4; v is an integer having a value of 1 or 0; T is a carbon atom, a nitrogen atom, a sulfur atom, or an oxygen atom, wherein when v has a value of 0 linking group L is covalently bonded to the phenyl ring to which T would have bonded; wherein $R^3$, $R^4$, $R^5$, L, and $Z^2$ are as defined for compound of Formula (A); and $R^6$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of the macrocyclic compound of Formula (B), each of $J^1$ and $J^2$ is independently selected from the group consisting of hydrogen, hydroxy, halogen, cyano, trifluoromethyl, trifluoromethoxy, nitro, trimethylsilanyl, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N-$R^a$)N($R^a$)$_2$, —N($R^a$)S(O)$_t R^a$, —N($R^a$)S(O)$_2 R^a$, —S(O)O$R^a$, —S(O)$_2 $O$R^a$, —S(O)N($R^a$)$_2$, —S(O)$_2$N($R^a$)$_2$, PO$_3$($R^a$)$_2$, alkyl, alkenyl, alkynyl, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, each being optionally substituted by one or more suitable substituents.

In at least one embodiment of the macrocyclic compound of Formula (B), each of $J^1$ and $J^2$ is independently selected from the group consisting of a hydrogen atom, an alkyl group, an alicyclic hydrocarbon group, an alkenyl group, an alkynyl group, an aryl group, an amino group, an alkoxy group, an aryloxy group, a heterocyclic oxy group, an acyl group, an alkoxycarbonyl group, an aryloxycarbonyl group, an acyloxy group, an acylamino group, an alkoxycarbonylamino group, an aryloxycarbonylamino group, a sulfonylamino group, a sulfamoyl group, a carbamoyl group, an alkylthio group, an arylthio group, a heterocyclic thio group, a sulfonyl group, a sulfinyl group, a ureido group, a phosphoric acid amide group, a hydroxyl group, a mercapto group, a halogen atom, a cyano group, a carboxyl group, a nitro group, a hydroxamic acid group, a sulfino group, a hydrazino group, an imino group, a heterocyclic group, a silyl group, and a silyloxy group.

In some preferred embodiments, the macrocyclic compound of Formula (B) has the structure of Formula (B1):

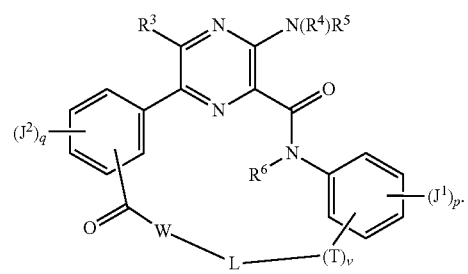

(B1)

wherein W is selected from the group consisting of C($R^7$)($R^6$), O, S, and N$R^7$, wherein each $R^7$ and $R^6$ is selected independently from the group consisting of hydrogen, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; wherein when there is a plurality of $R^6$ each instance of $R^6$ may be the same as or different from another instance of $R^6$; wherein each of $J^1$, $J^2$ p and q has the same meaning as defined with respect to the macrocyclic compound of Formula (B); and v is an integer having a value of 1 or 0; T is a carbon atom, a nitrogen atom, a sulfur atom, or an oxygen atom, wherein when v is 0 linking group L is covalently bonded to the phenyl ring to which T would have bonded.

In at least one embodiment of the macrocyclic compound of Formula (B1), each of $J^1$ and $J^2$ is independently selected from the group consisting of hydrogen, hydroxy, halogen, cyano, trifluoromethyl, trifluoromethoxy, nitro, trimethylsilanyl, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N-$R^a$)N($R^a$)$_2$, —N($R^a$)S(O)$_t R^a$, —N($R^a$)S(O)$_2 R^a$, —S(O)O$R^a$, —S(O)$_2 $O$R^a$, —S(O)N($R^a$)$_2$, —S(O)$_2$N($R^a$)$_2$, or PO$_3$($R^a$)$_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In some preferred embodiments, the macrocyclic compound of Formula (B) has the structure of Formula (B2):

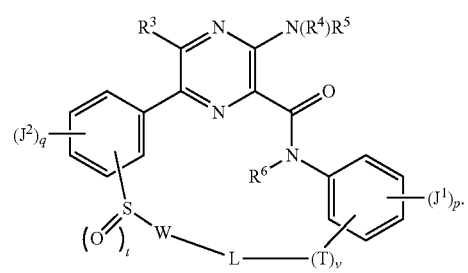

(B2)

wherein W is selected from the group consisting of C(R⁷)(R⁶), O, S, and NR⁷, wherein each R⁶ and R⁷ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; wherein when there is a plurality of R⁶ each instance of R⁶ may be the same as or different from another instance of R⁶; wherein each of J¹, J², p and q has the same meaning as defined with respect to the macrocyclic compound of Formula (B); t is an integer having a value of 1 or 2; and v is an integer having a value of 1 or 0; T is a carbon atom, a nitrogen atom, a sulfur atom, or an oxygen atom, wherein when v is 0 linking group L is covalently bonded to the phenyl ring to which T would have bonded.

In at least one embodiment of the macrocyclic compound of Formula (B2), each of J¹ and J² is independently selected from the group consisting of hydrogen, hydroxy, halogen, cyano, trifluoromethyl, trifluoromethoxy, nitro, trimethylsilanyl, —ORᵃ, —SRᵃ, —OC(O)—Rᵃ, —N(Rᵃ)₂, —C(O)Rᵃ, —C(O)ORᵃ, —OC(O)N(Rᵃ)₂, —C(O)N(Rᵃ)₂, —N(Rᵃ)C(O)ORᵃ, —N(Rᵃ)C(O)Rᵃ, —N(Rᵃ)C(O)N(Rᵃ)₂, N(Rᵃ)C(N-Rᵃ)N(Rᵃ)₂, —N(Rᵃ)S(O)ᵢRᵃ, —N(Rᵃ)S(O)₂Rᵃ, —S(O)ORᵃ, —S(O)₂ORᵃ, —S(O)N(Rᵃ)₂, —S(O)₂N(Rᵃ)₂, or PO₃(Rᵃ)₂, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each Rᵃ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In some preferred embodiments, the macrocyclic compound of Formula (B) has the structure of Formula (B3):

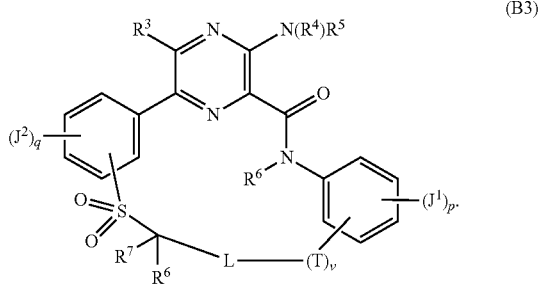

(B3)

wherein each R⁶ and R⁷ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; wherein when there is a plurality of R⁶ each instance of R⁶ may be the same as or different from another instance of R⁶; wherein each of J¹, J², R³, R⁴, R⁵, p and q has the same meaning as defined with respect to the macrocyclic compound of Formula (B); and v is an integer having a value of 1 or 0; T is a carbon atom, a nitrogen atom, a sulfur atom, or an oxygen atom, wherein when v is 0 linking group L is covalently bonded to the phenyl ring to which T would have bonded.

In at least one embodiment of the macrocyclic compound of Formula (B3), each of J¹ and J² is independently selected from the group consisting of hydrogen, hydroxy, halogen, cyano, trifluoromethyl, trifluoromethoxy, nitro, trimethylsilanyl, —ORᵃ, —SRᵃ, —OC(O)—Rᵃ, —N(Rᵃ)₂, —C(O)Rᵃ, —C(O)ORᵃ, —OC(O)N(Rᵃ)₂, —C(O)N(Rᵃ)₂, —N(Rᵃ)C(O)ORᵃ, —N(Rᵃ)C(O)Rᵃ, —N(Rᵃ)C(O)N(Rᵃ)₂, N(Rᵃ)C(N-Rᵃ)N(Rᵃ)₂, —N(Rᵃ)S(O)ᵢRᵃ, —N(Rᵃ)S(O)₂Rᵃ, —S(O)ORᵃ, —S(O)₂ORᵃ, —S(O)N(Rᵃ)₂, —S(O)₂N(Rᵃ)₂, or PO₃(Rᵃ)₂, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each Rᵃ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In some preferred embodiments, the macrocyclic compound of Formula (B) has the structure of Formula (B4):

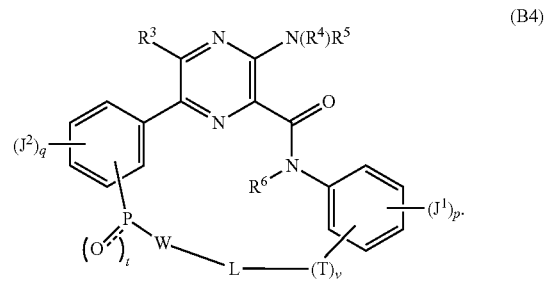

(B4)

wherein W is selected from the group consisting of C(R⁷)(R⁶), O, S, and NR⁷, wherein each R⁶ and R⁷ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; when there is a plurality of R⁶ each instance of R⁶ may be the same as or different from another instance of R⁶; and wherein each of J¹, J² p and q has the same meaning as defined with respect to the macrocyclic compound of Formula (B); whenever a bond is drawn as ====== the may be a single bond or a double bond, and where there is a plurality of ====== as in when t is 2, each instance of ====== may be same as or different from another instance of ======. In other words, each instance of ====== is independently a single bond or a double bond.

In some preferred embodiments, the macrocyclic compound of Formula (A1) has the structure of Formula (B5):

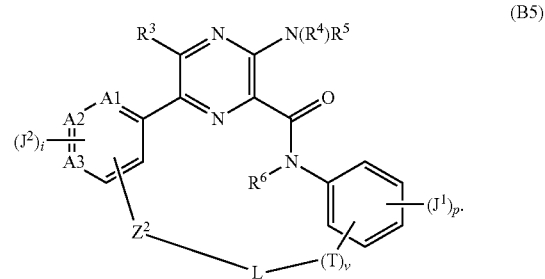

(B5)

wherein each of $R^6$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; each of $A^1$, $A^2$, and $A^3$ is independently selected from N and $CR^9$, wherein $R^9$ is independently a hydrogen atom or a substituent; wherein each of $J^1$, $J^2$, $Z^2$, and p has the same meaning as defined with respect to the macrocyclic compound of Formula (B); v is an integer having a value of 1 or 0; T is a carbon atom, a nitrogen atom, a sulfur atom, or an oxygen atom, wherein when v is 0 linking group L is covalently bonded to the phenyl ring to which T would have bonded.

In some preferred embodiments of the macrocyclic compound of Formula (B5), $J^1$, $J^2$ are independently hydroxy, halogen, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$, —N(R$^a$)S(O)$_2$R$^a$, —S(O)OR$^a$, —S(O)$_2$OR$^a$, —S(O)N(R$^a$)$_2$, —S(O)$_2$N(R$^a$)$_2$, or PO$_3$(R$^a$)$_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In some embodiments, the macrocyclic compound having the structure of Formula (A) has the structure of Formula (C):

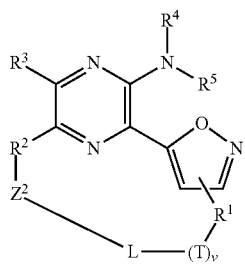

(C)

wherein $R^1$, $R^2$, $R^3$, $R^4$, $R^5$, L and $Z^2$ are as defined for compound of Formula (A); v is an integer having a value of 1 or 0; and T is a carbon atom, a nitrogen atom, a sulfur atom, or an oxygen atom, wherein when v is 0 linking group L is covalently bonded to $R^1$ to which T would have bonded.

In some embodiments, the macrocyclic compound having the structure of Formula (C) has the structure of Formulas (C1) or (C2):

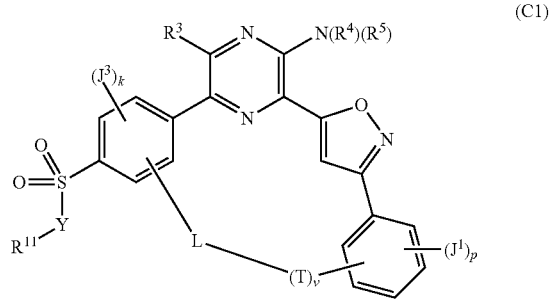

(C1)

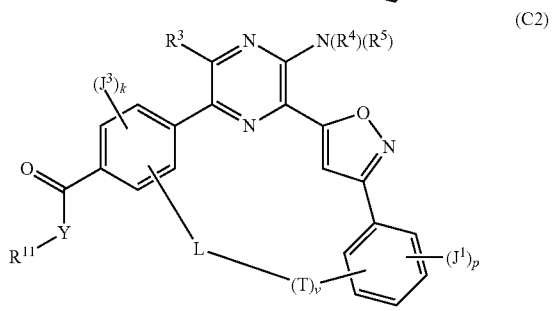

(C2)

wherein each of $R^3$, $R^4$, $R^5$, and $R^{11}$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; k is an integer having a value of 1, 2, or 3; p is the same as defined above and/or elsewhere in this disclosure (e.g., p is an integer having a value of 1, 2, 3, or 4); $J^3$ is hydrogen or any suitable substitutent; Y is selected from the group consisting of NR$^{12}$, C(R$^{13}$), and O; each of R$^{12}$ and R$^{13}$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; v is an integer having a value of 1 or 0; and T is a carbon atom, a nitrogen atom, a sulfur atom, or an oxygen atom, wherein when v is 0 linking group L is covalently bonded to the phenyl ring to which T would have bonded.

In some preferred embodiments of the macrocyclic compounds of Formulas (C1) or (C2), $J^1$ and $J^3$ are independently selected from the group consisting of hydrogen, hydroxy, halogen, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$, —N(R$^a$)S(O)$_2$R$^a$, —S(O)OR$^a$, —S(O)$_2$OR$^a$, —S(O)N(R$^a$)$_2$, —S(O)$_2$N(R$^a$)$_2$, or PO$_3$(R$^a$)$_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In some embodiments, the macrocyclic compound having the structure of Formula (A) has the structure of Formulas (D1) or (D2):

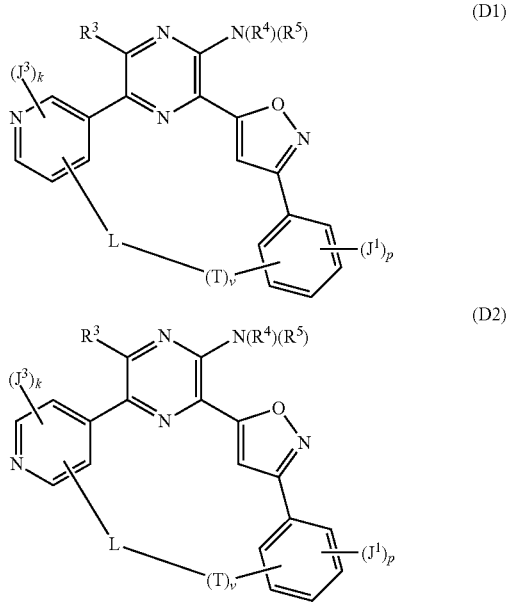

wherein each of $R^3$, $R^4$, and $R^5$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; k is an integer having a value of 1, 2, or 3; p is an integer having a value of 1, 2, 3, or 4; $J^3$ is hydrogen or any suitable substitutent; v is an integer having a value of 1 or 0; and T is a carbon atom, a nitrogen atom, a sulfur atom, or an oxygen atom, wherein when v is 0 linking group L is covalently bonded to the phenyl ring to which T would have bonded.

In some preferred embodiments of the compounds having the structures of Formulas (D1) and (D2), $J^1$ and $J^3$ are independently selected from the group consisting of hydroxy, halogen, cyano, trifluoromethyl, trifluoromethoxy, nitro, trimethylsilanyl, —$OR^a$, —$SR^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_x$$R^a$, —N($R^a$)S(O)$_2$$R^a$, —S(O)O$R^a$, —S(O)$_2$O$R^a$, —S(O)N($R^a$)$_2$, —S(O)$_2$N($R^a$)$_2$, or PO$_3$($R^a$)$_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In at least one embodiment of any one of macrocyclic compounds having the structure of Formulas (A1), (B), (B1)-(B5), (C), (C1), (C2), (D1), and (D2), L represents a backbone chain of at least 2 atoms in length.

In at least one embodiment of any one of macrocyclic compounds having the structure of Formulas (A1), (B), (B1)-(B5), (C), (C1), (C2), (D1), and (D2), L represents a backbone chain of at least 2 atoms and L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises a backbone chain of at least 3 atoms in length.

In at least one embodiment of any one of macrocyclic compounds having the structure of Formulas (A1), (B), (B1)-(B5), (C), (C1), (C2), (D1), and (D2), L represents a backbone chain of at least 3 atoms in length and L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises a backbone chain of at least 4 atoms in length.

In at least one embodiment of any one of macrocyclic compounds having the structure of Formulas (A1), (B), (B1)-(B5), (C), (C1), (C2), (D1), and (D2), L represents a backbone chain of at least 4 atoms in length and L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises a backbone chain of at least 5 atoms in length.

In at least one embodiment of any one of macrocyclic compounds having the structure of Formulas (A1), (B), (B1)-(B5), (C), (C1), (C2), (D1), and (D2), L represents a backbone chain of at least 5 atoms in length and L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises a backbone chain of at least 6 atoms in length.

In at least one embodiment of any one of macrocyclic compounds having the structure of Formulas (A1), (B), (B1)-(B5), (C), (C1), (C2), (D1), and (D2), L represents a backbone chain of at least 6 atoms in length and L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises a backbone chain of at least 7 atoms in length.

In at least one embodiment of any one of macrocyclic compounds having the structure of Formulas (A1), (B), (B1)-(B5), (C), (C1), (C2), (D1), and (D2), L represents a backbone chain of at least 7 atoms in length and L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises a backbone chain of at least 8 atoms in length.

In at least one embodiment of any one of macrocyclic compounds having the structure of Formulas (A1), (B), (B1)-(B5), (C), (C1), (C2), (D1), and (D2), L represents a backbone chain of at least 8 atoms in length and L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises a backbone chain of at least 9 atoms in length.

In at least one embodiment of any one of macrocyclic compounds having the structure of Formulas (A1), (B), (B1)-(B5), (C), (C1), (C2), (D1), and (D2), L represents a backbone chain of at least 9 atoms in length and L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises a backbone chain of at least 10 atoms in length.

In at least one embodiment of any one of macrocyclic compounds having the structure of Formulas (A1), (B), (B1)-(B5), (C), (C1), (C2), (D1), and (D2), L represents a backbone chain of at least 10 atoms in length and L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises a backbone chain of at least 11 atoms in length.

In at least one embodiment of any one of macrocyclic compounds having the structure of Formulas (A1), (B), (B1)-(B5), (C), (C1), (C2), (D1), and (D2), L represents a backbone chain of at least 11 atoms in length and L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises a backbone chain having from 2 atoms in length to 17 atoms in length.

In at least one embodiment of any one of macrocyclic compounds having the structure of Formulas (A1), (B), (B1)-(B5), (C), (C1), (C2), (D1), and (D2), L comprises a backbone chain having from 3 atoms in length to 17 atoms in length.

In at least one embodiment of any one of macrocyclic compounds having the structure of Formulas (A1), (B), (B1)-(B5), (C), (C1), (C2), (D1), and (D2), L comprises a backbone chain having from 4 atoms in length to 17 atoms in length.

In at least one embodiment of any one of macrocyclic compounds having the structure of Formulas (A1), (B), (B1)-(B5), (C), (C1), (C2), (D1), and (D2), L comprises a backbone chain having from 5 atoms in length to 17 atoms in length.

In at least one embodiment of any one of macrocyclic compounds having the structure of Formulas (A1), (B), (B1)-(B5), (C), (C1), (C2), (D1), and (D2), L comprises a backbone chain having from 6 atoms in length to 17 atoms in length.

In at least one embodiment of any one of macrocyclic compounds having the structure of Formulas (A1), (B), (B1)-(B5), (C), (C1), (C2), (D1), and (D2), L comprises a backbone chain having from 7 atoms in length to 17 atoms in length.

In at least one embodiment of any one of macrocyclic compounds having the structure of Formulas (A1), (B), (B1)-(B5), (C), (C1), (C2), (D1), and (D2), L comprises a backbone chain having from 8 atoms in length to 17 atoms in length.

In at least one embodiment of any one of macrocyclic compounds having the structure of Formulas (A1), (B), (B1)-(B5), (C), (C1), (C2), (D1), and (D2), L comprises a backbone chain having from 9 atoms in length to 17 atoms in length.

In at least one embodiment of any one of macrocyclic compounds having the structure of Formulas (A1), (B), (B1)-(B5), (C), (C1), (C2), (D1), and (D2), L comprises a backbone chain having from 10 atoms in length to 17 atoms in length.

In at least one embodiment of any one of macrocyclic compounds having the structure of Formulas (A1), (B), (B1)-(B5), (C), (C1), (C2), (D1), and (D2), L comprises a backbone chain having from 11 atoms in length to 17 atoms in length.

In at least one embodiment of any one of macrocyclic compounds having the structure of Formulas (A1), (B), (B1)-(B5), (C), (C1), (C2), (D1), and (D2), L represents an aliphatic backbone chain having at least 3 atoms in length.

In at least one embodiment of any one of macrocyclic compounds having the structure of Formulas (A1), (B), (B1)-(B5), (C), (C1), (C2), (D1), and (D2), L represents an alkylene backbone one or more times interrupted with a heteroatom.

In at least one embodiment of any one of macrocyclic compounds having the structure of Formulas (A1), (B), (B1)-(B5), (C), (C1), (C2), (D1), and (D2), L represents an alkylene backbone one or more times interrupted with a heteroatom, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L represents an alkylene backbone one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L represents an alkylene backbone one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L represents an aliphatic backbone chain having at least two contiguous carbon atoms, wherein L is interrupted by one or more —O—, —S—, —N(R$^g$)—, moieties, wherein each $R^g$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of any one of macrocyclic compounds having the structure of Formulas (A1), (B), (B1)-(B5), (C), (C1), (C2), (D1), and (D2), L represents an aliphatic backbone chain having at least two contiguous carbon atoms, wherein L is interrupted by one or more —O—, —S—, —N($R^g$)—,

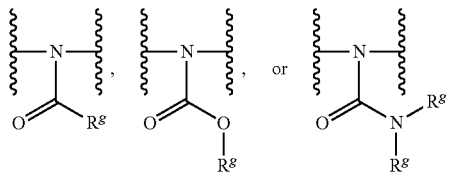

moieties, wherein each $R^g$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents, and wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L represents an aliphatic backbone chain having at least two contiguous carbon atoms, wherein L is interrupted by one or more —O—, —S—, —N($R^g$)—,

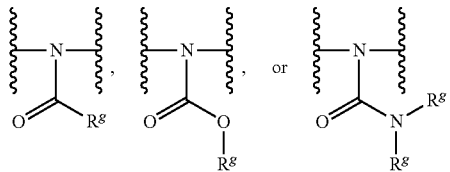

moieties, provided that each —O—, —S—, —N($R^g$)—,

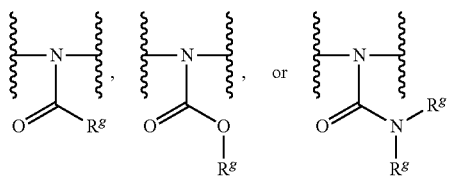

moiety, if present, is not contiguous with another —O—, —S—, N($R^g$)—,

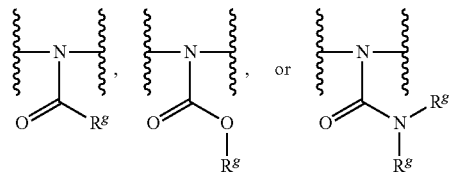

moiety, wherein each $R^g$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In at least one embodiment of any one of macrocyclic compounds having the structure of Formulas (A1), (B), (B1)-(B5), (C), (C1), (C2), (D1), and (D2), L represents an aliphatic backbone chain having at least two contiguous carbon atoms, wherein L is interrupted by one or more —O—, —S—, —N($R^g$)—,

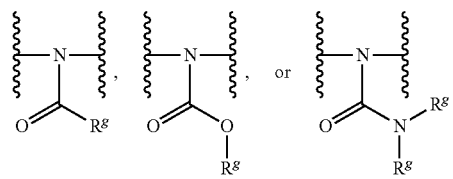

moieties, provided that each —O—, —S—, —N($R^g$)—,

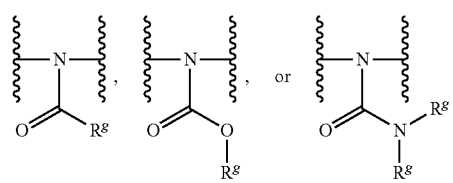

moiety, if present, is not contiguous with another —O—, —S—, —N($R^g$)—,

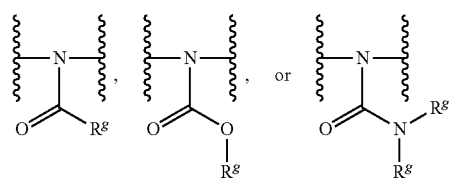

moiety, wherein each $R^g$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents, and wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L represents a polyalkylene oxide backbone.

In at least one embodiment of any one of macrocyclic compounds having the structure of Formulas (A1), (B1)-(B5), (C), (C1), (C2), (D1), and (D2), L represents a polyalkylene oxide backbone, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L represents a polyalkylene oxide backbone, wherein the polyalkylene oxide backbone comprises polyethylene oxide (PEO), polypropyleneoxide (PPO), polybutyleneoxide (PBO) or a mixture thereof.

In at least one embodiment of any one of macrocyclic compounds having the structure of Formulas (A1), (B), (B1)-(B5), (C), (C1), (C2), (D1), and (D2), L represents a polyalkylene oxide backbone, wherein the polyalkylene oxide backbone comprises polyethylene oxide (PEO), polypropyleneoxide (PPO), polybutyleneoxide (PBO) or a mixture thereof, and wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises an aliphatic backbone chain of at least 3 atoms one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone chain of at least 3 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises an aliphatic backbone chain of at least 4 atoms one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone chain of at least 4 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises an aliphatic backbone chain of at least 5 atoms one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone chain of at least 5 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises an aliphatic backbone chain of at least 6 atoms one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone chain of at least 6 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises an aliphatic backbone chain of at least 7 atoms one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone chain of at least 7 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises an aliphatic backbone chain of at least 8 atoms one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone chain of at least 8 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises an aliphatic backbone chain of at least 9 atoms one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone chain of at least 9 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises an aliphatic backbone chain of at least 10 atoms one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone chain of at least 10 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises an aliphatic backbone chain of at least 11 atoms one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone chain of at least 11 atoms one or more times interrupted by one or more heteroatoms independently selected from the group consisting of O, S, N and P, wherein L-(T)$_v$ represents a backbone chain having at most 25 atoms in length, wherein T, and v are as defined for the compound of Formula (A).

In at least one embodiment of any one of macrocyclic compounds having the structure of Formulas (A1), (B), (B1)-(B5), (C), (C1), (C2), (D1), and (D2), L comprises an aliphatic backbone of at least 2 atoms in length to 17 atoms in length, wherein the aliphatic backbone chain is one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone of at least 3 atoms in length to 17 atoms in length, wherein the aliphatic backbone chain is one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone of at least 4 atoms in length to 17 atoms in length, wherein the aliphatic backbone chain is one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone of at least 5 atoms in length to 17 atoms in length, wherein the aliphatic backbone chain is one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone of at least 6 atoms in length to 17 atoms in length, wherein the aliphatic backbone chain is one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone of at least 7 atoms in length to 17 atoms in length, wherein the aliphatic backbone chain is one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone of at least 8 atoms in length to 17 atoms in length, wherein the aliphatic backbone chain is one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone of at least 9 atoms in length to 17 atoms in length, wherein the aliphatic backbone chain is one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone of at least 10 atoms in length to 17 atoms in length, wherein the aliphatic backbone chain is one or more times interrupted by one or more heteroatoms independently selected from the group consisting of O, S, N and P.

In at least one embodiment of any one of macrocyclic compounds having the structure of Formulas (A1), (B), (B1)-(B5), (C), (C1), (C2), (D1), and (D2), L comprises an aliphatic backbone of at least 11 atoms in length to 17 atoms in length, wherein the aliphatic backbone chain is one or more times interrupted by one or more heteroatoms independently selected from the group consisting of O, S, N and P.

In some preferred embodiments, the macrocyclic compound of Formula (B) has the structures of Formulas (B6) and (B7):

$Z^3$ is:

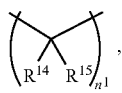

a covalent bond, or $G^3\text{-}(C_{1-20})$alkylene, wherein $n^1$ is an integer having a value of 0 to 20; each of $G^1$, $G^2$, and $G^3$ is independently selected from the group consisting of $N(R^{14})$,

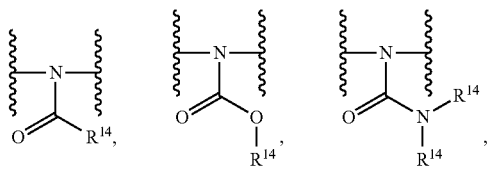

oxygen atom, sulfur atom, sulfoxide, and sulfone; each of $n^1$ and u is an integer having a value independently selected from the group consisting of 1 to 20; whenever it appears herein, an integer range such as "1 to 20" refers to each integer ranging in value from 0 to 20; each of $R^3$, $R^4$, $R^5$, $R^6$, $R^{14}$, and $R^{15}$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and each of $J^1$, $J^2$, p, and q has the same meaning as defined with respect to the macrocyclic compound of Formula (B).

In some preferred embodiments of the macrocyclic compounds of Formulas (B6) and (B7), $J^1$, $J^2$ are independently selected from the group consisting of hydroxy, halogen, cyano, trifluoromethyl, trifluoromethoxy, nitro, trimethylsilanyl, —$OR^a$, —$SR^a$, —$OC(O)$—$R^a$, —$N(R)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(N\text{-}R^a)N(R^a)_2$, —$N(R^a)S(O)_tR^a$, —$N(R)S(O)_2R^a$, —$S(O)OR^a$, —$S(O)_2OR^a$, —$S(O)N(R^a)_2$, —$S(O)_2N(R^a)_2$, or $PO_3(R^a)_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In some preferred embodiments of the macrocyclic compounds of Formulas (B6) and (B7), the substructure $(G^1\text{-}(C_{1-20})\text{alkylene})_u\text{-}G^2$ is an oxy-alkylene oxide, $(O\text{—}(C_{1-20})\text{alkylene})_u\text{-}O$. In some preferred embodiments of the macrocyclic compounds of Formulas (B6) and (B7), the substructure $(G^1\text{-}(C_{1-20})\text{alkylene})_u\text{-}G^2$ is an oxy-alkylene sulfide, $(O\text{—}(C_{1-2})\text{alkylene})_u\text{-}S$. In some preferred embodiments of the macrocyclic compounds of Formulas (B6) and (B7), the substructure $(G^1\text{-}(C_{1-20})\text{alkylene})_u\text{-}G^2$ is an oxy-alkylene amino, $(O\text{—}(C_{1-20})\text{alkylene})_u\text{-}N(R^{16})$, wherein $R^{16}$ is selected from the group consisting of hydrogen, —$C(O)R^{16a}$, —$C(O)OR^{16a}$, —$C(O)N(R^{16a})_2$, alkyl, alkenyl, alkynyl, cycloalkyl, cycloalkenyl, heterocyclyl, aryl, heteroaryl, aralkyl, and heteraralkyl, wherein each $R^{16a}$ is independently selected from the group consisting of hydrogen, alkyl, alkenyl, alkynyl, cycloalkyl, cycloalkenyl, heterocyclyl, aryl, heteroaryl, aralkyl, and heteraralkyl, and each alkyl, alkenyl, alkynyl, cycloalkyl, cycloalkenyl, heterocyclyl, aryl, heteroaryl, aralkyl, and heteraralkyl for $R^{16}$ or $R^{16a}$ is optionally substituted by one or more suitable substituents. In some preferred embodiments of the macrocyclic compounds of Formulas (B6) and (B7), the substructure $(G^1\text{-}(C_{1-20})\text{alkylene})_u\text{-}G^2$ is a sulfo-alkylene oxide, $(S\text{—}(C_{1-20})\text{alkylene})_u\text{-}O$. In some preferred embodiments of the macrocyclic compounds of Formulas (B6) and (B7), the substructure $(G^1\text{-}(C_{1-20})\text{alkylene})_u\text{-}G^2$ is a sulfo-alkylene sulfide, $(S\text{—}(C_{1-20})\text{alkylene})_u\text{-}S$. In some preferred embodiments of the macrocyclic compounds of Formulas (B6) and (B7), the substructure $(G^1\text{-}(C_{1-20})\text{alkylene})_u\text{-}G^2$ is a sulfo-alkylene amino, $(S\text{—}(C_{1-20})\text{alkylene})_u\text{-}N(R^{16})$, wherein $R^{16}$ is selected from the group consisting of hydrogen, —$C(O)R^{16a}$, —$C(O)OR^{16a}$, —$C(O)N(R^{16a})_2$, alkyl, alkenyl, alkynyl, cycloalkyl, cycloalkenyl, heterocyclyl, aryl, heteroaryl, aralkyl, and heteraralkyl, wherein each $R^{16a}$ is independently selected from the group consisting of hydrogen, alkyl, alkenyl, alkynyl, cycloalkyl, cycloalkenyl, heterocyclyl, aryl, heteroaryl, aralkyl, and heteraralkyl, and each alkyl, alkenyl, alkynyl, cycloalkyl, cycloalkenyl, heterocyclyl, aryl, heteroaryl, aralkyl, and heteraralkyl for $R^{16}$ or $R^{16a}$ is optionally substituted by one or more suitable substituents. In some preferred embodiments of the macrocyclic compounds of Formulas (B6) and (B7), the substructure $(G^1\text{-}(C_{1-20})\text{alkylene})_u\text{-}G^2$ is an amino-alkylene oxide, $(N(R^{16})\text{—}(C_{1-20})\text{alkylene})_u\text{-}O$, wherein $R^{16}$ is selected from the group consisting of hydrogen, —$C(O)R^{16a}$, —$C(O)OR^{16a}$, —$C(O)N(R^{16a})_2$, alkyl, alkenyl, alkynyl, cycloalkyl, cycloalkenyl, heterocyclyl, aryl, heteroaryl, aralkyl, and heteraralkyl, wherein each $R^{16a}$ is independently selected from the group consisting of hydrogen, alkyl, alkenyl, alkynyl, cycloalkyl, cycloalkenyl, heterocyclyl, aryl, heteroaryl, aralkyl, and heteraralkyl, and each alkyl, alkenyl, alkynyl, cycloalkyl, cycloalkenyl, heterocyclyl, aryl, heteroaryl, aralkyl, and heteraralkyl for $R^{16}$ or $R^{16a}$ is optionally substituted by one or more suitable substituents. In some preferred embodiments of the macrocyclic compounds of Formulas (B6) and (B7), $(G^1\text{-}(C_{1-20})\text{alkylene})_u\text{-}G^2$ is an amino-alkylene amino, $(N(R^{16})\text{—}(C_{1-20})\text{alkylene})_u\text{-}N(R^{16})$, wherein each $R^{16}$ is independently selected from the group consisting of hydrogen, —$C(O)R^{16a}$, —$C(O)OR^{16a}$, —$C(O)N(R^{16a})_2$, alkyl, alkenyl, alkynyl, cycloalkyl, cycloalkenyl, heterocyclyl, aryl, heteroaryl, aralkyl, and heteraralkyl, wherein each $R^{16a}$ is independently selected from the group consisting of hydrogen, alkyl, alkenyl, alkynyl, cycloalkyl, cycloalkenyl, heterocyclyl, aryl, heteroaryl, aralkyl, and heteraralkyl, and each alkyl, alkenyl, alkynyl, cycloalkyl, cycloalkenyl, heterocyclyl, aryl, heteroaryl, aralkyl, and heteraralkyl for $R^{16}$ or $R^{16a}$ is optionally substituted by one or more suitable substituents. In some preferred embodiments of the macrocyclic compounds of Formulas (B6) and (B7), $(G^1\text{-}(C_{1-20})\text{alkylene})_u\text{-}G^2$ is an amino-alkylene sulfide, $(N(R^{16})\text{—}(C_{1-20})\text{alkylene})_u\text{-}S$, wherein each $R^{16}$ is independently selected from the group consisting of hydrogen, —$C(O)R^{16a}$, —$C(O)OR^{16a}$, —$C(O)N(R^{16a})_2$, alkyl, alkenyl, alkynyl, cycloalkyl, cycloalkenyl, heterocyclyl, aryl, heteroaryl, aralkyl, and heteraralkyl, wherein each $R^{16a}$ is independently selected from the group consisting of hydrogen, alkyl, alkenyl, alkynyl, cycloalkyl, cycloalkenyl, heterocyclyl, aryl, heteroaryl, aralkyl, and heteraralkyl, and each alkyl, alkenyl, alkynyl, cycloalkyl, cycloalkenyl, heterocyclyl, aryl, heteroaryl, aralkyl, and heteraralkyl for $R^{16}$ or $R^{16a}$ is optionally substituted by one or more suitable substituents.

In some preferred embodiments of the macrocyclic compounds of Formulas (B6) and (B7), $G^1$ of the substructure $(G^1\text{-}(C_{1-20})\text{alkylene})_u\text{-}G^2$ is $N(R^{16})$, wherein each $R^{16}$ is independently selected from the group consisting of hydrogen, —C(O)$R^{16a}$, —C(O)O$R^{16a}$, —C(O)N($R^{16a}$)$_2$, alkyl, alkenyl, alkynyl, alkyl, alkenyl, alkynyl, cycloalkyl, cycloalkenyl, and the following:

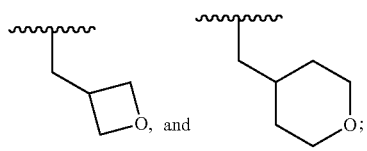

wherein each $R^{16a}$ is independently selected from the group consisting of hydrogen, alkyl, alkenyl, alkynyl, cycloalkyl, cycloalkenyl, heterocyclyl, aryl, heteroaryl, aralkyl, and heteraralkyl.

In at least one embodiment of any one of macrocyclic compounds having the structure of Formulas (B6) and (B7), $Z^3\text{-}(G^1\text{-}(C_{1-20})\text{alkylene})_u\text{-}G^2$ represents a backbone chain having at most 25 atoms in length.

In at least one embodiment of any one of macrocyclic compounds having the structure of Formulas (B6) and (B7), -$(G^1\text{-}(C_{1-20})\text{alkylene})_u$- represents a polyalkylene oxide backbone, wherein the polyalkylene oxide backbone comprises polyethylene oxide (PEO), polypropyleneoxide (PPO), polybutyleneoxide (PBO) or a mixture thereof.

In at least one embodiment of any one of macrocyclic compounds having the structure of Formulas (B6) and (B7), -$(G^1\text{-}(C_{1-20})\text{alkylene})_u$- represents a polyalkylene oxide backbone, wherein the polyalkylene oxide backbone comprises polyethylene oxide (PEO), polypropyleneoxide (PPO), polybutyleneoxide (PBO) or a mixture thereof, wherein $Z^3\text{-}(G^1\text{-}(C_{1-20})\text{alkylene})_u\text{-}G^2$ represents a backbone chain having at most 25 atoms in length.

In some preferred embodiments, the macrocyclic compound of Formula (B6) has the following structure of Formula (B6.1) or Formula (B6.2):

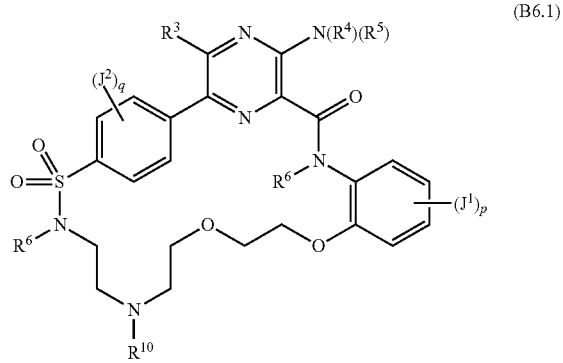

(B6.1)

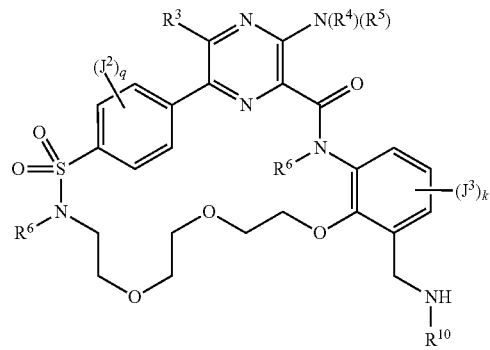

(B6.2)

wherein each of $R^3$, $R^4$, $R^5$, and $R^6$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; $R^{10}$ is selected from the group consisting of hydrogen, —C(O)$R^{10a}$, —C(O)O$R^{10a}$, —C(O)N($R^{10a}$)$_2$, alkyl, alkenyl, alkynyl, cycloalkyl, cycloalkenyl, heterocyclyl, aryl, heteroaryl, aralkyl, and heteraralkyl, wherein each $R^{10a}$ is selected from the group consisting of hydrogen, alkyl, alkenyl, alkynyl, cycloalkyl, cycloalkenyl, heterocyclyl, aryl, heteroaryl, aralkyl, and heteraralkyl; and each alkyl, alkenyl, alkynyl, cycloalkyl, cycloalkenyl, heterocyclyl, aryl, heteroaryl, aralkyl, and heteraralkyl for $R^{10}$ or $R^{10a}$ is optionally substituted by one or more suitable substituents; q and p are the same as defined above and/or elsewhere in this disclosure; $J^3$ is hydrogen or any suitable substitutent; and k is an integer having a value of 1, 2, or 3. In some preferred embodiments of the compounds having the structures of Formulas (B6.1) and (B6.2), $R^{10}$ is:

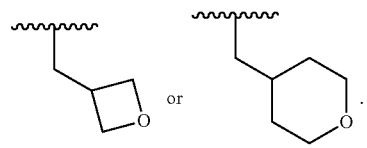 [SMILES: *CC1COC1 ; *CC1CCOCC1]

In some preferred embodiments of the compounds having the structures of Formulas (B6) and (B7), $J^1$ and $J^2$ are independently selected from the group consisting of hydrogen, hydroxy, halogen, cyano, trifluoromethyl, trifluoromethoxy, nitro, trimethylsilanyl, —O$R^a$, —S$R^a$, —OC(O)—$R^a$, —N($R^a$)$_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_r$$R^a$, —N($R^a$)S(O)$_2$$R^a$, —S(O)O$R^a$, —S(O)$_2$O$R^a$, —S(O)N($R^a$)$_2$, —S(O)$_2$N($R^a$)$_2$, or PO$_3$($R^a$)$_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In some preferred embodiments of the compounds having the structures of Formulas (B6.1) and (B6.2), $J^1$, $J^2$ and $J^3$ are independently selected from the group consisting of hydrogen, hydroxy, halogen, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_r$R$^a$, —N(R$^a$)S(O)$_2$R$^a$, —S(O)OR$^a$, —S(O)$_2$OR$^a$, —S(O)N(R$^a$)$_2$, —S(O)$_2$N(R$^a$)$_2$, or PO$_3$(R$^a$)$_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In some preferred embodiments, the macrocyclic compound of Formula (B) has the structures of Formulas (B8) and (B9):

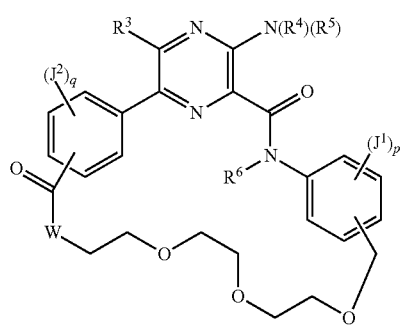

(B8)

(B9)

wherein each of R$^3$, R$^4$, R$^5$, and R$^6$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; J$^1$, J$^2$ q and p are the same as defined above and/or elsewhere in this disclosure; W selected from the group consisting of C(R$^7$)(R$^6$), O, S, and N(R$^7$), wherein R$^7$ selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In some preferred embodiments, the macrocyclic compound of Formula (B) has the structures of Formulas (B8.1) and (B9.1):

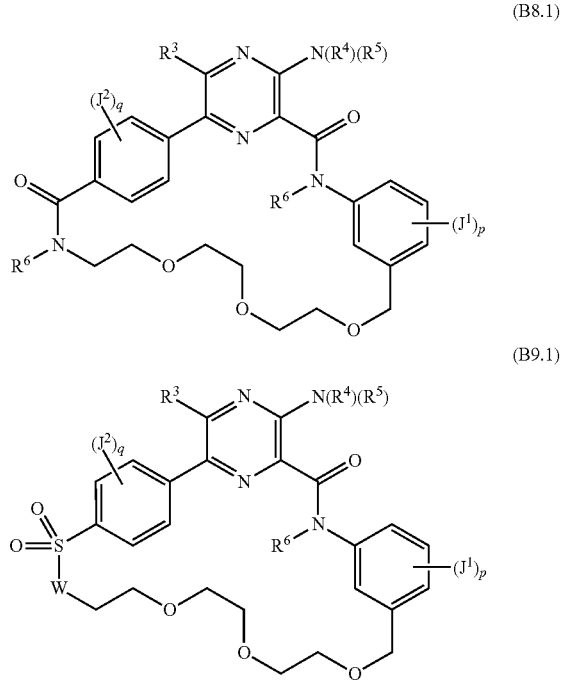

(B8.1)

(B9.1)

wherein each of R$^3$, R$^4$, R$^5$, and R$^6$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; J$^1$, J$^2$ q and p are the same as defined above and/or elsewhere in this disclosure; W selected from the group consisting of C(R$^7$)(R$^6$), O, S, and N(R$^7$), wherein R$^7$ selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents. In some preferred embodiments of the compounds having the structures of Formulas (B8.1) and (B9.1), J$^1$, J$^2$, R$^6$ and R$^7$ are independently any polar group, including nitro, hydroxyl, alkoxy, halogen, cyano, sulfonate, amino containing or amino-derived polar groups, carbohydrate groups, phosphorus containing polar groups, sulfur containing polar groups, and anions.

In some embodiments, the macrocyclic compound having the structure of Formula (B) has the structure of Formulas (B10) or (B11):

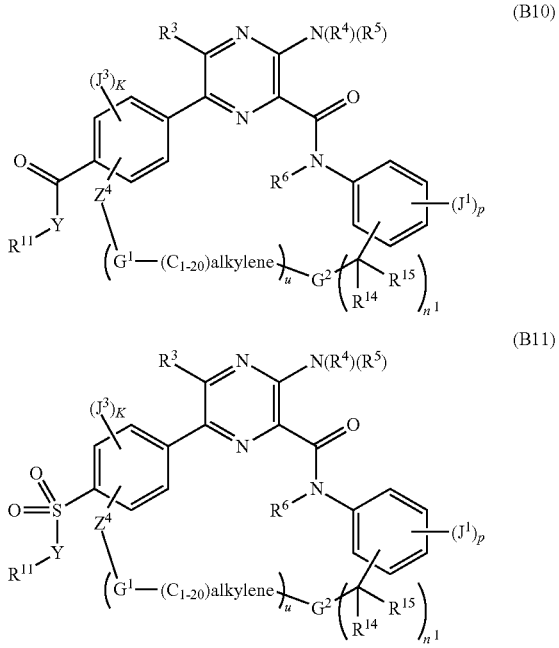

(B10)

(B11)

wherein each of $R^3$, $R^4$, $R^5$, $R^6$, and $R^{11}$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; k is an integer having a value of 1, 2, or 3; p is the same as defined above and/or elsewhere in this disclosure (e.g., p is an integer having a value of 1, 2, 3, or 4); $J^3$ is hydrogen or any suitable substitutent; Y is selected from the group consisting of $NR^{12}$, $C(R^{13})$, and O; each of $R^{12}$ and $R^{13}$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents;
$Z^4$ is:

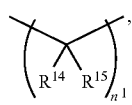

covalent bond, or $G^3$-($C_{1-20}$)alkylene; each of $G^1$, $G^2$, and $G^3$ is independently selected from the group consisting of $N(R^{14})$, oxygen atom, sulfur atom, sulfoxide, or sulfone; u is an integer having a value independently selected from the group consisting of 1 to 20; whenever it appears herein, an integer range such as "1 to 20" refers to each value in the given range up to and including 20—e.g., "u is an integer ranging in value from 1 to 20" means that u may have any one of the integer values 1, 2, 3, etc., up to and including 20;

$n^1$ is an integer ranging in value from 0 to 20; each of $R^{14}$ and $R^{15}$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and each of $J^1$ has the same meaning as defined with respect to the macrocyclic compound of Formula (B).

In some preferred embodiments of the macrocyclic compounds of Formulas (B10) or (B11), $J^1$ and $J^3$ are independently selected from the group consisting of hydrogen, hydroxy, halogen, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N($R^a$)$_2$, —C(O)N($R^a$)$_2$, —N($R^a$)C(O)O$R^a$, —N($R^a$)C(O)$R^a$, —N($R^a$)C(O)N($R^a$)$_2$, N($R^a$)C(N$R^a$)N($R^a$)$_2$, —N($R^a$)S(O)$_t$$R^a$, —N($R^a$)S(O)$_2$$R^a$, —S(O)O$R^a$, —S(O)$_2$O$R^a$, —S(O)N($R^a$)$_2$, —S(O)$_2$N($R^a$)$_2$, or PO$_3$($R^a$)$_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In at least one embodiment of any one of macrocyclic compounds having the structure of Formulas (B10) and (B11), $Z^4$-($G^1$-($C_{1-20}$)alkylene)$_u$-$G^2$ represents a backbone chain having at most 25 atoms in length.

In at least one embodiment of any one of macrocyclic compounds having the structure of Formulas (B10) and (B11), -($G^1$-($C_{1-20}$)alkylene)$_u$- represents a polyalkylene oxide backbone, wherein the polyalkylene oxide backbone comprises polyethylene oxide (PEO), polypropyleneoxide (PPO), polybutyleneoxide (PBO) or a mixture thereof.

In at least one embodiment of any one of macrocyclic compounds having the structure of Formulas (B10) and (B11), -($G^1$-($C_{1-20}$)alkylene)$_u$- represents a polyalkylene oxide backbone, wherein the polyalkylene oxide backbone comprises polyethylene oxide (PEO), polypropyleneoxide (PPO), polybutyleneoxide (PBO) or a mixture thereof, wherein $Z^4$-($G^1$-($C_{1-20}$)alkylene)$_u$-$G^2$ represents a backbone chain having at most 25 atoms in length.

In some preferred embodiments, the macrocyclic compound of Formula (B) has the structures of Formulas (B10.1) to (B11.2):

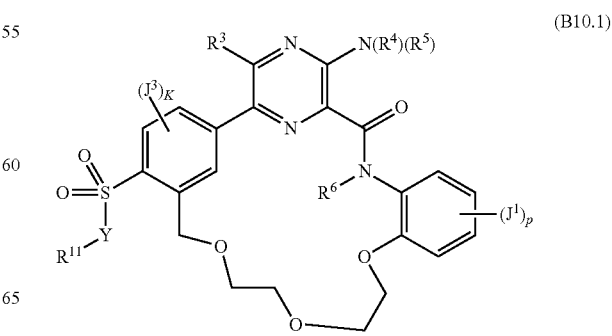

(B10.1)

-continued

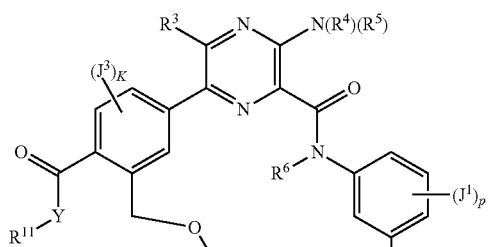
(B10.2)

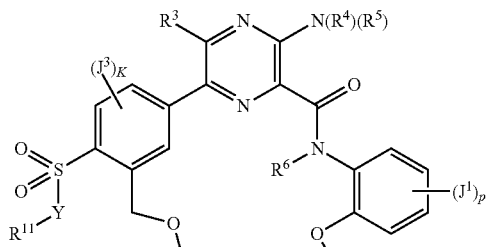
(B11.1)

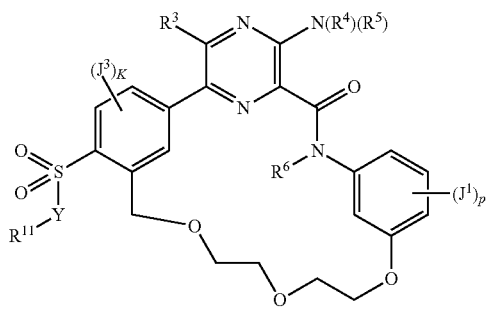
(B11.2)

wherein each of $R^3$, $R^4$, $R^5$, and $R^6$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; $J^1$ and p are the same as defined with respect to the macrocyclic compound of Formula (B); $J^3$ is hydrogen or any suitable substituent; k is an integer having a value of 1, 2, or 3; Y selected from the group consisting of CH, $C(R^{13})$, O, and $N(R^{13})$, wherein each of $R^{11}$, $R^{12}$ and $R^{13}$ is independently selected from the group consisting of hydrogen, alkyl, alkenyl, alkynyl, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents. In some preferred embodiments of the compounds having the structures of Formulas B10.1 to B11.2, $J^1$, $J^3$, $R^3$, and $R^{12}$ are independently any polar group including nitro, hydroxyl, alkoxy, halogen, cyano, sulfonate, amino containing or amino-derived polar groups, carbohydrate groups, phosphorus containing polar groups, sulfur containing polar groups, and anions; and $R^4$, $R^5$, $R^{11}$, $R^{13}$ are independently hydrogen, alkyl, alkenyl, alkynyl, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In some preferred embodiments of the macrocyclic compounds of Formulas (B10.1) to (B11.2), $J^1$ and $J^3$ are independently selected from the group consisting of hydrogen, hydroxy, halogen, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_tR^a$, —$N(R^a)S(O)_2R^a$, —$S(O)OR^a$, —$S(O)_2OR^a$, —$S(O)N(R^a)_2$, —$S(O)_2N(R^a)_2$, or $PO_3(R^a)_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In some preferred embodiments, the macrocyclic compound of Formula (A1) has the structures of Formulas (B12) to (B13):

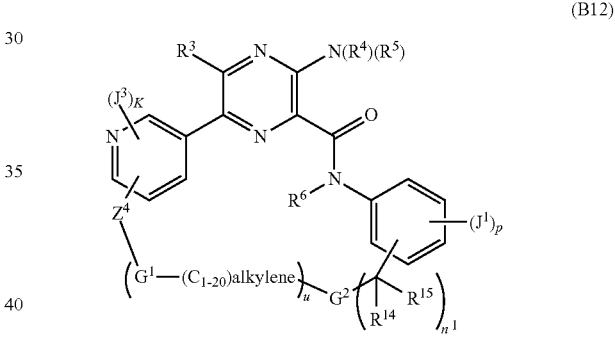
(B12)

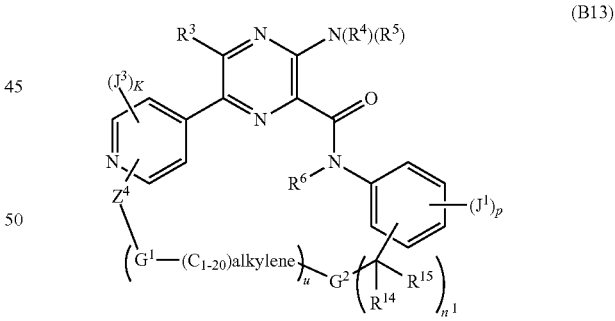
(B13)

wherein each of $R^3$, $R^4$, $R^5$, and $R^6$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; k is an integer having a value of 1, 2, or 3; p is the same as defined above and/or elsewhere in this disclosure (e.g., p is an integer having a value of 1, 2, 3, or 4); $J^3$ is hydrogen or any suitable substitutent;

$Z^4$ is:

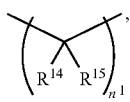

a covalent bond, or $G^3$-$(C_{1-20})$alkylene; each of $G^1$, $G^2$, and $G^3$ is independently selected from the group consisting of $N(R^{14})$, oxygen atom, sulfur atom, sulfoxide, or sulfone; u is an integer having a value independently selected from the group consisting of 1 to 20; whenever it appears herein, an integer range such as "1 to 20" refers to each value in the given range up to and including 20—e.g., "u is an integer ranging in value from 1 to 20" means that u may have any one of the integer values 1, 2, 3, etc., up to and including 20; $n^1$ is an integer ranging in value from 0 to 20; each of $R^3$, $R^4$, $R^5$, $R^6$, $R^{14}$, and $R^{15}$ is selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and each of $J^1$ has the same meaning as defined with respect to the macrocyclic compound of Formula (A1).

In some preferred embodiments of the macrocyclic compounds of Formulas (B12) and (B13), $J^1$ and $J^3$ are independently selected from the group consisting of hydrogen, hydroxy, halogen, cyano, trifluoromethyl, trifluoromethoxy, nitro, trimethylsilanyl, —$OR^a$, —$SR^a$, —$OC(O)$—$R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_2R^a$, —$N(R^a)S(O)_2R^a$, —$S(O)OR^a$, —$S(O)_2OR^a$, —$S(O)N(R^a)_2$, —$S(O)_2N(R^a)_2$, or $PO_3(R^a)_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In at least one embodiment of any one of macrocyclic compounds having the structure of Formulas (B12) and (B13), $Z^4$-$(G^1$-$(C_{1-20})$alkylene$)_u$-$G^2$ represents a backbone chain having at most 25 atoms in length.

In at least one embodiment of any one of macrocyclic compounds having the structure of Formulas (B12) and (B13), -$(G^1$-$(C_{1-20})$alkylene$)_u$- represents a polyalkylene oxide backbone, wherein the polyalkylene oxide backbone comprises polyethylene oxide (PEO), polypropyleneoxide (PPO), polybutyleneoxide (PBO) or a mixture thereof.

In at least one embodiment of any one of macrocyclic compounds having the structure of Formulas (B12) and (B13), -$(G^1$-$(C_{1-20})$alkylene$)_u$- represents a polyalkylene oxide backbone, wherein the polyalkylene oxide backbone comprises polyethylene oxide (PEO), polypropyleneoxide (PPO), polybutyleneoxide (PBO) or a mixture thereof, wherein $Z^4$-$(G^1$-$(C_{1-20})$alkylene$)_u$-$G^2$ represents a backbone chain having at most 25 atoms in length.

In some preferred embodiments of the compounds having the structures of Formulas (B12) and (B13), $J^1$, $J^3$, and $R^3$ are independently any polar group, including nitro, hydroxyl, alkoxy, halogen, cyano, sulfonate, amino containing or amino-derived polar groups, carbohydrate groups, phosphorus containing polar groups, sulfur containing polar groups, and anions; and $R^4$ and $R^5$ are independently hydrogen, alkyl, alkenyl, alkynyl, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In some preferred embodiments, the macrocyclic compound of Formula (B12) has the structures of Formulas (B12.1) and (B12.2) and the macrocyclic compound of Formula (B13) has the structures of Formulas (B13.1) and (B13.2):

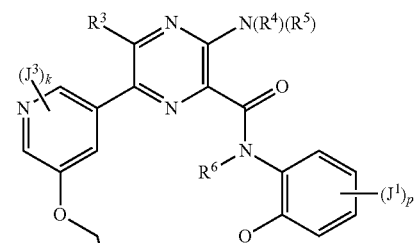

(B12.1)

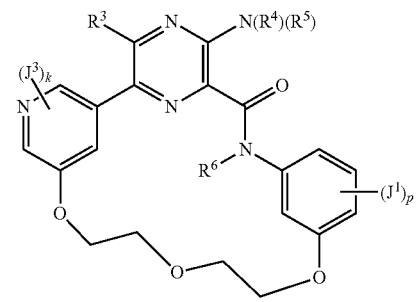

(B12.2)

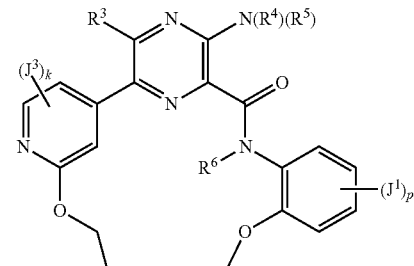

(B13.1)

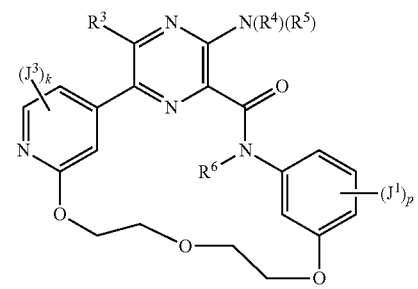

(B13.2)

wherein each of $R^3$, $R^4$, $R^5$, and $R^6$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; $J^1$, $J^3$ p, and k have the same meanings as defined with respect to the macrocyclic compound of Formulas (B12) and (B13) above. In some preferred embodiments of the compounds having the structures of Formulas (B12.1) to (B13.2), $J^1$, $J^2$, and $R^3$ are independently any polar group, including nitro, hydroxyl, alkoxy, halogen, cyano, sulfonate, amino containing or amino-derived polar groups, carbohydrate groups, phosphorus containing polar groups, sulfur containing polar groups, and anions; and $R^4$ and $R^5$ are independently hydrogen, alkyl, alkenyl, alkynyl, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In some preferred embodiments of the macrocyclic compounds of Formulas (B12.1) to (B13.2), $J^1$ and $J^3$ are independently selected from the group consisting of hydrogen, hydroxy, halogen, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N($R^a$)C(O)O$R^a$, —N($R^a$)C(O)$R^a$, —N($R^a$)C(O)N$(R^a)_2$, N($R^a$)C(N$R^a$)N$(R^a)_2$, —N($R^a$)S(O)$_rR^a$, —N($R^a$)S(O)$_2R^a$, —S(O)O$R^a$, —S(O)$_2$O$R^a$, —S(O)N$(R^a)_2$, —S(O)$_2$N$(R^a)_2$, or PO$_3(R^a)_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In some preferred embodiments, the macrocyclic compound of Formula (C) has the structures of Formulas (C3) and (C4):

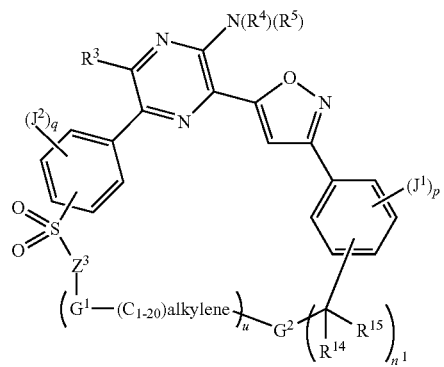

(C3)

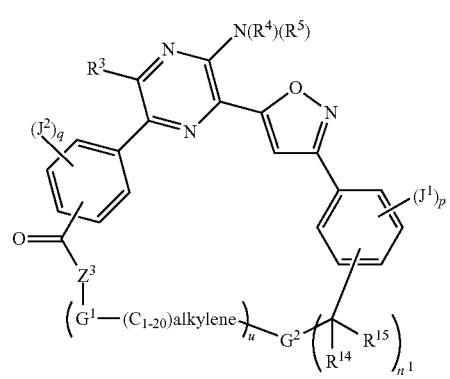

(C4)

wherein each of $R^3$, $R^4$, $R^5$, $R^{14}$, and $R^{15}$ is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; each of p and q is the same as defined above and/or elsewhere in this disclosure (e.g., p and q each is an integer having a value of 1, 2, 3, or 4); each of $J^1$ and $J^2$ is a hydrogen or any suitable substitutent;

$Z^3$ is:

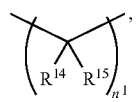

a covalent bond, or $G^3$-(C$_{1-20}$)alkylene; each of $G^1$, $G^2$, and $G^3$ is independently selected from the group consisting of $N(R^{14})$,

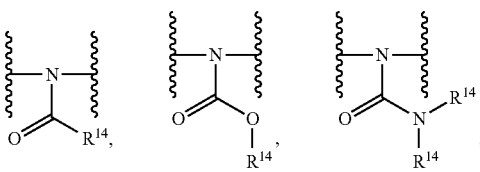

oxygen atom, sulfur atom, sulfoxide, or sulfone; u is an integer having a value selected from the group consisting of 1 to 20; whenever it appears herein, an integer range such as "1 to 20" refers to each value in the given range up to and including 20—e.g., "u is an integer ranging in value from 1 to 20" means that u may have any one of the integer values 1, 2, 3, etc., up to and including 20; $n^1$ is an integer ranging in value from 0 to 20, wherein $G^2$ is covalently bonded to the proximal phenyl ring when $n^1$ is 0.

In some preferred embodiments of the macrocyclic compounds of Formulas (C3) or (C4), $J^1$ and $J^2$ are independently selected from the group consisting of hydrogen, hydroxy, halogen, cyano, trifluoromethyl, trifluoromethoxy, nitro, trimethylsilanyl, —$OR^a$, —$SR^a$, —OC(O)—$R^a$, —$N(R^a)_2$, —C(O)$R^a$, —C(O)O$R^a$, —OC(O)N$(R^a)_2$, —C(O)N$(R^a)_2$, —N($R^a$)C(O)O$R^a$, —N($R^a$)C(O)$R^a$, —N($R^a$)C(O)N$(R^a)_2$, N($R^a$)C(N$R^a$)N$(R^a)_2$, —N($R^a$)

S(O)$_r$R$^a$, —N(R$^a$)S(O)$_2$R$^a$, —S(O)OR$^a$, —S(O)$_2$OR$^a$, —S(O)N(R$^a$)$_2$, —S(O)$_2$N(R$^a$)$_2$, or PO$_3$(R$^a$)$_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

In at least one embodiment of any one of macrocyclic compounds having the structure of Formulas (C3) and (C4), Z$^3$-(G$^1$-(C$_{1-20}$)alkylene)$_u$-G$^2$ represents a backbone chain having at most 25 atoms in length.

In at least one embodiment of any one of macrocyclic compounds having the structure of Formulas (C3) and (C4), -(G$^1$-(C$_{1-20}$)alkylene)$_u$- represents a polyalkylene oxide backbone, wherein the polyalkylene oxide backbone comprises polyethylene oxide (PEO), polypropyleneoxide (PPO), polybutyleneoxide (PBO) or a mixture thereof.

In at least one embodiment of any one of macrocyclic compounds having the structure of Formulas (C3) and (C4), -(G$^1$-(C$_{1-20}$)alkylene)$_u$- represents a polyalkylene oxide backbone, wherein the polyalkylene oxide backbone comprises polyethylene oxide (PEO), polypropyleneoxide (PPO), polybutyleneoxide (PBO) or a mixture thereof, wherein Z$^3$-(G$^1$-(C$_{1-20}$)alkylene)$_u$-G$^2$ represents a backbone chain having at most 25 atoms in length.

In some preferred embodiments, the macrocyclic compound of Formula (C3) has the structures of Formulas (C3.1) and (C3.2) and the macrocyclic compound of Formula (C4) has the structures of Formulas (C4.1) and (C4.2):

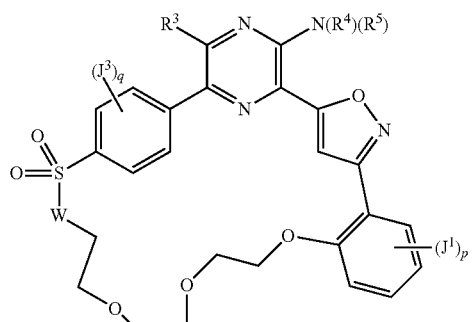

(C3.1)

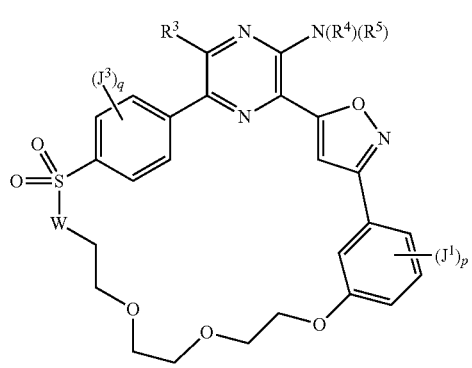

(C3.2)

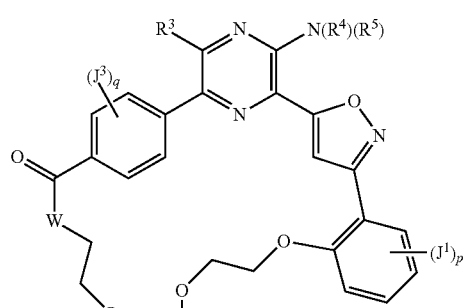

(C4.1)

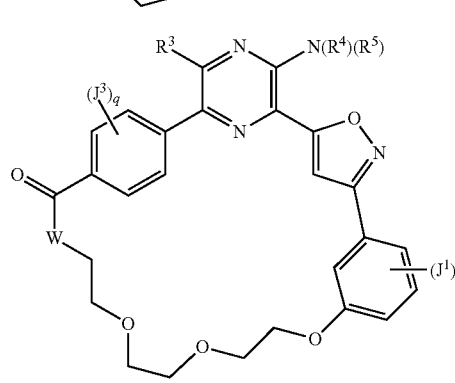

(C4.2)

Wherein W selected from the group consisting of C(R$^7$)(R$^6$), O, S, and N(R$^7$), wherein each of R$^3$, R$^4$, R$^5$, R$^6$, and R$^7$, is independently selected from the group consisting of hydrogen, alkyl, alkenyl, alkynyl, cycloalkyl, cycloalkenyl, heterocyclyl, aryl, heteroaryl, aralkyl, and heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; J$^1$, J$^2$ q and p are the same as defined above with respect to the structure of Formula (B). In some preferred embodiments of the compounds having the structures of Formulas (C3.1) to (C4.2), J$^1$, J$^2$, and R$^3$ are independently any polar group, including nitro, hydroxyl, alkoxy, halogen, cyano, sulfonate, amino containing or amino-derived polar groups, carbohydrate groups, phosphorus containing polar groups, sulfur containing polar groups, and anions; and R$^4$ and R$^5$ are independently hydrogen, alkyl, alkenyl, alkynyl, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents.

In some preferred embodiments of the compounds having the structures of Formulas (C3.1) to (C4.2), J$^1$ and J$^2$ are independently selected from the group consisting of:
H, CH$_2$NHCH$_3$,

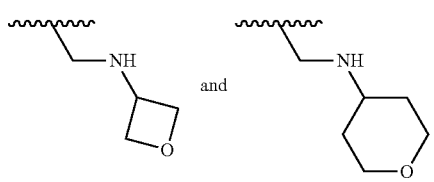 [SMILES: *CNC1COC1 ; *CNC1CCOCC1]

and

In some preferred embodiments of the compounds having the structures of Formulas (C3.1) to (C4.2), $J^1$, $J^2$, $R^3$, $R^4$, and $R^5$ are independently selected from the group consisting of hydrogen, hydroxy, halogen, cyano, trifluoromethyl, trifluoromethoxy, nitro, trimethylsilanyl, —$OR^a$, —$SR^a$, —OC(O)—$R^a$, —$N(R^a)_2$, —$C(O)R^a$, —$C(O)OR^a$, —OC(O)N$(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_rR^a$, —$N(R^a)S(O)_2R^a$, —$S(O)OR^a$, —$S(O)_2OR^a$, —$S(O)N(R^a)_2$, —$S(O)_2N(R^a)_2$, or $PO_3(R^a)_2$, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl is optionally substituted by one or more suitable substituents; and wherein each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl.

Representative macrocyclic compounds of Formula (A) include, but are not limited to, the macrocyclic compounds P(1) to P(41), which are listed in the following Table 1.

TABLE 1

Exemplary macrocyclic compounds of the invention:

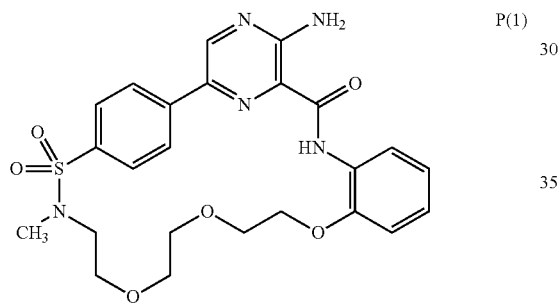
P(1)

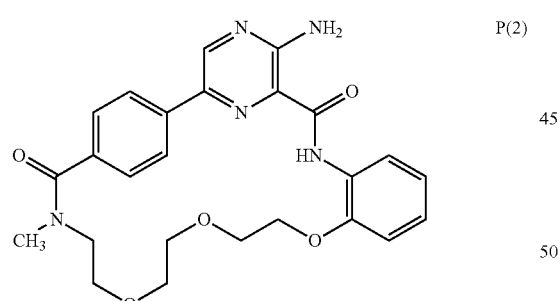
P(2)

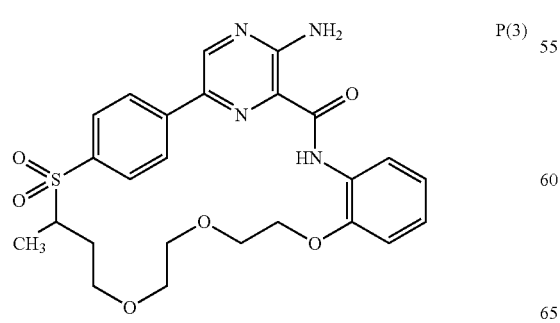
P(3)

TABLE 1-continued

Exemplary macrocyclic compounds of the invention:

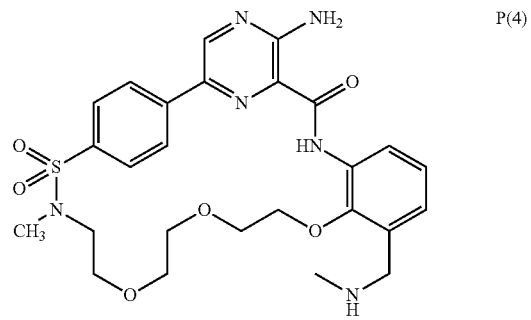
P(4)

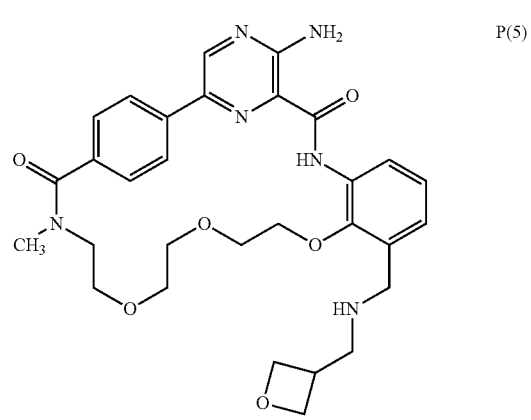
P(5)

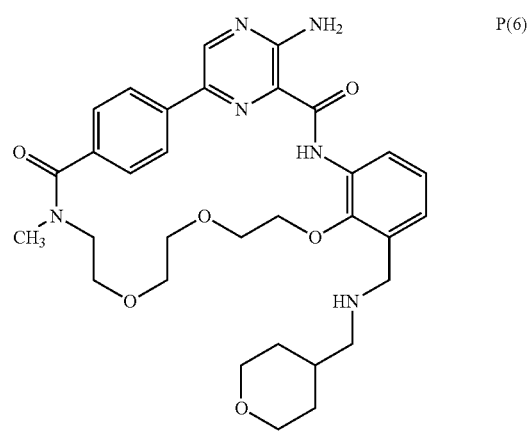
P(6)

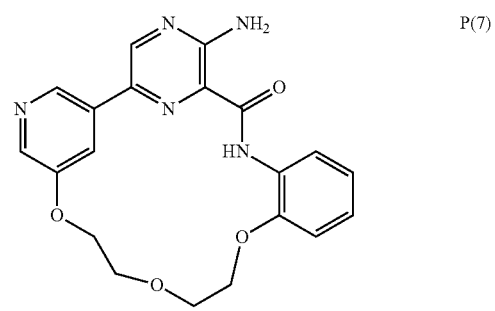
P(7)

TABLE 1-continued
Exemplary macrocyclic compounds of the invention:
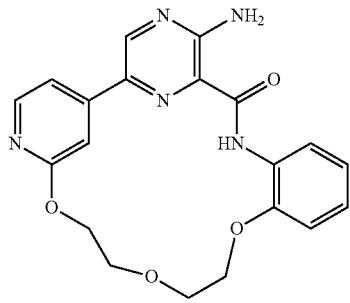 [SMILES: Nc1ncc2nc1C(=O)Nc1ccccc1OCCOCCOc1cc-2ccn1] P(8)
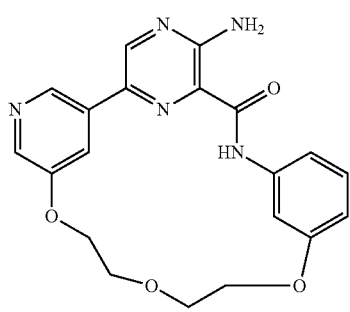 [SMILES: Nc1ncc2nc1C(=O)Nc1cccc(c1)OCCOCCOc1cncc-2c1] P(9)
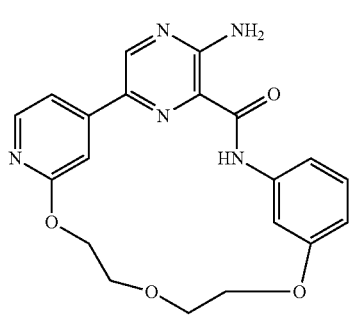 [SMILES: Nc1ncc2nc1C(=O)Nc1cccc(c1)OCCOCCOc1cc-2ccn1] P(10)
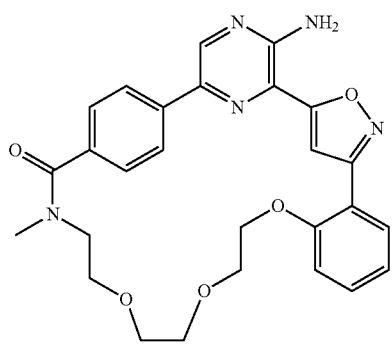 [SMILES: CN1CCOCCOCCOc2ccccc2-c2cc(on2)-c2nc(cnc2N)-c2ccc(cc2)C1=O] P(11)
TABLE 1-continued
Exemplary macrocyclic compounds of the invention:
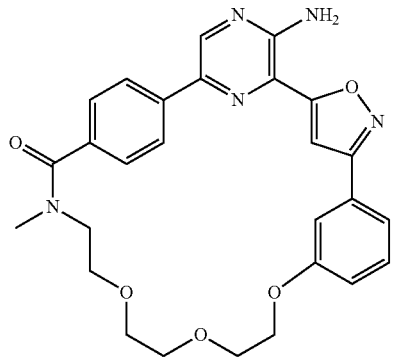 [SMILES: CN1CCOCCOCCOc2cccc(c2)-c2cc(on2)-c2nc(cnc2N)-c2ccc(cc2)C1=O] P(12)
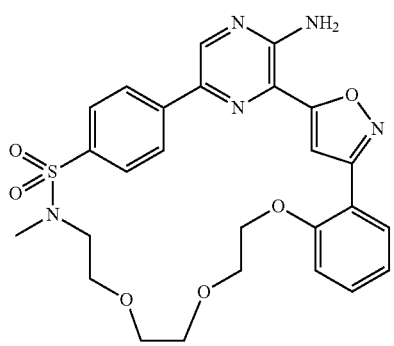 [SMILES: CN1CCOCCOCCOc2ccccc2-c2cc(on2)-c2nc(cnc2N)-c2ccc(cc2)S1(=O)=O] P(13)
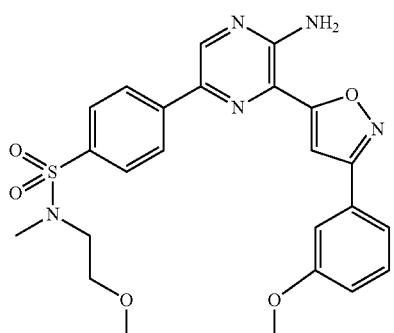 P(14)
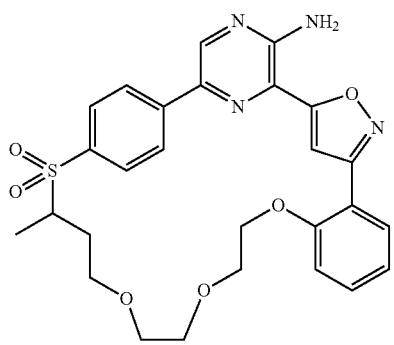 [SMILES: CC1CCOCCOCCOc2ccccc2-c2cc(on2)-c2nc(cnc2N)-c2ccc(cc2)S1(=O)=O] P(15)

TABLE 1-continued
Exemplary macrocyclic compounds of the invention:
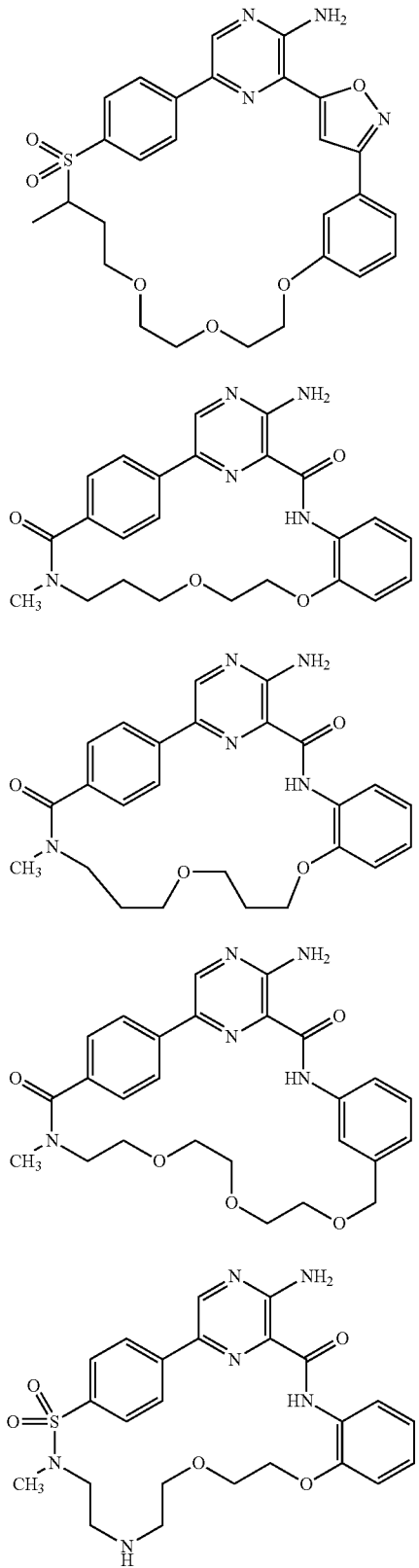
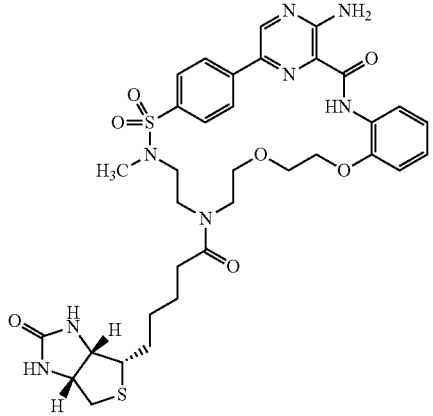 [SMILES: CN1CCN(C(=O)CCCC[C@@H]2SC[C@@H]3NC(=O)N[C@@H]32)CCOCCOc2ccccc2NC(=O)c2nc(cnc2N)-c2ccc(cc2)S1(=O)=O]
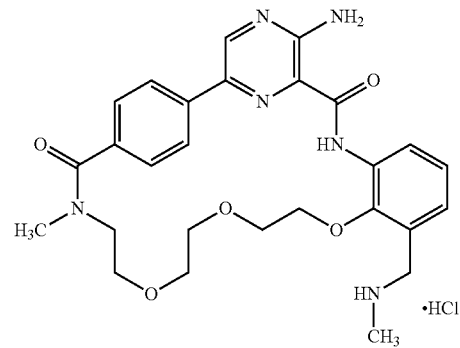 [SMILES: CNCc1cccc2c1OCCOCCOCCN(C)C(=O)c1ccc(cc1)-c1cnc(N)c(n1)C(=O)N2 ; Cl]
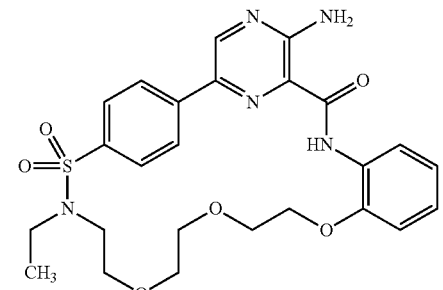
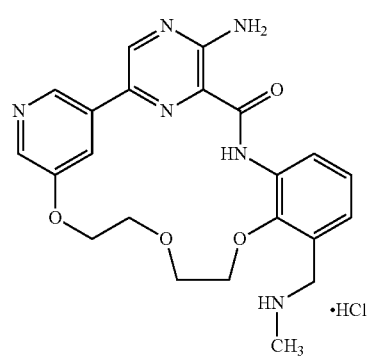 [SMILES: CNCc1cccc2c1OCCOCCOc1cncc(c1)-c1cnc(N)c(n1)C(=O)N2 ; Cl]

TABLE 1-continued
Exemplary macrocyclic compounds of the invention:
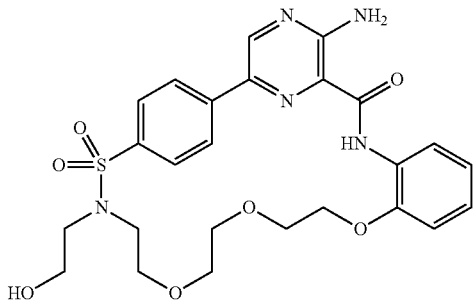 [SMILES: Nc1ncc2nc1C(=O)Nc1ccccc1OCCOCCOCCN(CCO)S(=O)(=O)c1ccc-2cc1]
P(25)
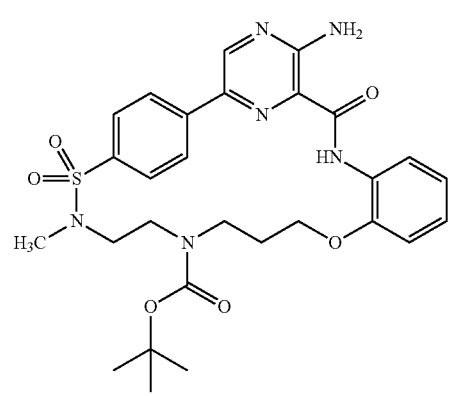 [SMILES: CN1CCN(C(=O)OC(C)(C)C)CCCOc2ccccc2NC(=O)c2nc(cnc2N)-c2ccc(cc2)S1(=O)=O]
P(26)
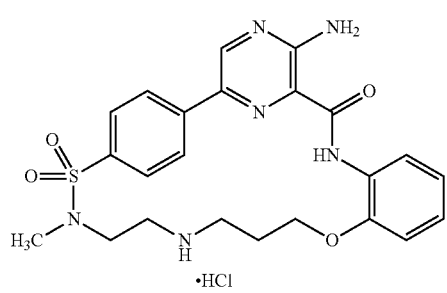 [SMILES: CN1CCNCCCOc2ccccc2NC(=O)c2nc(cnc2N)-c2ccc(cc2)S1(=O)=O ; Cl]
P(27)
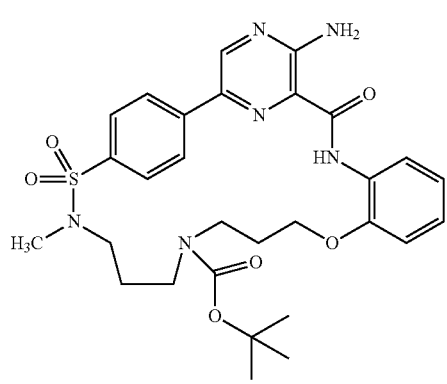 [SMILES: CN1CCCN(C(=O)OC(C)(C)C)CCCOc2ccccc2NC(=O)c2nc(cnc2N)-c2ccc(cc2)S1(=O)=O]
P(28)
TABLE 1-continued
Exemplary macrocyclic compounds of the invention:
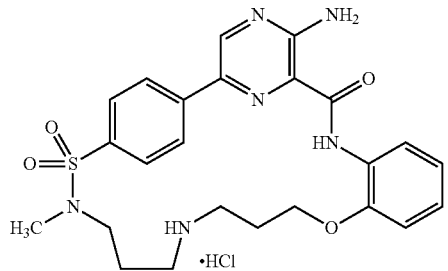 [SMILES: CN1CCCNCCCOc2ccccc2NC(=O)c2nc(cnc2N)-c2ccc(cc2)S1(=O)=O ; Cl]
P(29)
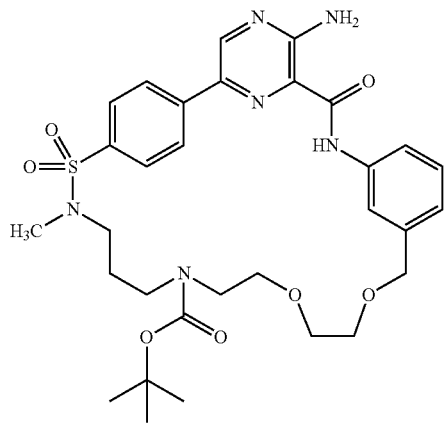 [SMILES: CN1CCCN(C(=O)OC(C)(C)C)CCOCCOCc2cccc(c2)NC(=O)c2nc(cnc2N)-c2ccc(cc2)S1(=O)=O]
P(30)
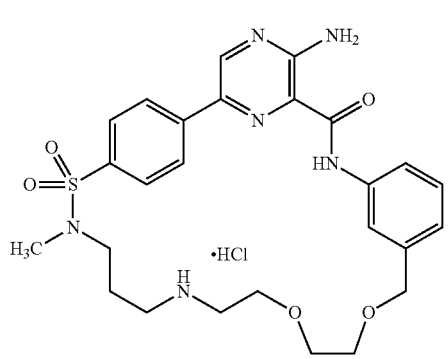 [SMILES: CN1CCCNCCOCCOCc2cccc(c2)NC(=O)c2nc(cnc2N)-c2ccc(cc2)S1(=O)=O ; Cl]
P(31)
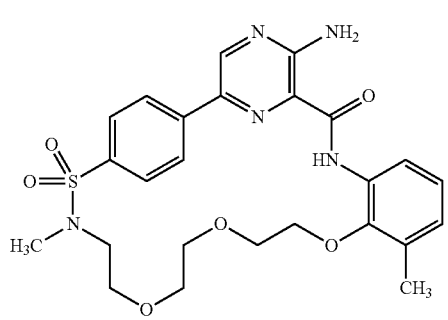 [SMILES: Cc1cccc2c1OCCOCCOCCN(C)S(=O)(=O)c1ccc(cc1)-c1cnc(N)c(n1)C(=O)N2]
P(32)

TABLE 1-continued
Exemplary macrocyclic compounds of the invention:
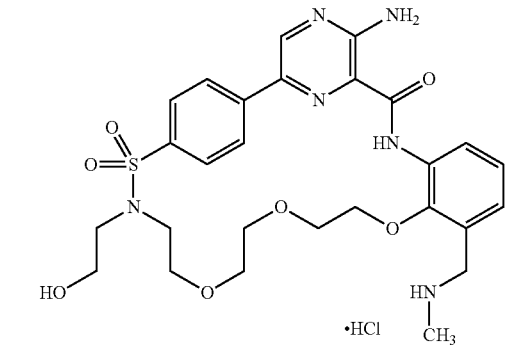 [SMILES: CNCc1cccc2c1OCCOCCOCCN(CCO)S(=O)(=O)c1ccc(cc1)-c1cnc(N)c(n1)C(=O)N2 ; Cl]
P(33)
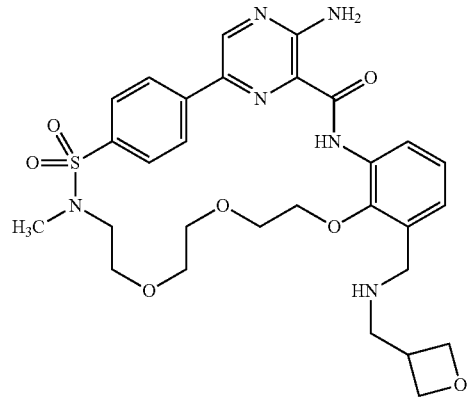 [SMILES: CN1CCOCCOCCOc2c(CNCC3COC3)cccc2NC(=O)c2nc(cnc2N)-c2ccc(cc2)S1(=O)=O]
P(37)
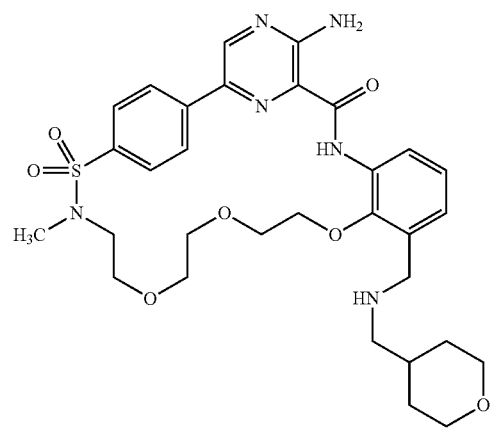
P(34)
P(38)
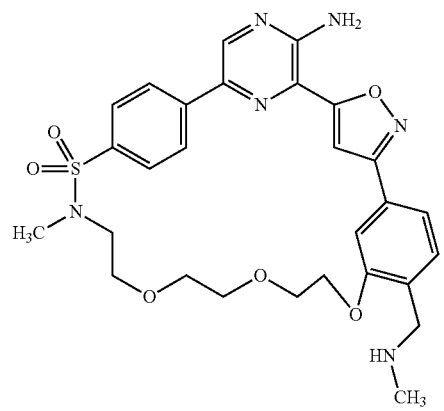 [SMILES: CNCc1ccc2cc1OCCOCCOCCN(C)S(=O)(=O)c1ccc(cc1)-c1cnc(N)c(n1)-c1cc-2no1]
P(35)
P(39)
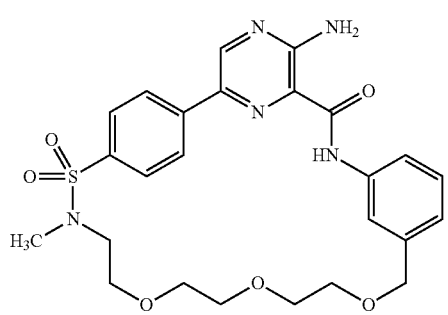 [SMILES: CN1CCOCCOCCOCc2cccc(c2)NC(=O)c2nc(cnc2N)-c2ccc(cc2)S1(=O)=O]
P(36)
P(40)

TABLE 1-continued

Exemplary macrocyclic compounds of the invention:

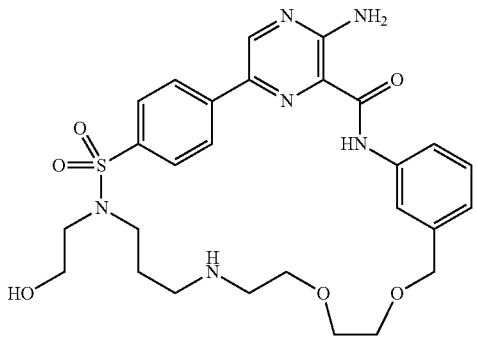 [SMILES: Nc1ncc2nc1C(=O)Nc1cccc(c1)COCCOCCNCCCN(CCO)S(=O)(=O)c1ccc-2cc1]

P(41)

III. SYNTHESIS

The compounds of the disclosure may be prepared in light of the specification using steps generally known to those of ordinary skill in the art. Those compounds may be analyzed by known methods, including but not limited to LCMS (liquid chromatography mass spectrometry) and NMR (nuclear magnetic resonance). Below are a set of generic schemes that illustrate generally how to prepare the compounds of the present disclosure.

In some embodiments, macrocyclic compound of Formula (A1) can be prepared according to the general synthetic Scheme 1, wherein $R^1$ to $R^5$, $Z^2$, and L all are as defined for the macrocyclic compound having the structure of Formula (A). As illustrated in Scheme 1, amidation of pyrazine carboxylic acid S-1 and amine S-2 produces amide S-3. Suzuki-Miyaura reaction between amide S-3 and boronic acid S-4 produces substituted pyrazine S-5, wherein Q and M are functionalities necessary to effect ring closing reaction(s) to produce macrocyclic compound of Formula (A1).

Scheme 1: A General Scheme for the Preparation of Compounds of Formula (A1)

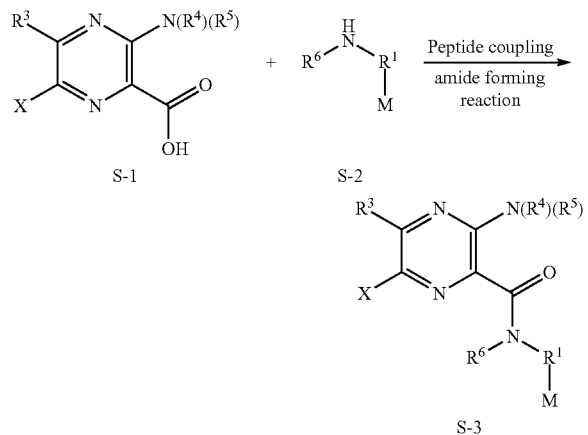

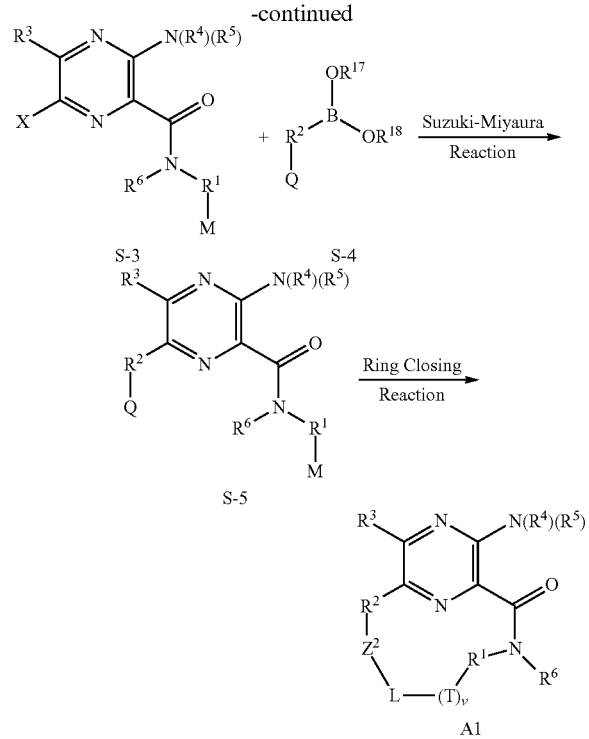

A. Starting Materials of Scheme 1:

Carboxylic acid (S-1) is commercially available or can be readily synthesized from commercially available precursors according to well known literature procedures, including procedures reported by R. C. Ellingson and R. L. Henry in 1949 (Pyrazine Chemistry. IV. Bromination of 2-Amino-3-carbomethoxypyrazine, *J. Am. Chem. Soc.*, 1949, 71 (8), pp 2798-2800). X in (S-1) is a halogen. Each of $R^3$, $R^4$, and $R^5$ in (S-1) has the meaning and scope disclosed throughout this disclosure with respect to the compound of Formula (A) and various subgenuses thereof, including the compound of Formula (A1).

Amine starting material (S-2) is either commercially available or can be readily prepared from commercially available precursors. $R^1$ and $R^6$ in (S-2) have the meanings and scope disclosed throughout this disclosure with respect to the compound of Formula (A) and various subgenuses thereof, including the compound of Formula (A1). M is any substructure or a functional group sufficient to allow for a ring closing reaction to form the compound of Formula (A1).

Boronic acid or ester (S-4) is commercially available, can readily be synthesized from commercially available precursors according to well known literature procedures or is synthesized according to procedures disclosed herein. Each of $R^{17}$ and $R^{18}$ can independently be hydrogen, alkyl, cycloalkyl, or aryl; or $R^{17}$ and $R^{18}$ may combine together to form a ring. $R^2$ in (S-4) has the meaning and scope disclosed throughout this disclosure with respect to the compound of Formula (A) and various subgenuses thereof, including the compound of Formula (A1). Q is any substructure or a functional group sufficient to allow for a ring closing reaction between Q and M to form the compound of Formula (A1).

B. Reactions of Scheme 1:

Carboxylic acid (S-1) and amine (S-2) can be reacted utilizing any suitable amide forming reaction, including various known peptide coupling reactions, to form amide (S-3), which in turn is coupled with boronic acid derivative (S-4), for example, via a Suzuki-Miyaura reaction to form intermediary compound (S-5). Other reactions and starting materials may be used to arrive at intermediary compound (S-5).

Any suitable ring closing reaction between M and Q of intermediary compound (S-5) can be used to form macrocyclic compound (A1). For example, Ring-Closing Metathesis (RCM) may be used to form the macrocyle when M and Q contain terminal olefinic groups. The resulting ring double bond may be used as site for further modification of the macrocycle. For example, dihydroxylation of the ring double (e.g., by Sharpless bishydroxylation) could be used to introduce hydroxyl groups along the backbone of the macrocyclic ring. The hydroxyl may in turn be further modified through esterification, oxidation, or etherification reactions. The ring double bond may be reduced with, for example, diimide ($N_2H_2$). Other reactions that may be performed on the ring double bond include hydroamination, hydroxyamination, and hydroboration.

In some embodiments, a ring closing reaction between M and Q of intermediary compound (S-5) is an intramolecular amide coupling between an amino function group and a carboxylic acid group. The amino function group or the carboxylic acid group may be located in either M or Q of intermediary compound (S-5).

In some embodiments, a ring closing reaction between M and Q of intermediary compound (S-5) is a Mitsunobu Reaction (involving a hydroxyl group and a carboxylic acid) to form a macrolactone. In some embodiments, a ring closing reaction between M and Q of intermediary compound (S-5) is a Mitsunobu Reaction in which a sulfonamide moiety (located in either M or Q of compound (S-5)) is directly coupled with a primary or a secondary alcohol (located in either M or Q of compound (S-5) which is not having the sulfonamide moiety) under Mitsunobu reaction conditions to afford various sulfonamide macrocycles. In some preferred embodiments, the sulfone amide moiety is selected from the group consisting of N-alkyl-sulfonamide (e.g., N—BOC protected sulfonamide), N-alkenyl-sulfonamide, N-alkynyl-sulfonamide, N-alkyl-sulfonamide, N-alkenyl-sulfonamide, N-alkynyl-sulfonamide, N-aryl-sulfonamide, N-heteroaryl-sulfonamide, N-aralkyl-sulfonamide, and N-heteraralkyl-sulfonamide, any one of which may be located in either M or Q of compound (S-5) while primary and secondary alcohol is located in the other of M or Q of compound (S-5) lacking the sulfonamide moeity. In some embodiments, a ring closing reaction between M and Q of intermediary compound (S-5) is a Heck reaction (also called the Mizoroki-Heck reaction), involving an unsaturated halide (or triflate) and an alkene group, to effect macrocyclization.

In some embodiments, a ring closing reaction between M and Q of intermediary compound (S-5) is a Buchwald-Hartwig amination in which macrocyclization is effected by a carbon-nitrogen bond formation via a palladium-catalyzed cross-coupling of an amine group with an aryl halide or aryl triflate. The amine group or the aryl halide may be located in either M or Q of intermediary compound (S-5).

In some embodiments, a ring closing reaction between M and Q of intermediary compound (S-5) is a macrocyclization via peptide coupling involving an amino function group and a carboxylic acid group either of which may be located either in M or Q of intermediary compound (S-5). Peptide coupling reagents suitable for the macrocylization include BOP (Benzotriazol-1-yloxy)tris(dimethylamino)phosphonium hexafluorophosphate; carbodiimides such as dicyclohexylcarbodiimide (DCC) and diisopropylcarbodiimide (DIC); triazoles such as 1-hydroxy-benzotriazole (HOBt) and 1-hydroxy-7-aza-benzotriazole (HOAt); and Uronium based peptide coupling reagents, including HBTU, HATU, HCTU, COMU, and TBTU; and others include PyBOP, and TOTU (O-[(Ethoxycarbonyl)cyanomethylenamino]-N,N,N',N'-tetra methyluronium tetrafluoroborate).

Scheme 1A: an exemplary synthetic scheme for the preparation of exemplary compound P(2)

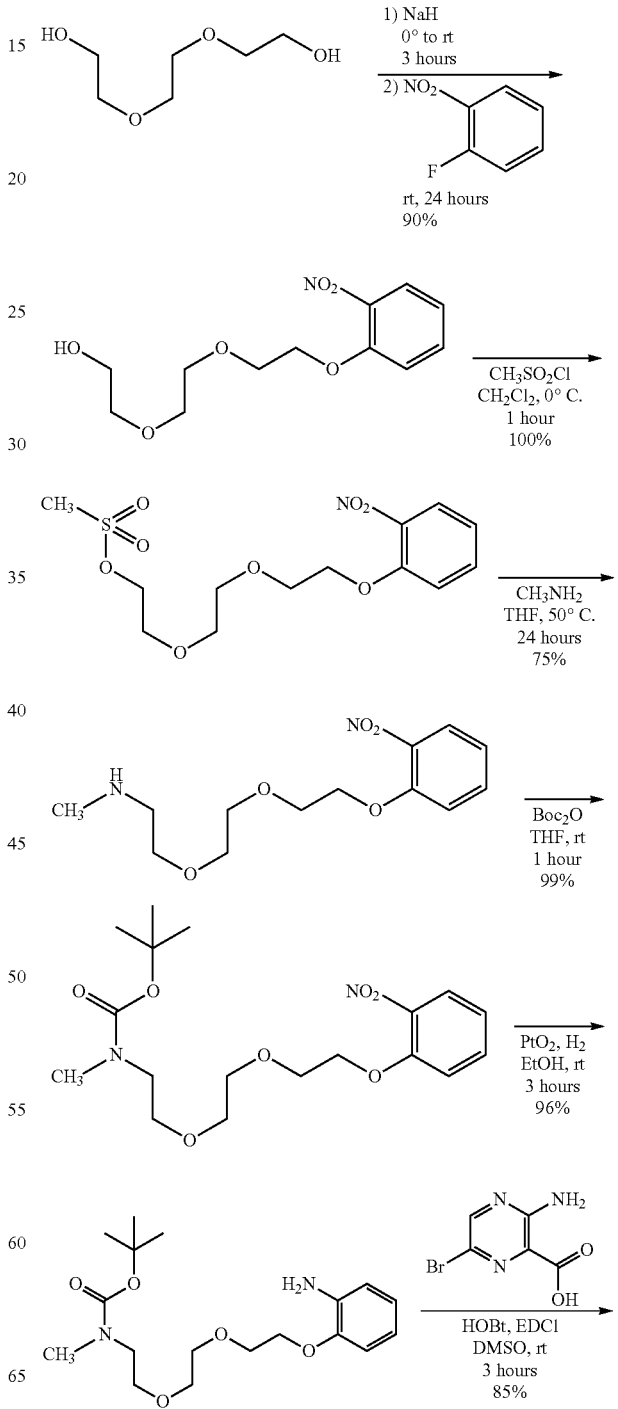

81
-continued
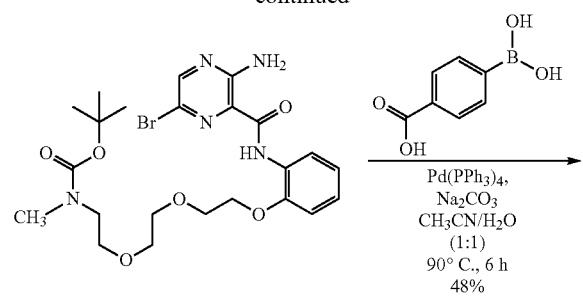
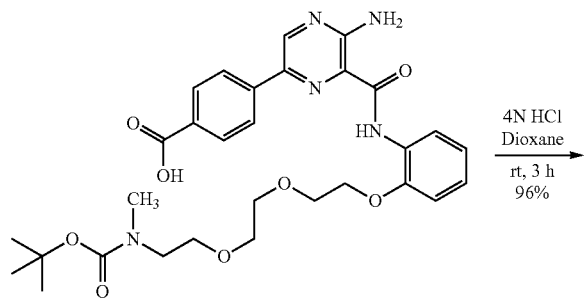
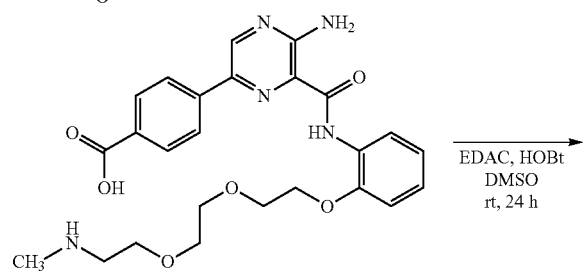
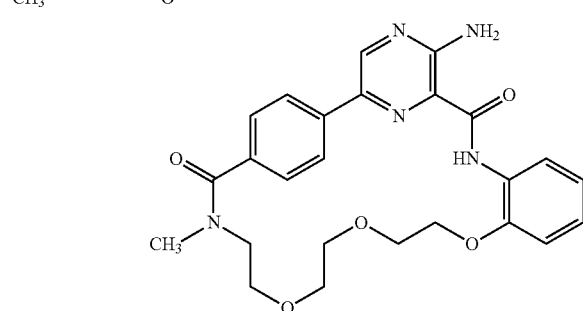
Scheme 1B: an exemplary synthetic scheme for the preparation of exemplary compound P(1)
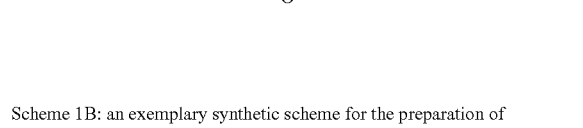
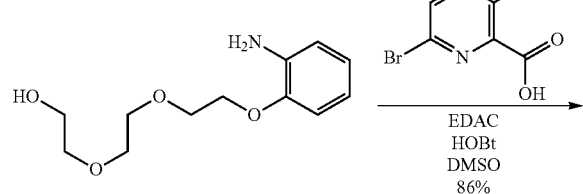
82
-continued
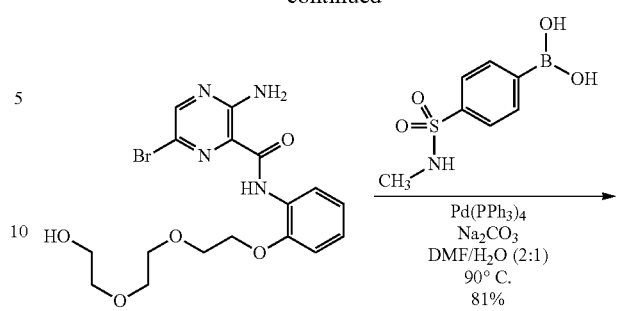
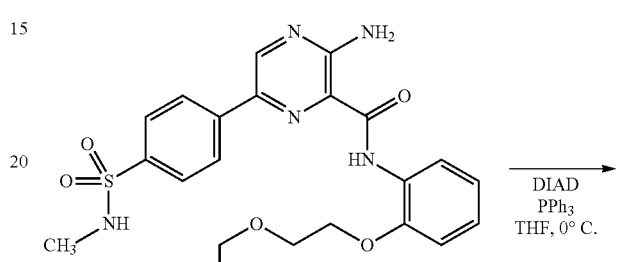
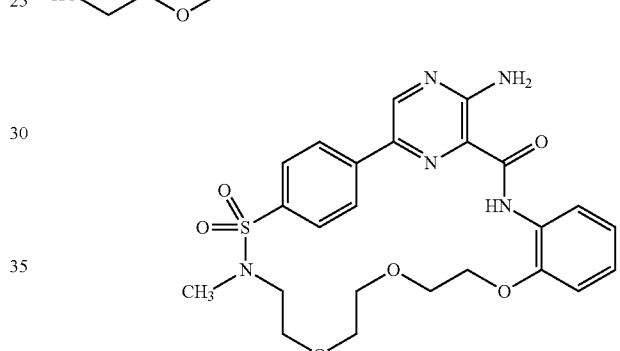
Scheme 1C: an exemplary synthetic scheme for the preparation of exemplary compound P(20)
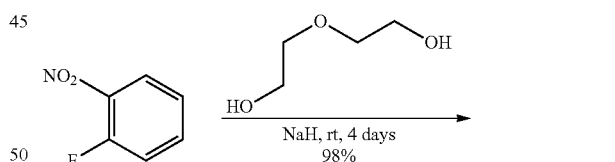
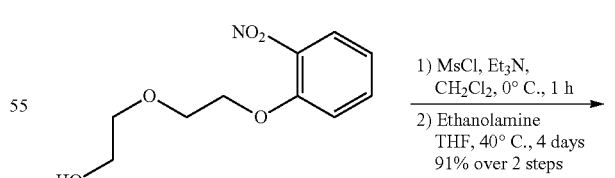

83
-continued
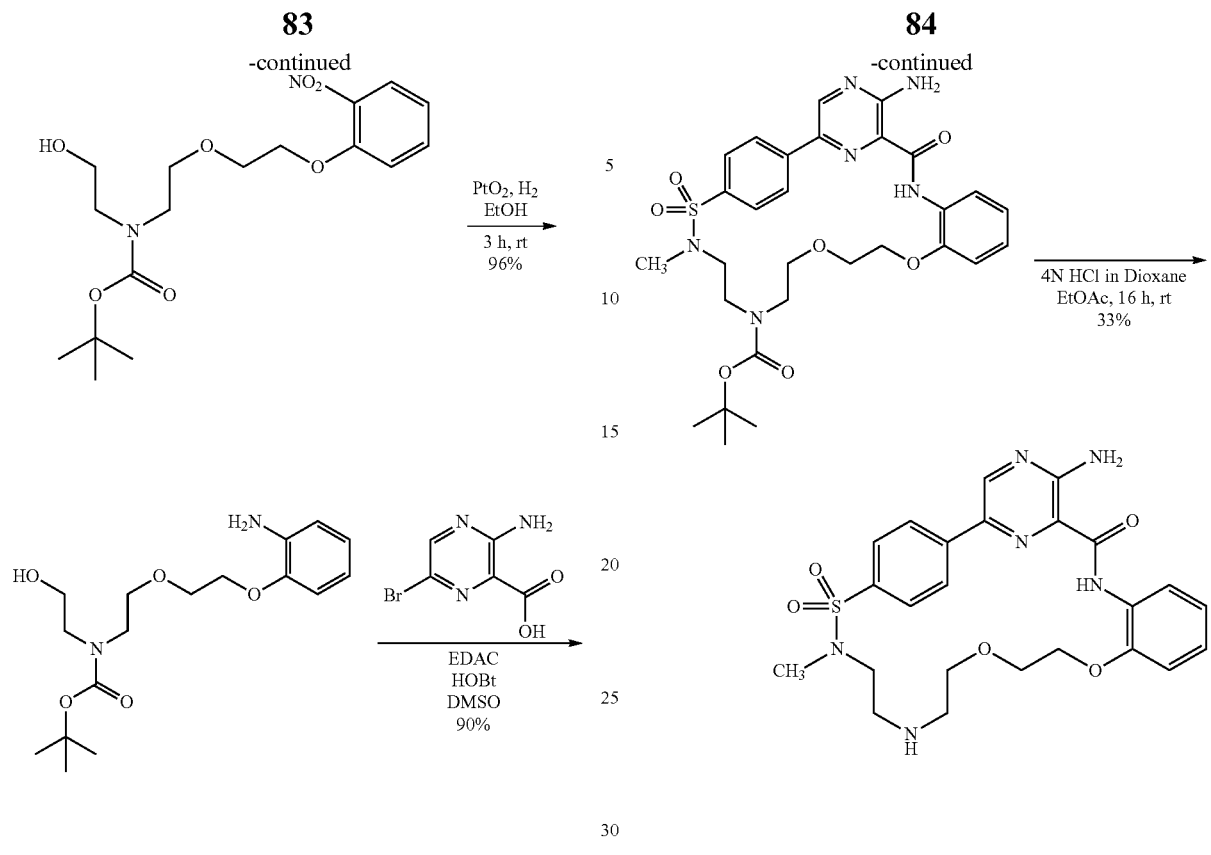
84
-continued
Scheme: P(21)
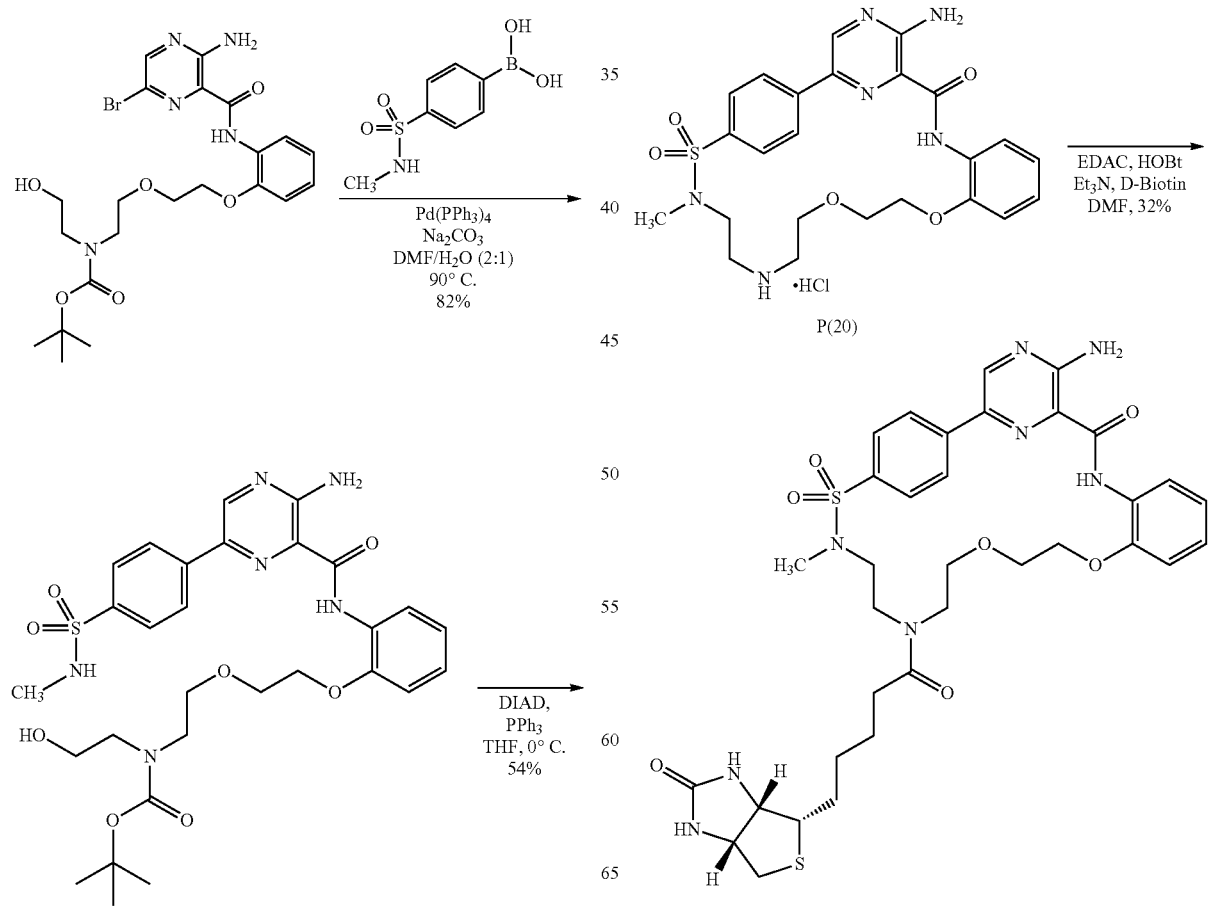
P(20)

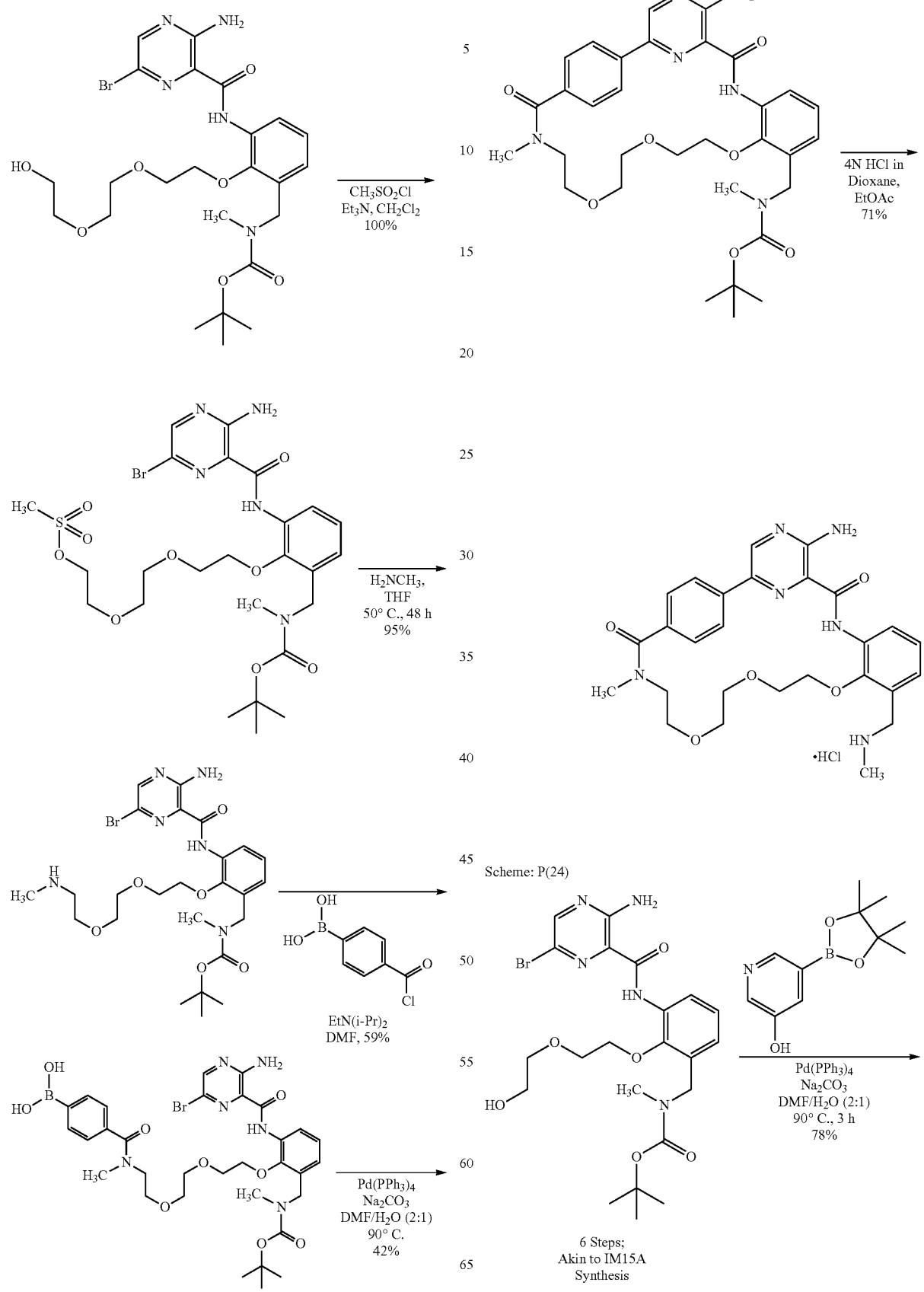

87
-continued
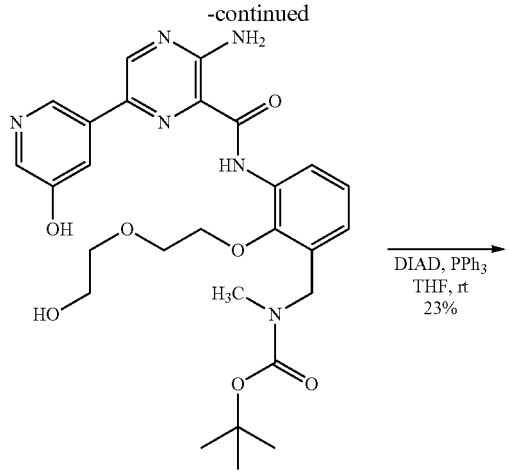
DIAD, PPh₃
THF, rt
23%
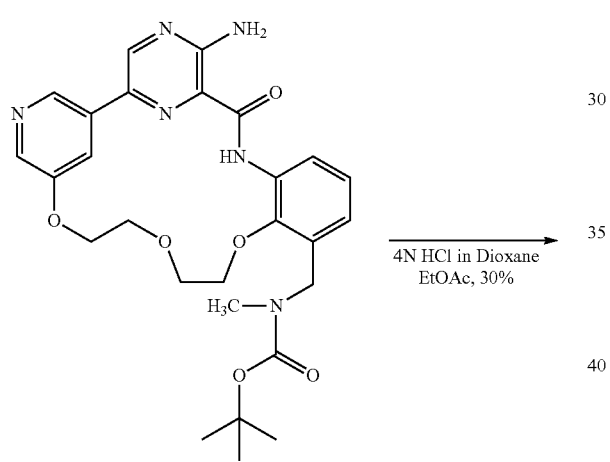
4N HCl in Dioxane
EtOAc, 30%
88
Scheme: P(25)
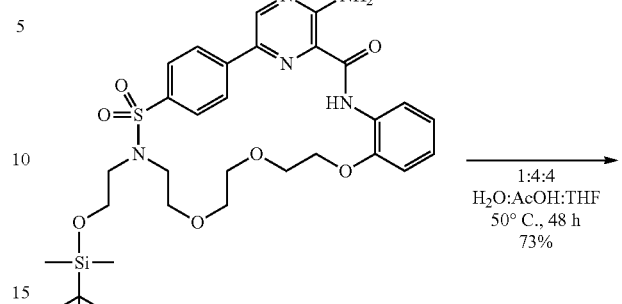
Prepared in a similar manner as
IM9, but with appropriate Starting Materials
1:4:4
H₂O:AcOH:THF
50° C., 48 h
73%
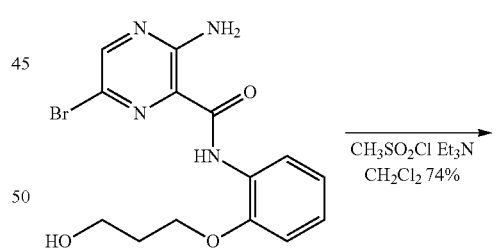
Scheme: P(26), P(27):
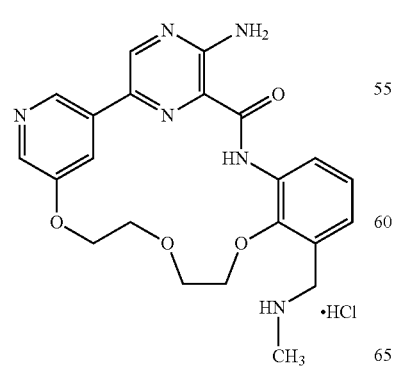
CH₃SO₂Cl Et₃N
CH₂Cl₂ 74%
Prepared in a similar
manner as intermediate
for P(1)
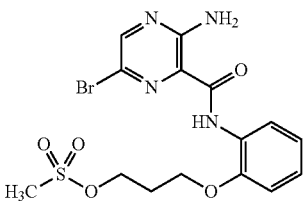
H₂NCH₂CH₂CH₂OH
THF 94%

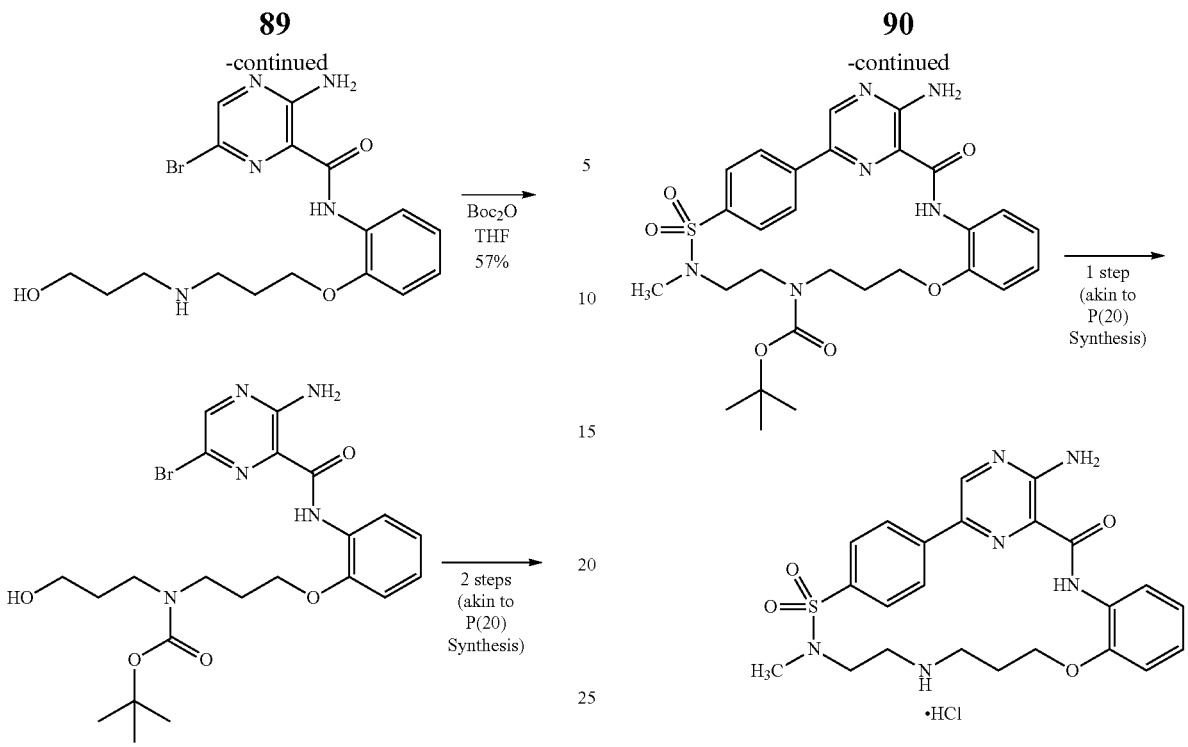
Scheme: P(30), P(31)
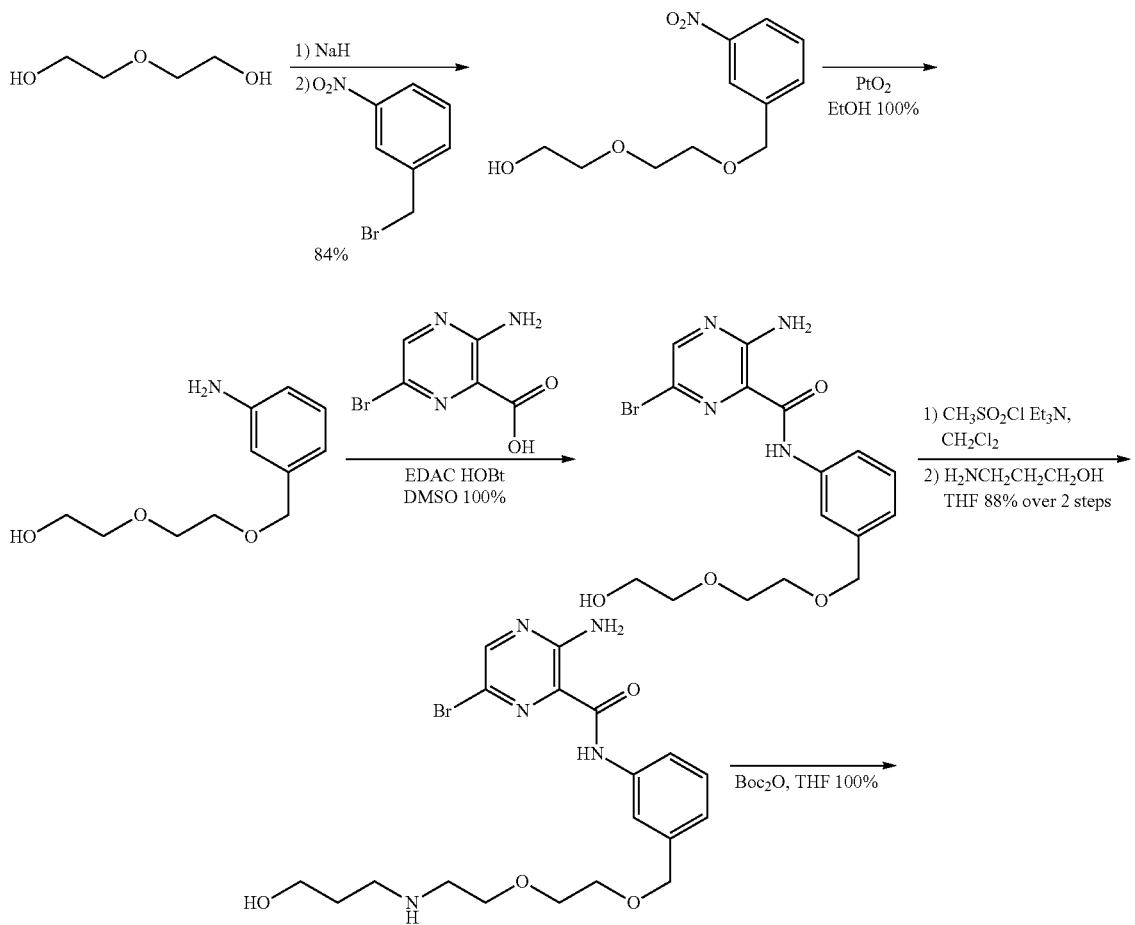

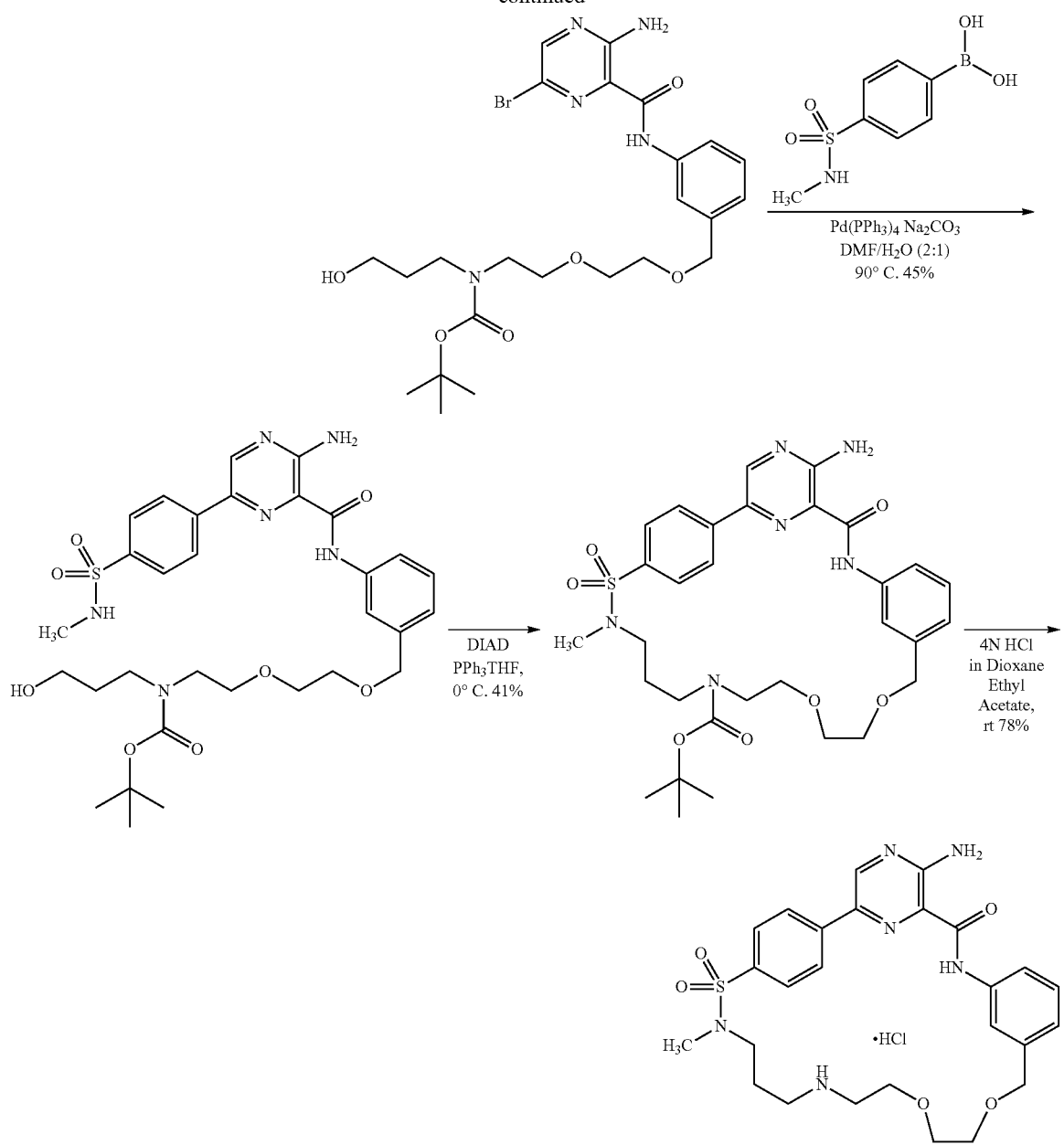
Scheme: P(33), P(34)
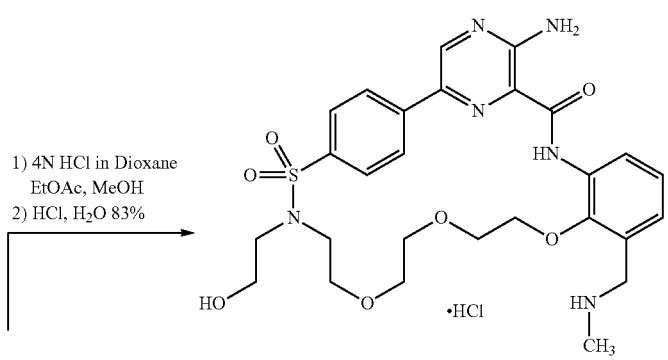

93 94
-continued
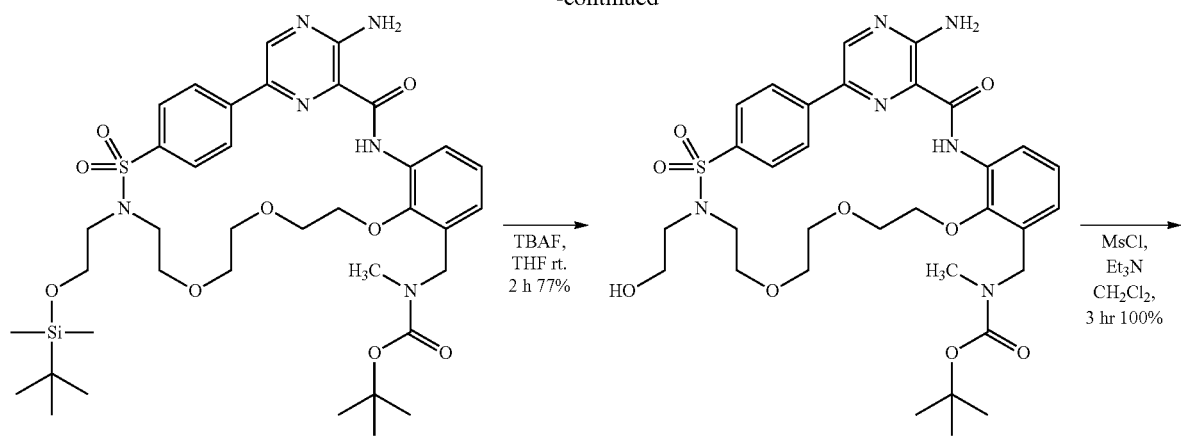
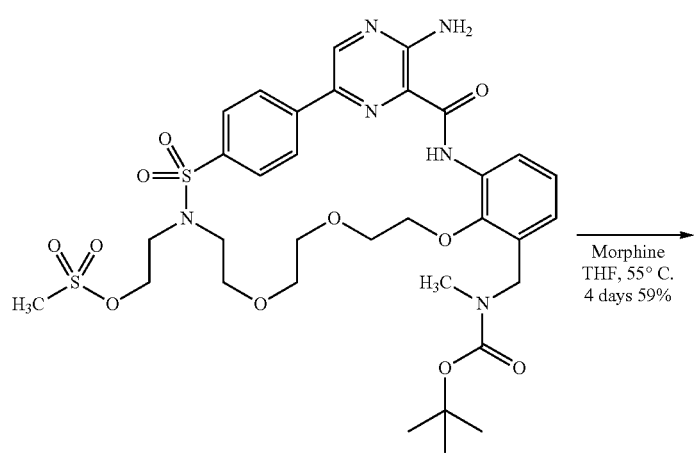
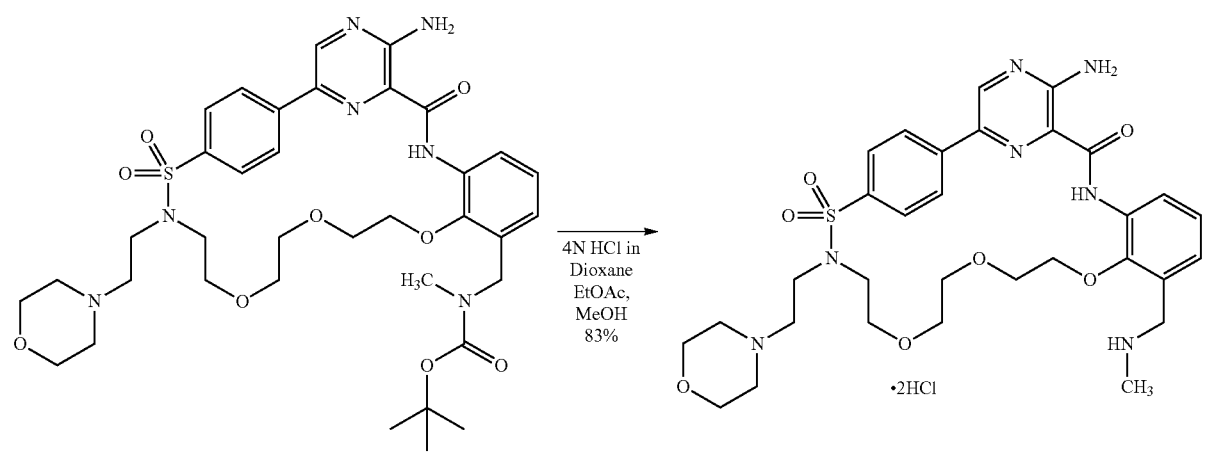

Isoxazole containing compounds according to the present invention may be prepared according to synthetic Scheme 2.

Scheme 2: A General Scheme for the Preparation of Isoxazole Containing Compounds

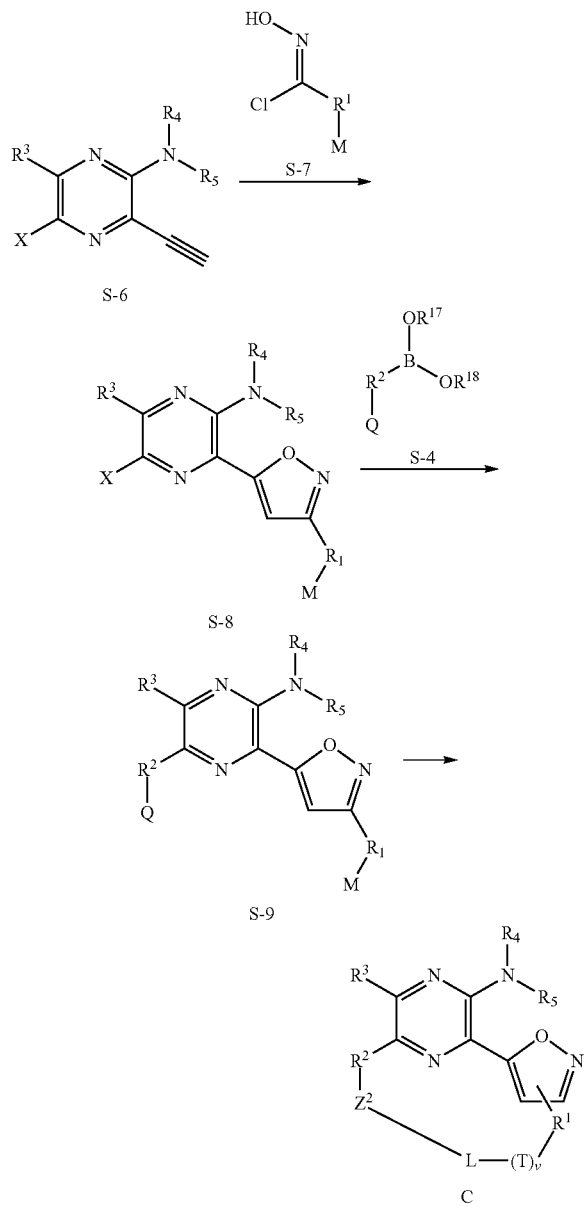

A. Starting Materials of Scheme 2:

Pyrazine alkyne (S-6) is commercially available or can be readily synthesized from commercially available precursors according to well known Sonogashira cross-coupling literature procedures. X in (S-6) is a halogen. Each of $R^3$, $R^4$, and $R^5$ in (S-6) has the meaning and scope disclosed throughout this disclosure with respect to the compound of Formula (A) and various subgenuses thereof, including the compound of Formula (A1).

Nitrile oxide precursor (S-7) is either commercially available or can be readily prepared from commercially available materials. M is any substructure or a functional group sufficient to allow for a ring closing reaction to form the compound of Formula (C).

Boronic acid or ester (S-4) is commercially available, can readily be synthesized from commercially available precursors according to well known literature procedures or is synthesized according to procedures disclosed herein. Each of $R^{17}$ and $R^{18}$ can independently be hydrogen, alkyl, cycloalkyl, or aryl; or $R^{17}$ and $R^{18}$ may combine together to form a ring. $R^2$ in (S-4) has the meaning and scope disclosed throughout this disclosure with respect to the compound of Formula (A) and various subgenuses thereof, including the compound of Formula (A1). Q is any substructure or a functional group sufficient to allow for a ring closing reaction between Q and M to form the compound of Formula (A1).

B. Reactions of Scheme 2:

Pyrazine alkyne (S-6) and Nitrile oxide precursor (S-7) undergo a [3+2]cycloaddition reaction, similar to literature procedures reported by A. Ricca in 1961 (Synthesis of polyphenyl isoxazoles. *Gazzetta Chimica Italiana*, 91, 83-9; 1961) and M. A. Weidner-Wells et al. in 2004 (Synthesis and structure-activity relationships of 3,5-diarylisoxazoles and 3,5-diaryl-1,2,4-oxadiazoles, novel classes of small molecule interleukin-8 (IL-8) receptor antagonists. *Bioorganic & Medicinal Chemistry Letters*, 14(16), 4307-4311; 2004) to produce isoxazolyl containing compound (S-8), which in turn is coupled with boronic acid derivative (S-4), for example, via a Suzuki-Miyaura reaction to form intermediary compound (S-9). Any suitable ring closing reaction between M and Q of intermediary compound (S-5) can be used to form macrocyclic compound (C). For example, Ring-Closing Metathesis (RCM) may be used to form the macrocycle when M and Q contain terminal olefinic groups. The resulting ring double bond may be used as site for further modification of the macrocycle. For example, dihydroxylation of the ring double (e.g., by Sharpless bishydroxylation) could be used to introduced hydroxyl groups along the backbone of the macrocyclic ring. The hydroxyl may in turn be further modified through esterification, oxidation, or etherification reactions. The ring double bond may be reduced with, for example, diimide ($N_2H_2$). Other reactions that may be performed on the ring double bond include hydroamination, hydroxyamination, and hydroboration.

In some embodiments, a ring closing reaction between M and Q of intermediary compound (S-9) is an intramolecular amide coupling between an amino function group and a carboxylic acid group. The amino function group or the carboxylic acid group may be located in either M or Q of intermediary compound (S-9).

In some embodiments, a ring closing reaction between M and Q of intermediary compound (S-9) is a Mitsunobu Reaction (involving a hydroxyl group and a carboxylic acid) to form a macrolactone. In some embodiments, a ring closing reaction between M and Q of intermediary compound (S-9) is a Mitsunobu Reaction in which a sulfonamide moiety (located in either M or Q of compound (S-9)) is directly coupled with a primary or a secondary alcohol (located in either M or Q of compound (S-9) which is not having the sulfonamide moiety) under Mitsunobu reaction conditions to afford various sulfonamide macrocycles. In some preferred embodiments, the sulfone amide moiety is selected from the group consisting of N-alkyl-sulfonamide (e.g., N—BOC protected sulfonamide), N-alkenyl-sulfonamide, N-alkynyl-sulfonamide, N-alkyl-sulfonamide, N-alkenyl-sulfonamide, N-alkynyl-sulfonamide, N-aryl-sulfonamide, N-heteroaryl-sulfonamide, N-aralkyl-sulfonamide, and N-heteraralkyl-sulfonamide, any one of which may be located in either M or Q of compound (S-9) while primary and secondary alcohol is located in the other of M or Q of compound (S-9) lacking the sulfonamide moeity. In some embodiments, a ring closing reaction between M and Q of intermediary compound (S-9) is a Heck reaction (also called the Mizoroki-Heck reaction), involving an unsaturated halide (or triflate) and an alkene group, to effect macrocyclization.

In some embodiments, a ring closing reaction between M and Q of intermediary compound (S-9) is a Buchwald-Hartwig amination in which macrocyclization is effected by a carbon-nitrogen bond formation via a palladium-catalyzed cross-coupling of an amine group with an aryl halide (or an aryl triflate). The amine group or the aryl halide may be located in either M or Q of intermediary compound (S-9).

In some embodiments, a ring closing reaction between M and Q of intermediary compound (S-9) is a macrocyclization via peptide coupling involving an amino function group and a carboxylic acid group either of which may be located either in M or Q of intermediary compound (S-9). Peptide coupling reagents suitable for the macrocylization include BOP (Benzotriazol-1-yloxy)tris(dimethylamino)phosphonium hexafluorophosphate; carbodiimides such as dicyclohexylcarbodiimide (DCC) and diisopropylcarbodiimide (DIC); triazoles such as 1-hydroxy-benzotriazole (HOBt) and 1-hydroxy-7-aza-benzotriazole (HOAt); and Uronium based peptide coupling reagents, including HBTU, HATU, HCTU, COMU, and TBTU; and others include PyBOP, and TOTU (O-[(Ethoxycarbonyl)cyanomethylenamino]-N,N,N', N'-tetra methyluronium tetrafluoroborate).

As shown in Scheme 2, compound of Formula (C) includes $Z^2$ and L each of which has the meaning and scope disclosed throughout this disclosure with respect to the compound of Formula (A) and various subgenuses thereof, including the compound of Formula (C). The variable v in the compound of Formula (C) is an integer having a value of 1 or 0; and T is a carbon atom, a nitrogen atom, a sulfur atom, or an oxygen atom, wherein when v is 0 linking group L is covalently bonded to $R^1$ to which T would have bonded.

Scheme 2A: an exemplary synthetic scheme showing preparation of exemplary compound P(13)

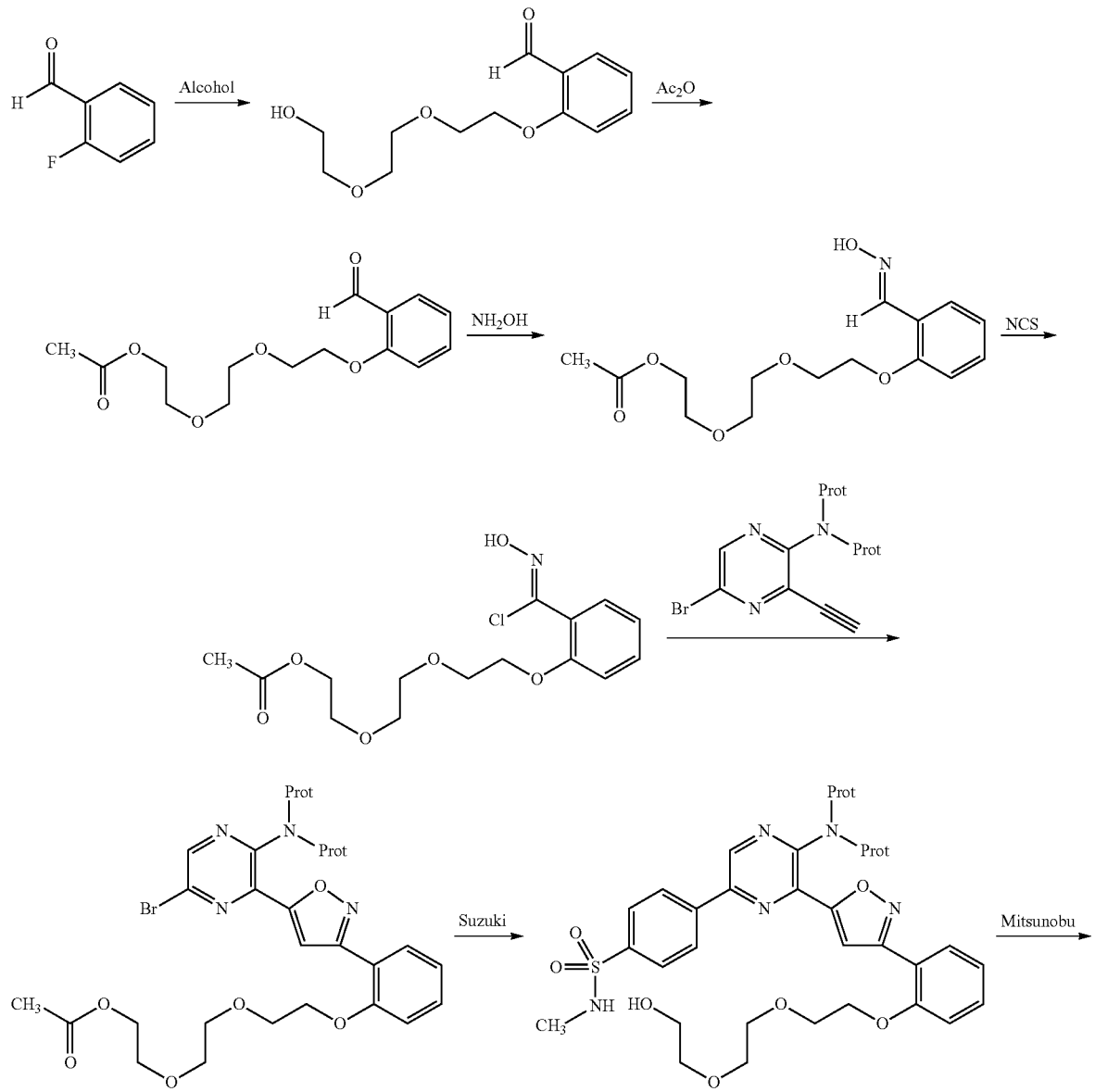

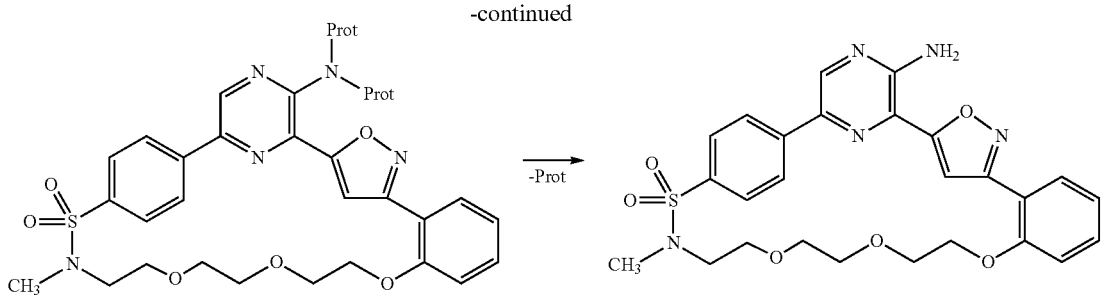

"Prot" as used in Scheme 2A denotes any suitable amine protecting group including, but not limited to, benzyloxycarbonyl (CBz), tert-Butyloxycarbonyl (BOC), phthaloyl, allyloxycarbonyl, 9-fluorenylmethyloxycarbonyl, acetyl, formyl, benzoyl, and pivaloyl groups.

Scheme 2B: an exemplary synthetic scheme showing preparation of exemplary compound P(15)

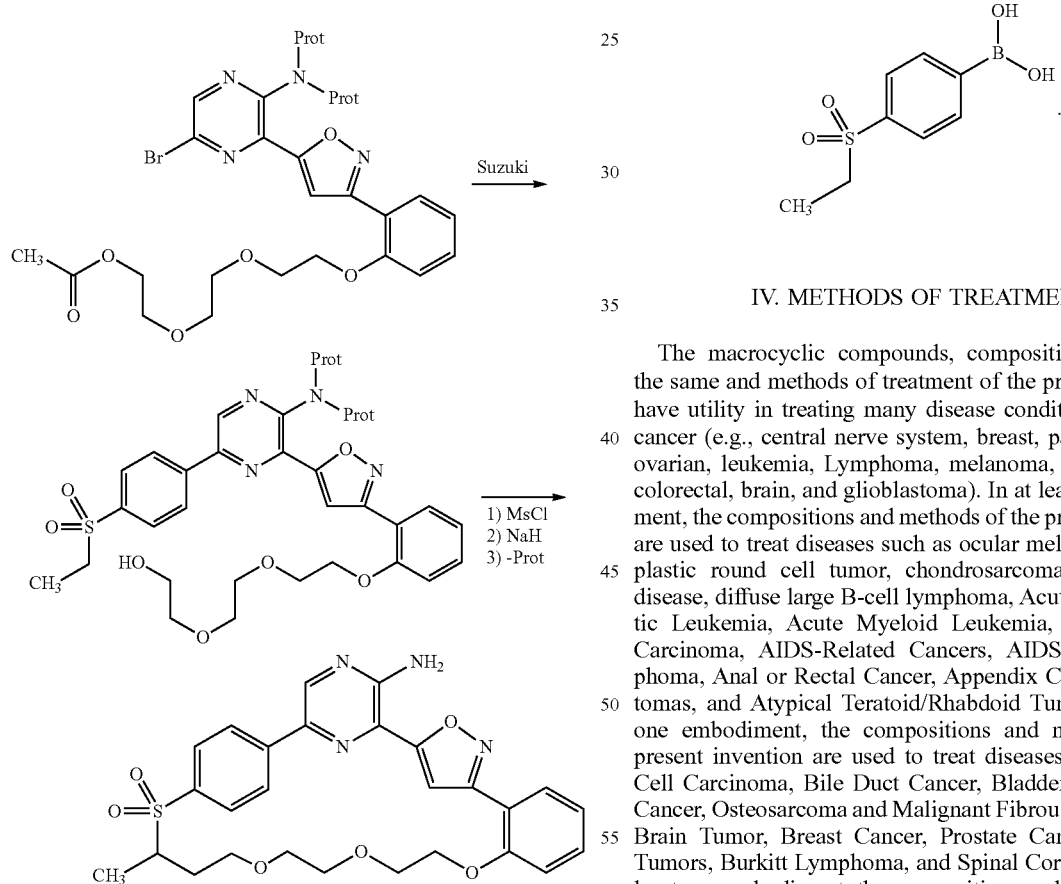

"Prot" as used in Scheme 2B denotes any suitable amine protecting group including, but not limited to, benzyloxycarbonyl (CBz), tert-Butyloxycarbonyl (BOC), phthaloyl, allyloxycarbonyl, 9-fluorenylmethyloxycarbonyl, acetyl, formyl, benzoyl, and pivaloyl groups.

Exemplary aryl bornic acids suitable for use in the Suzuki-Miyaura reaction of Schemes 2A and 2B, include, but are not limited to, the following:

IV. METHODS OF TREATMENT

The macrocyclic compounds, compositions containing the same and methods of treatment of the present invention have utility in treating many disease conditions, including cancer (e.g., central nerve system, breast, pancreatic, lung, ovarian, leukemia, Lymphoma, melanoma, renal, prostate, colorectal, brain, and glioblastoma). In at least one embodiment, the compositions and methods of the present invention are used to treat diseases such as ocular melanoma, desmoplastic round cell tumor, chondrosarcoma, leptomengial disease, diffuse large B-cell lymphoma, Acute Lymphoblastic Leukemia, Acute Myeloid Leukemia, Adrenocortical Carcinoma, AIDS-Related Cancers, AIDS-Related Lymphoma, Anal or Rectal Cancer, Appendix Cancer, Astrocytomas, and Atypical Teratoid/Rhabdoid Tumor. In at least one embodiment, the compositions and methods of the present invention are used to treat diseases such as Basal Cell Carcinoma, Bile Duct Cancer, Bladder Cancer, Bone Cancer, Osteosarcoma and Malignant Fibrous Histiocytoma, Brain Tumor, Breast Cancer, Prostate Cancer, Bronchial Tumors, Burkitt Lymphoma, and Spinal Cord Tumors. In at least one embodiment, the compositions and methods of the present invention are used to treat diseases such as Carcinoid Tumor, Carcinoma of Unknown Primary, Central Nervous System Atypical Teratoid/Rhabdoid Tumor, Leptomeningeal Disease, Central Nervous System Embryonal Tumors, Central Nervous System Lymphoma, Cervical Cancer, Chordoma, Chronic Lymphocytic Leukemia, Chronic Myelogenous Leukemia, Chronic Myeloproliferative Disorders, Colon Cancer, Colorectal Cancer, Craniopharyngioma, and Cutaneous T-Cell Lymphoma. In at least one embodiment, the compositions and methods of the present invention are used to treat diseases such as Endometrial Cancer, Ependymoblastoma, Ependymoma, Esophageal Cancer, Ewing Sarcoma Family of Tumors, Extracranial Germ Cell Tumor, Extragonadal Germ Cell Tumor, Extrahepatic Bile Duct Cancer, and Eye Cancer. In at least one embodiment, the compositions and methods of the present invention are used to treat diseases such as Gallbladder Cancer, Gastric (Stomach) Cancer, Gastrointestinal Carcinoid Tumor, Gastrointestinal Stromal Tumor (GIST), Germ Cell Tumor, Gestational Trophoblastic Tumor, and Glioma. In at least one embodiment, the compositions and methods of the present invention are used to treat cancer selected from the group consisting of Hairy Cell Leukemia, Head and Neck Cancer, Hepatocellular (Liver) Cancer, Histiocytosis, Hodgkin Lymphoma, and Hypopharyngeal Cancer. In at least one embodiment, the compositions and methods of the present invention are used to treat diseases such as Kaposi Sarcoma, and Kidney (Renal Cell) Cancer. In at least one embodiment, the compositions and methods of the present invention are used to treat diseases such as Langerhans Cell Histiocytosis, Laryngeal Cancer, Lip and Oral Cavity Cancer, Liver Cancer, Lung Cancer, Non-Hodgkin Lymphoma, and Primary Central Nervous System Lymphoma. In at least one embodiment, the compositions and methods of the present invention are used to treat diseases such as Waldenström's macroglobulinemia (lymphoplasmacytic lymphoma), Malignant Fibrous Histiocytoma of Bone and Osteosarcoma, Medulloblastoma, Medulloepithelioma, Melanoma, Merkel Cell Carcinoma, Mesothelioma, Metastatic Squamous Neck Cancer with Occult Primary, Multiple Endocrine Neoplasia Syndrome, Mouth Cancer, Multiple Myeloma/Plasma Cell Neoplasm, Mycosis Fungoides, Myelodysplastic Syndromes, Myelodysplastic/Myeloproliferative Neoplasms, Multiple Myeloma, and Myeloproliferative Disorders. In at least one embodiment, the compositions and methods of the present invention are used to treat cancer. In at least one embodiment, the compositions and methods of the present invention are used to treat diseases such as Nasal Cavity and Paranasal Sinus Cancer, Nasopharyngeal Cancer, and Neuroblastoma. In at least one embodiment, the compositions and methods of the present invention are used to treat diseases such as Oral Cancer, Lip and Oral Cavity Cancer, Oropharyngeal Cancer, Osteosarcoma and Malignant Fibrous Histiocytoma of Bone, Ovarian Cancer, Ovarian Germ Cell Tumor, Ovarian Epithelial Cancer, and Ovarian Low Malignant Potential Tumor. In at least one embodiment, the compositions and methods of the present invention are used to treat diseases such as Pancreatic Cancer, Papillomatosis, Paranasal Sinus and Nasal Cavity Cancer, Parathyroid Cancer, Penile Cancer, Pharyngeal Cancer, Pineal Parenchymal Tumors of Intermediate Differentiation, Pineoblastoma and Supratentorial Primitive Neuroectodermal Tumors, Pituitary Tumor, Pleuropulmonary Blastoma, Pregnancy and Breast Cancer, and Prostate Cancer. In at least one embodiment, the compositions and methods of the present invention are used to treat cancer selected from the group consisting of Rectal Cancer, Renal Pelvis and Ureter, Respiratory Tract Carcinoma Involving the NUT Gene on Chromosome 15, Retinoblastoma, and Rhabdomyosarcoma. In at least one embodiment, the compositions and methods of the present invention are used to treat high grade prostate cancer. In at least one embodiment, the compositions and methods of the present invention are used to treat medium grade prostate cancer. In at least one embodiment, the compositions and methods of the present invention are used to treat low grade prostate cancer. In at least one embodiment, the compositions and methods of the present invention are used to treat castration-resistant prostate cancer.

In at least one embodiment, the compositions and methods of the present invention are used to treat a proliferative skin disorder. In at least one embodiment, the compositions and methods of the present invention are used to treat a proliferative skin disorder, wherein the proliferative skin disorder is psoriasis. In at least one embodiment, the compositions and methods of the present invention are used to treat cancer selected from the group consisting of Salivary Gland Cancer, Sarcoma, Sezary Syndrome, Skin Cancer, Ocular Cancer, Skin Carcinoma, Small Intestine Cancer, Soft Tissue Sarcoma, Squamous Cell Carcinom, Squamous Neck Cancer with Occult Primary, and Supratentorial Primitive Neuroectodermal Tumors. In at least one embodiment, the compositions and methods of the present invention are used to treat cancer selected from the group consisting of T-Cell Lymphoma, Testicular Cancer, Throat Cancer, Thymoma and Thymic Carcinoma, Thyroid Cancer, Transitional Cell Cancer of the Renal Pelvis and Ureter, and Gestational Trophoblastic Tumor. In at least one embodiment, the compositions and methods of the present invention are used to treat cancer selected from the group consisting of Carcinoma of Unknown Primary Site, Cancer of Unknown Primary Site, Unusual Cancers of Childhood, Urethral Cancer, and Uterine Sarcoma. In at least one embodiment, the compositions and methods of the present invention are used to treat cancer selected from the group consisting of Vaginal Cancer, and Vulvar Cancer. In at least one embodiment, the compositions and methods of the present invention are used to treat cancer selected from the group consisting of Wilms Tumor, and Women's Cancers.

The utility of the methods and compositions of the present invention is not limited to any particular animal species. In at least one embodiment, a subject treated according to methods and using compositions of the present invention, can be mammalian or non-mammalian. In at least one embodiment, a mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. In at least one embodiment, a non-mammalian subject can be any non-mammal including, but not limited to, a bird such as a duck, goose, chicken, or turkey. In at least one embodiment, subjects can be either gender and can be any age. In at least one embodiment, the compositions and methods can also be used to prevent cancer. In at least one embodiment, the compositions and methods of the present invention can also be used to stimulate the immune system.

EXAMPLES

The invention will be illustrated by the following non-limiting examples: The following examples describe the preparation of representative compounds of the present invention. Melting points are reported as uncorrected in degrees centigrade. The infrared data is reported as wave numbers at maximum absorption, $v_{max}$, in reciprocal centimeters, $cm^{-1}$. Mass spectral data is reported as the mass-to-charge ratio, m/z; and for high resolution mass spectral data, the calculated and experimentally found masses, $[M^+H]^+$, for the neutral formulae M are reported. Nuclear magnetic resonance data is reported as $\delta$ in parts per million (ppm) downfield from the standard, tetramethylsilane, along with the solvent, nucleus, and field strength parameters. The spin-spin homonuclear coupling constants are reported as J values in hertz; and the multiplicities are reported as: s, singlet; d, doublet; t, triplet; q, quartet; quintet; or br, broadened.

Preparation of Intermediary Compounds

Example 1: tert-butyl (2-(2-(2-(2-aminophenoxy)ethoxy)ethoxy)ethyl)(methyl)carbamate

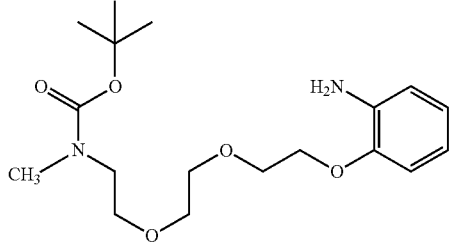 [SMILES: CN(CCOCCOCCOc1ccccc1N)C(=O)OC(C)(C)C]

IM1: tert-butyl (2-(2-(2-(2-aminophenoxy)ethoxy)ethoxy)ethyl)(methyl)carbamate

Example 1A: 2-(2-(2-(2-nitrophenoxy)ethoxy)ethoxy)ethan-1-ol (IM1A)

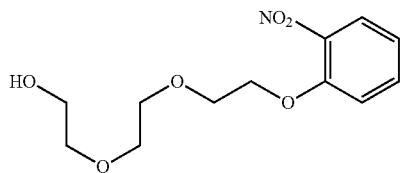 [SMILES: O=[N+]([O-])c1ccccc1OCCOCCOCCO]

IM1A: N-methyl-2-(2-(2-(2-nitrophenoxy)ethoxy)ethoxy)ethan-1-amine

NaH (60% in mineral oil; 1.30 g, 32.5 mmol) was added neat over 10 minutes to a rapidly stirring solution of triethyleneglycol (83.4 mL, 0.625 mol) at 0° C. After 30 minutes the reaction mixture was warmed to room temperature. After 1.5 hours the reaction mixture was virtually homogeneous and evolution of gas had ceased. Then at room temperature 1-fluoro-2-nitrobenzene was added neat dropwise over 1 minute. The resulting reaction mixture was stirred overnight at room temperature. After 16 hours the reaction mixture was diluted with ~225 mL of water, then extracted with ~50 mL of hexane. The aqueous phase was then extracted with EtOAc 2× (225 mL and 50 mL respectively). The combined EtOAc extracts were washed with water 2× (~75 mL each), then with brine (50 mL), dried over $Na_2SO_4$, filtered, and concentrated under reduced pressure to give 6.07 g (90%) of desired product 2-(2-(2-(2-nitrophenoxy)ethoxy)ethoxy)ethan-1-ol as a tan tinted oil. LC/MS: basically a single peak (M+Na=294.1; minor peak for M+H=272.1); TLC: 1:1 EtOAc:Hexane Rf=0.2, homogeneous. Proceeded and used the isolated material for the subsequent steps without further manipulation.

Example 1B: 2-(2-(2-(2-aminophenoxy)ethoxy)ethoxy)ethan-1-ol

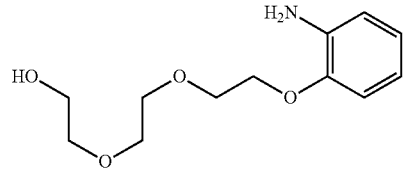 [SMILES: Nc1ccccc1OCCOCCOCCO]

IM1B: 2-(2-(2-(2-aminophenoxy)ethoxy)ethoxy)ethan-1-ol

At room temperature added a solution 2-(2-(2-(2-nitrophenoxy)ethoxy)ethoxy)ethan-1-ol (814 mg, 3 mmol) in Ethanol (30 mL) to $PtO_2$ (100 mg, 0.45 mmol) in a Parr bottle and place onto a Parr apparatus under a hydrogen atmosphere at 38 psi. After 3 hours filtered the reaction mixture carefully though Celite, then concentrated the filtrate under reduced pressure to yield 720 mg (99%) of slightly purple tinted oil 2-(2-(2-(2-aminophenoxy)ethoxy)ethoxy)ethan-1-ol. TLC: 100% EtOAc Rf=0.4, homogeneous (Starting Material 2-(2-(2-(2-nitrophenoxy)ethoxy)ethoxy)ethan-1-ol Rf=0.45; confirmed by co-spot) and the product discolors upon sitting on plate; LC/MS: (dissolved in EtOH) ~95% (M+H=242.2, consistent with desired product). This isolated 2-(2-(2-(2-aminophenoxy)ethoxy)ethoxy)ethan-1-ol was used for subsequent steps without further manipulation.

Example 1C: Methanesulfonic acid 2-{2-[2-(2-nitro-phenoxy)-ethoxy]-ethoxy}-ethyl ester

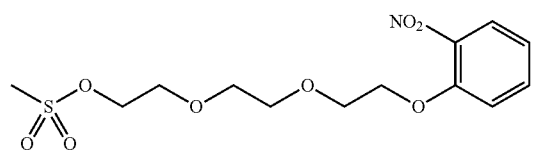 [SMILES: CS(=O)(=O)OCCOCCOCCOc1ccccc1[N+](=O)[O-]]

IM1C: Methanesulfonic acid 2-{2-[2-(2-nitro-phenoxy)-ethoxy]-ethoxy}-ethyl ester A 0° C. solution of 2-(2-(2-(2-nitrophenoxy)ethoxy)ethoxy)ethan-1-ol (3.26 g, 12 mmol) and triethylamine (2.51 mL, 18 mmol) in $CH_2Cl_2$ (80 mL) was treated with methanesulfonyl chloride (1.11 mL, 14.4 mmol) dropwise over 30 seconds. After 1 hour 1N HCl (30 mL) was added to the 0° C. solution, then an additional 20 mL of $CH_2Cl_2$ was added. After separation of layers the aqueous phase was washed with 20 mL more of $CH_2Cl_2$, the organic phases were combined, dried over $MgSO_4$, filtered, and concentrated under reduced pressure to give 4.21 g (T.W. 4.19 g) of the desired methanesulfonic acid 2-{2-[2-(2-nitro-phenoxy)-ethoxy]-ethoxy}-ethyl ester as a yellow oil. TLC: 1:1 EtOAc:Hexane Rf=0.35, homogenous (SM: Rf=0.2); LC/MS: one major peak with purity >95% (M+23=372.0, consistent with desired mesylated intermediate, which was used for the subsequent step without further manipulation.

105

Example 1D: N-methyl-2-(2-(2-(2-nitrophenoxy)ethoxy)ethoxy)ethan-1-amine

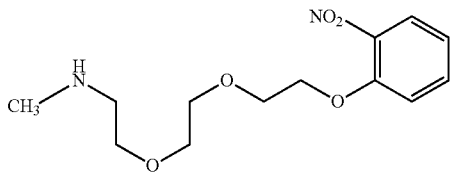 [SMILES: CNCCOCCOCCOc1ccccc1[N+](=O)[O-]]

IM1D: N-methyl-2-(2-(2-(2-nitrophenoxy)ethoxy)ethoxy)ethan-1-amine

In a pressure flask at room temperature Methanesulfonic acid 2-{2-[2-(2-nitro-phenoxy)-ethoxy]-ethoxy}-ethyl ester (0.91 g, 2.6 mmol) in THF (10 mL) was added to a stirring solution of 2M Methylamine in THF (35 mL, 70 mmol). The homogenous reaction mixture was sealed and warmed to 500. After 14 hours the reaction mixture was cooled to room temperature, the vessel opened and the reaction mixture subsequently concentrated under reduced pressure. The residue was partitioned between 10 mL of saturated aqueous NaHCO$_3$ and Et$_2$O (2×; 10 mL and 5 mL respectively). The aqueous phase was then washed 3× with CHCl$_3$ (30 mL each). The CHCl$_3$ extracts were combined, dried over Na$_2$SO$_4$, filtered, and concentrated under reduced pressure to give 450 mg (62%) of N-methyl-2-(2-(2-(2-nitrophenoxy)ethoxy)ethoxy)ethan-1-amine as a yellow oil. LC/MS: one major peak (>95%), M+H=285.2, consistent with desired product. Proceeded and used N-methyl-2-(2-(2-(2-nitrophenoxy)ethoxy)ethoxy)ethan-1-amine for subsequent step without further manipulation.

Example 1E: Methyl-(2-{2-[2-(2-nitro-phenoxy)-ethoxy]-ethoxy}-ethyl)-carbamic acid tert-butyl ester

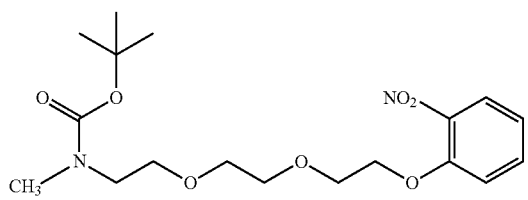 [SMILES: CN(CCOCCOCCOc1ccccc1[N+](=O)[O-])C(=O)OC(C)(C)C]

IM1E: Methyl-(2-{2-[2-(2-nitro-phenoxy)-ethoxy]-ethoxy}-ethyl)-carbamic acid tert-butyl ester In a reaction vial Di-tert-butyl dicarbonate (253 mg, 1.16 mmol) in THF (3 mL) was added to a solution of N-methyl-2-(2-(2-(2-nitrophenoxy)ethoxy)ethoxy)ethan-1-amine (330 mg, 1.16 mmol) in THF (10 mL). After 2 hours the reaction solution was concentrated under reduced pressure. The residue was partitioned between CH$_2$Cl$_2$ (25 mL) and 1N HCl (25 mL). The organic phase was then washed with saturated aqueous NaHCO$_3$, dried over Na$_2$SO$_4$, filtered,

106 and concentrated under reduced pressure to give 440 mg (99%) of the desired BOC protected intermediate as a clear oil, which was used for the subsequent step without further purification. TLC: 20:1 CH$_2$Cl$_2$:MeOH Rf=0.8, homogenous; 1:1 EtOAc:Hexane Rf=0.5, trace impurity at origin. LC/MS (sample dissolved in CH$_3$CN): Basically a single peak, with correct M+23 for desired product (407.2), with a base peak of 285.2, which is M+1-Boc.

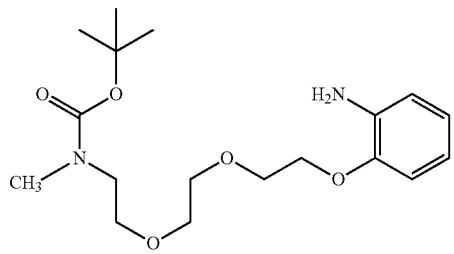 [SMILES: CN(CCOCCOCCOc1ccccc1N)C(=O)OC(C)(C)C]

IM1: tert-butyl (2-(2-(2-(2-aminophenoxy)ethoxy)ethoxy)ethyl)(methyl)carbamate

A solution of Methyl-(2-{2-[2-(2-nitro-phenoxy)-ethoxy]-ethoxy}-ethyl)-carbamic acid tert-butyl ester (430 mg, 1.12 mmol) in Ethanol (30 mL) was combined with PtO$_2$ (50 mg, 0.22 mmol) in a Parr bottle and placed onto a Parr apparatus under a hydrogen atmosphere at 41 psi (11:30 AM). After 3 hours filtered off the Pt catalyst through a bed of Celite, then concentrated the clear solution under reduced pressure to yield a clear oil, which was placed under high vacuum overnight. There remained 380 mg (96%) of tert-butyl (2-(2-(2-(2-aminophenoxy)ethoxy)ethoxy)ethyl)(methyl)carbamate as clear oil. LC/MS: ~90% at rt 3.60 min (strong base peak at 255.2 (mass of desired+1-Boc), with a rather small M+H=355.2 for desired, and slightly stronger at M+23=377.2); TLC: 20:1 CH$_2$Cl$_2$:MeOH Rf=0.8, homogenous and discolors on the plate (SM A Rf=0.85, which was confirmed different by co-spot). Intermediate tert-butyl (2-(2-(2-(2-aminophenoxy)ethoxy)ethoxy)ethyl)(methyl)carbamate was used for subsequent reactions without further manipulation.

Example 2: tert-butyl (2-(2-(2-aminophenoxy)ethoxy)ethyl)(2-hydroxyethyl)carbamate

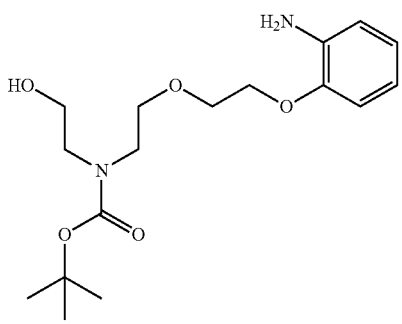 [SMILES: CC(C)(C)OC(=O)N(CCO)CCOCCOc1ccccc1N]

IM2: tert-butyl (2-(2-(2-aminophenoxy)ethoxy)ethyl)(2-hydroxyethyl)carbamate

Example 2A:
2-[2-(2-Nitro-phenoxy)-ethoxy]-ethanol

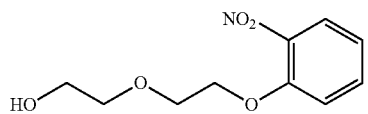 [SMILES: O=[N+]([O-])c1ccccc1OCCOCCO]

IM2A: 2-[2-(2-Nitro-phenoxy)-ethoxy]-ethanol

2-[2-(2-Nitro-phenoxy)-ethoxy]-ethanol (im-2A), was prepared in a similar manner as described in Example 1A for 2-(2-(2-(2-nitrophenoxy)ethoxy)ethoxy)ethan-1-ol, after replacing diethyleneglycol for triethyleneglycol. Yield: 98%. LC/MS: a single peak (M+Na=250.13; minor peak for M+H=228.2); TLC: 1:1 EtOAc:Hexane Rf=0.35, homogeneous.

Example 2B: Methanesulfonic acid 2-[2-(2-nitro-phenoxy)-ethoxy]-ethyl ester

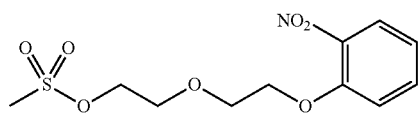 [SMILES: CS(=O)(=O)OCCOCCOc1ccccc1[N+](=O)[O-]]

IM2B: Methanesulfonic acid 2-[2-(2-nitro-phenoxy)-ethoxy]-ethyl ester

Methanesulfonic acid 2-[2-(2-nitro-phenoxy)-ethoxy]-ethyl ester was prepared in a similar manner as described in Example 1C Methanesulfonic acid 2-{2-[2-(2-nitro-phenoxy)-ethoxy]-ethoxy}-ethyl ester after replacing 2-[2-(2-Nitro-phenoxy)-ethoxy]-ethanol for 2-(2-(2-(2-nitrophenoxy)ethoxy)ethoxy)ethan-1-ol. Yield: 100%. TLC: 1:1 EtOAc:Hexane Rf=0.5, homogenous (SM A: Rf=0.3); LC/MS: major peak >95% (M+23=328.1, consistent with desired product), also trace of SM (A) at rt 3.36 min.

Example 2C: 2-{2-[2-(2-Nitro-phenoxy)-ethoxy]-ethylamino}-ethanol

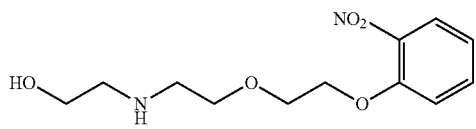 [SMILES: O=[N+]([O-])c1ccccc1OCCOCCNCCO]

IM2C: 2-{2-[2-(2-Nitro-phenoxy)-ethoxy]-ethylamino}-ethanol

At room temperature a solution of Methanesulfonic acid 2-[2-(2-nitro-phenoxy)-ethoxy]-ethyl ester (1.53 g, 5 mmol) in THF (10 mL) was added to a stirring solution of ethanolamine (7.5 mL, 125 mmol) in THF (20 mL) and the flask was then sealed. After stirring for 3 days at room temperature the reaction was warmed to 40° C. for 16 hours. The reaction solution was concentrated under reduced pressure, and the resulting residue was partitioned between saturated aqueous NaHCO$_3$ (15 mL) and Et$_2$O (15 mL). The aqueous phase was then washed 2× with CHCl$_3$ (75 mL and 25 mL respectively). The CHCl$_3$ extracts were combined, dried over Na$_2$SO$_4$, filtered, and concentrated under reduced pressure. Left with 1.58 g (T.W. 1.35 g) of yellow oil. 1H NMR supported this material had considerable ethanolamine remaining, so the 1.58 g was dissolved in CHCl$_3$ (60 mL) and washed twice with brine (40 mL each). The organic phase was dried over Na$_2$SO$_4$, filtered and concentrated to give 1.23 g (91%) of 2-{2-[2-(2-Nitro-phenoxy)-ethoxy]-ethylamino}-ethanol as a yellow oil. TLC: 5:1 CH$_2$Cl$_2$: MeOH Rf=0.80, homogeneous; LC/MS: (M+H=271.4). 2-{2-[2-(2-Nitro-phenoxy)-ethoxy]-ethylamino}-ethanol was used for subsequent steps without further manipulation.

Example 2D: (2-Hydroxy-ethyl)-{2-[2-(2-nitro-phenoxy)-ethoxy]-ethyl}-carbamic acid tert-butyl ester

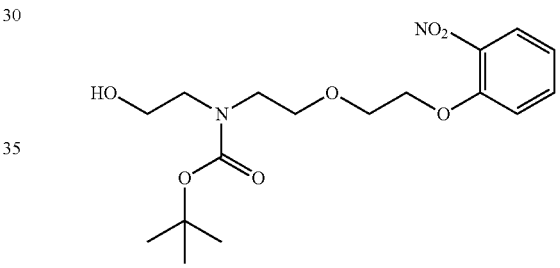

IM2D: (2-Hydroxy-ethyl)-{2-[2-(2-nitro-phenoxy)-ethoxy]-ethyl}-carbamic acid tert-butyl ester At room temperature Di-tert-butyl dicarbonate (912 mg, 4.18 mmol) in THF (3 mL) was added to a solution of 2-{2-[2-(2-Nitro-phenoxy)-ethoxy]-ethylamino}-ethanol (1.13 g, 4.18 mmol) in THF (20 mL). After 16 hours added CH$_3$NHCH$_2$CH$_2$NHCH$_3$ (0.10 mL, 0.93 mmol) to the homogeneous solution. After one additional hour the reaction mixture was concentrated under reduced pressure. The residue was partitioned between CH$_2$Cl$_2$ (25 mL) and 1N HCl (25 mL). The organic phase was then washed with saturated aqueous NaHCO$_3$, dried over Na$_2$SO$_4$, filtered, and concentrated under reduced pressure to give 1.40 g (90%) of (2-Hydroxy-ethyl)-{2-[2-(2-nitro-phenoxy)-ethoxy]-ethyl}-carbamic acid tert-butyl ester as a yellow oil. TLC: 1:1 EtOAc:Hexane Rf=0.4, homogeneous; LC/MS: M+H for desired, albeit smaller peak (M+H=370.9); M+23 was more significant (392.8), with the base peak being M+H-Boc (271.0). Used (2-Hydroxy-ethyl)-{2-[2-(2-nitro-phenoxy)-ethoxy]-ethyl}-carbamic acid tert-butyl ester for subsequent steps without further manipulation.

Example 2E: tert-butyl (2-(2-(2-aminophenoxy)ethoxy)ethyl)(2-hydroxyethyl)carbamate

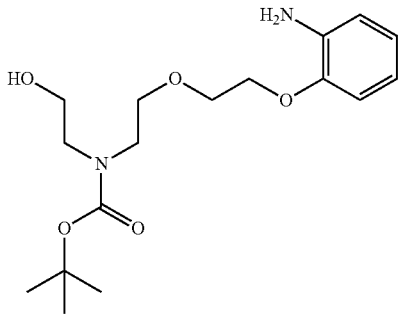

IM2: tert-butyl (2-(2-(2-aminophenoxy)ethoxy)ethyl)(2-hydroxyethyl)carbamate

Tert-butyl (2-(2-(2-aminophenoxy)ethoxy)ethyl)(2-hydroxyethyl)carbamate was prepared in a similar manner as described in Example 1B for 2-(2-(2-(2-aminophenoxy)ethoxy)ethoxy)ethan-1-ol, after replacing (2-Hydroxyethyl)-{2-[2-(2-nitro-phenoxy)-ethoxy]-ethyl}-carbamic acid tert-butyl ester for 2-(2-(2-(2-nitrophenoxy)ethoxy)ethoxy)ethan-1-ol. Yield: 96%. LC/MS: virtually clean with a M+H=340.8, consistent with desired product; also saw a significant M+23=362.9.

Example 3: tert-butyl (3-amino-2-(2-(2-(2-hydroxyethoxy)ethoxy)ethoxy)benzyl)(methyl)carbamate

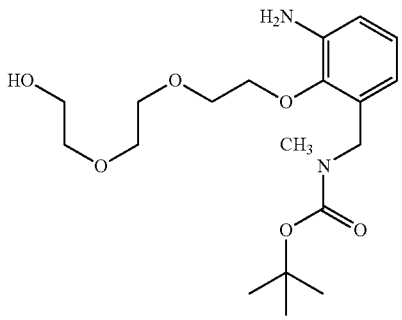

IM3: tert-butyl (3-amino-2-(2-(2-(2-hydroxyethoxy)ethoxy)ethoxy)benzyl)(methyl)carbamate Example 3A: 2-(2-(2-(2-hydroxyethoxy)ethoxy)ethoxy)-3-nitrobenzoic acid

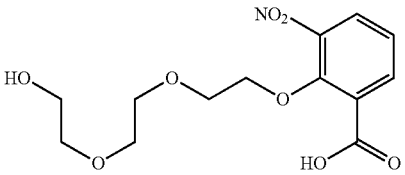 [SMILES: O=C(O)c1cccc([N+](=O)[O-])c1OCCOCCOCCO]

IM3A: 2-(2-(2-(2-hydroxyethoxy)ethoxy)ethoxy)-3-nitrobenzoic acid

A heterogenous mixture of triethyleneglycol (33 mL, 250 mmol), 2-fluoro-3-nitrobenzoic acid (1.85 g, 10 mmol), and cesium carbonate (7.2 g, 22 mmol) was warmed to 60° C. to give a homogenous solution. After 5 hours, heating was discontinued and the mixture was cooled to room temperature. The cooled reaction mixture was diluted with water (100 mL), and with swirling slowly acidified with 12N HCl to pH 2 (~3.5 mL of 12 N HCl; 42 mmol). The resulting acidic solution was then extracted with $Et_2O$ (~15 mL). The layers were separated and the aqueous phase was washed with $CHCl_3$ (2×; 100 mL and 75 mL respectively). The $CHCl_3$ layers were combined and washed with water (2×; 30 mL each), and then with brine (50 mL). The $CHCl_3$ organic phase was then dried over $Na_2SO_4$, filtered, and concentrated under reduced pressure to give 1.95 g (62%) of 2-(2-(2-(2-hydroxyethoxy)ethoxy)ethoxy)-3-nitrobenzoic acid as a yellow tinted oil. TLC: 10:1:0.5 EtOAc:MeOH:$NH_4OH$ Rf=0.05, with smallest trace impurity at Rf=0.15; LC/MS: Virtually clean and consistent with desired product (M+H=315.9). The isolated 2-(2-(2-(2-hydroxyethoxy)ethoxy)-3-nitrobenzoic acid was used for subsequent steps without further manipulation.

Example 3B: 2-(2-(2-(2-hydroxyethoxy)ethoxy)ethoxy)-N-methyl-3-nitrobenzamide

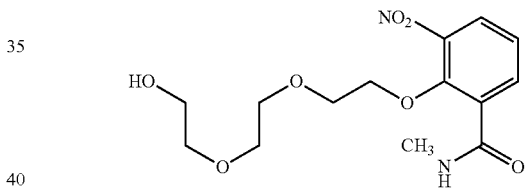

IM3B: 2-(2-(2-(2-hydroxyethoxy)ethoxy)ethoxy)-N-methyl-3-nitrobenzamide

EDCI was added neat (1.59 g, 8.3 mmol) to a room temperature, homogeneous solution of 2-(2-(2-(2-hydroxyethoxy)ethoxy)ethoxy)-3-nitrobenzoic acid (1.74 g, 5.52 mmol), Methylamine Hydrochloride (745 mg, 11.04 mmol), N,N-Diisopropylethylamine (2.1 mL, 12.1 mmol) and hydroxybenzotriazole (373 mg, 2.76 mmol) in DMF (50 mL). After 3 hours the mixture was concentrated under reduced pressure at 45° C. The semi-concentrated reaction mixture was partitioned between EtOAc (2×; 150 mL and 50 mL respectively) and water (50 mL). The combined organics were then washed sequentially with saturated aqueous $NaHCO_3$ (50 mL) and brine (40 mL), dried over $Na_2SO_4$, filtered and concentrated under reduced pressure at 50° C. to yield 1.23 g (68%) of desired 2-(2-(2-(2-hydroxyethoxy)ethoxy)ethoxy)-N-methyl-3-nitrobenzamide as an oil. LC/MS: clean (M+H=329.3, consistent with desired product; also saw a rather strong M+23=350.9); TLC: 10:1:0.5 EtOAc:MeOH:$NH_4OH$: Rf=0.7 (Starting Material 2-(2-(2-(2-hydroxyethoxy)ethoxy)ethoxy)-3-nitrobenzoic acid Rf=0.05).

Example 3C: 2-{2-[2-(2-Methylaminomethyl-6-nitro-phenoxy)-ethoxy]-ethoxy}-ethanol

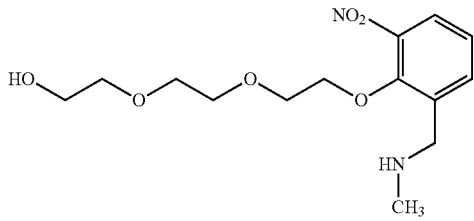 [SMILES: CNCc1cccc([N+](=O)[O-])c1OCCOCCOCCO]

IM3C: 2-{2-[2-(2-Methylaminomethyl-6-nitro-phenoxy)-ethoxy]-ethoxy}-ethanol

A solution of 2-(2-(2-(2-hydroxyethoxy)ethoxy)ethoxy)-N-methyl-3-nitrobenzamide (1.15 g, 3.5 mmol) in THF (30 mL) was added dropwise over 15 minutes to a stirring 0° C. solution of 1M BH$_3$.THF in THF (17.5 mL, 17.5 mmol). After 30 minutes the reaction solution was warmed to room temperature. After an additional 1 hour the reaction was warmed to 60° C. After 16 hours the reaction was cooled to 0° C. and slowly diluted with 1N HCl (50 mL). Upon completion of addition of the HCl the reaction was warmed to room temperature. After a half hour the reaction was warmed to 60° C. After 1 hour the reaction mixture was re-cooled to 0° C. and treated with NaOH to reach a pH of 8-9. The resulting solution was used for the subsequent step without further manipulation. TLC: 10:1:0.5 EtOAc:MeOH:NH$_4$OH Rf=0.6 (major spot); trace of starting material amide at Rf=0.75.

Example 3D: tert-butyl (2-(2-(2-(2-hydroxyethoxy)ethoxy)ethoxy)-3-nitrobenzyl)(methyl)carbamate

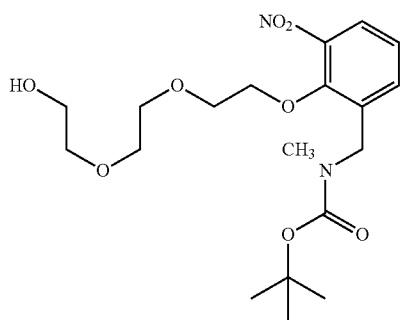

IM3D: tert-butyl (2-(2-(2-(2-hydroxyethoxy)ethoxy)ethoxy)-3-nitrobenzyl)(methyl)carbamate Added a solution of Di-tert-butyl dicarbonate (993 mg, 4.55 mmol) in THF (5 mL) to the reaction solution of 2-{2-[2-(2-Methylaminomethyl-6-nitro-phenoxy)-ethoxy]-ethoxy}-ethanol, which was stirring at 0° C. After 1 hour the mixture was warmed to room temperature. After stirring an additional 2 hours the reaction mixture was concentrated under reduced pressure to remove the majority of THF, then the remaining solution was extracted with CHCl$_3$ (2×; 100 mL and 25 mL respectively). The organic phases were combined and washed sequentially with 1N HCl (25 mL) and saturated aqueous NaHCO$_3$ (100 mL). The resulting organic phase was dried over Na$_2$SO$_4$, filtered, and concentrated under reduced pressure to yield a golden oil, which was placed under high vacuum overnight to yield 1.65 g (T.W. 1.45 g) of crude tert-butyl (2-(2-(2-(2-hydroxyethoxy)ethoxy)ethoxy)-3-nitrobenzyl)(methyl)carbamate as an amber oil. This material was adsorbed onto a silica gel column with CH$_2$Cl$_2$, and then purified by normal phase chromatography eluting with a gradient solvent system (20%-100% EtOAc/Hexane). The desired fractions were combined and concentrated under reduced pressure to give 580 mg (40%) of desired tert-butyl (2-(2-(2-(2-hydroxyethoxy)ethoxy)ethoxy)-3-nitrobenzyl)(methyl)carbamate as a yellow oil. TLC: 100% EtOAc Rf=0.75, homogeneous; LC/MS: M+H=415.2, consistent with desired product (a relatively small peak), with a stronger peak for M+23=437.3 and the base peak at M+H-Boc=315.0. The purified tert-butyl (2-(2-(2-(2-hydroxyethoxy)ethoxy)ethoxy)-3-nitrobenzyl)(methyl)carbamate was used for subsequent steps without further manipulation.

Example 3E: tert-butyl (3-amino-2-(2-(2-(2-hydroxyethoxy)ethoxy)ethoxy)benzyl)(methyl)carbamate

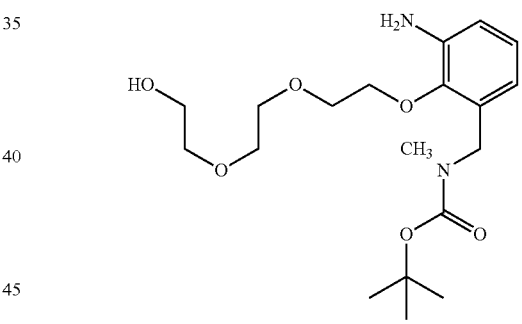

IM3: tert-butyl (3-amino-2-(2-(2-(2-hydroxyethoxy)ethoxy)ethoxy)benzyl)(methyl)carbamate Tert-butyl (3-amino-2-(2-(2-(2-hydroxyethoxy)ethoxy)ethoxy)benzyl)(methyl)carbamate was prepared in a similar manner as described in Example 1B for 2-(2-(2-(2-aminophenoxy)ethoxy)ethoxy)ethan-1-ol, after replacing tert-butyl (2-(2-(2-(2-hydroxyethoxy)ethoxy)ethoxy)-3-nitrobenzyl)(methyl)carbamate for 2-(2-(2-(2-nitrophenoxy)ethoxy)ethoxy)ethan-1-ol. Yield: 100%. TLC: 100% EtOAc Rf=0.6, homogeneous (Starting Material tert-butyl (2-(2-(2-(2-hydroxyethoxy)ethoxy)ethoxy)-3-nitrobenzyl)(methyl)carbamate Rf=0.75; confirmed by co-spot); LC/MS: (M+H=385.0, consistent with desired product). Proceeded and used tert-butyl (3-amino-2-(2-(2-(2-hydroxyethoxy)ethoxy)ethoxy)benzyl)(methyl)carbamate for subsequent steps without further manipulation.

Example 4: tert-butyl (2-(2-(2-(2-(3-amino-6-bromopyrazine-2-carboxamido)phenoxy)-ethoxy)ethoxy)ethyl)(methyl)carbamate

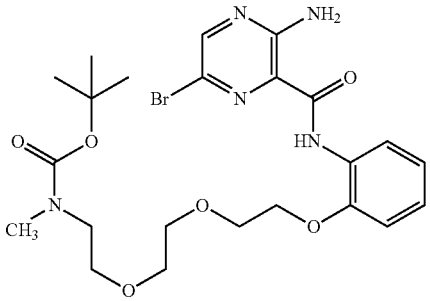 [SMILES: CN(CCOCCOCCOc1ccccc1NC(=O)c1nc(Br)cnc1N)C(=O)OC(C)(C)C]

IM4: tert-butyl (2-(2-(2-(2-(3-amino-6-bromopyrazine-2-carboxamido)phenoxy)ethoxy)ethoxy)ethyl)(methyl)carbamate EDAC (359 mg, 1.88 mmol) was added neat to a room temperature solution of 3-Amino-6-bromo-pyrazine-2-carboxylic acid (164 mg, 0.75 mmol), tert-butyl (2-(2-(2-(2-aminophenoxy)ethoxy)ethoxy)ethyl)(methyl)carbamate (319 mg, 0.9 mmol), and hydroxybenzotriazole (51 mg, 0.375 mmol) in DMSO (2 mL). After 2.5 hours the reaction mixture was cooled towards 0° C., and then with rapid stirring the mixture was diluted with water (4.5 mL). The mixture was shaken to get a free flowing solid, and then stirred for 15 minutes. The solid was then filtered and rinsed liberally with water three times. After air drying for two hours there remained 354 mg (85%) of desired product tert-butyl (2-(2-(2-(2-(3-amino-6-bromopyrazine-2-carboxamido)phenoxy)ethoxy)ethoxy)ethyl)(methyl)carbamate as a golden rod colored solid. LC/MS: >95% (Small M+23 with Br pattern; no significant M+H, but do see base peak as M+1-Boc=455, with Br pattern; TLC: 1:1 EtOAc:Hexane Rf=0.85, homogeneous; 1:2 EtOAc:Hexane Rf=0.5, homogeneous. The isolated tert-butyl (2-(2-(2-(2-(3-amino-6-bromopyrazine-2-carboxamido)phenoxy)ethoxy)ethoxy)ethyl)(methyl)carbamate was used for subsequent steps without further manipulation.

Example 5: tert-butyl (2-(2-(2-(3-amino-6-bromopyrazine-2-carboxamido)phenoxy)ethoxy)ethyl)(2-hydroxyethyl)carbamate

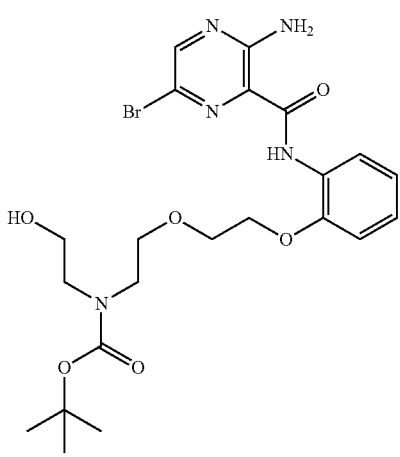 [SMILES: CC(C)(C)OC(=O)N(CCO)CCOCCOc1ccccc1NC(=O)c1nc(Br)cnc1N]

IM5: tert-butyl (2-(2-(2-(3-amino-6-bromopyrazine-2-carboxamido)phenoxy)ethoxy)ethyl)(2-hydroxyethyl)carbamate Tert-butyl (2-(2-(2-(3-amino-6-bromopyrazine-2-carboxamido)phenoxy)ethoxy)ethyl)(2-hydroxyethyl)carbamate was prepared in a similar manner as described in Example (4) for tert-butyl (2-(2-(2-(2-(3-amino-6-bromopyrazine-2-carboxamido)phenoxy)ethoxy)ethoxy)ethyl)(methyl)carbamate, after replacing tert-butyl (2-(2-(2-aminophenoxy)ethoxy)ethyl)(2-hydroxyethyl)carbamate for tert-butyl (2-(2-(2-(2-aminophenoxy)ethoxy)ethoxy)ethyl)(methyl)carbamate. Yield: 100%. TLC: 100% EtOAc Rf=0.85, homogeneous; LC/MS: (M+H=541, consistent with desired product). Proceeded and used tert-butyl (2-(2-(2-(3-amino-6-bromopyrazine-2-carboxamido)phenoxy)ethoxy)ethyl)(2-hydroxyethyl)carbamate for subsequent steps without further manipulation.

Example 6: 4-(5-amino-6-((2-((2,2,5-trimethyl-4-oxo-3,8,11-trioxa-5-azatridecan-13-yl)oxy)phenyl)carbamoyl)pyrazin-2-yl)benzoic acid

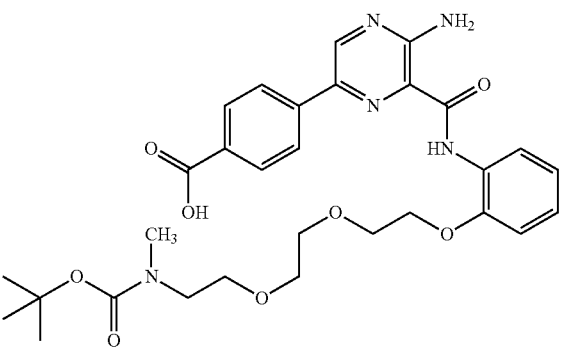 [SMILES: CN(CCOCCOCCOc1ccccc1NC(=O)c1nc(-c2ccc(C(=O)O)cc2)cnc1N)C(=O)OC(C)(C)C]

IM6: 4-(5-amino-6-((2-((2,2,5-trimethyl-4-oxo-3,8,11-trioxa-5-azatridecan-13-yl)oxy)phenyl)carbamoyl)pyrazin-2-yl)benzoic acid A suspension of tert-butyl (2-(2-(2-(2-(3-amino-6-bromopyrazine-2-carboxamido)phenoxy)ethoxy)ethoxy)ethyl)(methyl)carbamate (333 mg, 0.6 mmol), 4-Carboxyphenylboronic acid (100 mg, 0.6 mmol), and Sodium carbonate (134 mg, 1.3 mmol) in a mixed solvent system of $CH_3CN$ (4 mL)/water (4 mL) was de-gassed with nitrogen in a small pressure flask and then $Pd(PPh_3)_4$ (69 mg, 0.06 mmol) was added neat. The reaction mixture was placed under a nitrogen atmosphere, capped and heated to 90° C.

After 6 hours the reaction was cooled to room temperature. The $CH_3CN$ layer was concentrated under reduced pressure. The aqueous phase was diluted with 20 mL $H_2O$ and extracted with $Et_2O$ (~20 mL), which yielded a bit of an emulsion. After about an hour the layers separated and the aqueous phase was washed with a second portion of $Et_2O$. After sitting for an additional 1.5 hours the layers had almost completely resolved and the resulting aqueous phase was cooled to 0° C. and acidified to pH ~2-4 by addition of 1N HCl (~2.5 mL). The resulting precipitate was collected and washed with water liberally (3×). The sample was air dried overnight. There remained 172 mg (48%) of desired 4-(5-amino-6-((2-((2,2,5-trimethyl-4-oxo-3,8,11-trioxa-5-azatridecan-13-yl)oxy)phenyl)carbamoyl)pyrazin-2-yl)benzoic acid as a brown solid. LC/MS: virtually clean and consistent with desired product (M+H=596.4), also significant M+23=618.4 and a strong base peak of 496.3 (M+H-Boc); TLC: 100% EtOAc Rf=0.8, homogeneous. The isolated 4-(5-amino-6-((2-((2,2,5-trimethyl-4-oxo-3,8,11-trioxa-5-azatridecan-13-yl)oxy)phenyl)carbamoyl)pyrazin-2-yl)benzoic acid was used for subsequent reactions without further manipulation.

Example 7: tert-butyl (2-(2-(2-(3-amino-6-(4-(N-methylsulfamoyl)phenyl)pyrazine-2-carboxamido)phenoxy)ethoxy)ethyl)(2-hydroxyethyl)carbamate

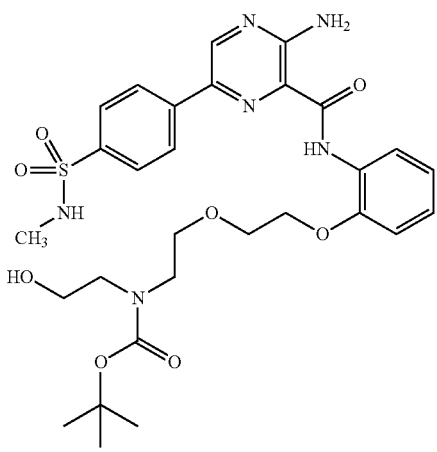 [SMILES: CNS(=O)(=O)c1ccc(-c2cnc(N)c(C(=O)Nc3ccccc3OCCOCCN(CCO)C(=O)OC(C)(C)C)n2)cc1]

IM7: tert-butyl (2-(2-(2-(3-amino-6-(4-(N-methylsulfamoyl)phenyl)pyrazine-2-carboxamido)phenoxy)ethoxy)ethyl)(2-hydroxyethyl)carbamate In a small pressure reaction vessel tert-butyl (2-(2-(2-(3-amino-6-bromopyrazine-2-carboxamido)phenoxy)ethoxy)ethyl)(2-hydroxyethyl)carbamate (405 mg, 0.75 mmol) and methyl 4-boronobenzenesulfonamide (194 mg, 0.90 mmol) were mixed with DMF (12 mL), then 2M Na$_2$CO$_3$ (6 mL) was added and the resulting solution degassed under a stream of nitrogen. Then under nitrogen, Pd(PPh$_3$)$_4$ (87 mg, 0.075 mmol) was added and the whole was capped and warmed to 90° C. After 4 hours the reaction mixture was cooled to room temperature and the heterogeneous reaction mixture was partitioned between EtOAc (75 mL) and water (60 mL). The aqueous phase was washed with a second portion of EtOAc (25 mL) and then the combined organic phases were washed with water (15 mL) followed by brine (50 mL). The organic phase was dried over Na$_2$SO$_4$, filtered and concentrated to give 880 mg of brown oil (T.W. 473 mg). The oil was dissolved in MeOH (~5 mL) and cooled to 4° C. for 3 days. The resulting solid was filtered and rinsed three times with small amounts of ice cold MeOH. After air drying there remained 387 mg (82%) of desired tert-butyl (2-(2-(2-(3-amino-6-(4-(N-methylsulfamoyl)phenyl)pyrazine-2-carboxamido)phenoxy)ethoxy)ethyl)(2-hydroxyethyl)carbamate as a yellow solid. TLC: 100% EtOAc Rf=0.65, homogeneous; LC/MS (M+H=631.2, consistent with desired product). Proceeded and used tert-butyl (2-(2-(2-(3-amino-6-(4-(N-methylsulfamoyl)phenyl)pyrazine-2-carboxamido)phenoxy)ethyl)(2-hydroxyethyl)carbamate for subsequent steps without further manipulation.

Example 8: 4-(5-amino-6-((2-(2-(2-(2-(methylamino)ethoxy)ethoxy)ethoxy)phenyl)carbamoyl)pyrazin-2-yl)benzoic acid HCl adduct

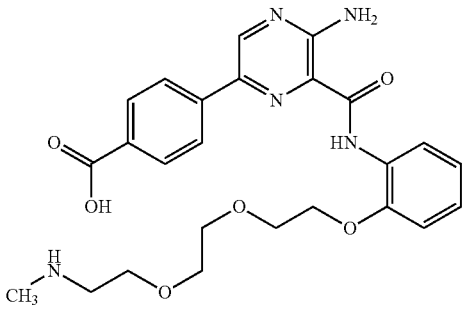 [SMILES: CNCCOCCOCCOc1ccccc1NC(=O)c1nc(-c2ccc(C(=O)O)cc2)cnc1N]

IM8: 4-(5-amino-6-((2-(2-(2-(2-(methylamino)ethoxy)ethoxy)ethoxy)phenyl)carbamoyl)pyrazin-2-yl)benzoic acid.HCl adduct To a solution of 4-(5-amino-6-((2-((2,2,5-trimethyl-4-oxo-3,8,11-trioxa-5-azatridecan-13-yl)oxy)phenyl)carbamoyl)pyrazin-2-yl)benzoic acid (149 mg, 0.25 mmol) in dioxane (7.5 mL) was added 4N HCl in Dioxane (4 mL, 16 mmol)) at room temperature. After 2 hours the reaction mixture was concentrated under reduced pressure and the resulting yellow residue was treated with Et$_2$O (~15 mL). The resulting solid was filtered off and rinsed twice with Et$_2$O (5 mL each). As air drying, appeared possibly may be hygroscopic, so the yellow powder was transferred to a small sample bottle and sealed. Left with 127 mg (96%) of 4-(5-amino-6-((2-(2-(2-(2-(methylamino)ethoxy)ethoxy)ethoxy)phenyl)carbamoyl)pyrazin-2-yl)benzoic acid HCl salt as a golden colored solid. LC/MS: virtually clean (M+H=496.2, consistent with desired product). 4-(5-amino-6-((2-(2-(2-(2-(methylamino)ethoxy)ethoxy)ethoxy)phenyl)carbamoyl)pyrazin-2-yl)benzoic acid. HCl adduct was used directly in subsequent reactions without further manipulation.

Example 9: tert-butyl 2$^5$-amino-15-methyl-3-oxo-6,9-dioxa-16-thia-4,12,15-triaza-2(2,6)-pyrazina-1(1,4),5(1,2)-dibenzenacyclohexadecaphane-12-carboxylate 16,16-dioxide

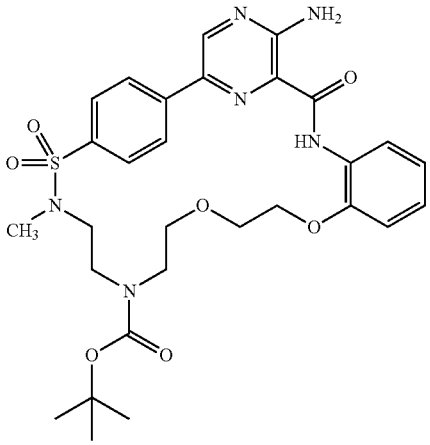 [SMILES: CN1CCN(C(=O)OC(C)(C)C)CCOCCOc2ccccc2NC(=O)c2nc(cnc2N)-c2ccc(cc2)S1(=O)=O]

IM9: tert-butyl 2⁵-amino-15-methyl-3-oxo-6,9-di-oxa-16-thia-4,12,15-triaza-2(2,6)-pyrazina-1(1,4),5 (1,2)-dibenzenacyclohexadecaphane-12-carboxylate 16,16-dioxide To a 0° C. solution of tert-butyl (2-(2-(2-(3-amino-6-(4-(N-methylsulfamoyl)phenyl)pyrazine-2-carboxamido)phenoxy)ethoxy)ethyl)(2-hydroxyethyl)carbamate (331 mg, 0.525 mmol) and Triphenylphosphine (551 mg, 2.10 mmol) in THF (20 mL) was added neat Diisopropyl azodicarboxylate (310 µL, 1.575 mmol). After 1.5 hours the reaction mixture was warmed to room temperature and stirred an additional 2 hours. The reaction mixture was then concentrated under reduced pressure, the residue treated with 10 mL of MeOH and then cooled to 4° C. for 16 hours. The solid was filtered from the MeOH and rinsed twice with ice cold MeOH (~2 mL each). After air drying there remained 136 mg (42%) of desired tert-butyl 2⁵-amino-15-methyl-3-oxo-6,9-dioxa-16-thia-4,12,15-triaza-2(2,6)-pyrazina-1(1,4),5(1,2)-dibenzenacyclohexadecaphane-12-carboxylate 16,16-dioxide yellow solid, which was used for subsequent steps without further manipulation. TLC: 100% EtOAc Rf=0.9.

Example 10: 3-amino-6-bromo-N-(2-(2-(2-(2-hydroxyethoxy)ethoxy)ethoxy)phenyl)pyrazine-2-carboxamide

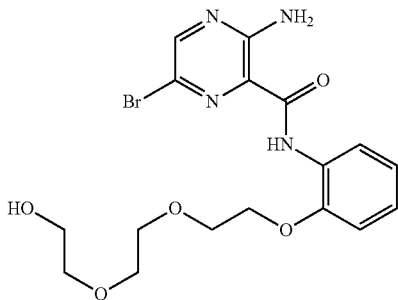 [SMILES: Nc1ncc(Br)nc1C(=O)Nc1ccccc1OCCOCCOCCO]

IM10: 3-amino-6-bromo-N-(2-(2-(2-(2-hydroxyethoxy)ethoxy)ethoxy)phenyl)pyrazine-2-carboxamide 3-amino-6-bromo-N-(2-(2-(2-(2-hydroxyethoxy)ethoxy)ethoxy)phenyl)pyrazine-2-carboxamide was prepared in a similar manner as described in Example (4) for tert-butyl (2-(2-(2-(2-(3-amino-6-bromopyrazine-2-carboxamido)phenoxy)ethoxy)ethoxy)ethyl)(methyl)carbamate, after replacing 2-(2-(2-(2-aminophenoxy)ethoxy)ethoxy)ethan-1-ol for tert-butyl (2-(2-(2-(2-aminophenoxy)ethoxy)ethoxy)ethyl)(methyl)carbamate. Yield: 86%. TLC: 100% EtOAc Rf=0.75, homogeneous; LC/MS: (M+H=442, consistent with desired product). Proceeded and used 3-amino-6-bromo-N-(2-(2-(2-(2-hydroxyethoxy)ethoxy)ethoxy)phenyl)pyrazine-2-carboxamide for subsequent steps without further manipulation.

Example 11: 3-amino-N-(2-(2-(2-(2-hydroxyethoxy)ethoxy)ethoxy)phenyl)-6-(4-(N-methylsulfamoyl)phenyl)pyrazine-2-carboxamide

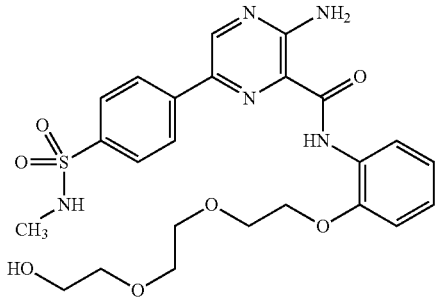 [SMILES: CNS(=O)(=O)c1ccc(-c2cnc(N)c(C(=O)Nc3ccccc3OCCOCCOCCO)n2)cc1]

IM11: 3-amino-N-(2-(2-(2-(2-hydroxyethoxy)ethoxy)ethoxy)phenyl)-6-(4-(N-methylsulfamoyl)phenyl)pyrazine-2-carboxamide 3-amino-N-(2-(2-(2-(2-hydroxyethoxy)ethoxy)ethoxy)phenyl)-6-(4-(N-methylsulfamoyl)phenyl)pyrazine-2-carboxamide was prepared in a similar manner as described in Example (7) for tert-butyl (2-(2-(2-(3-amino-6-(4-(N-methylsulfamoyl)phenyl)pyrazine-2-carboxamido)phenoxy)ethoxy)ethyl)(2-hydroxyethyl)carbamate, after replacing 3-amino-6-bromo-N-(2-(2-(2-(2-hydroxyethoxy)ethoxy)ethoxy)phenyl)pyrazine-2-carboxamide for tert-butyl (2-(2-(2-(3-amino-6-bromopyrazine-2-carboxamido)phenoxy)ethoxy)ethyl)(2-hydroxyethyl)carbamate. Yield: 81%. TLC: 100% EtOAc Rf=0.55, homogeneous; LC/MS: (M+H=532.3, consistent with desired product). Proceeded and used 3-amino-N-(2-(2-(2-(2-hydroxyethoxy)ethoxy)ethoxy)phenyl)-6-(4-(N-methylsulfamoyl)phenyl)pyrazine-2-carboxamide for subsequent steps without further manipulation.

Preparation of Exemplary Compounds of the Invention

Example 12: 2⁵-amino-15-methyl-6,9-dioxa-16-thia-4,12,15-triaza-2(2,6)-pyrazina-1(1,4),5(1,2)-dibenzenacyclohexadecaphan-3-one 16,16-dioxide

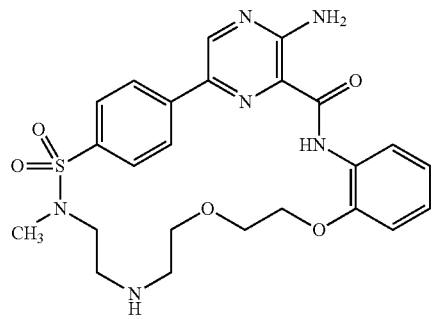 [SMILES: CN1CCNCCOCCOc2ccccc2NC(=O)c2nc(cnc2N)-c2ccc(cc2)S1(=O)=O]

P(20): 2⁵-amino-15-methyl-6,9-dioxa-16-thia-4,12,15-triaza-2(2,6)-pyrazina-1(1,4),5(1,2)-dibenzenacyclohexadecaphan-3-one 16,16-dioxide A suspension of tert-butyl 2⁵-amino-15-methyl-3-oxo-6,9-dioxa-16-thia-4,12,15-triaza-2(2,6)-pyrazina-1(1,4),5(1, 2)-dibenzenacyclohexadecaphane-12-carboxylate 16,16-dioxide (37 mg, 0.06 mmol) in Dioxane (3 mL) and Ethyl Acetate (3 mL) was treated at room temperature with 4N HCl in Dioxane (3 mL, 12 mmol), which greatly helped dissolution initially. The mixture was stirred at room temperature and saw considerable solid forming over time. After 16 hours the resulting solid was filtered and rinsed liberally with EtOAc. On drying started as a yellow powder, then began gumming a bit, and then appeared as a orange/yellow solid. Possibly suggestive of a hydrate? Left with 28 mg of crude $2^5$-amino-15-methyl-6,9-dioxa-16-thia-4,12,15-triaza-2(2,6)-pyrazina-1(1,4),5(1,2)-dibenzenacyclohexadecaphan-3-one 16,16-dioxide.HCl adduct as a yellow/orange solid. This material was partitioned between CHCl$_3$/EtOAc and saturated aqueous NaHCO$_3$. The aqueous layer was extracted twice more with straight CHCl$_3$. The organic layers were combined, dried over Na$_2$SO$_4$, filtered, and concentrated to yield 24 mg of a yellow solid. This solid was dissolved in ~3 mL of CH$_2$Cl$_2$ and adsorbed on a 20×20 silica plate (1000 micron), then eluted with a 10:1:0.5 EtOAc:MeOH:NH$_4$OH solvent system. The desired band of silica was isolated (Rf~0.55), suspended in MeOH, filtered and rinsed liberally with MeOH (2×), CH$_2$Cl$_2$ (2×), and then MeOH once again (total volume of ~70 mL). The filtrate was concentrated under reduced pressure to yield 14 mg of residue. This material was treated with ~2 mL of CH$_2$Cl$_2$, filtered into a pre-weighed sample bottle and then blown to dryness under a stream of N$_2$. This residue was placed under high vacuum for 2 hour to yield 10 mg (32%) of desired $2^5$-amino-15-methyl-6,9-dioxa-16-thia-4,12,15-triaza-2(2,6)-pyrazina-1(1,4),5(1,2)-dibenzenacyclohexadecaphan-3-one 16,16-dioxide as a yellow solid. LC/MS: (dissolved sample in warm MeOH), (M+H=513.0, consistent with desired product); TLC: 10:1:0.5 EtOAc:MeOH:NH$_4$OH system Rf=0.8, homogeneous.

Example 13: $2^5$-amino-15-methyl-6,9,12-trioxa-4,15-diaza-2(2,6)-pyrazina-1(1,4),5(1,2)-dibenzenacyclohexadecaphane-3,16-dione 2-yl)benzoic acid.HCl adduct (106 mg, 0.2 mmol) and triethylamine (52 mg, 0.52 mmol) were combined in DMSO (2 mL) at room temperature. A milky suspension resulted. At room temperature the milky mix was added dropwise over 20 minutes to a stirring mixture of EDAC (153 mg, 0.8 mmol) and hydroxybenzotriazole (13.5 mg, 0.1 mmol) in DMSO (1 mL). After stirring 16 hours at room temperature the reaction mixture was cooled and diluted with water, resulting in a solid precipitating. After stirring for 15 minutes the solid was filtered and rinsed liberally with water 3×. After air drying there remained 69 mg (77%) of crude $2^5$-amino-15-methyl-6,9,12-trioxa-4,15-diaza-2(2,6)-pyrazina-1(1,4),5(1,2)-dibenzenacyclohexadecaphane-3,16-dione as a yellow solid. This crude solid was dissolved in ~4 mL of CH$_2$Cl$_2$ and adsorbed onto a 20×20 silica plate (1000 micron), then the plate was eluted with 100% EtOAc. Collected silica streaking from Rf=0.2 to 0.05 and rinsed this band of silica with EtOAc (3×33 mL). The filtrates were concentrated under reduced pressure to give 28 mg of yellow solid. Triturated the 28 mg of yellow solid with 2 mL ice cold MeOH, then filtered and rinsed with 2 mL of ice cold MeOH. After air drying for about an hour found left with 16 mg (18%) of desired $2^5$-amino-15-methyl-6,9,12-trioxa-4,15-diaza-2(2,6)-pyrazina-1(1,4),5(1,2)-dibenzenacyclohexadecaphane-3,16-dione as a yellow solid. LC: (dissolved in DMSO) single peak (M+H=478.2, consistent with desired product); TLC: 10:1:0.5 EtOAc:MeOH:NH$_4$OH Rf=0.75, homogeneous, 100% EtOAc Rf=0.25, homogeneous.

Example 14: $2^5$-amino-15-methyl-12-(5-((3aS,4S,6aR)-2-oxohexahydro-1H-thieno[3,4-d]imidazol-4-yl)pentanoyl)-6,9-dioxa-16-thia-4,12,15-triaza-2(2,6)-pyrazina-1(1,4),5(1,2)-dibenzenacyclohexadecaphan-3-one 16,16-dioxide

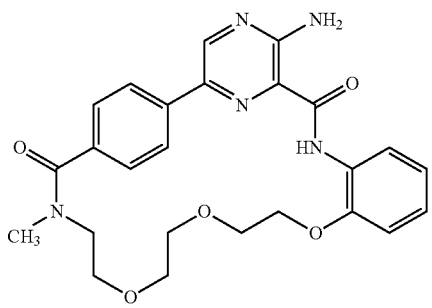 [SMILES: CN1CCOCCOCCOc2ccccc2NC(=O)c2nc(cnc2N)-c2ccc(cc2)C1=O]

P(2): $2^5$-amino-15-methyl-6,9,12-trioxa-4,15-diaza-2(2,6)-pyrazina-1(1,4),5(1,2)-dibenzenacyclohexadecaphane-3,16-dione In a small reaction vial 4-(5-amino-6-((2-(2-(2-(2-(methylamino)ethoxy)ethoxy)ethoxy)phenyl)carbamoyl)pyrazin-

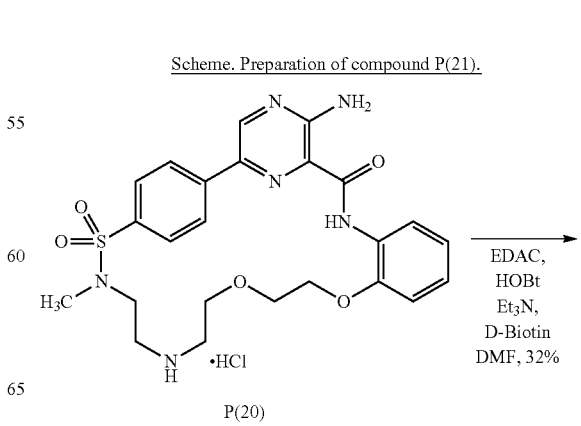

Scheme. Preparation of compound P(21).

P(20)

121
-continued

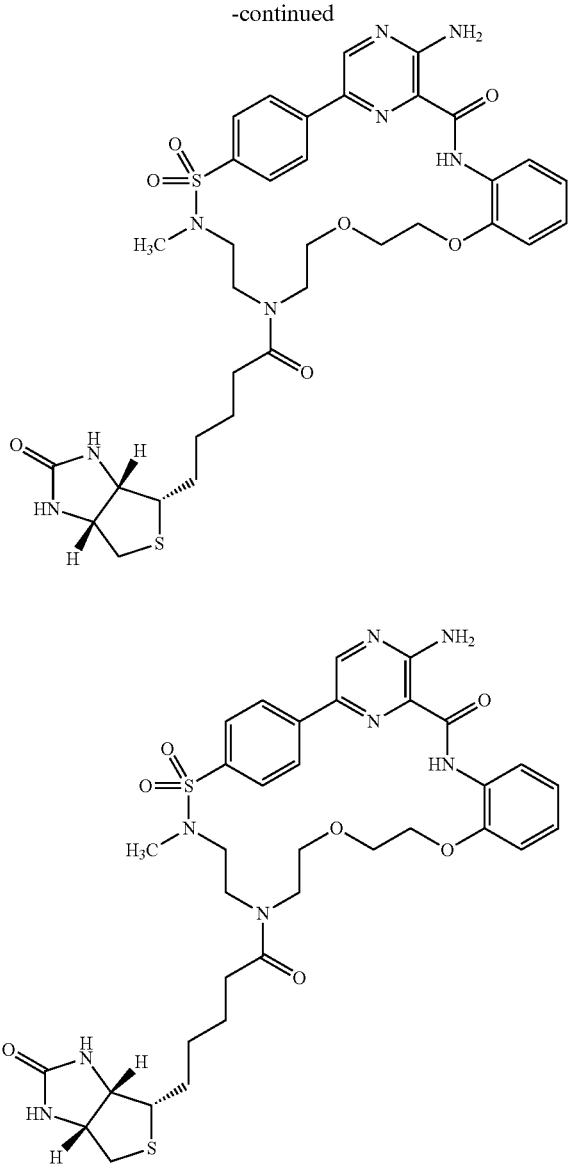

122

P(21): $2^5$-amino-15-methyl-12-(5-((3 aS,4S,6aR)-2-oxohexahydro-1H-thieno[3,4-d]imidazol-4-yl)pentanoyl)-6,9-dioxa-16-thia-4,12,15-triaza-2(2,6)-pyrazina-1(1,4),5(1,2)-dibenzenacyclohexadecaphan-3-one 16,16-dioxide P(20) as its HCl salt (16.5 mg, 0.030 mmol), hydroxybenzotriazole (2 mg, 0.015 mmol), and D-Biotin (8.8 mg, 0.036 mmol) were combined in DMF (0.33 mL) to give a heterogeneous mixture. Triethylamine (13.8 mL, 0.099 mmol) was added, which led to an almost homogeneous solution. EDAC (17 mg, 0.090 mmol) was then added at room temperature with stirring. After 3 hours the reaction mixture was treated with 1 mL of saturated aqueous NaHCO$_3$ followed by 2 mL water. The resulting heterogeneous mixture was stirred for 5 minutes; the resulting solid was filtered and rinsed liberally with water (3×). The collected solid was air dried overnight to give 17 mg of desired product as a yellow solid. This solid was dissolved in a CH$_2$Cl$_2$:MeOH solution, adsorbed onto a 10×20 silica plate (1000 micron) and eluted with a 10:1:0.5 EtOAc:MeOH:NH$_4$OH system. The desired band was suspended in a 1:1 CH$_2$Cl$_2$:MeOH solution (~10 mL), filtered and the silica solid rinsed liberally with the same 1:1 solution (total volume of ~50 mL). The filtrate was concentrated under reduced pressure. There remained 13 mg of residue. This material was treated with ~2 mL of CH$_2$Cl$_2$, the solution filtered into a pre-weighed sample bottle and then blown to dryness under a stream of N$_2$. This residue was placed under high vacuum for 1 hour to give 7 mg (32%) of desired P(21) as a yellow solid. LC/MS: (M+H=739.0, consistent with desired product); TLC: 10:1:0.5 EtOAc:MeOH:NH$_4$OH Rf=0.45, homogeneous.

Example 15: $2^5$-amino-15-methyl-$5^3$-((methylamino)methyl)-6,9,12-trioxa-4,15-diaza-2(2,6)-pyrazina-1(1,4),5(1,2)-dibenzenacyclohexadecaphane-3,16-dione Scheme. Preparation of compound P(22).

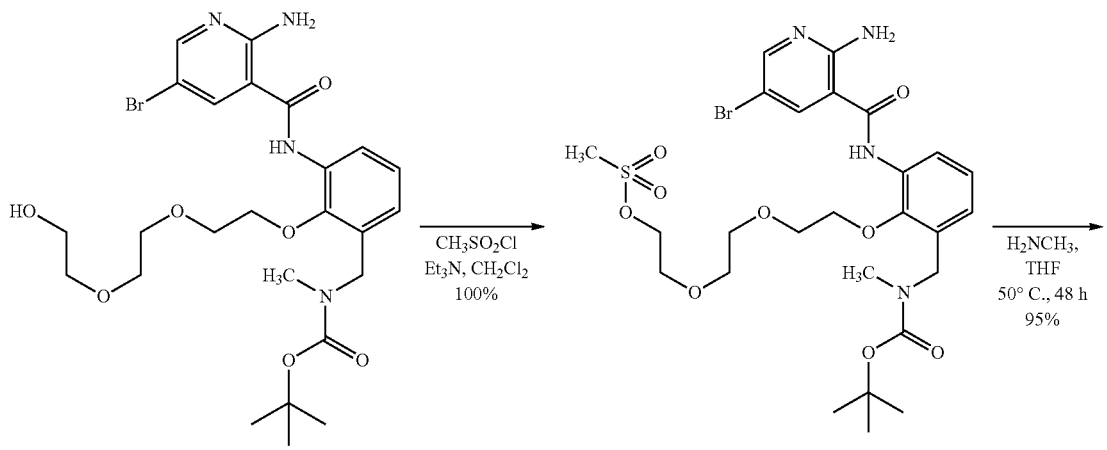

-continued
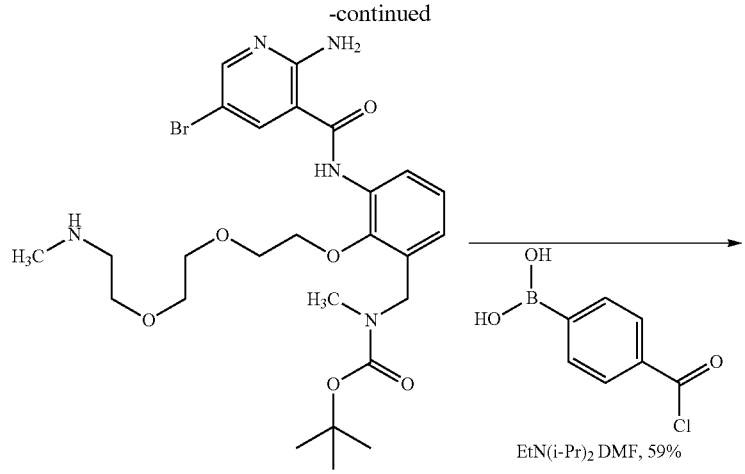
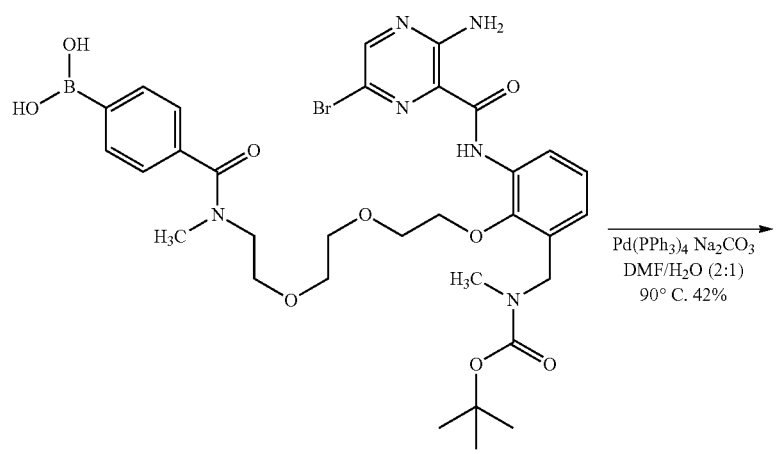
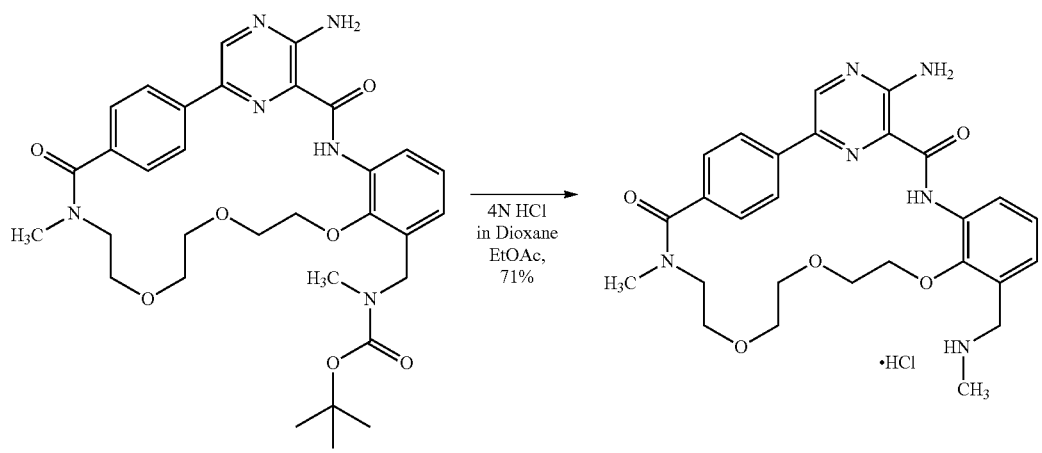

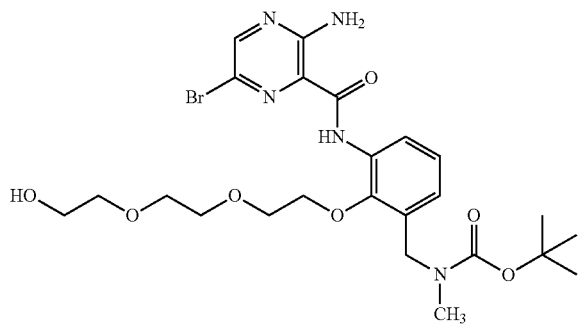

IM15A

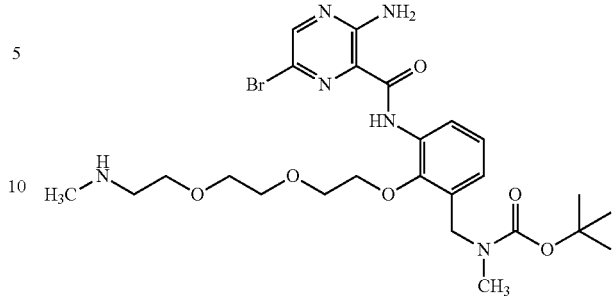

IM15C

EDAC (4.79 g, 25 mmol) was added to a stirring, room temperature solution of IM3 (4.61 g, 12 mmol), 3-amino-6-bromopyrazine-2-carboxylic acid (2.18 g, 10 mmol), and hydroxybenzotriazole (0.68 g, 5 mmol) in DMSO (16 mL). After stirring for three hours, 50 mL of water was added to the reaction mixture, to give a gooh. Decanted off liquid and repeated water rinse and decanting 2× more. The residue was partitioned between EtOAc (200 mL) and water (50 mL). The resulting organic phase was extracted sequentially with saturated aqueous NaHCO$_3$, 1N HCl (~30 mL), and saturated aqueous NaHCO$_3$ once again. The organic phase was dried over Na$_2$SO$_4$, filtered, and concentrated under reduced pressure to give an amber colored oil, which placed under high vacuum to remove any residual solvent. Left with 4.97 g (85%) of desired IM15A as an amber oil, which was used for subsequent steps without further manipulation.

A room temperature solution of IM15B (0.99 g, 1.5 mmol) in THF (5 mL) was added to a stirring solution of 2M methylamine in THF (75 mmol, 37.5 mL) in a pressure flask. The flask was sealed and the reaction was warmed to 50° C. After 48 hours the reaction mixture was removed from the heat, cooled in an ice bath and then opened. The reaction mixture was concentrated under reduced pressure and the residue was partitioned between EtOAc (50 mL) and saturated aqueous NaHCO$_3$ (40 mL). The aqueous phase was extracted with a second portion of EtOAc (40 mL). The organics were combined, dried over Na$_2$SO$_4$, filtered, and concentrated under reduced pressure to give a brown oil. This material was placed under high vacuum for 1 hour. There remained 0.85 g (95%) of desired IM15C as a brown oil. LC/MS: >95% (M+H=598, with Br pattern, consistent for desired product); TLC: 10:1:0.5 EtOAc:MeOH:NH$_4$OH Rf=0.4. Proceeded and used IM15C for subsequent step without further manipulation.

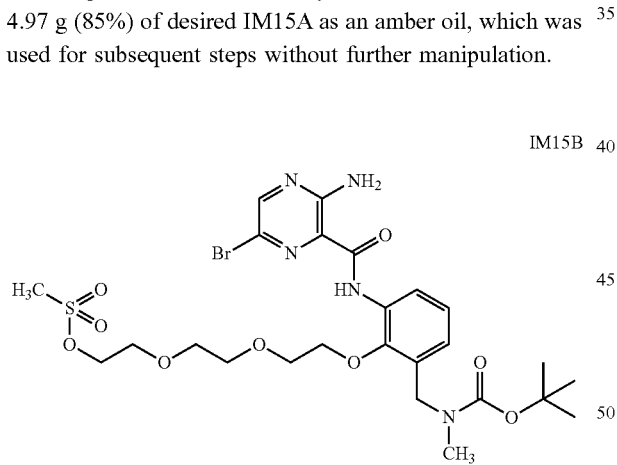

IM15B

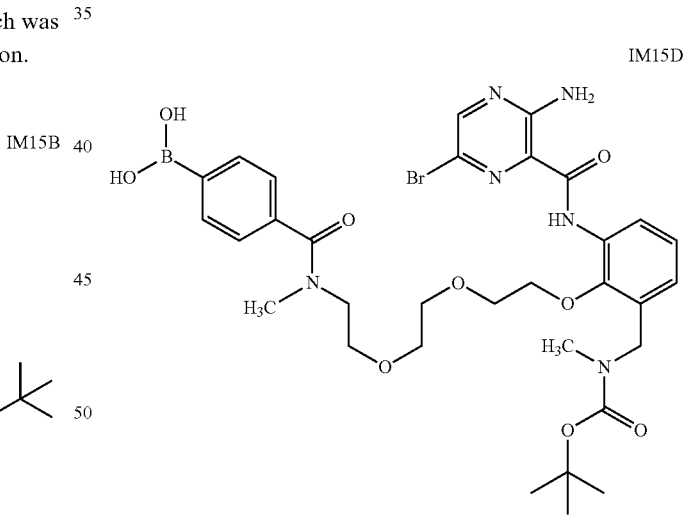

IM15D

A 0° C. solution of IM15A (877 mg, 1.5 mmol) and triethylamine (313 µL, 2.25 mmol) in DCM (20 mL) was treated dropwise with a solution of methanesulfonyl chloride (151 µL, 1.95 mmol) in DCM (5 mL). After 45 minutes the 0° C. reaction solution was treated with 1N HCl (10 mL). After separating the layers, the organic phase was dried over MgSO$_4$, filtered, and concentrated under reduced pressure, then placed under high vacuum for a ½ hour. There remained 0.99 g (100%) of desired IM15B as a yellow oil. This material was used for the subsequent step without further manipulation.

4-Chlorocarbonylphenylboronic acid (155 mg, 0.84 mmol) was added neat to a 0° C. solution of IM15C (418 mg, 0.70 mmol) and N,N-diisopropylethylamine (164 µL, 0.945 mmol) in DMF (6 mL). After 15 minutes the ice bath was removed and the mixture stirred at room temperature. After stirring for 2.5 hours, additional portions of N,N-diisopropylethylamine (82 µL, 0.473 mmol) and 4-chlorocarbonylphenylboronic acid (78 mg, 0.42 mmol) were added to the room temperature reaction mixture. After stirring another 30 minutes, third portions of N,N-diisopropylethylamine (41 µL, 0.237 mmol) and 4-chlorocarbonylphenylboronic acid (39 mg, 0.21 mmol) were added to the reaction mixture. After an additional 30 minutes, the reaction solution was partitioned between EtOAc (50 mL) and saturated aqueous NaHCO₃ (50 mL). Then a small amount of water was added, to give clear biphasic solution. Separated layers and washed aqueous phase with a second portion of EtOAc (25 mL). The organic phases were combined and washed sequentially with another portion of saturated aqueous NaHCO₃ (20 mL), 1 N HCl (25 mL), and brine (30 mL). The organic phase was dried over Na₂SO₄, filtered and concentrated to give 0.63 g (T.W. 0.52 g) of crude product as a tan oil. TLC: 10:1:0.5 EtOAc:MeOH:NH₄OH Rf=0.15, clearly darkest (~70%), also small spots at Rf=solvent front, Rf 0.85, streak at Rf 0.75, Rf 0.5 (=trace of SM A), Rf 0.1 and origin. The crude product was dissolved in a small amount of EtOAc and loaded onto a 12 g ISCO column. The chromatography was performed with a gradient eluent system, starting with 100% EtOAc up to 10% MeOH/EtOAc. The desired fractions were concentrated under reduced pressure to yield 310 mg (59%) of desired IM15D as a slightly yellow colored foam. TLC: 10:1:0.5 EtOAc:MeOH:NH₄OH Rf=0.15, homogeneous; LC/MS: (~100%) (M+H=746, with Br pattern rather weak, a stronger M+23=768, with a Br pattern and a very strong M+H-Boc=646, with Br pattern). IM15D was used for its subsequent step without further manipulation.

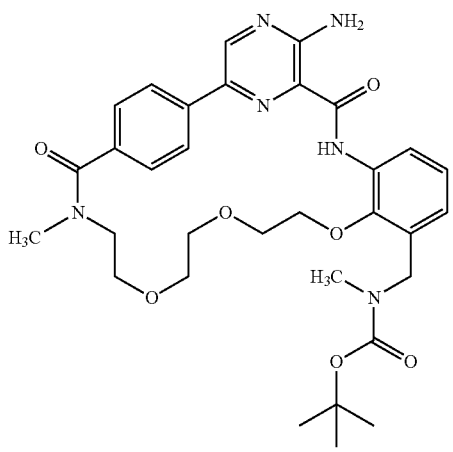

IM15E

In a pressure reaction vessel IM15D was dissolved in DMF (28 mL), then 2M Na₂CO₃ (7 mL) was added and the solution degassed under a stream of N₂ for 2 minutes. Under nitrogen, Pd(PPh₃)₄(40 mg, 0.035 mmol) was added to the heterogeneous reaction mixture, after which the whole was capped and warmed to 90-95° C. After 1.5 hours the reaction mixture was removed from heating, and upon cooling the reaction was partitioned between EtOAc (100 mL) and water (100 mL). The aqueous phase was extracted with a second portion of EtOAc (75 mL). The organic phases were combined and washed sequentially with water (60 mL×2; slow separation) and then brine (50 mL). The organic phase was dried over Na₂SO₄, filtered and concentrated to give crude product as a brown oil. TLC: 10:1:0.5 EtOAc:MeOH:NH₄OH Rf=0.8, major spot. Saw solid started to form when trying to dissolve up the crude product in a small amount of EtOAc for transfer. The EtOAc was blown off under a stream of nitrogen, and the resulting residue was treated with ~5 mL of ice cold MeOH. The mixture sat for ~½ hour in an ice bath, then the resulting solid was filtered and rinsed with ice cold MeOH. After air drying there remained 91 mg (42%) of desired IM15E as a gold colored solid. TLC: 10:1:0.5 EtOAc:MeOH:NH₄OH Rf=0.8, homogeneous. LC/MS (dissolved in CH₃CN): >95% pure (M+H=621.6, consistent with desired product). Proceeded onto subsequent step with IM15E being used without further manipulation.

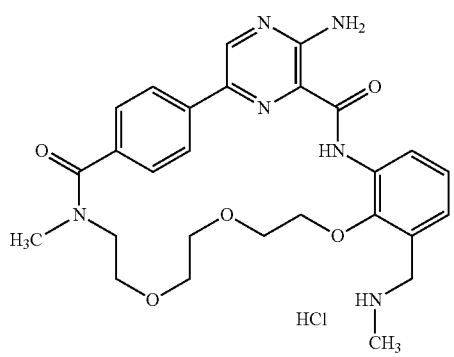 [SMILES: CNCc1cccc2c1OCCOCCOCCN(C)C(=O)c1ccc(cc1)-c1cnc(N)c(n1)C(=O)N2 ; Cl]

P(22): 2⁵-amino-15-methyl-5³-((methylamino) methyl)-6,9,12-trioxa-4,15-diaza-2(2,6)-pyrazina-1 (1,4),5(1,2)-dibenzenacyclohexadecaphane-3,16-dione hydrochloride The Boc deprotection of IM15E was performed similar to that for P(20) after substituting the appropriate macrocycle.

Example 16: 2⁵-amino-5³-((methylamino)methyl)-6, 9,12-trioxa-4-aza-2(2,6)-pyrazina-1(3,5)-pyridina-5 (1,2)-benzenacyclododecaphan-3-one Scheme. Preparation of compound P(24).

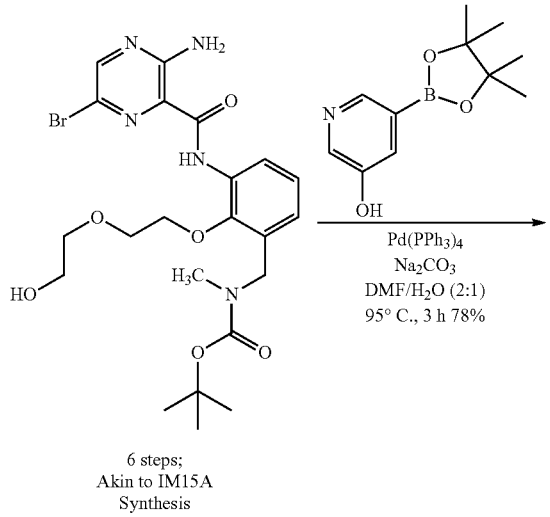

6 steps;
Akin to IM15A
Synthesis

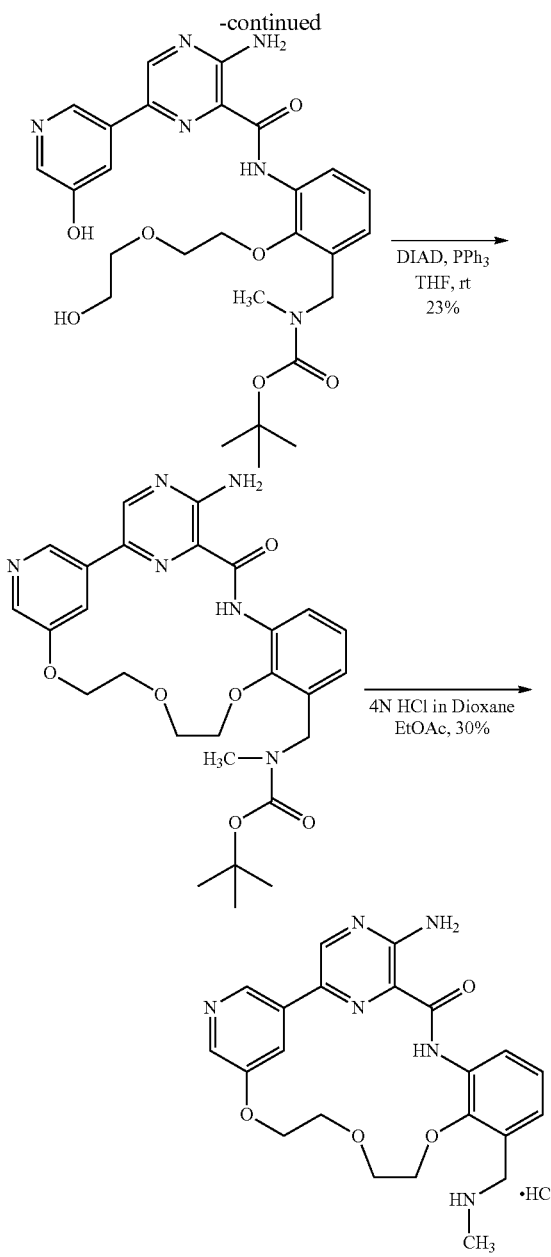

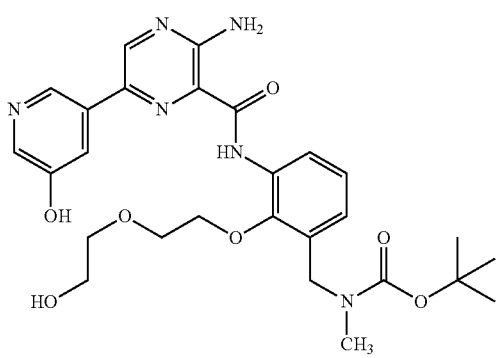

In a small pressure reaction vessel tert-butyl (3-(3-amino-6-bromopyrazine-2-carboxamido)-2-(2-(2-hydroxyethoxy)ethoxy)benzyl)(methyl)carbamate (245 mg, 0.453 mmol), prepared in a similar manner as IM15A (intermediate in the preparation of P(22), cf. Example 15), and 5-(4,4,5,5-tetramethyl-1,3,2-dioxaborolan-2-yl)-3-pyridol (120 mg, 0.544 mmol) were mixed with DMF (6 mL) until almost homogeneous, then 2M Na$_2$CO$_3$ (3 mL) was added and the resulting heterogeneous mixture degassed under a stream of N$_2$ for 3 minutes. Under nitrogen, Pd(PPh$_3$)$_4$(52 mg, 0.045 mmol) was added and the whole was capped and warmed to 95° C. After 3 hours, heating was discontinued. Once cooled, the heterogeneous mixture was partitioned between EtOAc (2×30 mL) and water (20 mL). The EtOAc extracts were combined, washed again with water, then with brine, dried over Na$_2$SO$_4$, filtered, and concentrated under reduced pressure. The residue was placed under high vacuum for 16 hours, to yield 196 mg (78%) of desired IM16A as a tan oil. LC/MS: (M+H=555.6; also ~equal M+23=577.6 and a strong base peak for M+H-Boc=455.5). Also saw ~10% of rt 4.61 minutes, corresponding to Ph$_3$P=O (M+H=279.4). TLC: 10:1:0.5 EtOAc:MeOH:NH$_4$OH~90% at Rf=0.25, with faint spots at origin and at Rf=0.85. Proceeded on to subsequent step using this material without further manipulation.

IM16B

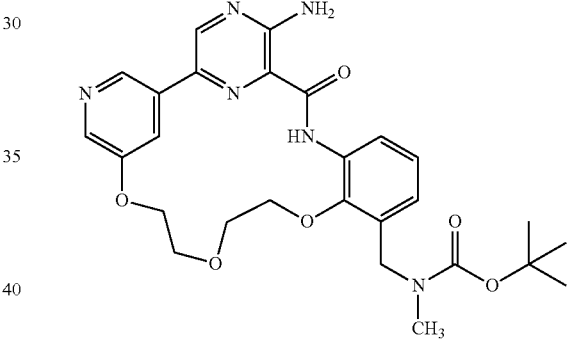

A 0° C. solution of IM16A (180 mg, 0.325 mmol) and triphenylphospine (341 mg, 1.30 mmol) in THF (12 mL) was treated with diisopropyl azodicarboxylate (192 µL, 0.974 mmol). After 15 minutes the cooling bath was removed and the reaction warmed to room temperature. After 3 hours the reaction mixture was concentrated under reduced pressure. The residue was partitioned between EtOAc and saturated aqueous NaHCO$_3$. The organic phase was dried over Na$_2$SO$_4$, filtered and concentrated to give a brownish oil. The oil was partitioned between Et$_2$O (10 mL) and 1N HCl (10 mL). An oil filmed on the side of the separatory funnel, suggesting the desired compound as a salt is not soluble in Et$_2$O or water. The aqueous phase, along with the oil, was washed with a second portion of Et$_2$O (5 mL). The aqueous phase and oil film were then carefully treated with NaHCO$_3$. The resulting basic solution was extracted with EtOAc (2×10 mL). The combined EtOAc extracts were dried over Na$_2$SO$_4$, filtered, and concentrated under reduced pressure to give 108 mg (62%) of crude product residue. LC/MS: Saw was ~70% of desired product, with ~15% Ph$_3$P=O, and a number of small peaks (~1-2% each). This material was loaded onto a 12 g silica gel column and purified on an ISCO apparatus. The column was eluted with an EtOAc/hexane gradient system, starting at 50%

EtOAc (hold 1 minute) and working up to 100% EtOAc (at 8 minutes) and then held at 100% for an additional 8 minutes. One major peak came off between 8-10 minutes, which showed mainly desired product. Combined and concentrated these fractions to give 40 mg (23%) of semi-pure desired IM16B. LC/MS showed same relative ratio of desired to Ph$_3$P=O (85%:15%), so these two materials co-eluted, but other minor impurities gone. Proceeded and used this semi-crude material to subsequent deprotection step without further manipulation.

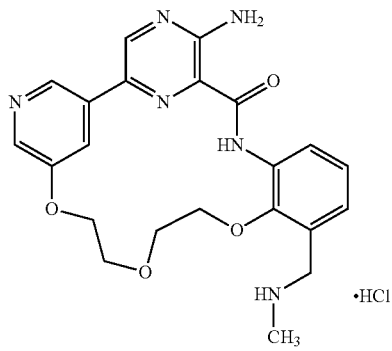 [SMILES: CNCc1cccc2c1OCCOCCOc1cncc(c1)-c1cnc(N)c(n1)C(=O)N2 ; Cl]

P(24): $2^5$-amino-$5^3$-((methylamino)methyl)-6,9,12-trioxa-4-aza-2(2,6)-pyrazina-1(3,5)-pyridina-5(1,2)-benzenacyclododecaphan-3-one hydrochloride A room temperature, homogeneous solution of IM16B (31 mg, 0.058 mmol) in ethyl acetate (2 mL) was treated with 4N HCl in dioxane (1 mL, 4 mmol HCl). An intense yellow color resulted and no appreciable exotherm was noted. Solid started to precipitate after 5 minutes. The reaction mixture was then stirred 16 hours, after which the fine solid was collected and rinsed liberally with EtOAc. After air drying 10 mg (37%) of desired P(24) was isolated as a yellow solid. TLC: 10:1:0.5 EtOAc:MeOH:NH$_4$OH: (dissolved in MeOH/CH$_3$CN) Rf=0.6, homogeneous; LC/MS: virtually clean (M+H=437.5, consistent with desired product and also see a M+23=459.5).

Example 17: $2^5$-amino-15-(2-hydroxyethyl)-6,9,12-trioxa-16-thia-4,15-diaza-2(2,6)-pyrazina-1(1,4),5(1,2)-dibenzenacyclohexadecaphan-3-one 16,16-dioxide Scheme. Preparation of compound P(25).

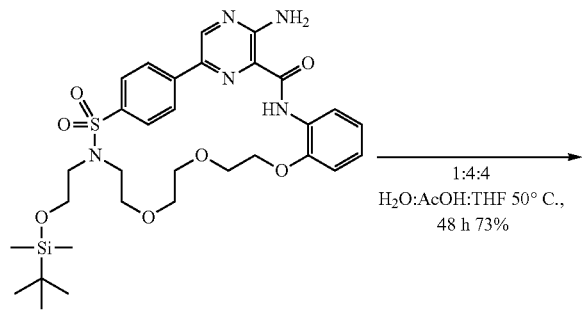

Prepared in a similar manner as IM9, but with appropriate Starting Materials

-continued

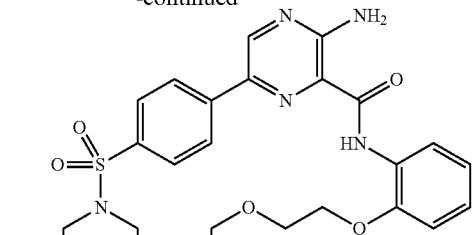

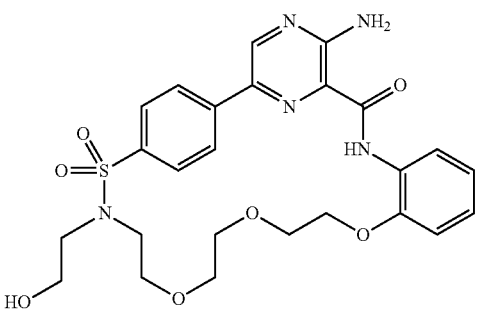 [SMILES: Nc1ncc2nc1C(=O)Nc1ccccc1OCCOCCOCCN(CCO)S(=O)(=O)c1ccc-2cc1]

P(25): $2^5$-amino-15-(2-hydroxyethyl)-6,9,12-trioxa-16-thia-4,15-diaza-2(2,6)-pyrazina-1(1,4),5(1,2)-dibenzenacyclohexadecaphan-3-one 16,16-dioxide A room temperature solution of $2^5$-amino-15-(2-((tert-butyldimethylsilyl)oxy)ethyl)-6,9,12-trioxa-16-thia-4,15-diaza-2(2,6)-pyrazina-1(1,4),5(1,2)-dibenzenacyclohexadecaphan-3-one 16,16-dioxide (IM17A) (36 mg, 0.055 mmol), prepared in a similar manner as IM9 after substituting the appropriate boronic acid coupled with IM15A, in THF (200 μL) was treated with AcOH (200 μL) followed by water (50 μL). The resulting solution was capped and warmed to 50° C. After warming 48 hours, the resulting heterogeneous mixture was cooled to 0° C. for 1 hour, then the solid was filtered off and rinsed liberally with CH$_3$CN. After air drying the solid was dried under high vacuum to yield 22 mg (73%) of desired P(25) as a yellow solid. LC/MS (dissolved in MeOH/CH$_3$CN with sonication): ~95% (M+H=544.51, consistent with desired product P(25)) and ~5% (M+H=658.6, consistent with starting material IM17A). P(25) was currently tested without further purification.

Example 18: tert-butyl $2^5$-amino-13-methyl-3-oxo-6-oxa-14-thia-4,10,13-triaza-2(2,6)-pyrazina-1(1,4),5(1,2)-dibenzenacyclotetradecaphane-10-carboxylate 14,14-dioxide and $2^5$-amino-13-methyl-6-oxa-14-thia-4,10,13-triaza-2(2,6)-pyrazina-1(1,4), 5 (1,2)-dibenzenacyclotetradecaphan-3-one 14,14-dioxide Scheme. Preparation of compounds P(26) and P(27).

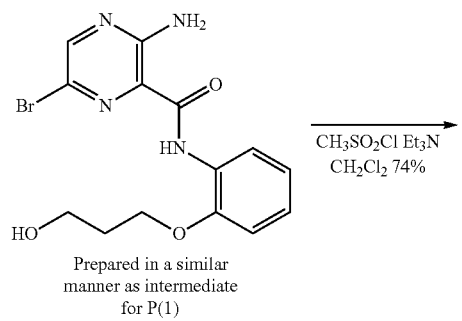

Prepared in a similar manner as intermediate for P(1)

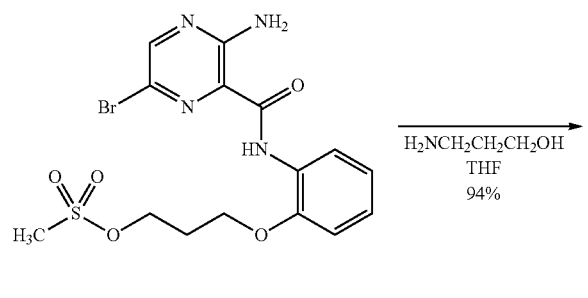

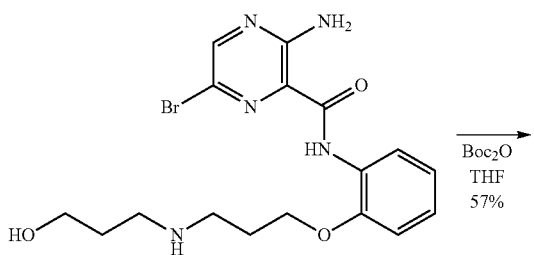

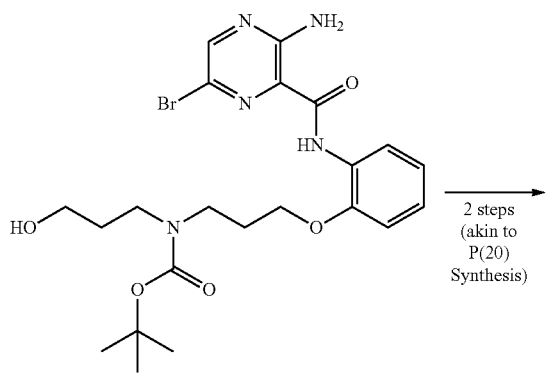

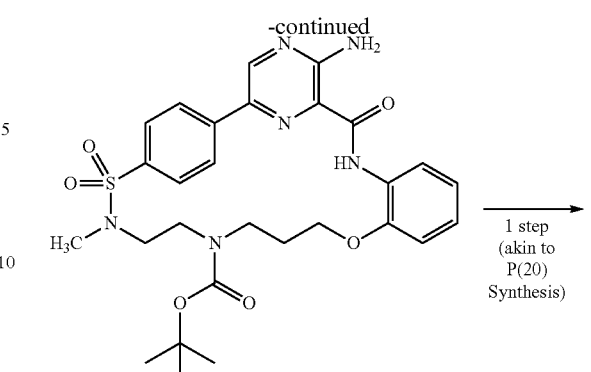

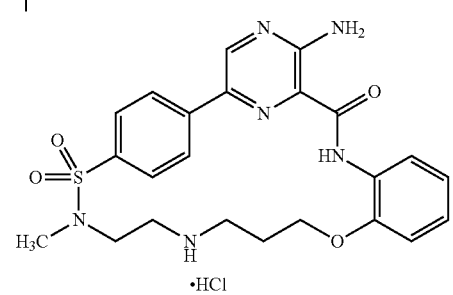

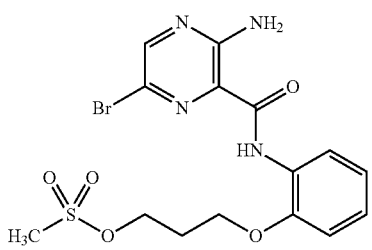

A 0° C. mixture of 3-amino-6-bromo-N-(2-(3-hydroxypropoxy)phenyl)pyrazine-2-carboxamide (2.57 g, 1.5 mmol), prepared in a similar manner as IM10 after substituting the appropriate diol, and triethylamine (1.37 mL, 9.8 mmol) in DCM (150 mL) was treated dropwise with methanesulfonyl chloride (0.65 mL, 8.4 mmol). After 20 minutes the reaction was warmed to room temperature and stirred for 3 days. The reaction mixture was filtered and the solid rinsed liberally with DCM to give 2.30 g (74%) of desired IM18A as a yellow solid. LC/MS (dissolved in DMSO): >95% (M+H=446, with Br pattern, consistent for desired product); TLC: 1:1 EtOAc:Hexane Rf=0.75, homogenous (SM Rf=0.70). IM18A was used for the subsequent step without further manipulation.

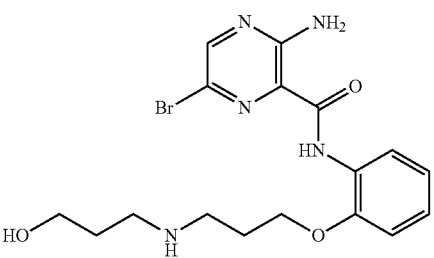

A room temperature solution of IM18A (1.11 g, 2.5 mmol) in THF (100 mL) was combined with 3-amino-1-propanol (4.8 mL, 62.5 mmol), then the flask was sealed and warmed to 55° C. After 3 days the reaction mixture was cooled and concentrated under reduced pressure. The residue was treated with aqueous NaHCO$_3$ and the resulting solid filtered, rinsed liberally with water, and air dried overnight. There remained 1.00 g (94%) of desired IM18B as a yellow solid. LC/MS: >90% (M+H=367, with Br pattern, consistent for desired product). Proceeded and used IM18B for subsequent step without further manipulation.

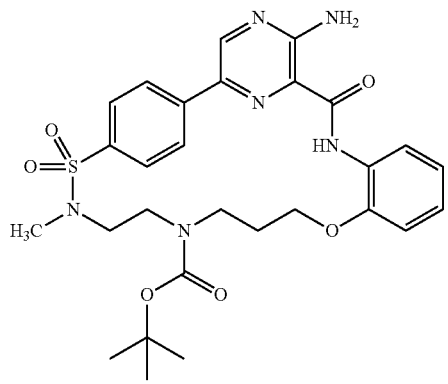 [SMILES: CN1CCN(C(=O)OC(C)(C)C)CCCOc2ccccc2NC(=O)c2nc(cnc2N)-c2ccc(cc2)S1(=O)=O]

P(26): tert-butyl 2$^5$-amino-13-methyl-3-oxo-6-oxa-14-thia-4,10,13-triaza-2(2,6)-pyrazina-1(1,4),5(1,2)-dibenzenacyclotetradecaphane-10-carboxylate 14,14-dioxide

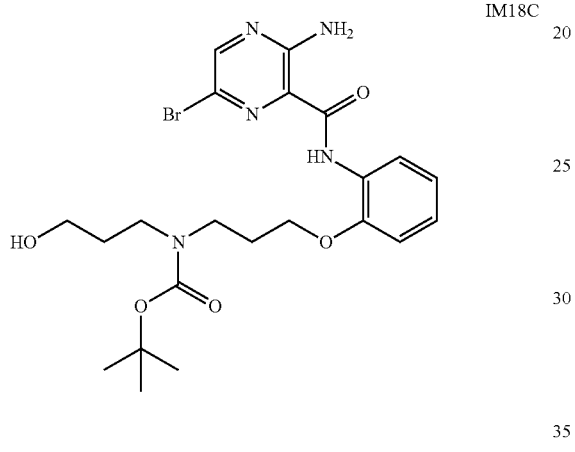

IM18C

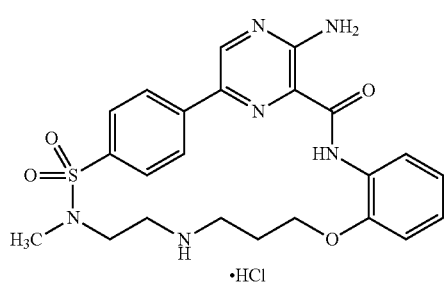 [SMILES: CN1CCNCCCOc2ccccc2NC(=O)c2nc(cnc2N)-c2ccc(cc2)S1(=O)=O ; Cl]

·HCl

Di-tert-butyl dicarbonate (552 mg, 2.53 mmol) in THF (3 mL) was added to a room temperature mixture of IM18B (976 mg, 2.30 mmol) in THF (150 mL). After 25 hours the reaction mixture had become homogenous and was concentrated under reduced pressure to give a copper colored oil. Upon sitting, the oil solidified. The solid was triturated in CH$_3$CN (25 mL) and the solid filtered and rinsed with ice cold CH$_3$CN. Left with 0.69 g (57%) of desired IM18C as a yellow solid. TLC: 1:1 EtOAc:Hexane Rf=0.55. LC/MS (in MeOH/CH$_3$CN): >95% (M+23=547, with Br pattern, consistent with desired product). Proceeded on using IM18C without further manipulation.

P(27): 2$^5$-amino-13-methyl-6-oxa-14-thia-4,10,13-triaza-2(2,6)-pyrazina-1(1,4),5(1,2)-dibenzenacyclo-tetradecaphan-3-one 14,14-dioxide hydrochloride Compounds P(26) and P(27) are prepared similar to compound P(20).

Example 19: tert-butyl 2$^5$-amino-17-methyl-3-oxo-7,10-dioxa-18-thia-4,13,17-triaza-2(2,6)-pyrazina-1(1,4),5(1,3)-dibenzenacyclooctadecaphane-13-carboxylate 18,18-dioxide and 2$^5$-amino-17-methyl-7,10-dioxa-18-thia-4,13,17-triaza-2(2,6)-pyrazina-(1,4),5(1,3)-dibenzenacyclooctadecaphan-3-one 18,18-dioxide Scheme. Preparation of compounds P(30) and P(31).

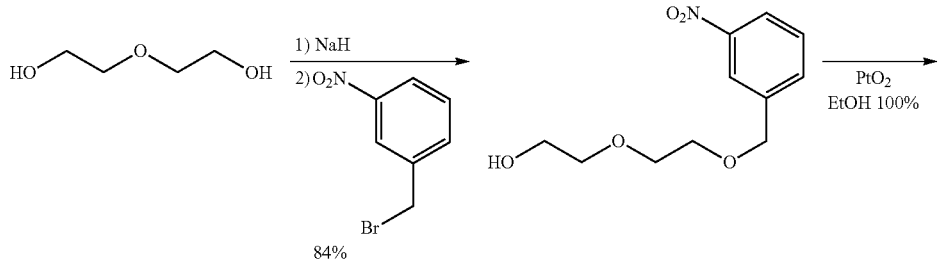

84%

137 138
-continued
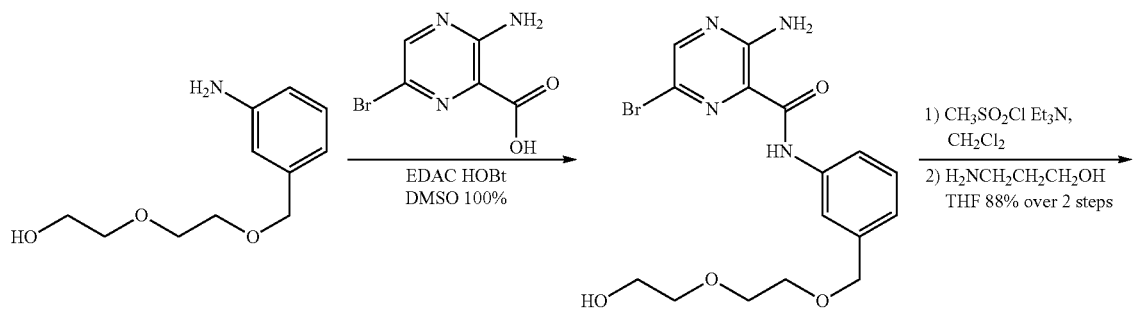
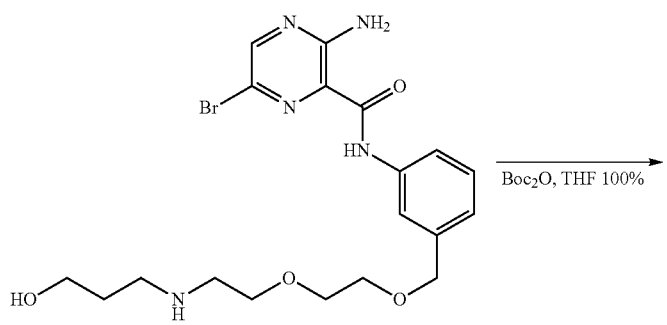
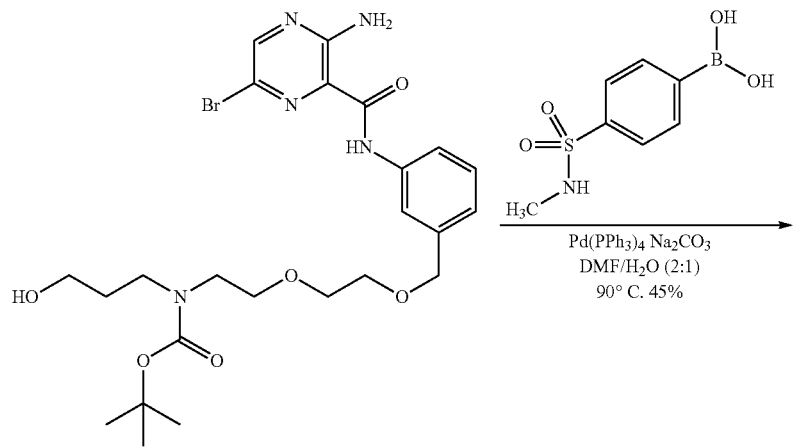
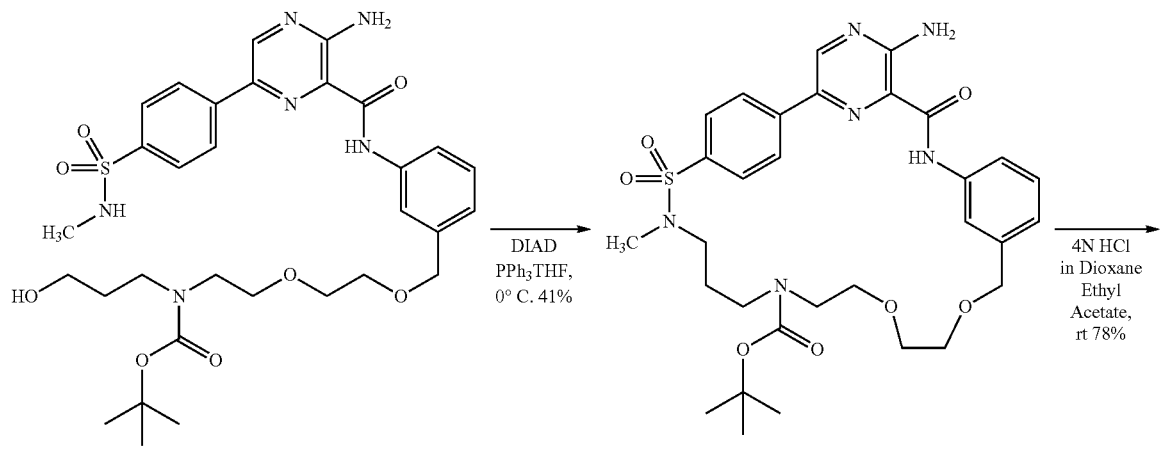

-continued

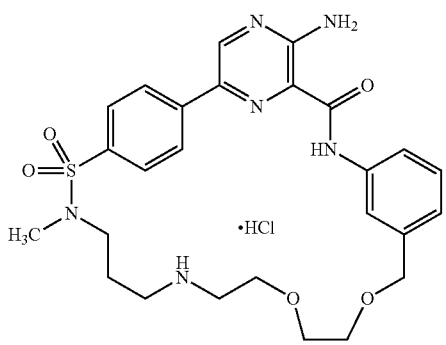

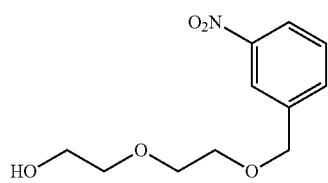

IM19A

To rapidly stirring, room temperature diethylene glycol (45 mL; 0.50 mol), NaH (60% Dispersion in mineral oil; 1.04 g, 26 mmol) was added neat over 2 minutes. A homogeneous solution resulted after gas evolution had ceased, then 3-nitrobenzylbromide (4.32 g, 20 mmol) was added neat. After stirring four days at room temperature, the reaction mixture was diluted with ~300 mL of water and extracted with ~100 mL of hexane. The aqueous phase was then extracted with EtOAc 2× (200 mL and 50 mL respectively). The combined EtOAc extracts were washed with water 3× (~75 mL each), then with brine (50 mL), dried over $Na_2SO_4$, filtered, and concentrated under reduced pressure to give 4.07 g (84%) of desired IM19A as a clear oil. LC/MS: 100% (M+Na=264.1; minor peak for M+H=242.2); TLC: 1:1 EtOAc:Hexane Rf=0.3, homogeneous. Proceeded and used IM19A for subsequent reaction without further manipulation.

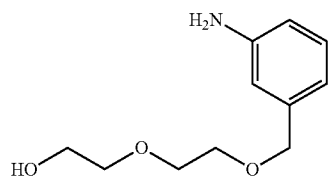

IM19B

A solution of IM19A (1.81 g, 7.5 mmol) in EtOH (100 mL) was combined with $PtO_2$ (113 mg, 0.5 mmol) in a Parr bottle and the resulting mixture was placed under a hydrogen atmosphere (47 psi). After 7 hours the chamber was evacuated of hydrogen and the mixture carefully filtered though Celite 545. The filtrate was concentrated under reduced pressure to give 1.64 g (T.W. 1.58 g) of desired IM19B as a tan solid. LC/MS: major peak (M+H=212.34, with a strong M+23=234.4, consistent with desired product). TLC: 100% EtOAc Rf=0.3, small impurity at Rf=0.15. Proceeded and used IM19B for subsequent reaction without further manipulation.

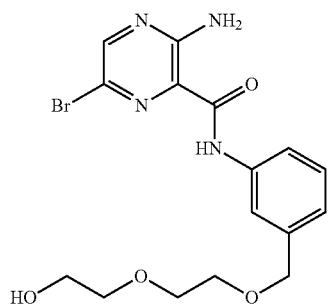

IM19C

EDAC (2.79 g, 14.5 mmol) was added to a stirring, room temperature solution of IM19B (1.48 g, 7 mmol), 3-amino-6-bromopyrazine-2-carboxylic acid (1.27 g, 5.83 mmol), and hydroxybenzotriazole (0.39 g, 2.9 mmol) in DMSO (9 mL). After stirring for 1 day, 50 mL of water was added to the reaction mixture, to give a gooh. This residue was partitioned between EtOAc (2×100 mL) and additional water (50 mL). The combined organic phases were then extracted with saturated aqueous $NaHCO_3$, dried over $Na_2SO_4$, filtered, and concentrated under reduced pressure to give 2.50 g (T.W. 2.40 g) of desired IM19C as a brown oil. TLC: 100% EtOAc Rf=0.55, with slight impurities at Rf=0.75 and Rf=0.9; LC/MS (dissolved in $CH_3CN/MeOH$) >98% (M+H=412, with Br pattern, consistent with desired product, and also a M+23=434, also with Br pattern and also consistent with the desired product). Proceeded and used IM19C for subsequent reaction without further manipulation.

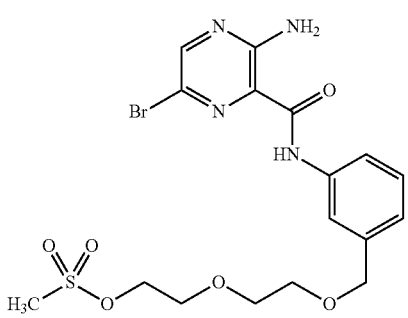

IM19D

A 0° C. solution of IM19C (2.40 g, 5.83 mmol) and triethylamine (1.13 mL, 8.16 mmol) in DCM (60 mL) was treated dropwise with methanesulfonyl chloride (0.54 mL, 7 mmol) over 2 minutes. After 45 minutes the 0° C. reaction solution was treated with 1N HCl (12 mL). After separating the layers, the organic phase was dried over MgSO$_4$, filtered, and concentrated under reduced pressure. There remained 2.92 g (T.W. 2.85 g) of desired IM19D as a yellow oil. TLC: 100% EtOAc Rf=0.8 major spot; LC/MS: one major peak (M+H=490, with Br pattern consistent with desired product). IM19D was used for the subsequent step without further manipulation.

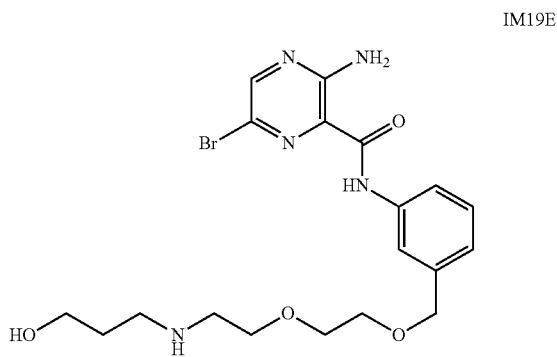 [SMILES: Nc1ncc(Br)nc1C(=O)Nc1cccc(COCCOCCNCCCO)c1]

IM19E

A room temperature solution of IM19D (1.42 g, 2.91 mmol) in THF (11 mL) was combined with 3-amino-1-propanol (5.6 mL, 72.75 mmol), then the flask was sealed and stirred. After 5 days the reaction mixture was concentrated under reduced pressure and the residue was partitioned between EtOAc (40 mL) and saturated aqueous NaHCO$_3$ (30 mL). The aqueous phase was extracted with a second portion of EtOAc (25 mL). The organics were combined, washed 3× with brine (25 mL each), dried over Na$_2$SO$_4$, filtered, and concentrated under reduced pressure to give a bronze oil. This material was placed under high vacuum for ½ hour. There remained 1.19 g (88%) of desired IM19E as a bronze oil. LC/MS: >95% (M+H=469, with Br pattern, consistent for desired product). Proceeded and used IM19E for subsequent step without further manipulation.

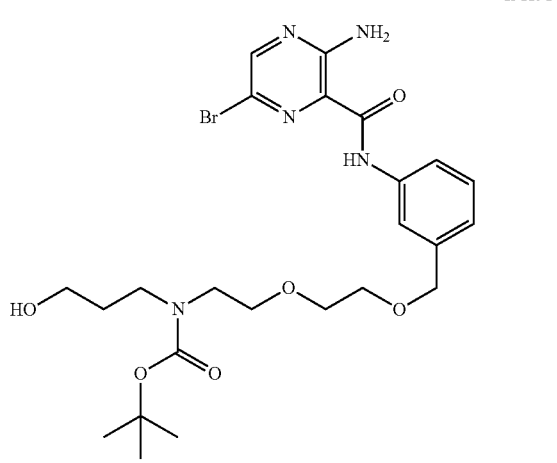

IM19F

Di-tert-butyl dicarbonate (576 mg, 2.64 mmol) in THF (3 mL) was added to a room temperature solution of IM19E (1.12 g, 2.40 mmol) in THF (10 mL). After 2.5 hours the reaction mixture was concentrated under reduced pressure. The residue was partitioned between CH$_2$Cl$_2$ (25 mL) and 1N HCl (25 mL). The organic phase was then washed with saturated aqueous NaHCO$_3$, dried over Na$_2$SO$_4$, filtered, and concentrated under reduced pressure and then dried overnight under high vacuum. Left with 1.40 g (T.W. 1.36 g) of desired IM19F as a yellow oil. TLC: 100% EtOAc: Hexane Rf=0.75; 1:1 EtOAc:Hexane Rf=0.25. LC/MS (in MeOH): >95% (very weak M+H=569, with Br pattern; slightly stronger M+23=591, with Br pattern; very strong base peak at M+H-Boc=469, with Br pattern). Proceeded on using IM19F without further manipulation.

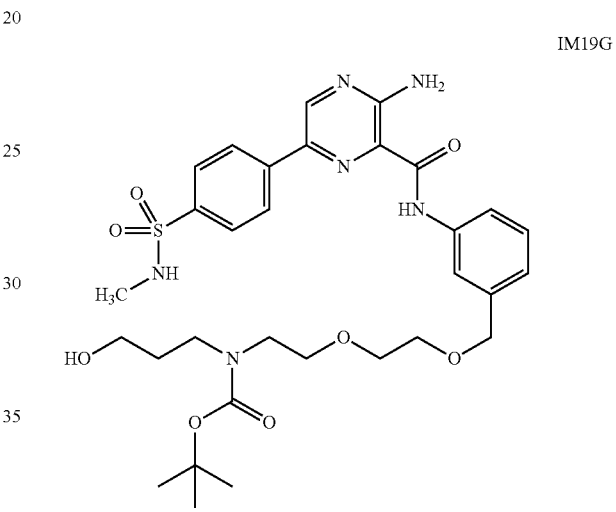

IM19G

In a small pressure reaction vessel a solution of IM19F (284 mg, 0.50 mmol) and methyl 4-boronobenzenesulfonamide (129 mg, 0.60 mmol) in DMF (8 mL) was combined with 2M Na$_2$CO$_3$ (4 mL) and the resulting heterogeneous mixture degassed under a stream of N$_2$ for 3 minutes. Under nitrogen, Pd(PPh$_3$)$_4$ (57 mg, 0.05 mmol) was added and the whole was capped and warmed to 90° C. After 2 hours, heating was discontinued. Once cooled, the heterogeneous mixture was partitioned between EtOAc (2×75 mL) and water (60 mL). The EtOAc extracts were combined, washed again with water (2×25 mL), then with brine (50 mL), dried over Na$_2$SO$_4$, filtered, and concentrated under reduced pressure to yield 510 mg (T.W. 329 mg) of crude product. This crude material was dissolved in EtOAc (1 mL) and adsorbed onto a 12 g Isco column, and eluted with a gradient EtOAc/hexane system (25% EtOAc/hexane to 100% EtOAc over 10 minutes and held at 100% EtOAc for an additional 7 minutes). The purest fractions were combined and concentrated under reduced pressure to give 147 mg (45%) of desired IM19G as a yellow oil. LC/MS: >95% (M+H=659.4, consistent with desired product). TLC: 100% EtOAc Rf=0.7, homogenous. Proceeded on to subsequent step using this material without further manipulation.

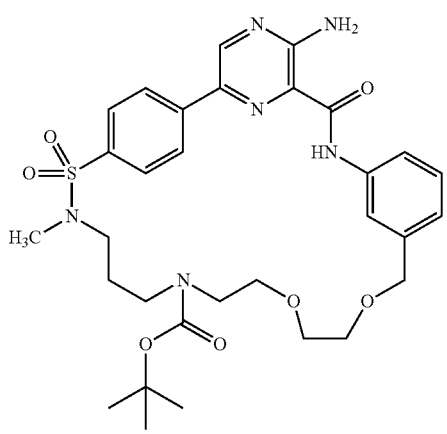 [SMILES: CN1CCCN(C(=O)OC(C)(C)C)CCOCCOCc2cccc(c2)NC(=O)c2nc(cnc2N)-c2ccc(cc2)S1(=O)=O]

P(30): tert-butyl 2⁵-amino-17-methyl-3-oxo-7,10-dioxa-18-thia-4,13,17-triaza-2(2,6)-pyrazina-1(1,4),5(1,3)-dibenzenacyclooctadecaphane-13-carboxylate 18,18-dioxide A room temperature solution of IM19G (132 mg, 0.20 mmol) and triphenylphospine (210 mg, 0.80 mmol) in THF (8 mL) was treated with diisopropyl azodicarboxylate (118 µL, 0.60 mmol). After 3 hours the reaction mixture was concentrated under a stream of nitrogen. The residue was suspended in MeOH (4 mL) and treated with water (0.11 mL, 6 mmol) followed by AcOH (0.165 mL, 3 mmol). This homogenous solution was chilled to 4° C. and held 4 days. The resulting solid was filtered and rinsed 3× with ice cold MeOH (1 mL each). After air drying there remained 74 mg (58%) of crude product as yellow solid. The crude product was dissolved in CH₂Cl₂ (1 mL) and adsorbed onto a 12 g Isco silica gel column. The column was eluted with a gradient of 10% EtOAc/Hexane (hold 1 minute) up to 75% EtOAc/Hexane (12 minutes) and held an extra 4 minutes at 75%. The purest fractions were combined and concentrated under reduced pressure to give 53 mg (41%) of desired P(30) as a yellow solid. TLC: 1:1 EtOAc:Hexane Rf=0.4, homogenous and 100% EtOAc Rf=0.85, homogeneous; LC/MS (DMSO solution): (100%) (M+H=641.4, consistent with desired product). This material was carried onto the subsequent step without further manipulation.

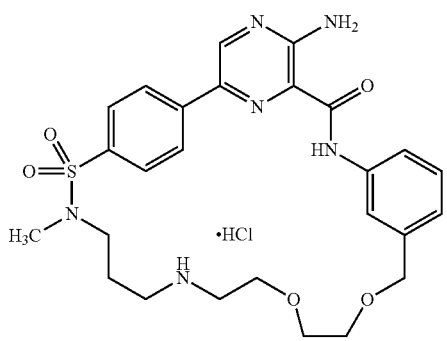 [SMILES: CN1CCCNCCOCCOCc2cccc(c2)NC(=O)c2nc(cnc2N)-c2ccc(cc2)S1(=O)=O ; Cl]

P(31): 2⁵-amino-17-methyl-7,10-dioxa-18-thia-4,13,17-triaza-2(2,6)-pyrazina-1(1,4),5(1,3)-dibenzenacyclooctadecaphan-3-one 18,18-dioxide hydrochloride 4 N HCl in Dioxane (2.5 mL, 10 mmol) was combined with a heterogeneous mixture of P(30) (45 mg, 0.070 mmol) in EtOAc (4 mL), which resulted in the mixture becoming virtually homogenous. After an hour, solid started to precipitate from the reaction mixture. The mixture was stirred for 16 hours. The resulting solid was filtered, rinsed liberally with EtOAc, and then air dried. There remained 32 mg (78%) of desired P(31) as a light yellow solid. LC/MS (DMSO): ~100% (M+H=541.2, consistent with the desired product).

Example 20: 2⁵-amino-15-(2-hydroxyethyl)-5³-((methylamino)methyl)-6,9,12-trioxa-16-thia-4,15-diaza-2(2,6)-pyrazina-1(1,4),5(1,2)-dibenzenacyclohexadecaphan-3-one 16,16-dioxide Scheme. Preparation of compound P(33).

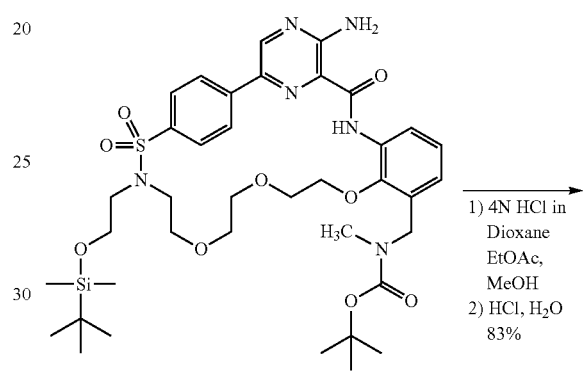

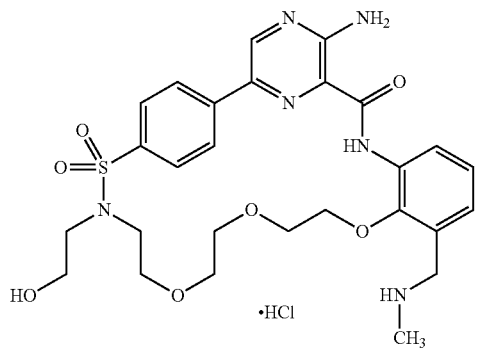

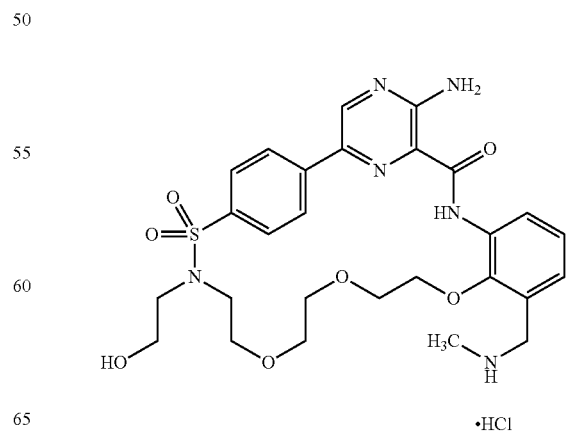

145

P(33): $2^5$-amino-15-(2-hydroxyethyl)-$5^3$-((methylamino)methyl)-6,9,12-trioxa-16-thia-4,15-diaza-2(2,6)-pyrazina-1(1,4),5(1,2)-dibenzenacyclohexadecaphan-3-one 16,16-dioxide hydrochloride A room temperature, homogeneous solution of tert-butyl (($2^5$-amino-15-(2-((tert-butyldimethylsilyl)oxy)ethyl)-16,16-dioxido-3-oxo-6,9,12-trioxa-16-thia-4,15-diaza-2(2,6)-pyrazina-1(1,4),5(1,2)-dibenzenacyclohexadecaphane-$5^3$-yl)methyl)(methyl)carbamate, (IM20), (32 mg, 0.04 mmol), prepared in a similar manner as IM9 after substituting the appropriate boronic acid coupled with IM15A, in ethyl acetate (1.2 mL) was treated with 4N HCl in dioxane (700 µL, 2.8 mmol). An intense yellow color resulted and no appreciable exotherm was noted. Solid started to precipitate after 5 minutes. The reaction mixture was then stirred 16 hours, after which the fine solid was collected and rinsed liberally with EtOAc. After air drying 23 mg (92%) of crude product was collected. This material was dissolved in water (~3 mL) and treated with concentrated HCl (250 µL). Again, solid started to crash out and this mixture was stirred at room temperature. After 2 days and additional portion of concentrated HCl (500 µL) was added to the reaction mixture and stirring was continued. After 24 hours the mixture was cooled in an ice bath, the solid filtered off and rinsed with EtOAc. There remained 14 mg of desired P(33) as a yellow solid. LC/MS: >98% (M+H=587.3, consistent with desired product).

Example 21: $2^5$-amino-$5^3$-((methylamino)methyl)-15-(2-morpholinoethyl)-6,9,12-trioxa-16-thia-4,15-diaza-2(2,6)-pyrazina-1(1,4),5(1,2)-dibenzenacyclohexadecaphan-3-one 16,16-dioxide and $2^5$-amino-15-(2-(dimethylamino)ethyl)-$5^3$-((methylamino)methyl)-6,9,12-trioxa-16-thia-4,15-diaza-2(2,6)-pyrazina-1(1,4),5(1,2)-dibenzenacyclohexadecaphan-3-one 16,16-dioxide

146

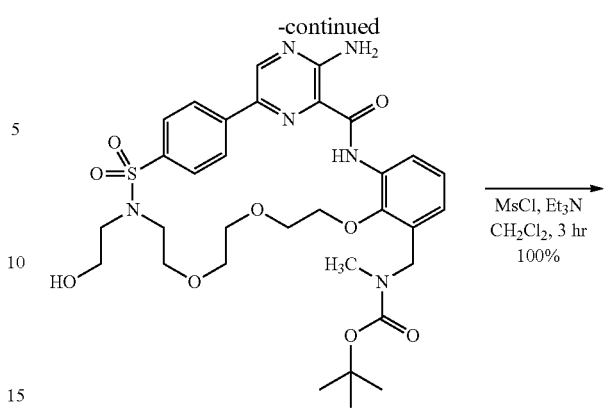

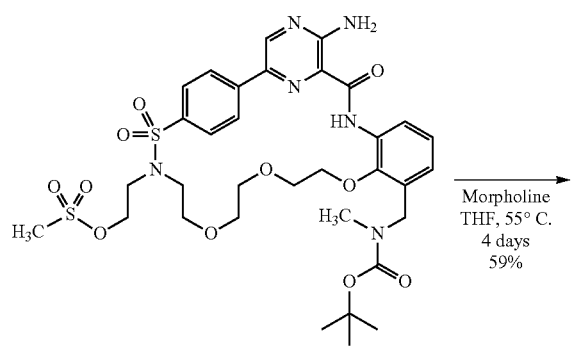

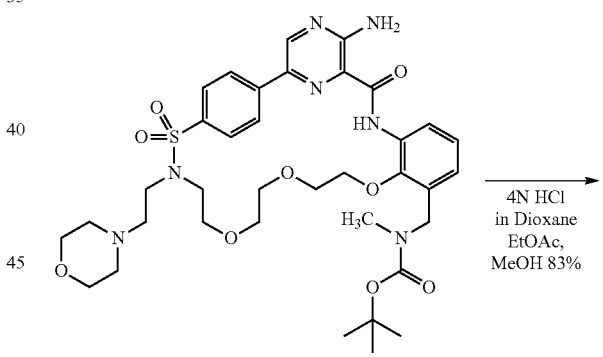

Scheme. Preparation of compound P(34).

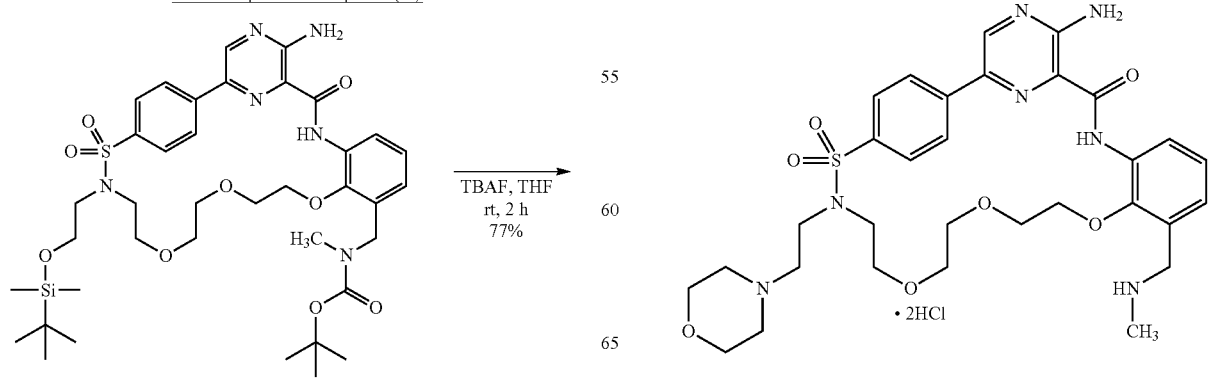

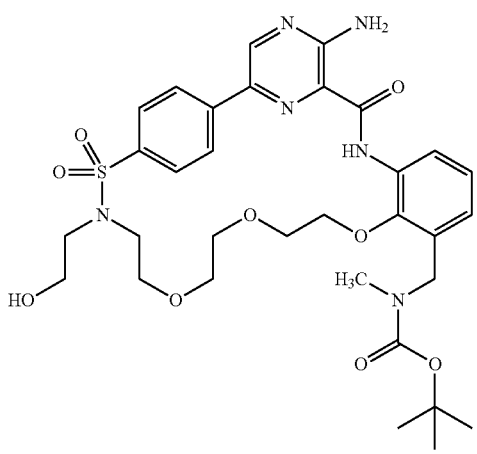

IM21A

A solution of TBAF (1M in THF; 1.1 equivalents) was added dropwise to a stirring, room temperature solution of tert-butyl ((2⁵-amino-15-(2-((tert-butyldimethylsilyl)oxy)ethyl)-16,16-dioxido-3-oxo-6,9,12-trioxa-6-thia-4,15-diaza-2(2,6)-pyrazina-1(1,4),5(1,2)-dibenzenacyclohexadecaphane-5³-yl)methyl)(methyl)carbamate, (IM20), (60 mg, 0.075 mmol), prepared in a similar manner as IM9 after substituting the appropriate boronic acid coupled with IM15A, in THF (1.5 mL). After 2 hours the reaction solution was concentrated under a stream of nitrogen. The residue was mixed with water (5 mL) and cooled to 4° C. After 4 days the resulting yellow solid was filtered and rinsed liberally with water, then air dried. There remained 40 mg (77%) of desired IM21A as a yellow solid. LC/MS: (~98%) (M+H=687.5, consistent with desired product); TLC: 100% EtOAc Rf=0.65. Proceeded and used IM21A for subsequent step without further manipulation.

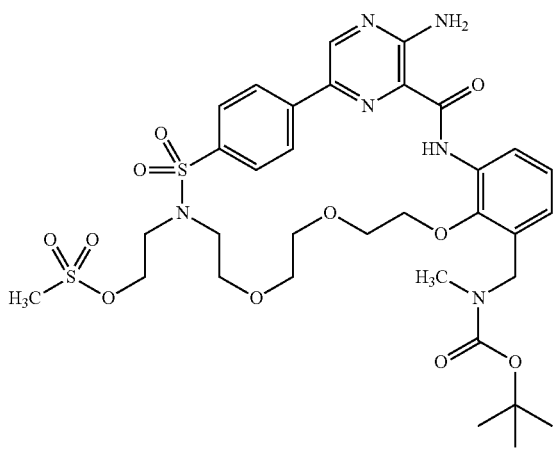

IM21B

A 0° C. solution of IM21A (40 mg, 0.058 mmol) and triethylamine (11.3 μL, 0.081 mmol) in DCM (1 mL) was treated with methanesulfonyl chloride (5.4 μL, 0.07 mmol) over 2 minutes. After 5 minutes the reaction mixture was warmed to room temperature. After two 45 minute intervals, two additional portions of triethylamine (22.6 μL, 0.162 mmol and 11.3 μL, 0.081 mmol respectively) and methanesulfonyl chloride (10.8 μL, 0.14 mmol and 5.4 μL, 0.07 mmol respectively) were added to the reaction mixture (to push the reaction to completion). After then treating the reaction mixture with 1N HCl (1 mL), the layers were separated, the organic phase was dried over MgSO₄, filtered, and concentrated under reduced pressure. There remained 49 mg (T.W. 44 mg) of desired IM21B as a yellow oil. TLC: 100% EtOAc Rf=0.8, homogeneous; LC/MS (dissolved in CH₃CN): >98% (M+H=765.5, consistent with desired product). IM21B was used for the subsequent step without further manipulation.

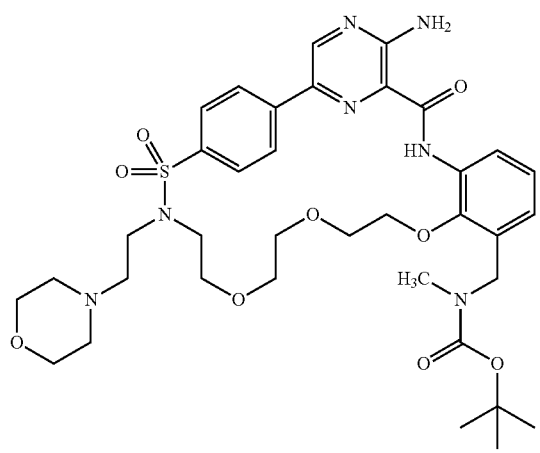

IM21C

A room temperature solution of IM21B (22 mg, 0.029 mmol) in THF (1 mL) was combined with morpholine in portions (142 μL, 1.62 mmol), then the flask was sealed and warmed to 55° C. After 4 days the reaction mixture was concentrated under a stream of nitrogen and the residue was treated with saturated aqueous NaHCO₃ (~¾ mL). A solid precipitated and the mixture was stirred for 2 hours. The resulting solid was filtered and rinsed liberally with water. After air drying there remained 21 mg of crude product. This material was triturated with a small amount of ice cold MeOH and the resulting solid was filtered and rinsed with a small amount of ice cold MeOH. After air drying there remained 13 mg (59%) of desired IM21C as a yellow solid. LC/MS: >95% (M+H=756.4, consistent with desired product), ~2% (M+H=656.4, consistent with Boc deprotected of product, which is fine, as that will be the final target product). Proceeded and used IM21C for subsequent step without further manipulation.

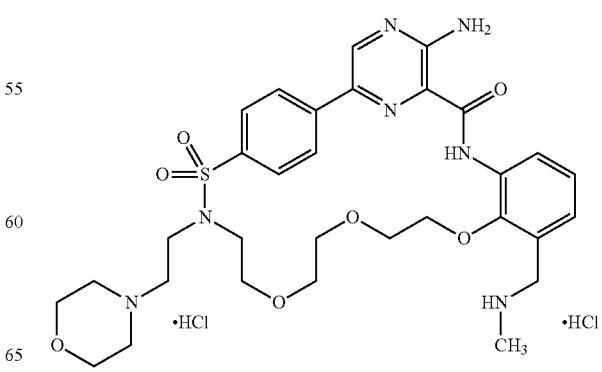

P(34): $2^5$-amino-$5^3$-((methylamino)methyl)-15-(2-morpholinoethyl)-6,9,12-trioxa-16-thia-4,15-diaza-2(2,6)-pyrazina-1(1,4),5(1,2)-dibenzenacyclohexadecaphan-3-one 16,16-dioxide dihydrochloride 4 N HCl in Dioxane (175 µL, 0.7 mmol) was combined with a heterogeneous mixture of IM21C (8 mg, 0.010 mmol) in EtOAc (0.35 mL), which resulted in the mixture becoming gummy. To help dissolution, added 130 µL of MeOH, which helped considerably. After an hour, solid started to precipitate from the reaction mixture. The mixture was stirred for 16 hours. The reaction mixture was then treated with 1.5 mL of EtOAc and stirred for 15 minutes. The resulting solid was filtered, rinsed liberally with EtOAc, and then air dried. There remained 5.8 mg (83%) of desired P(34) as a yellow solid. LC/MS (dissolved in water): >95% (M+H=656.4, consistent with the desired product).

P(35): $2^5$-amino-5-(2-(dimethylamino)ethyl)-$5^3$-((methylamino)methyl)-6,9,12-trioxa-16-thia-4,15-diaza-2(2,6)-pyrazina-1(1,4),5(1,2)-dibenzenacyclohexadecaphan-3-one 16,16-dioxide dihydrochloride The dimethylamine analog P(35) was made in a similar manner to morpholine analog P(34).

Example 22: $2^5$-amino-16-methyl-7,10,13-trioxa-17-thia-4,16-diaza-2(2,6)-pyrazina-1(1,4),5(1,3)-dibenzenacycloheptadecaphan-3-one 17,17-dioxide Scheme. Preparation of compound P(40).

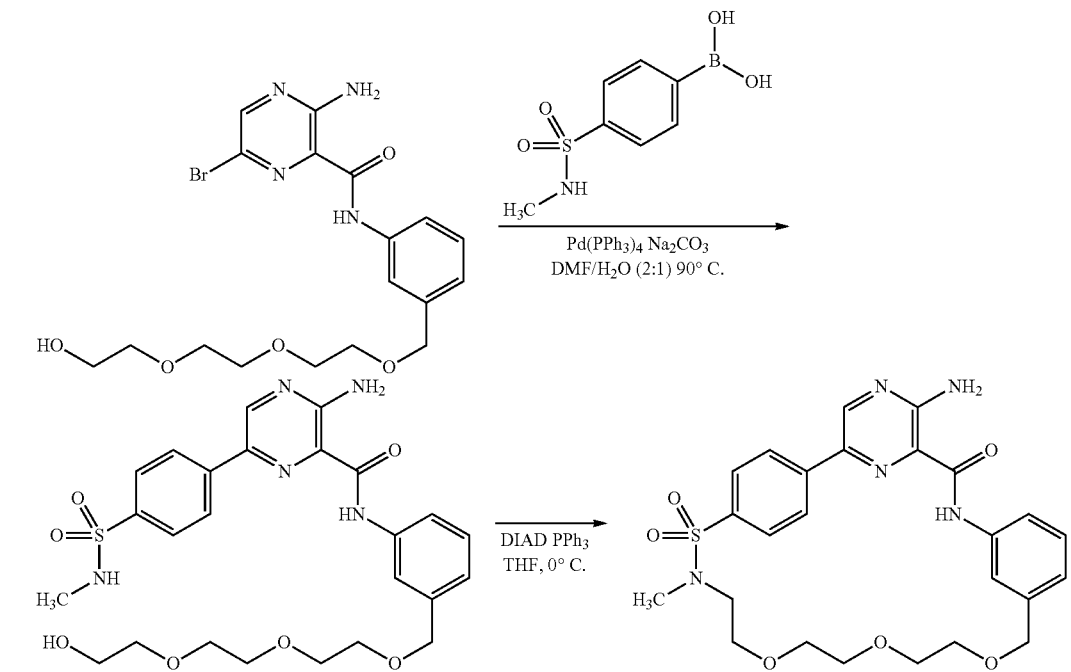

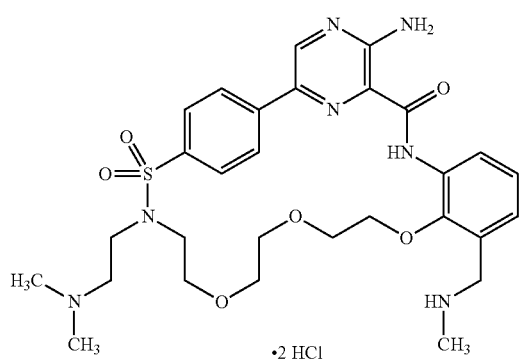 [SMILES: CNCc1cccc2c1OCCOCCOCCN(CCN(C)C)S(=O)(=O)c1ccc(cc1)-c1cnc(N)c(n1)C(=O)N2 ; "·2 HCl"]

A solution of 3-amino-6-bromo-N-(3-((2-(2-(2-hydroxyethoxy)ethoxy)ethoxy)methyl)phenyl)pyrazine-2-carboxamide (455 mg, 1 mmol), prepared in a similar manner as IM19C, and methyl 4-boronobenzenesulfonamide (258 mg, 1.2 mmol) in DMF (16 mL) was combined with 2M $Na_2CO_3$ (8 mL) and the resulting heterogeneous mixture degassed under a stream of $N_2$ for 3 minutes. Under nitrogen, Pd(PPh$_3$)$_4$ (116 mg, 0.10 mmol) was added and the whole was capped and warmed to 90° C. After 2.5 hours, heating was discontinued. Once cooled, the heterogeneous mixture was partitioned between EtOAc (2×50 mL) and water (20 mL). The EtOAc extracts were combined, washed again with water (3×40 mL), then with brine, dried over Na$_2$SO$_4$, filtered, and concentrated under reduced pressure to give 610 mg of crude product. The crude material was loaded onto a 12 g column after dissolving most of oil in ~3 mL of EtOAc, then set on Isco eluting with a gradient system starting with 90% EtOAc/Hexane and running out to 100% EtOAc (2 minutes) and held at 100% for an additional 10 minutes. The purest fractions were combined and concentrated under reduced pressure to give 310 mg (57%) of desired IM22A as a tan oil. LC/MS of 149B: (dissolved in MeOH/CH$_3$CN): >95% (M+H=546.3, consistent with desired product); TLC: 100% EtOAc Rf=0.25, homogeneous. Proceeded and used IM22A for subsequent reaction without further manipulation.

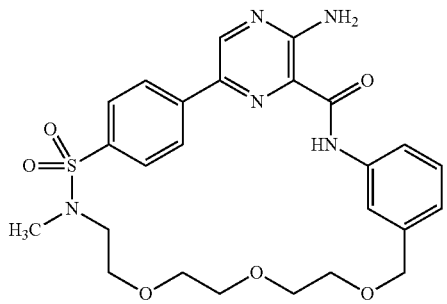 [SMILES: CN1CCOCCOCCOCc2cccc(c2)NC(=O)c2nc(cnc2N)-c2ccc(cc2)S1(=O)=O]

P(40): 2$^5$-amino-16-methyl-7,10,13-trioxa-17-thia-4,16-diaza-2(2,6)-pyrazina-1(1,4),5(1,3)-dibenzenacycloheptadecaphan-3-one 17,17-dioxide A 0° C. solution of IM22A (300 mg, 0.55 mmol) and triphenylphospine (577 mg, 2.2 mmol) in THF (15 mL) was treated with diisopropyl azodicarboxylate (325 µL, 1.65 mmol). After 15 minutes the cooling bath was removed and the reaction warmed to room temperature. After 3 hours the reaction mixture was concentrated under reduced pressure. The residue was partitioned between EtOAc and saturated aqueous NaHCO$_3$. The organic phase was dried over Na$_2$SO$_4$, filtered and concentrated to give an orange residue. The orange residue was suspended in MeOH (10 mL) and then treated with 99 µL of water (10 equivalents; 5.5 mmol) followed by 126 µL of AcOH (4 equivalents; 2.2 mmol) and the mixture left stirring at room temperature. After 3 days the resulting solid was filtered and rinsed liberally with MeOH, and air dried. There remained 113 mg (39%) of desired P(40) as a yellow solid. LC/MS (dissolved in DMSO): (M+H=528.2, consistent with desired product).

Cellular Assays for Evaluation of ATR Kinase Inhibition and Selectivity

Example 23: Phenotypical Evaluation of ATR Inhibition

It is known that inhibition of ATR in cells under replicative stress stalls DNA replication, which prevents cells from progressing through S-phase, leading to an accumulation of cells in this cell cycle phase (Kevin D. Smith, et al., Tim-Tipin dysfunction creates an indispensable reliance on the ATR-Chk1 pathway for continued DNA synthesis, *J. Cell Biol.* 2009, 187, 15-23). In the present experiment Jurkat cells were treated with 0.2 µM aphidicolin to induce replication stress in the presence of test compounds, at concentrations ranging from 10 µM to 0.1 µM, for 24 hours. Cells were fixed and cell-cycle profiles examined by flow cytometry as in Smith, J. Cell Bio. 2009. Test compounds were considered active if stalling of the cells in S-phase was observed.

Exemplary compound P(1) demonstrated significant inhibition of cell cycle progression by accumulation of cells in S-phase at concentrations of 10 µM, 2.5 µM, and 1.25 µM (FIGS. 1, 2, and 3A respectively). Testing compound IM11 at 1.25 µM (FIG. 3B) exemplifies a normal cell-cycle profile and thus is considered inactive at this dose.

Exemplary compound P(4) at a concentration of 300 nM showed a similar phenotypical response to that seen upon genetic knock-down of ATR when combined with replicative stress (FIG. 4A) of Smith (Kevin D. Smith, et al., Tim-Tipin dysfunction creates an indispensable reliance on the ATR-Chk1 pathway for continued DNA synthesis, *J. Cell Biol.* 2009, 187, 15-23).

Example 24: ATR Cellular Kinase Activity and Selectivity

Chk1 phosphorylation, ATR's primary downstream target, is used as a read-out for ATR activity (Liu Q. et al., Chk1 is an essential kinase that is regulated by Atr and required for the G(2)/M DNA damage checkpoint, *Genes Dev.* 2000, June 15, 14(12), 1448-1459; and (Jia Li and David F. Stern, Regulation of CHK2 by DNA-dependent Protein Kinase, *J. Biol. Chem.* 2005, 280, 12041-12050). Chk2 phosphorylation (stimulated by 5 Gy irradiation), is a marker of ATM and DNA-PKcs activity, which together with ATR are closely related DNA-damage responsive PIKK family kinases (Shuhei Matsuoka et al., Ataxia telangiectasia-mutated phosphorylates Chk2 in vivo and in vitro, *Proceedings of the National Academy of Sciences of the USA*, 2000, 97(19), 10389-10394; Li J and Stern D F, Regulation of CHK2 by DNA-dependent protein kinase. *The Journal of biological chemistry*, 2005, 280, 12041-12050).

ATR Kinase Activity:

HCT119 WT BCL/XL-GFP cells were incubated with decreasing concentrations of test compounds (10-0.003 µM) and 5 µM aphidicolin for 4 hours prior to lysis. Cell lysis and western blotting were performed as in Gilad, Cancer Res, 2010, using the following antibodies as per manufacturers' instructions: pCHK1 (Ser345) (Cell signaling 133D3), pH2AX (S 139) (Millipore 05636), GAPDH (loading control, Chemicon MAB374), and MCM3 (loading control, Santa Cruz sc-9850). Test compounds were considered active if significant inhibition of Chk1 phosphorylation was observed.

ATR Kinase Selectivity:

HCT119 WT BCL/XL-GFP cells were incubated with decreasing concentrations of test compounds (5-0.01 µM) alone for 30 minutes followed by 5 Gy irradiation and cell lysis 20 minutes post irradiation. Cell lysis and western blotting were performed as in Gilad, Cancer Res, 2010, using the following antibodies as per manufacturers' instructions: pChk2 (T68) (Cell Signaling 2661S), GAPDH (loading control, Chemicon MAB374), and MCM3 (loading control, Santa Cruz sc-9850). Test compounds were considered ATR selective if significantly less inhibition of Chk2 phosphorylation was observed relative to Chk1 phosphorylation.

ATR Kinase Activity:

Exemplary compound P(4) completely inhibited Chk1 phosphorylation at concentrations of 1 µM and above, and was able to limit phosphorylation of Chk1 at doses as low as 30 nM (FIG. 4B). Concomitant with decreased Chk1 phosphorlation, inhibition of ATR activity leads to an increase in DNA double strand breaks as detected by increased H2AX phosphorylation (FIG. 4B).

ATR Kinase Selectivity:

Exemplary compound P(4) did not affect levels of Chk2 phosphorylation (stimulated by 5 Gy irradiation) (FIG. 4C).

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

All references, including publications, patent applications, and patents, cited herein are hereby incorporated by reference to the same extent as if each reference were individually and specifically indicated to be incorporated by reference and were set forth in its entirety herein.

We claim:

1. A macrocyclic compound having the structure of Formula (A) or a pharmaceutically acceptable salt thereof:

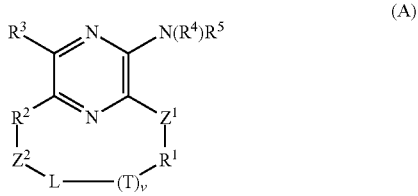

wherein:
$R^1$ and $R^2$ are phenyl independently optionally substituted by 1, 2, 3, or 4 substituents, as permitted;
$Z^1$ and $Z^2$ are, independently, —SO—, —SO$_2$—, —S(=O)N(R$^6$)—, —S(=O)C(R$^7$)(R$^6$), —S(=O)$_2$N(R$^6$)—, —S(=O)$_2$C(R$^7$)(R$^6$)—, —C(=O)—, —C(=O)N(R$^6$)—, —C(=O)C(R$^7$)(R$^6$), —C(S)C(R$^7$)(R$^6$)— or —C(S)N(R$^6$)—;

$R^6$ and $R^7$ are, independently, hydrogen, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted with a substituent;
v is an integer which is 1 or 0;
T is —CH$_2$—, —NH—, —S—, or —O—;
L is an aliphatic chain having at least two contiguous carbon atoms, wherein L is interrupted by one or more —O—, —S—, —N(R$^g$)—,

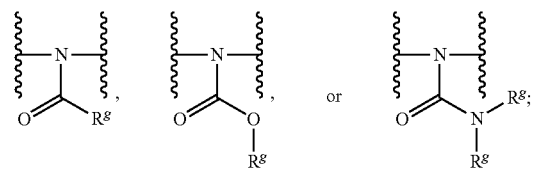

each $R^g$ is, independently, hydrogen, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl, is optionally substituted by one or more suitable substituents;
L-(T)$_v$ is a chain having at most 25 atoms in length; and
each $R^3$, $R^4$ and $R^5$ is, independently, hydrogen, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted by one or more suitable substituent.

2. The macrocyclic compound of claim 1, wherein $Z^1$ is —C(=O)N(R$^6$)—.

3. The macrocyclic compound of claim 1, wherein $Z^2$ is —S(=O)$_2$N(R$^6$)—.

4. The macrocyclic compound of claim 1, wherein:
$Z^2$ is —S(=O)$_2$N(R$^6$)—; and
$Z^1$ is —C(=O)N(R$^6$)—.

5. The macrocyclic compound of claim 1, wherein L is an aliphatic chain having at least 3 contiguous carbon atoms.

6. The macrocyclic compound of claim 1, wherein $R^3$, $R^4$, and $R^5$ are each H.

7. The macrocyclic compound of claim 1, wherein:
$Z^1$ is —C(=O)N(R$^6$); and
$Z^2$ is —C(=O)N(R$^6$), —S(O)$_2$—, or —S(=O)$_2$N(R$^6$).

8. The macrocyclic compound of claim 7, wherein each $R^6$ is independently H, alkyl, or substituted alkyl.

9. The compound of claim 1, wherein $R^6$ is hydrogen, alkyl, alkenyl, or alkynyl.

10. The compound of claim 1, wherein L is a chain of at least 4 contiguous carbon atoms in length.

11. The compound of claim 1, wherein L is an alkylene chain one or more times interrupted with a heteroatom which is O, S, or N, r P.

12. The compound of claim 1, wherein L is a polyalkylene oxide.

13. The compound of claim 12, wherein L is a polyethylene oxide, polypropylene oxide, polybutylene oxide, or a mixture thereof.

14. The macrocyclic compound of claim 1, having the structure of Formula (B1) or a pharmaceutically acceptable salt thereof:

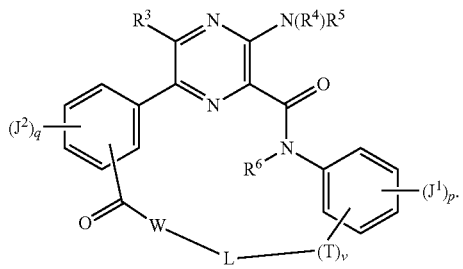

wherein:
W is C(R$^7$)(R$^6$), S, or NR$^7$; and
J$^1$ and J$^2$ are, independently, hydrogen, hydroxy, halogen, cyano, trifluoromethyl, trifluoromethoxy, nitro, trimethylsilanyl, —OR$^a$, —SR$^a$, —OC(O)R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$, —N(R$^a$)S(O)$_2$R$^a$, —S(O)OR$^a$, —S(O)$_2$OR$^a$, —S(O)N(R$^a$)$_2$, —S(O)$_2$N(R$^a$)$_2$, PO$_3$(R$^a$)$_2$, alkyl, alkenyl, alkynyl, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted by one or more suitable substituent;
each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, each being optionally substituted by one or more suitable substituent; and
p and q are, independently, an integer of 1 to 4.

15. The macrocyclic compound of claim 1, having the structure of Formula (B2) or a pharmaceutically acceptable salt thereof:

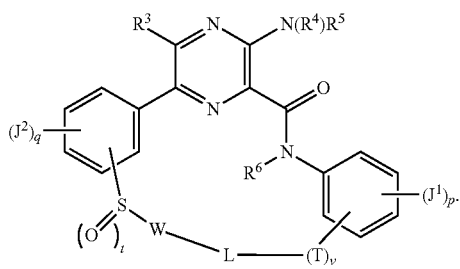

wherein:
W is C(R$^7$)(R$^6$), S, or NR$^7$;
t is an integer of 1 or 2;
each J$^1$ and J$^2$ are, independently, hydrogen, hydroxy, halogen, cyano, trifluoromethyl, trifluoromethoxy, nitro, trimethylsilanyl, —OR$^a$, —SR$^a$, —OC(O)R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_2$R$^a$, —N(R$^a$)S(O)$_2$R$^a$, —S(O)OR$^a$, —S(O)$_2$OR$^a$, —S(O)N(R$^a$)$_2$, —S(O)$_2$N(R$^a$)$_2$, PO$_3$(R$^a$)$_2$, alkyl, alkenyl, alkynyl, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted by one or more suitable substituent;
each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, being optionally substituted by one or more suitable substituent; and
p and q are, independently, an integer of 1 to 4.

16. The macrocyclic compound of claim having the structure of Formula (B3) or a pharmaceutically acceptable salt thereof:

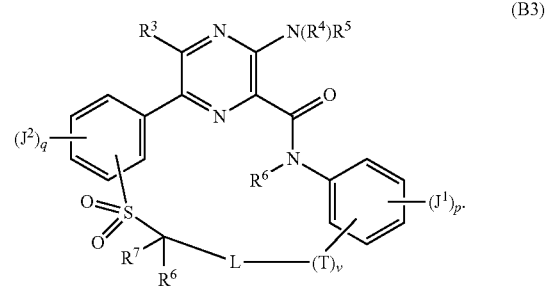

17. The macrocyclic compound of claim 1, having the structure of Formula (B6) or a pharmaceutically acceptable salt thereof:

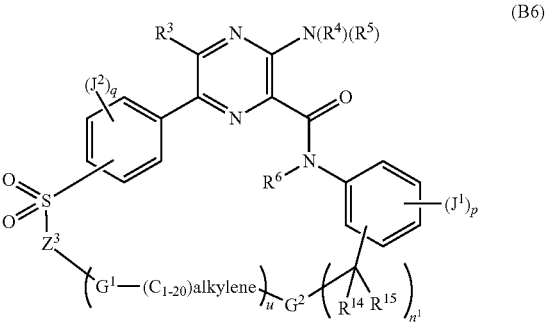

wherein:
Z$^3$ is

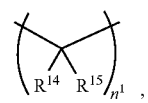

a covalent bond or G$^3$-(C$_{1-20}$)alkylene;
each G$^1$, G$^2$, and G$^3$ is, independently, N(R$^{14}$), —O—, —S—, sulfoxide, or sulfone;
each n' and u is, independently, an integer of 1 to 20;
each R$^{14}$ and R$^{15}$ is hydrogen, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted by one or more suitable substituent;

each $J^1$ and $J^2$ is, independently, hydrogen, hydroxy, halogen, cyano, trifluoromethyl, trifluoromethoxy, nitro, trimethylsilanyl, —$OR^a$, —$SR^a$, —$OC(O)R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_rR^a$, —$N(R^a)S(O)_2R^a$, —$S(O)OR^a$, —$S(O)_2OR^a$, —$S(O)N(R^a)_2$, —$S(O)_2N(R^a)_2$, $PO_3(R^a)_2$, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted by one or more suitable substituent;

each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl; and p and q are, independently, an integer of 1 to 4.

18. The macrocyclic compound of claim 15, having the structure of Formula (B6.1) or a pharmaceutically acceptable salt thereof:

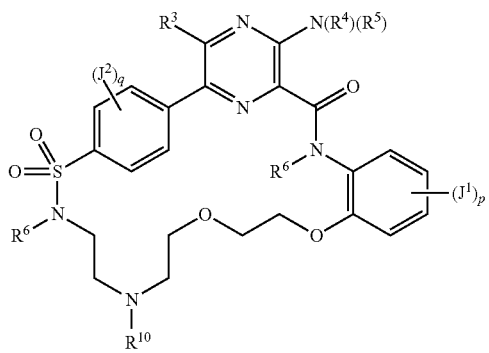
(B6.1)

wherein, $R^{10}$ is hydrogen, —$C(O)R^{10a}$, —$C(O)OR^{10a}$, —$C(O)N(R^{10a})_2$, alkyl, alkenyl, alkynyl, cycloalkyl, cycloalkenyl, heterocyclyl, aryl, heteroaryl, aralkyl, or heteroaralkyl; and $R^{10a}$ is hydrogen, alkyl, alkenyl, alkynyl, cycloalkyl, cycloalkenyl, heterocyclyl, aryl, heteroaryl, aralkyl, or heteraralkyl.

19. The macrocyclic compound of claim 17, having the structure of Formula (B6.2) or a pharmaceutically acceptable salt thereof:

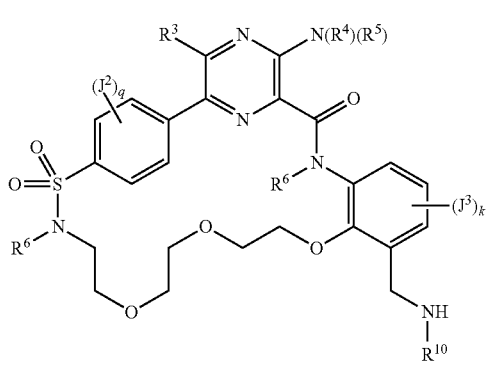
(B6.2)

wherein:
$R^{10}$ is hydrogen, —$C(O)R^{10a}$, —$C(O)OR^{10a}$, —$C(O)N(R^{10a})_2$, alkyl, alkenyl, alkynyl, cycloalkyl, cycloalkenyl, heterocyclyi, aryl, heteroaryl, aralkyl, or heteroaralkyl;

$R^{10a}$ is hydrogen, alkyl, alkenyl, alkynyl, cycloalkyl, cycloalkenyl, heterocyclyl, aryl, heteroaryl, aralkyl, or heteraralkyl;

$J^3$ is hydrogen, hydroxy, halogen, cyano, trifluoromethyl, trifluoromethoxy, nitro, trimethylsilanyl, —$OR^a$, —$SR^a$, —$OC(O)R^a$, —$N(R^a)_2$, —$C(O)R^a$, —$C(O)OR^a$, —$OC(O)N(R^a)_2$, —$C(O)N(R^a)_2$, —$N(R^a)C(O)OR^a$, —$N(R^a)C(O)R^a$, —$N(R^a)C(O)N(R^a)_2$, $N(R^a)C(NR^a)N(R^a)_2$, —$N(R^a)S(O)_rR^a$, —$N(R^a)S(O)_2R^a$, —$S(O)OR^a$, —$S(O)_2OR^a$, —$S(O)N(R^a)_2$, —$S(O)_2N(R^a)_2$, $PO_3(R^a)_2$, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted by one or more suitable substituent; and k is an integer of 1, 2, or 3.

20. The macrocyclic compound of claim 1, having the structure of Formula (B7) or a pharmaceutically acceptable salt thereof:

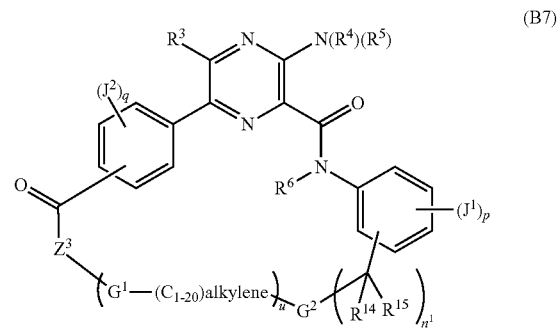
(B7)

wherein:
$Z^3$ is

, a covalent bond or $G^3$-$(C_{1-20})$alkylene;

each $G^1$, $G^2$, and $G^3$ is, independently, $N(R^{14})$, —O—, —S—, sulfoxide, or sulfone;

each $n^1$ and u is, independently, an integer of 1 to 20;

each $R^{14}$ and $R^{15}$ is hydrogen, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted by one or more suitable substituent;

each $J^1$ and $J^2$ is, independently, hydrogen, hydroxy, halogen, cyano, trifluoromethyl, trifluoromethoxy, nitro, trimethylsilanyl, —$OR^a$, $SR^a$, —$OC(O)R^a$, —$N(R^a)_2$, —$C(O)R^a$, —$C(O)OR^a$, —$OC(O)N(R^a)_2$, —$C(O)N(R^a)_2$, —$N(R)C(O)OR^a$, —$N(R^a)C(O)R^a$, —$N(R^a)C(O)N(R^a)_2$, $N(R^a)$ $C(NR^a)N(R^a)_2$, —$N(R^a)S(O)_rR^a$, —$N(R^a)S(O)_2R^a$, —$S(O)OR^a$, —$S(O)_2OR^a$, —S(O)N(R$^a$)$_2$, —S(O)$_2$N(R$^a$)$_2$, or PO$_2$(R$^a$)$_2$, alkyl, alkenyl, alkynyl, cycloalkyl, cycloalkenyl, heterocyclyl, aryl, heteroaryl, aralkyl, or heteroaralkyl, wherein each alkyl; alkenyl, alkynyl, cycloalkyl, cycloalkenyl, heterocyclyl, aryl, heteroaryl, aralkyl, or heteroaralkyl is optionally substituted by one or more suitable substituent;

each R$^a$ is, independently, hydrogen, alkyl, haloalkyl, carbocyclyl, carbocyclylalkyl, aryl, aralkyl, heterocycloalkyl, heterocycloalkylalkyl, heteroaryl or heteroarylalkyl; and p and q are, independently, an integer of 1 to 4.

21. The macrocyclic compound of claim 1, having the structure of Formula (B8) or a pharmaceutically acceptable salt thereof:

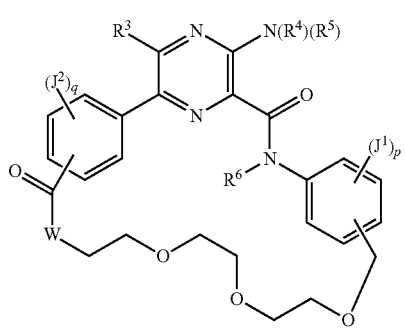

(B8)

wherein:

W is C(R$^7$)(R$^6$), S, or N(R$^7$);

J$^1$ and J$^2$ are, independently, hydrogen, hydroxy, halogen, cyano, trifluoromethyl, trifluoromethoxy, nitro, trimethylsilanyl, —OR$^a$, —SR$^a$, —OC(O)R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$C(NR$^a$)N(R$^a$)$_2$, —N(R$^a$)S(O)$_t$R$^a$, —N(R$^a$)S(O)$_2$R$^a$, —S(O)OR$^a$, —S(O)$_2$OR$^a$, —S(O)N(R$^a$)$_2$, —S(O)$_2$N(R$^a$)$_2$, or PO$_3$(R$^a$)$_2$, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted by one or more suitable substituent;

each R$^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl; and p and q are, independently, an integer of 1 to 4.

22. The macrocyclic compound of claim 21, having the structure of Formula (B8.1) or a pharmaceutically acceptable salt thereof:

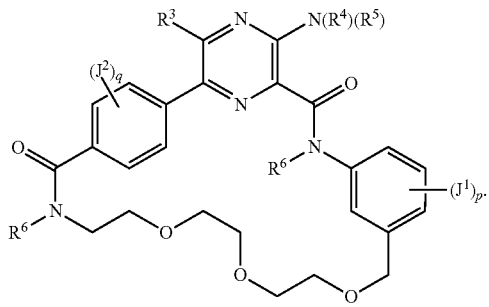

(B8.1)

23. The macrocyclic compound of claim 1, having the structure of Formula (B9) or a pharmaceutically acceptable salt thereof:

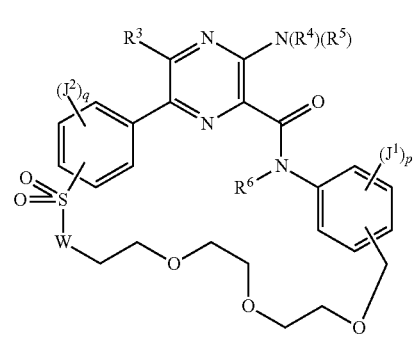

(B9)

wherein:

W is C(R$^7$)(R$^6$), S, or N(R$^7$);

J$^1$ and J$^2$ are, independently, hydrogen, hydroxy, halogen, cyano, trifluoromethyl, trifluoromethoxy, nitro, trimethylsilanyl, —OR$^a$, —SR$^a$, —OC(O)R$^a$, —N(R$^a$)$_2$, —C(O)R$^3$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, —N(R$^a$)C(NR$^a$)N(R$^a$)$_2$, —N(R$^a$)S(O)R$^a$, —N(R$^a$)S(O)$_2$R$^a$, —S(O)OR$^a$, —S(O)$_2$OR$^a$, —S(O)N(R$^a$)$_2$, —S(O)$_2$N(R$^a$)$_2$, or PO$_3$(R$^a$)$_2$, alkyl, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted by one or more suitable substituent;

each R$^a$ is, independently, hydrogen, alkyl, haloalkyl, carbocyclyl, carbocyclylalkyl, alkyl, aralkyl, heterocycloalkyl, heterocycloalkylalkyl, heteroaryl or heteroarylalkyl; and p and q are, independently, an integer of 1 to 4.

24. The macrocyclic compound of claim 1, having the structure of Formula (B9.1) or a pharmaceutically acceptable salt thereof:

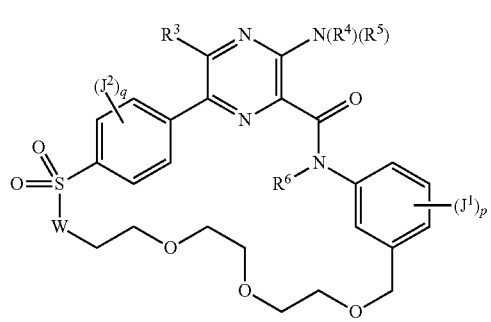

(B9.1)

wherein:

W is C(R⁷)(R⁶), S, or N(R⁷);

J¹ and J² are, independently, hydrogen, hydroxy, halogen, cyano, trifluoromethyl, trifluoromethoxy, nitro, trimethylsilanyl, —ORᵃ, —SRᵃ, —OC(O)Rᵃ, —N(Rᵃ)₂, —C(O)Rᵃ, —C(O)ORᵃ, —OC(O)N(Rᵃ)₂, —C(O)N(Rᵃ)₂, —N(Rᵃ)C(O)ORᵃ, —(Rᵃ)C(O)Rᵃ, —N(Rᵃ)C(O)N(Rᵃ)₂, N(Rᵃ)C(NRᵃ)N(Rᵃ)₂, —N(Rᵃ)S(O)ᵣRᵃ, —N(Rᵃ)S(O)₂Rᵃ, —(O)ORᵃ, —S(O)₂ORᵃ, —S(O)N(Rᵃ)₂, —S(O)₂N(Rᵃ)₂, or PO₃(Rᵃ)₂, alkenyl, alkynyl, cycloalkyl, cycloalkenyl, heterocyclyl, aryl, heteroaryl, aralkyl, or heteroaralkyl, wherein each alkyl, alkenyl, alkynyl, cycloalkyl, cycloalkenyl, heterocyclyl, aryl, heteroaryl, aralkyl, or heteroaralkyl is optionally substituted by one or more suitable substituent;

each Rᵃ is, independently, hydrogen, alkyl, haloalkyl, carbocyclyl, carbocyclylalkyl, aryl, aralkyl, heterocycloalkyl, heterocycloalkylalkyl, heteroaryl or heteroarylalkyl; and p and q are, independently, an integer of 1 to 4.

25. A unit dose comprising an effective amount of a macrocyclic compound according to claim 1.

26. A pharmaceutical composition comprising an effective amount of a macrocyclic compound according to claim 1 and a pharmaceutically acceptable carrier.

27. The macrocyclic compound of claim 1, wherein the compound is:

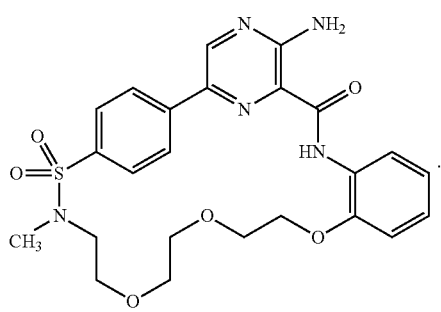 [SMILES: CN1CCOCCOCCOc2ccccc2NC(=O)c2nc(cnc2N)-c2ccc(cc2)S1(=O)=O]

28. The macrocyclic compound of claim 1, wherein the compound is:

29. The macrocyclic compound of claim 1, wherein the compound is:

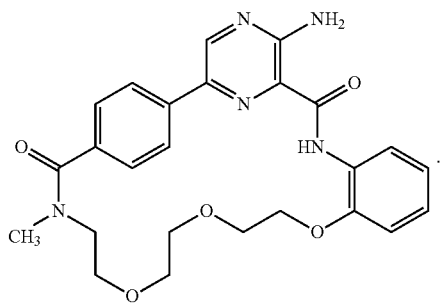 [SMILES: CN1CCOCCOCCOc2ccccc2NC(=O)c2nc(cnc2N)-c2ccc(cc2)C1=O]

30. The macrocyclic compound of claim 1, wherein the compound is:

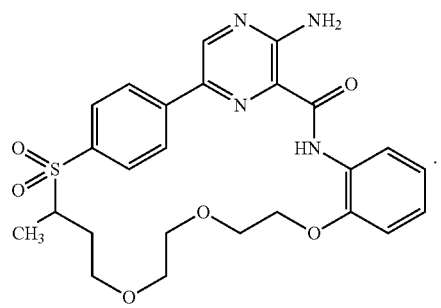 [SMILES: CC1CCOCCOCCOc2ccccc2NC(=O)c2nc(cnc2N)-c2ccc(cc2)S1(=O)=O]

31. The macrocyclic compound of claim 1, wherein the compound is:

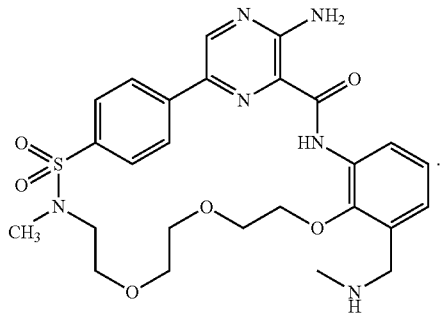 [SMILES: CNCc1cccc2c1OCCOCCOCCN(C)S(=O)(=O)c1ccc(cc1)-c1cnc(N)c(n1)C(=O)N2]

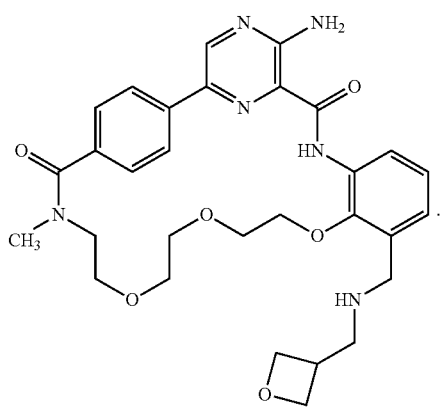 [SMILES: CN1CCOCCOCCOc2c(CNCC3COC3)cccc2NC(=O)c2nc(cnc2N)-c2ccc(cc2)C1=O]

32. The macrocyclic compound of claim 1, wherein the compound is:

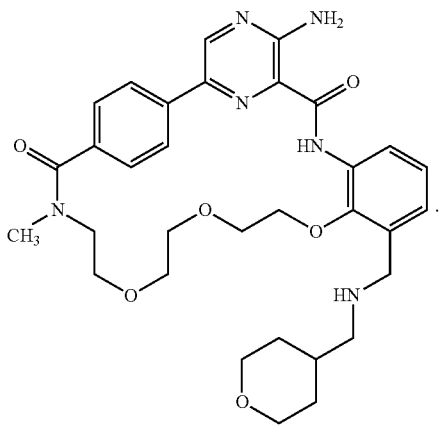 [SMILES: CN1CCOCCOCCOc2c(CNCC3CCOCC3)cccc2NC(=O)c2nc(cnc2N)-c2ccc(cc2)C1=O]

33. The macrocyclic compound of claim 1, wherein the compound is:

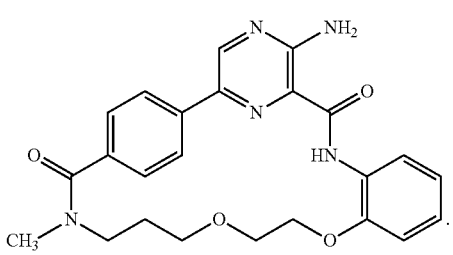 [SMILES: CN1CCCOCCOc2ccccc2NC(=O)c2nc(cnc2N)-c2ccc(cc2)C1=O]

34. The macrocyclic compound of claim 1, wherein the compound is:

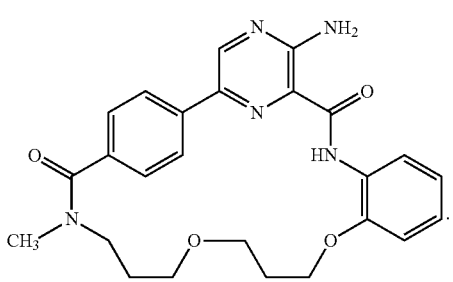 [SMILES: CN1CCCOCCCOc2ccccc2NC(=O)c2nc(cnc2N)-c2ccc(cc2)C1=O]

35. The macrocyclic compound of claim 1, wherein the compound is:

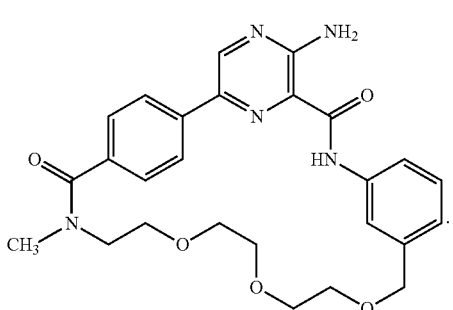

36. The macrocyclic compound of claim 1, wherein the compound is:

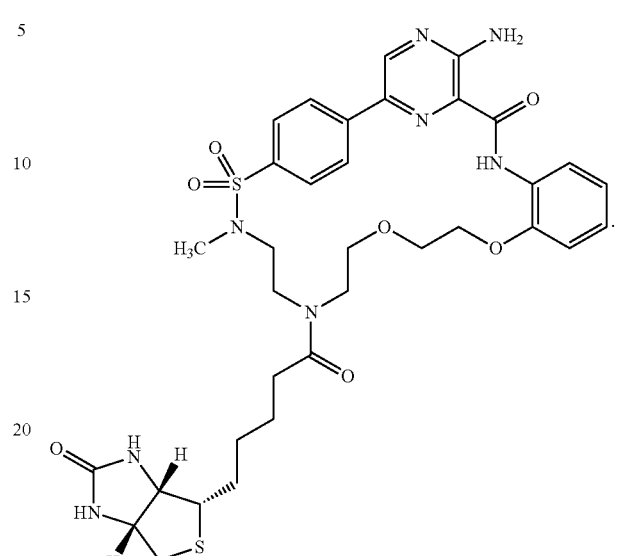

37. The macrocyclic compound of claim 1, wherein the compound is:

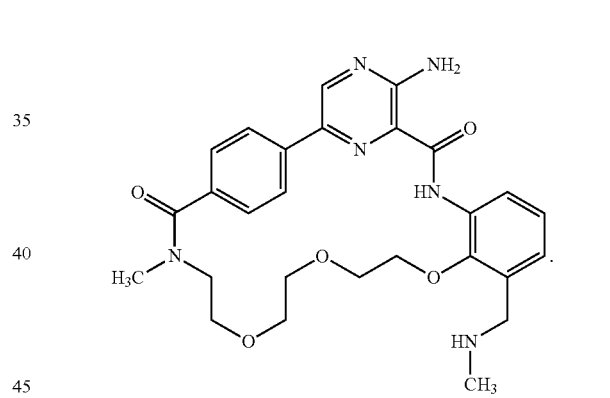

38. The macrocyclic compound of claim 1, wherein the compound is:

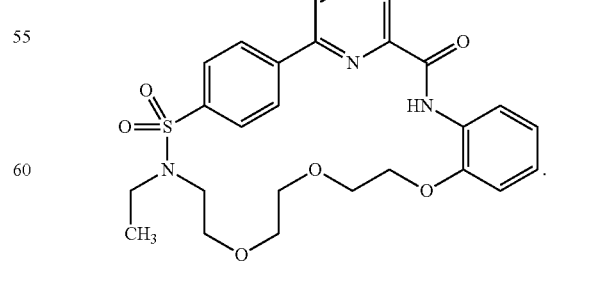

39. The macrocyclic compound of claim 1, wherein the compound is:

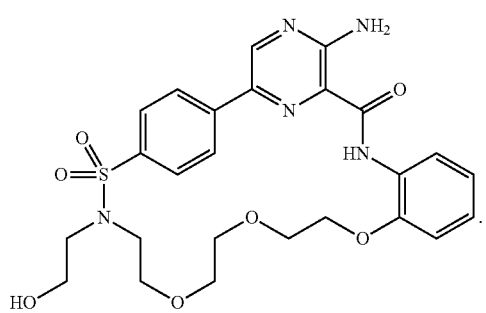 [SMILES: Nc1ncc2nc1C(=O)Nc1ccccc1OCCOCCOCCN(CCO)S(=O)(=O)c1ccc-2cc1]

40. The macrocyclic compound of claim 1, wherein the compound is:

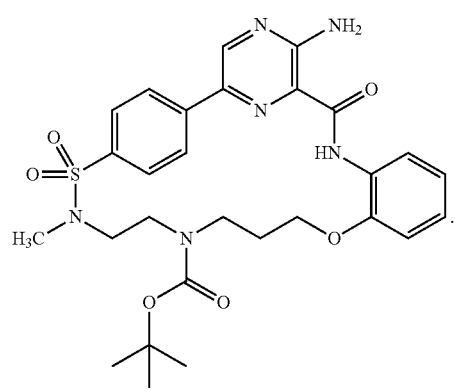 [SMILES: CN1CCN(C(=O)OC(C)(C)C)CCCOc2ccccc2NC(=O)c2nc(cnc2N)-c2ccc(cc2)S1(=O)=O]

41. The macrocyclic compound of claim 1, wherein the compound is:

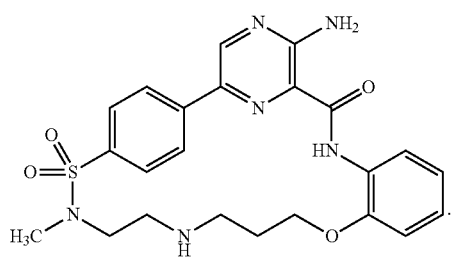 [SMILES: CN1CCNCCCOc2ccccc2NC(=O)c2nc(cnc2N)-c2ccc(cc2)S1(=O)=O]

42. The macrocyclic compound of claim 1, wherein the compound is:

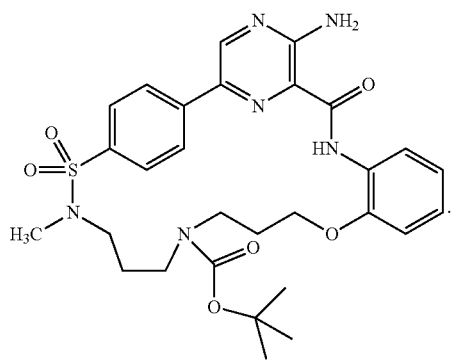 [SMILES: CN1CCCN(C(=O)OC(C)(C)C)CCCOc2ccccc2NC(=O)c2nc(cnc2N)-c2ccc(cc2)S1(=O)=O]

43. The macrocyclic compound of claim 1, wherein the compound is:

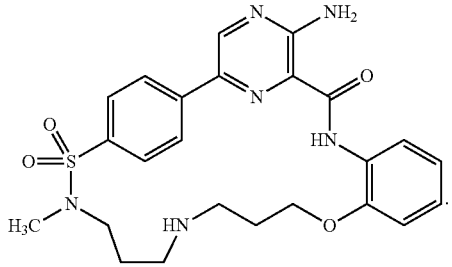 [SMILES: CN1CCCNCCCOc2ccccc2NC(=O)c2nc(cnc2N)-c2ccc(cc2)S1(=O)=O]

44. The macrocyclic compound of claim 1, wherein the compound is:

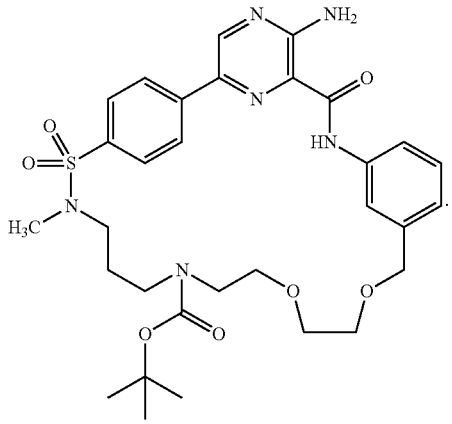 [SMILES: CN1CCCN(C(=O)OC(C)(C)C)CCOCCOCc2cccc(c2)NC(=O)c2nc(cnc2N)-c2ccc(cc2)S1(=O)=O]

45. The macrocyclic compound of claim 1, wherein the compound is:

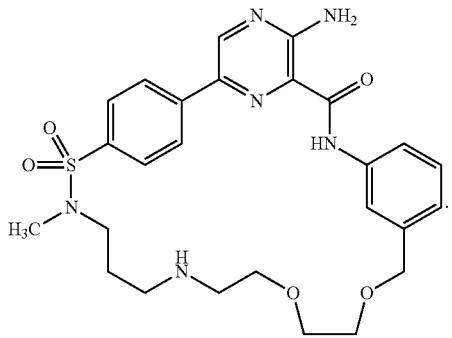 [SMILES: CN1CCCNCCOCCOCc2cccc(c2)NC(=O)c2nc(cnc2N)-c2ccc(cc2)S1(=O)=O]

46. The macrocyclic compound of claim 1, wherein the compound is:

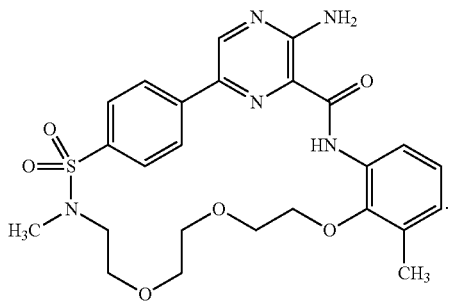 [SMILES: Cc1cccc2c1OCCOCCOCCN(C)S(=O)(=O)c1ccc(cc1)-c1cnc(N)c(n1)C(=O)N2]

47. The macrocyclic compound of claim 1, wherein the compound is:

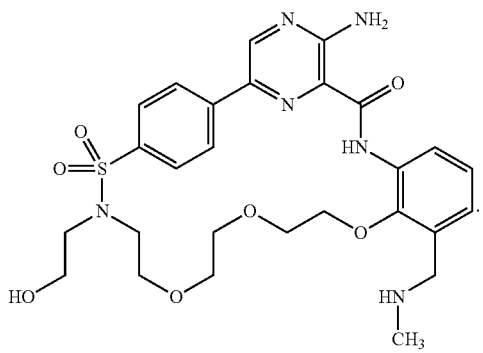 [SMILES: CNCc1cccc2c1OCCOCCOCCN(CCO)S(=O)(=O)c1ccc(cc1)-c1cnc(N)c(n1)C(=O)N2]

48. The macrocyclic compound of claim 1, wherein the compound is:

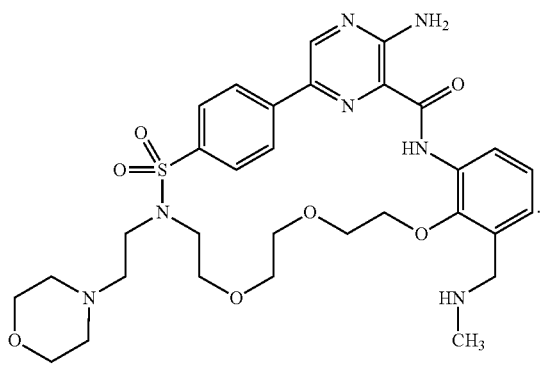 [SMILES: CNCc1cccc2c1OCCOCCOCCN(CCN1CCOCC1)S(=O)(=O)c1ccc(cc1)-c1cnc(N)c(n1)C(=O)N2]

49. The macrocyclic compound of claim 1, wherein the compound is:

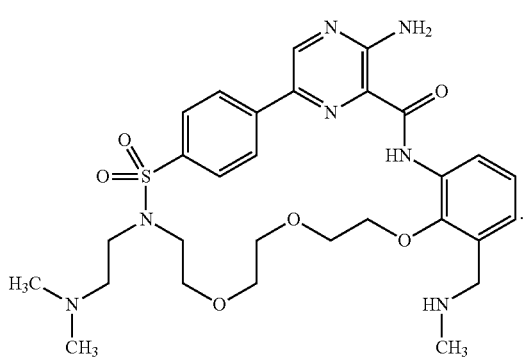 [SMILES: CNCc1cccc2c1OCCOCCOCCN(CCN(C)C)S(=O)(=O)c1ccc(cc1)-c1cnc(N)c(n1)C(=O)N2]

50. The macrocyclic compound of claim 1, wherein the compound is:

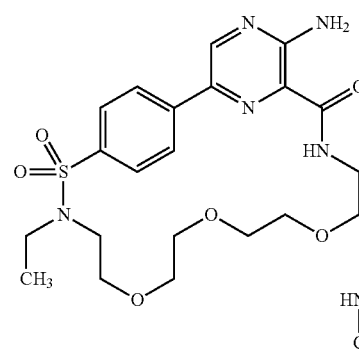

51. The macrocyclic compound of claim 1, wherein the compound is:

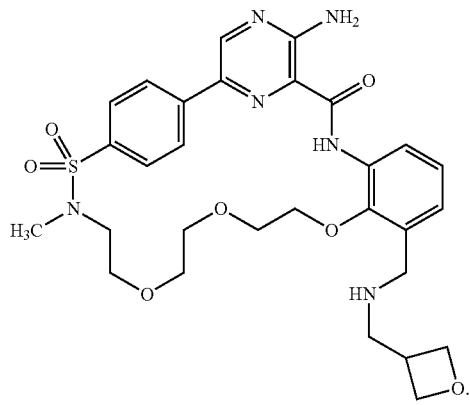

52. The macrocyclic compound of claim 1, wherein the compound is:

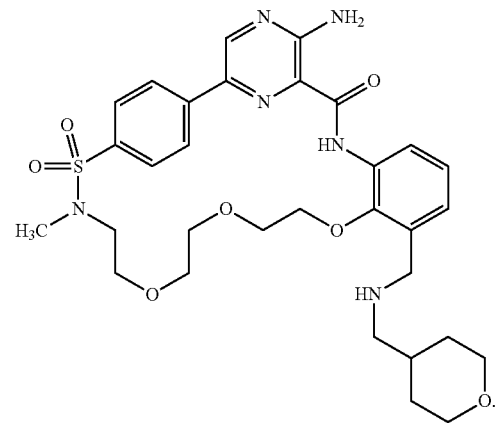 [SMILES: CN1CCOCCOCCOc2c(CNCC3CCOCC3)cccc2NC(=O)c2nc(cnc2N)-c2ccc(cc2)S1(=O)=O]

53. The macrocyclic compound of claim 1, wherein the compound is:

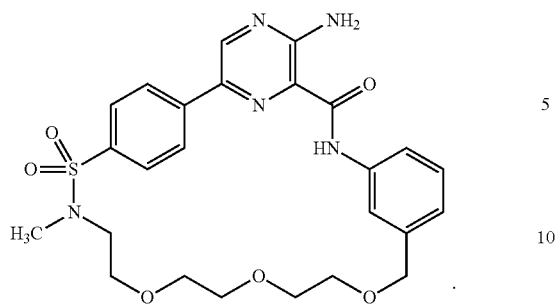
54. The macrocyclic compound of claim 1, wherein the compound is:
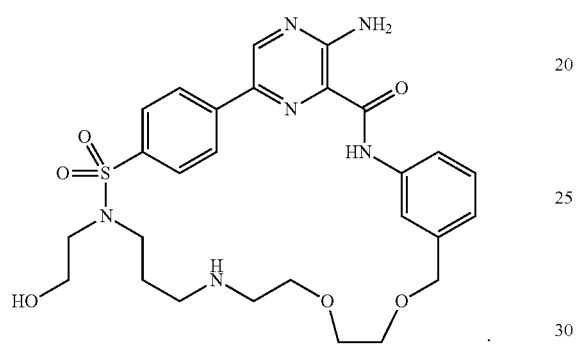
* * * * *